US008383668B2

United States Patent
Ebdrup et al.

(10) Patent No.: US 8,383,668 B2
(45) Date of Patent: Feb. 26, 2013

(54) 11-BETA-HYDROXYSTEROID DEHYDROGENASE TYPE 1 ACTIVE COMPOUNDS

(75) Inventors: Soren Ebdrup, Roskilde (DK); Henrik Sune Andersen, Holte (DK)

(73) Assignee: High Point Pharmaceuticals, LLC, High Point, NC (US)

( * ) Notice: Subject to any disclaimer, the term of this patent is extended or adjusted under 35 U.S.C. 154(b) by 0 days.

(21) Appl. No.: 13/235,200

(22) Filed: Sep. 16, 2011

(65) Prior Publication Data

US 2012/0010194 A1   Jan. 12, 2012

Related U.S. Application Data

(62) Division of application No. 12/307,999, filed as application No. PCT/EP2007/056467 on Jun. 28, 2007, now Pat. No. 8,048,908.

(30) Foreign Application Priority Data

Jul. 13, 2006   (EP) .................................... 06117119

(51) Int. Cl.
*A61K 31/402* (2006.01)
*C07D 207/08* (2006.01)
*C07D 207/12* (2006.01)
*C07D 207/14* (2006.01)

(52) U.S. Cl. ......... 514/424; 514/426; 514/428; 548/577

(58) Field of Classification Search .................. 514/424, 514/426, 428; 548/577
See application file for complete search history.

(56) References Cited

PUBLICATIONS

Miyazaki, et al. Document No. 144:36258, retrieved from CAPLUS on Nov. 19, 2010.*

Office Action for U.S. Appl. No. 13/128,045 dated Sep. 26, 2012.
Rauz et al., "Inhibition of 11 beta-hydroxysteroid dehydrogenase type 1 lowers intraocular pressure in patients with ocular hypertension" Q. J. Med., 96:481-490 (2003).
Tomlinson, et al., "11 beta-Hydroxysteroid Dehydrogenase Type 1: A Tissue-Specific Regulator of Glucocorticoid Response," Endocrine Reviews, 25(5):831-866 (2004).

* cited by examiner

*Primary Examiner* — Shawquia Young
(74) *Attorney, Agent, or Firm* — Samuel B. Rollins

(57) ABSTRACT

The use of substituted amides for modulating the activity of 11β-hydroxysteroid dehydrogenase type 1 (11βHSD1) and the use of these compounds as pharmaceutical compositions, are described. Also a novel class of substituted amides, of the general formula I. Their use in therapy, pharmaceutical compositions comprising the compounds, as well as their use in the manufacture of medicaments are described. The present compounds are modulators and more specifically inhibitors of the activity of 11βHSDI and may be useful in the treatment of a range of medical disorders where a decreased intracellular concentration of active glucocorticoid is desirable.

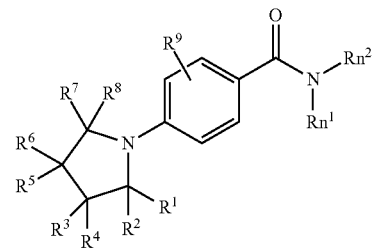

3 Claims, No Drawings

11-BETA-HYDROXYSTEROID DEHYDROGENASE TYPE 1 ACTIVE COMPOUNDS

The present application is a divisional application of U.S. patent application Ser. No. 12/307,999, which is the United States national-stage application, pursuant to 35 U.S.C. §371, of international application No. PCT/EP2007/056467, filed Jun. 28, 2007, which claims the benefit of priority to European Patent App. No. 06117119.5, filed Jul. 13, 2006.

FIELD OF INVENTION

The present invention relates to novel substituted amides, to their use in therapy, to pharmaceutical compositions comprising the same, to the use of said compounds in the manufacture of medicaments, and to therapeutic methods comprising the administration of the compounds. The present invention also relates to pharmaceutical compositions comprising the present compounds for treating disorders where it is desirable to modulate the activity of 11β-hydroxysteroid dehydrogenase type 1 (11βHSD1). The present compounds modulate the activity of 11β-hydroxysteroid dehydrogenase type 1 (11βHSD1) and are accordingly useful in the treatment of diseases in which such a modulation is beneficial, such as the metabolic syndrome.

BACKGROUND OF THE INVENTION

The metabolic syndrome is a major global health problem. In the US, the prevalence in the adult population is currently estimated to be approximately 25%, and it continues to increase both in the US and worldwide. The metabolic syndrome is characterised by a combination of insulin resistance, dyslipidemia, obesity and hypertension leading to increased morbidity and mortality of cardiovascular diseases. People with the metabolic syndrome are at increased risk of developing frank type 2 diabetes, the prevalence of which is equally escalating.

In type 2 diabetes, obesity and dyslipidemia are also highly prevalent and around 70% of people with type 2 diabetes additionally have hypertension once again leading to increased mortality of cardiovascular diseases.

In the clinical setting, it has long been known that glucocorticoids are able to induce all of the cardinal features of the metabolic syndrome and type 2 diabetes.

11β-hydroxysteroid dehydrogenase type 1 (11βHSD1) catalyses the local generation of active glucocorticoid in several tissues and organs including predominantly the liver and adipose tissue, but also e.g., skeletal muscle, bone, pancreas, endothelium, ocular tissue and certain parts of the central nervous system. Thus, 11βHSD1 serves as a local regulator of glucocorticoid actions in the tissues and organs where it is expressed (Tannin et al., *J. Biol. Chem.*, 266, 16653 (1991); Bujalska et al., *Endocrinology*, 140, 3188 (1999); Whorwood et al., *J. Clin Endocrinol Metab.*, 86, 2296 (2001); Cooper et al., *Bone*, 27, 375 (2000); Davani et al., *J. Biol. Chem.*, 275, 34841 (2000); Brem et al., *Hypertension*, 31, 459 (1998); Rauz et al., *Invest. Ophthalmol. Vis. Sci.*, 42, 2037 (2001); Moisan et al., *Endocrinology*, 127, 1450 (1990)).

The role of 11βHSD1 in the metabolic syndrome and type 2 diabetes is supported by several lines of evidence. In humans, treatment with the non-specific 11βHSD1 inhibitor carbenoxolone improves insulin sensitivity in lean healthy volunteers and people with type 2 diabetes. Likewise, 11βHSD1 knock-out mice are resistant to insulin resistance induced by obesity and stress. Additionally, the knock-out mice present with an anti-atherogenic lipid profile of decreased VLDL triglycerides and increased HDL-cholesterol. Conversely, mice that overexpress 11βHSD1 in adipocytes develop insulin resistance, hyperlipidemia and visceral obesity, a phenotype that resembles the human metabolic syndrome (Andrews et al., *J. Clin. Endocrinol. Metab.*, 88, 285 (2003); Walker et al., *J. Clin. Endocrinol. Metab.*, 80, 3155 (1995); Morton et al., *J. Biol. Chem.*, 276, 41293 (2001); Kotelevtsev et al., *Proc. Natl. Acad. Sci. USA*, 94, 14924 (1997); Masuzaki et al., *Science*, 294, 2166 (2001)).

The more mechanistic aspects of 11βHSD1 modulation and thereby modulation of intracellular levels of active glucocorticoid have been investigated in several rodent models and different cellular systems. 11βHSD1 promotes the features of the metabolic syndrome by increasing hepatic expression of the rate-limiting enzymes in gluconeogenesis, namely phosphoenolpyruvate carboxykinase and glucose-6-phosphatase, promoting the differentiation of preadipocytes into adipocytes thus facilitating obesity, directly and indirectly stimulating hepatic VLDL secretion, decreasing hepatic LDL uptake and increasing vessel contractility (Kotelevtsev et al., *Proc. Natl. Acad. Sci. USA*, 94, 14924 (1997); Morton et al., *J. Biol. Chem.* 276, 41293 (2001); Bujalska et al., *Endocrinology*, 140, 3188 (1999); Souness et al., *Steroids*, 67, 195 (2002), Brindley & Salter, *Prog. Lipid Res.*, 30, 349 (1991)).

WO 01/90090, WO 01/90091, WO 01/90092, WO 01/90093, and WO 01/90094 discloses various thiazol-sulfonamides as inhibitors of the human 11β-hydroxysteroid dehydrogenase type 1 enzyme, and further states that said compounds may be useful in treating diabetes, obesity, glaucoma, osteoporosis, cognitive disorders, immune disorders and depression. WO 04/089470 discloses various substituted amides as modulators of the human 11β-hydroxysteroid dehydrogenase type 1 enzyme, and further states that said compounds may be useful in treating medical disorders where a decreased intracellular concentration of active glucocorticoid is desirable. WO 2004/089415 and WO 2004/089416 discloses various combination therapies using an 11β-hydroxysteroid dehydrogenase type 1 inhibitor and respectively a glucocorticoid receptor agonist or an anti-hypertensive agent.

We have now found substituted amides that modulate the activity of 11βHSD1 leading to altered intracellular concentrations of active glucocorticoid. More specifically, the present compounds inhibit the activity of 11βHSD1 leading to decreased intracellular concentrations of active glucocorticoid. Thus, the present compounds can be used to treat disorders where a decreased level of active intracellular glucocorticoid is desirable, such as e.g., the metabolic syndrome, type 2 diabetes, impaired glucose tolerance (IGT), impaired fasting glucose (IFG), dyslipidemia, obesity, hypertension, diabetic late complications, cardiovascular diseases, arteriosclerosis, atherosclerosis, myopathy, muscle wasting, osteoporosis, neurodegenerative and psychiatric disorders, and adverse effects of treatment or therapy with glucocorticoid receptor agonists.

One object of the present invention is to provide compounds, pharmaceutical compositions and use of compounds that modulate the activity of 11βHSD1.

DEFINITIONS

In the following structural formulas and throughout the present specification, the following terms have the indicated meaning. The examples provided in the definitions present in this application are non-inclusive unless otherwise stated. They include but are not limited to the recited examples.

The term "halogen" or "halo" includes fluorine, chlorine, bromine, and iodine.

The term "trihalomethyl" includes trifluoromethyl, trichloromethyl, tribromomethyl, and triiodomethyl.

The term "trihalomethoxy" or "trihalomethyloxy" includes trifluorometoxy, trichlorometoxy, tribromometoxy, and triiodometoxy.

The term "alkyl" as used herein represents a saturated, branched or straight hydrocarbon group having the indicated number of carbon atoms, e.g. $C_{1-2}$-alkyl, $C_{1-3}$ alkyl, $C_{1-4}$-alkyl, $C_{1-6}$-alkyl, $C_{2-6}$-alkyl, $C_{3-6}$-alkyl, $C_{1-8}$-alkyl, $C_{1-10}$-alkyl, $C_{3-12}$-alkyl, $C_{6-12}$-alkyl, and the like. Representative examples are methyl, ethyl, propyl (e.g. prop-1-yl, prop-2-yl (or iso-propyl)), butyl (e.g. 2-methylprop-2-yl (or tert-butyl), but-1-yl, but-2-yl), pentyl (e.g. pent-1-yl, pent-2-yl, pent-3-yl), 2-methylbut-1-yl, 3-methylbut-1-yl, hexyl (e.g. hex-1-yl), heptyl (e.g. hept-1-yl), octyl (e.g. oct-1-yl), nonyl (e.g. non-1-yl), and the like.

The term "alkenyl" as used herein represents a branched or straight hydrocarbon group having the indicated number of carbon atoms and at least one double bond, e.g. $C_{2-6}$-alkenyl, $C_{2-7}$-alkenyl, $C_{2-8}$-alkenyl, $C_{2-10}$-alkenyl, $C_{3-6}$-alkenyl, and the like. Representative examples are ethenyl (or vinyl), propenyl (e.g. prop-1-enyl, prop-2-enyl), butadienyl (e.g. buta-1,3-dienyl), butenyl (e.g. but-1-en-1-yl, but-2-en-1-yl), pentenyl (e.g. pent-1-en-1-yl, pent-2-en-2-yl), hexenyl (e.g. hex-1-en-2-yl, hex-2-en-1-yl), 1-ethylprop-2-enyl, 1,1-(dimethyl)prop-2-enyl, 1-ethylbut-3-enyl, 1,1-(dimethyl)but-2-enyl, and the like.

The term "alkynyl" as used herein represents a branched or straight hydrocarbon group having the indicated number of carbon atoms and at least one triple bond, e.g. $C_{2-6}$-alkynyl, $C_{2-7}$-alkynyl, $C_{2-8}$-alkynyl, $C_{2-10}$-alkynyl, $C_{3-6}$-alkynyl, and the like. Alkynyl includes $C_2$-$C_6$ straight chain unsaturated aliphatic hydrocarbon groups and $C_4$-$C_6$ branched unsaturated aliphatic hydrocarbon groups having the specified number of carbon atoms. Representative examples are ethynyl, propynyl (e.g. prop-1-ynyl, prop-2-ynyl), butynyl (e.g. but-1-ynyl, but-2-ynyl), pentynyl (e.g. pent-1-ynyl, pent-2-ynyl), hexynyl (e.g. hex-1-ynyl, hex-2-ynyl), 1-ethylprop-2-ynyl, 1,1-(dimethyl)prop-2-ynyl, 1-ethylbut-3-ynyl, 1,1-(dimethyl)but-2-ynyl, and the like.

The term "saturated or partially saturated monocyclic, bicyclic, or tricyclic ring system" represents but is not limited to aziridinyl, azepanyl, azocanyl, pyrrolinyl, pyrrolidinyl, 2-imidazolinyl, imidazolidinyl, 2-pyrazolinyl, morpholinyl, piperidinyl, thiomorpholinyl, piperazinyl, phthalimide, 1,2,3,4-tetrahydro-quinolinyl, 1,2,3,4-tetrahydro-isoquinolinyl, 1,2,3,4-tetrahydro-quinoxalinyl, indolinyl, 1,6-aza-bicyclo[3.2.1]octane, 2-aza-bicyclo-[4.1.1]octane, 2-aza-bicyclo[3.2.1]octanyl, 7-aza-bicyclo[4.1.1]octanyl, 9-aza-bicyclo-[3.3.2]decanyl, 4-aza-tricyclo[4.3.1.1$^{3,8}$]undecanyl, 9-aza-tricyclo[3.3.2.0$^{3,7}$]decanyl.

The term "saturated or partially saturated ring" represents cyclopropyl, cyclobutyl, cyclopentyl, cyclohexyl, cyclobutenyl, cyclopentenyl, cyclohexenyl, cycloheptenyl, cyclooctenyl, cyclononenyl, cyclodecenyl, tetrahydrofuranyl, and tetrahydropyranyl.

The term "saturated or partially saturated aromatic ring" represents cyclopentyl, cyclohexyl, cyclobutenyl, cyclopentenyl, cyclohexenyl, cycloheptenyl, cyclooctenyl, cyclononenyl, cyclodecenyl, tetrahydrofuranyl, tetrahydropyranyl, phenyl, pyridyl, and pyrimidinyl.

The term "cycloalkyl" as used herein represents a saturated monocyclic carbocyclic ring having the specified number of carbon atoms, e.g. $C_{3-6}$-alkyl, $C_{3-8}$-alkyl, $C_{3-10}$-alkyl, $C_{3-12}$ alkyl, $C_{6-12}$-alkyl, $C_{7-11}$ alkyl, $C_{8-12}$ alkyl, $C_{3-15}$-alkyl, $C_{5-12}$ alkyl, $C_{6-12}$ alkyl, $C_{5-15}$-alkyl, $C_{6-15}$-alkyl, and the like. Representative examples are cyclopropyl, cyclobutyl, cyclopentyl, cyclohexyl, cycloheptyl, cyclooctyl, and the like. Cycloalkyl is also intended to represent a saturated bicyclic carbocyclic ring having from 4 to 10 carbon atoms. Representative examples are decahydronaphthalenyl, bicyclo[3.3.0]octanyl, and the like. Cycloalkyl is also intended to represent a saturated carbocyclic ring having from 3 to 10 carbon atoms and containing one or two carbon bridges. Representative examples are adamantyl, norbornanyl, nortricyclyl, bicyclo[3.2.1]octanyl, bicyclo[2.2.2]octanyl, tricyclo[5.2.1.0/2,6]decanyl, bicyclo[2.2.1]heptyl, and the like.

The term "spirocycloalkyl" represents a saturated carbocyclic ring having from 3 to 10 carbon atoms and containing one or more spiro rings. Representative examples are spiro[2.5]octanyl, spiro[4.5]decanyl, and the like.

The term "cycloalkylalkyl" represents a cycloalkyl group as defined above attached through an alkyl group having the indicated number of carbon atoms or substituted alkyl group as defined above (e.g., cyclopropylmethyl, cyclobutylethyl, and adamantylmethyl).

The term "cycloalkenyl" represents a partially saturated, mono-, bi-, tri- or spirocarbocyclic group having the specified number of carbon atoms (e.g., cyclobutenyl, cyclopentenyl, cyclohexenyl, cycloheptenyl, cyclooctenyl, cyclononenyl, and cyclodecenyl).

The term "cycloalkylcarbonyl" represents a cycloalkyl group as defined above having the indicated number of carbon atoms attached through a carbonyl group (e.g., cyclopropylcarbonyl and cyclohexylcarbonyl).

The term "cycloalkylalkylcarbonyl" represents a cycloalkyl group as defined above attached through an alkyl group having the indicated number of carbon atoms or substituted alkyl group as defined above (e.g., cyclohexylmethylcarbonyl and cycloheptylethylcarbonyl).

The term "cycloalkyloxy" represents a cycloalkyl group as defined above having the indicated number of carbon atoms attached through an oxygen atom (e.g., cyclopropyloxy and cyclohexyloxy).

The term "cycloalkyloxyalkyl" represents a cycloalkyloxy group as defined above having the indicated number of carbon atoms attached through an alkyl group having the indicated number of carbon atoms (e.g., cyclopropyloxymethylene and cyclohexyloxyethylene).

The term "cycloalkyl-alkyloxy" represents a cycloalkyl group as defined above having the indicated number of carbon atoms attached through an alkyloxy group as defined above having the indicated number of carbon atoms (e.g., cyclohexylmethoxy and cyclopropyl-ethoxy).

The term "hetcycloalkyl" represents a saturated mono-, bi-, tri-, or spirocarbocyclic group having the specified number of atoms with 1-4 of the specified number being heteroatoms or groups selected from nitrogen, oxygen, sulphur, and $S(O)_m$ (m=0-2) (e.g., tetrahydrofuranyl, tetrahydropyranyl, tetrahydrothiopyranyl, piperidine, and pyridazine).

The term "spirohetcycloalkyl" represents a hetcycloalkyl group as defined above having the specified number of atoms with 1-4 of the specified number being heteroatoms or groups selected from nitrogen, oxygen, sulphur, and $S(O)_m$ (m=0-2) and containing one or more spiro cycloalkyl rings as defined above or one or more hetcycloalkyl rings as defined above. Representative examples are 8-aza-spiro[4.5]decane, 2,8-diaza-spiro[4.5]decan-1-one and the like.

The term "hetcycloalkylalkyl" represents a hetcycloalkyl group as defined above attached through an alkyl group having the indicated number of carbon atoms (e.g., tetrahydrofuranylmethyl, tetrahydropyranylethyl, and tertahydrothiopyranylmethyl).

The term "hetcycloalkylcarbonyl" represents a hetcycloalkyl group as defined above having the indicated number of carbon atoms attached through a carbonyl group (e.g., 1-piperidin-4-yl-carbonyl and 1-(1,2,3,4-tetrahydro-isoquinolin-6-yl)carbonyl).

The term "hetcycloalkyloxy" represents a hetcycloalkyl group as defined above attached through an oxygen atom (e.g. pyrrolidin-3-oxy, and piperidin-4-oxy).

The term "hetcycloalkyloxyalkyl" represents a hetcycloalkyloxy group as defined above attached through an alkyl having the indicated number of carbon atoms (e.g. (decahydro-quinolin-4-yl)-methoxy, and piperidin-4-yl-methoxy).

The term "alkyloxy" represents an alkyl group having the indicated number of carbon atoms attached through an oxygen bridge (e.g., methoxy, ethoxy, propyloxy, allyloxy, and cyclohexyloxy).

The term "alkyloxyalkyl" represents an alkyloxy group as defined above attached through an alkyl group having the indicated number of carbon atoms (e.g., methyloxy-methyl).

The term "aryl" as used herein is intended to include monocyclic, bicyclic or polycyclic carbocyclic aromatic rings. Representative examples are phenyl, naphthyl (e.g. naphth-1-yl, naphth-2-yl), anthryl (e.g. anthr-1-yl, anthr-9-yl), phenanthryl (e.g. phenanthr-1-yl, phenanthr-9-yl), azulenyl and the like. Aryl is also intended to include monocyclic, bicyclic or polycyclic carbocyclic aromatic rings substituted with carbocyclic aromatic rings. Representative examples are biphenyl (e.g. biphenyl-2-yl, biphenyl-3-yl, biphenyl-4-yl), phenylnaphthyl (e.g. 1-phenylnaphth-2-yl, 2-phenylnaphth-1-yl), biphenylenyl and the like. Aryl is also intended to include partially saturated bicyclic or polycyclic carbocyclic rings with at least one unsaturated moiety (e.g. a benzo moiety). Representative examples are, indanyl (e.g. indan-1-yl, indan-5-yl), indenyl (e.g. inden-1-yl, inden-5-yl), 1,2,3,4-tetrahydronaphthyl (e.g. 1,2,3,4-tetrahydronaphth-1-yl, 1,2,3,4-tetrahydronaphth-2-yl, 1,2,3,4-tetrahydronaphth-6-yl), 1,2-dihydronaphthyl (e.g. 1,2-dihydronaphth-1-yl, 1,2-dihydronaphth-4-yl, 1,2-dihydronaphth-6-yl), fluorenyl (e.g. fluoren-1-yl, fluoren-4-yl, fluoren-9-yl), and the like. Aryl is also intended to include partially saturated bicyclic or polycyclic carbocyclic aromatic rings containing one or two bridges. Representative examples are, benzonorbornyl (benzonorborn-3-yl, benzonorborn-6-yl), 1,4-ethano-1,2,3,4-tetrahydronapthyl (e.g. 1,4-ethano-1,2,3,4-tetrahydronapth-2-yl, 1,4-ethano-1,2,3,4-tetrahydronapth-10-yl), and the like. Aryl is also intended to include partially saturated bicyclic or polycyclic carbocyclic aromatic rings containing one or more spiro atoms. Representative examples are spiro[cyclopentane-1,1'-indane]-4-yl, spiro[cyclopentane-1,1'-indene]-4-yl, spiro[piperidine-4,1'-indane]-1-yl, spiro[piperidine-3,2'-indane]-1-yl, spiro-[piperidine-4,2'-indane]-1-yl, spiro[piperidine-4,1-indane]-3'-yl, spiro[pyrrolidine-3,2'-indane]-1-yl, spiro[pyrrolidine-3,1'-(3',4'-dihydronaphthalene)]-1-yl, spiro[piperidine-3,1'-(3',4'-dihydronaphthalene)]-1-yl, spiro[piperidine-4,1'-(3',4'-dihydronaphthalene)]-1-yl, spiro[piperidine-4,1'-indene]-1-yl, and the like.

The term "hetaryl" includes pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), isoxazolyl (3-isoxazolyl, 4-isoxazolyl, 5-isoxazolyl), thiazolyl (2-thiazolyl, 4-thiazolyl, 5-thiazolyl), thiophenyl (2-thiophenyl, 3-thiophenyl, 4-thiophenyl, 5-thiophenyl), furanyl (2-furanyl, 3-furanyl, 4-furanyl, 5-furanyl), pyridyl (2-pyridyl, 3-pyridyl, 5-pyridyl), 5-tetrazolyl, pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]-furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo-[b]furanyl), 3-(2,3-dihydro-benzo[b]furanyl), 4-(2,3-dihydro-benzo[b]furanyl), 5-(2,3-dihydro-benzo-[b]furanyl), 6-(2,3-dihydro-benzo-[b]furanyl), 7-(2,3-dihydro-benzo[b]-furanyl)), 1,4-benzodioxin (2-(1,4-benzodioxin), 3-(1,4-benzodioxin), 5-(1,4-benzodioxin), 6-(1,4-benzodioxin), 7-(1,4-benzodioxin), 8-(1,4-benzodioxin)), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl (2-(2,3-dihydro-benzo[b]thiophenyl), 3-(2,3-dihydro-benzo[b]thiophenyl), 4-(2,3-dihydrobenzo-[b]thiophenyl), 5-(2,3-dihydro-benzo[b]thiophenyl), 6-(2,3-dihydro-benzo[b]thiophenyl), 7-(2,3-dihydro-benzo[b]thiophenyl)), 4,5,6,7-tetrahydro-benzo[b]thiophenyl (2-(4,5,6,7-tetrahydro-benzo[b]thiophenyl), 3-(4,5,6,7-tetrahydro-benzo[b]thiophenyl), 4-(4,5,6,7-tetrahydro-benzo[b]thiophenyl), 5-(4,5,6,7-tetrahydro-benzo[b]thiophenyl), 6-(4,5,6,7-tetrahydro-benzo[b]thiophenyl), 7-(4,5,6,7-tetrahydro-benzo[b]thiophenyl)), thieno[2,3-b]thiophenyl, 4,5,6,7-tetrahydro-thieno[2,3-c]pyridyl (4-(4,5,6,7-tetrahydro-thieno[2,3-c]pyridyl), 5-4,5,6,7-tetrahydro-thieno[2,3-c]pyridyl), 6-(4,5,6,7-tetrahydro-thieno[2,3-c]pyridyl), 7-(4,5,6,7-tetrahydro-thieno[2,3-c]pyridyl)), indolyl (1-indolyl, 2-indolyl, 3-indolyl, 4-indolyl, 5-indolyl, 6-indolyl, 7-indolyl), isoindolyl (1-isoindolyl, 2-isoindolyl, 3-isoindolyl, 4-isoindolyl, 5-isoindolyl, 6-isoindolyl, 7-isoindolyl), 1,3-dihydro-isoindolyl(1-(1,3-dihydro-isoindolyl), 2-(1,3-dihydro-isoindolyl), 3-(1,3-dihydro-isoindolyl), 4-(1,3-dihydro-isoindolyl), 5-(1,3-dihydro-isoindolyl), 6-(1,3-dihydro-isoindolyl), 7-(1,3-dihydro-isoindolyl)), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benz-oxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), benzo-[1,2,5]oxadiazolyl, (4-benzo[1,2,5]oxadiazole, 5-benzo[1,2,5]oxadiazole), carbazolyl (1-carbazolyl, 2-carbazolyl, 3-carbazolyl, 4-carbazolyl), piperidinyl (2-piperidinyl, 3-piperidinyl, 4-piperidinyl), and pyrrolidinyl (1-pyrrolidinyl, 2-pyrrolidinyl, 3-pyrrolidinyl).

The term "arylalkyl" represents an aryl group as defined above attached through an alkyl group having the indicated number of carbon atoms (e.g., benzyl, phenylethyl, 3-phenylpropyl, 1-naphtylmethyl, and 2-(1-naphtyl)ethyl).

The term "hetarylalkyl" or "hetaralkyl" represents a hetaryl group as defined above attached through an alkyl group having the indicated number of carbon atoms (e.g., (2-furyl)methyl, (3-furyl)methyl, (2-thienyl)methyl, (3-thienyl)methyl, (2-pyridyl)methyl, and 1-methyl-1-(2-pyrimidyl)ethyl).

The term "aryloxyhetaryl" represents an aryloxy group as defined above attached through a hetaryl group (e.g., 2-phenoxy-pyridyl).

The term "aryloxy" represents an aryl group as defined above attached through an oxygen bridge (e.g., phenoxy and naphthyloxy).

The term "hetaryloxy" represents a hetaryl group as defined above attached through an oxygen bridge (e.g., 2-pyridyloxy).

The term "arylalkyloxy" represents an arylalkyl group as defined above attached through an oxygen bridge (e.g., phenethyloxy and naphthylmethyloxy).

The term "hetarylalkyloxy" represents a hetarylalkyl group as defined above attached through an oxygen bridge (e.g., 2-pyridylmethyloxy).

The term "alkyloxycarbonyl" represents an alkyloxy group as defined above attached through a carbonyl group (e.g., methylformiat and ethylformiat).

The term "aryloxycarbonyl" represents an aryloxy group as defined above attached through a carbonyl group (e.g., phenylformiat and 2-thiazolylformiat).

The term "arylalkyloxycarbonyl" represents an "arylalkyloxy" group as defined above attached through a carbonyl group (e.g., benzylformiat and phenyletylformiat).

The term "alkylthio" represents an alkyl group having the indicated number of carbon atoms attached through a sulphur bridge (e.g., methylthio and ethylthio).

The term "arylthio" represents an aryl group as defined above attached through a sulphur bridge (e.g., benzenthiol and naphthylthiol).

The term "hetarylthio" represents a hetaryl group as defined above attached through a sulphur bridge (e.g., pyridine-2-thiol and thiazole-2-thiol).

The term "arylthioalkyl" represents an arylthio group as defined above attached through an alkyl group having the indicated number of carbon atoms (e.g., methylsulfanyl benzene, and ethylsulfanyl naphthalene).

The term "hetarylthioalkyl" represents a hetarylthio group as defined above attached through an alkyl group having the indicated number of carbon atoms (e.g., 2-methylsulfanyl-pyridine and 1-ethylsulfanyl-isoquinoline).

The term "hetaryloxyaryl" represents a hetaryloxy group as defined above attached through an aryl group as defined above (e.g., 1-phenoxy-isoquinolyl and 2-phenoxypyridyl).

The term "hetaryloxyhetaryl" represents a hetaryloxy group as defined above attached through a hetaryl group as defined above (e.g., 1-(2-pyridyloxy-isoquinoline) and 2-(imidazol-2-yloxy-pyridine)).

The term "aryloxyalkyl" represents an aryloxy group as defined above attached through an alkyl group having the indicated number of carbon atoms (e.g., phenoxymethyl and naphthyloxyethyl).

The term "aryloxyaryl" represents an aryloxy group as defined above attached through an aryl group as defined above (e.g., 1-phenoxy-naphthalene and phenyloxy-phenyl).

The term "arylalkyloxyalkyl" represents an arylalkyloxy group as defined above attached through an alkyl group having the indicated number of carbon atoms (e.g., ethoxymethyl-benzene and 2-methoxymethyl-naphthalene).

The term "hetaryloxyalkyl" represents a hetaryloxy group as defined above attached through an alkyl group having the indicated number of carbon atoms (e.g., 2-pyridyloxymethyl and 2-quinolyloxyethyl).

The term "hetarylalkyloxyalkyl" represents a hetarylalkyloxy group as defined above attached through an alkyl group having the indicated number of carbon atoms (e.g., 4-methoxymethyl-pyrimidine and 2-methoxymethyl-quinoline).

The term "alkylcarbonyl" represents an alkyl group as defined above having the indicated number of carbon atoms attached through a carbonyl group (e.g., octylcarbonyl, pentylcarbonyl, and 3-hexenylcarbonyl).

The term "arylcarbonyl" represents an aryl group as defined above attached through a carbonyl group (e.g., benzoyl).

The term "hetarylcarbonyl" represents a hetaryl group as defined above attached through a carbonyl group (e.g., 2-thiophenylcarbonyl, 3-methoxy-anthrylcarbonyl, and oxazolylcarbonyl).

The term "carbonylalkyl" represents a carbonyl group attached through an alkyl group having the indicated number of carbon atoms (e.g., acetyl).

The term "alkylcarbonylalkyl" represents an alkylcarbonyl group as defined above attached through an alkyl group having the indicated number of carbon atoms (e.g., propan-2-one and 4,4-dimethyl-pentan-2-one).

The term "arylcarbonylalkyl" represents a arylcarbonyl group as defined above attached through an alkyl group having the indicated number of carbon atoms (e.g., 1-phenyl-propan-1-one and 1-(3-chloro-phenyl)-2-methyl-butan-1-one).

The term "hetarylcarbonylalkyl" represents a hetarylcarbonyl group as defined above attached through an alkyl group having the indicated number of carbon atoms (e.g., 1-pyridin-2-yl-propan-1-one and 1-(1-H-imidazol-2-yl)-propan-1-one).

The term "arylalkylcarbonyl" represents an arylalkyl group as defined above having the indicated number of carbon atoms attached through a carbonyl group (e.g., phenylpropylcarbonyl and phenylethylcarbonyl).

The term "hetarylalkylcarbonyl" represents a hetarylalkyl group as defined above wherein the alkyl group is in turn attached through a carbonyl (e.g., imidazolylpentylcarbonyl).

The term "alkylcarbonylamino" represents an "alkylcarbonyl" group as defined above wherein the carbonyl is in turn attached through the nitrogen atom of an amino group (e.g., methylcarbonylamino, cyclopentylcarbonyl-aminomethyl, and methylcarbonylaminophenyl). The nitrogen atom may itself be substituted with an alkyl or aryl group.

The term "alkylcarbonylaminoalkyl" represents an "alkylcarbonylamino" group attached through an alkyl group having the indicated number of carbon atoms (e.g. N-propyl-acetamide and N-butyl-propionamide).

The term "arylalkylcarbonylamino" represents an "arylalkylcarbonyl" group as defined above attached through an amino group (e.g., phenylacetamide and 3-phenyl-propionamide).

The term "arylalkylcarbonylaminoalkyl" represents an "arylalkylcarbonylamino" group attached through an alkyl group having the indicated number of carbon atoms (e.g., N-ethyl-phenylacetamide and N-butyl-3-phenyl-propionamide).

The term "arylcarbonylamino" represents an "arylcarbonyl" group as defined above attached through an amino group (e.g., benzamide and naphthalene-1-carboxylic acid amide).

The term "arylcarbonylaminoalkyl" represents an "arylcarbonylamino" group attached through an alkyl group having the indicated number of carbon atoms (e.g., N-propyl-benzamide and N-butyl-naphthalene-1-carboxylic acid amide).

The term "alkylcarboxy" represents an alkylcarbonyl group as defined above wherein the carbonyl is in turn attached through an oxygen bridge (e.g., heptylcarboxy, cyclopropylcarboxy, and 3-pentenylcarboxy).

The term "arylcarboxy" represents an arylcarbonyl group as defined above wherein the carbonyl is in turn attached through an oxygen bridge (e.g., benzoic acid).

The term "alkylcarboxyalkyl" represents an alkylcarboxy group as defined above wherein the oxygen is attached via an alkyl bridge (e.g., heptylcarboxymethyl, propylcarboxy tert-butyl, and 3-pentylcarboxyethyl).

The term "arylalkylcarboxy" represents an arylalkylcarbonyl group as defined above wherein the carbonyl is in turn attached through an oxygen bridge (e.g., benzylcarboxy and phenylpropylcarboxy).

The term "arylalkylcarboxyalkyl" represents an arylalkylcarboxy group as defined above wherein the carboxy group is in turn attached through an alkyl group having the indicated number of carbon atoms (e.g., benzylcarboxymethyl and phenylpropylcarboxypropyl).

The term "hetarylcarboxy" represents a hetarylcarbonyl group as defined above wherein the carbonyl is in turn attached through an oxygen bridge (e.g., pyridine-2-carboxylic acid).

The term "hetarylalkylcarboxy" represents a hetarylalkylcarbonyl group as defined above wherein the carbonyl is in turn attached through an oxygen bridge (e.g., (1-H-imidazol-2-yl)-acetic acid and 3-pyrimidin-2-yl-propionic acid).

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent, the substituents may be the same or different.

The term "treatment" or "treating" is defined as the management and care of a patient for the purpose of combating or alleviating the disease, condition, or disorder, and the term includes the administration of the active compound to prevent or delay the onset of the symptoms or complications; alleviating (both temporary and permanent) the symptoms or complications; and/or eliminating the disease, condition, or disorder. Thus, "treatment" or "treating" includes prevention and/or prophylaxis of the disease, condition, or disorder.

The term "pharmaceutically acceptable" is defined as being suitable for administration to humans without adverse events.

The term "prodrug" is defined as a chemically modified form of the active drug, said prodrug being administered to the patient and subsequently being converted to the active drug. Techniques for development of prodrugs are well known in the art.

DETAILED DESCRIPTION OF THE INVENTION

Thus, in an embodiment, the present invention provides a substituted amide of formula (I):

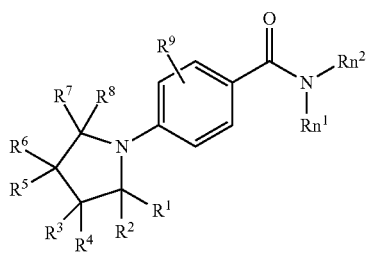

(I)

wherein:
$R^1$, $R^2$, $R^3$, $R^4$, $R^5$, $R^6$, $R^7$ and $R^8$ are each independently selected from H, halo, $C_2$-$C_{10}$-alkenyl, $C_2$-$C_{10}$alkynyl, $NR^{10}R^{11}$, $C(O)R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, arylC$_1$-C$_6$alkyl, hetarylC$_1$-C$_6$alkyl, arylC$_1$-C$_6$alkyloxy, hetarylC$_1$-C$_6$alkyloxy, $C_3$-$C_{10}$cycloalkyl, $C_3$-$C_{10}$cycloalkyloxy, $C_3$-$C_{10}$cycloalkylC$_1$-C$_6$alkyloxy, $C_3$-$C_{10}$hetcycloalkyl, $C_3$-$C_{10}$hetcycloalkyloxy, aryloxyC$_1$-C$_6$alkyl, hetaryloxyC$_1$-C$_6$alkyl, $C_3$-$C_{10}$cycloalkyloxyC$_1$-C$_6$alkyl, and $C_3$-$C_{10}$hetcycloalkyloxyC$_1$-C$_6$alkyl, wherein each alkyl, cykloalkyl, hetcycloalkyl, and aryl/hetaryl group is substituted with 0-3 $R^{18}$; or $R^2$, $R^3$, $R^4$, $R^6$, $R^7$ and $R^8$ are each independently selected from H, halo, $C_2$-$C_{10}$alkenyl, $C_2$-$C_{10}$alkynyl, $NR^{10}R^{11}$, $C(O)R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, arylC$_1$-C$_6$alkyl, hetarylC$_1$-C$_6$alkyl, arylC$_1$-C$_6$alkyloxy, hetarylC$_1$-C$_6$alkyloxy, $C_3$-$C_{10}$cycloalkyl, $C_3$-$C_{10}$cycloalkyloxy, $C_3$-$C_{10}$cycloalkylC$_1$-C$_6$alkyloxy, $C_3$-$C_{10}$hetcycloalkyl, $C_3$-$C_{10}$hetcycloalkyloxy, aryloxyC$_1$-C$_6$alkyl, hetaryloxyC$_1$-C$_6$alkyl, $C_3$-$C_{10}$cycloalkyloxyC$_1$-C$_6$alkyl, and $C_3$-$C_{10}$-hetcycloalkyloxyC$_1$-C$_6$alkyl, wherein each alkyl, cykloalkyl, hetcycloalkyl, and aryl/hetaryl group is substituted with 0-3 $R^{18}$; and $R^1$ and $R^5$ together with the carbons to which they are attached form a 4-8 membered saturated, partially saturated or aromatic ring consisting of 2-8 carbon atoms, and 0-2 additional heteroatoms selected from nitrogen, oxygen, and $S(O)_n$, wherein this ring is substituted with 0-3 groups selected from fluoro, $C_1$-$C_6$alkyl, $C_3$-$C_{10}$-cycloalkyl, $C_3$-$C_{10}$hetcycloalkyl, $C_3$-$C_6$spirocycloalkyl, 3-6 membered spirohetcycloalkyl, aryl, hetaryl, arylC$_1$-C$_6$alkyl, hetarylC$_1$-C$_6$alkyl, —C(O)R$^{12}$, —S(O)$_n$R$^{12}$, —S(O)$_n$NR$^{14}$R$^{15}$, —N(R$^{14}$)S(O)$_n$R$^{12}$, —N(R$^{16}$)C(=Y)NR$^{14}$R$^{15}$, —C(=NR$^{17}$)NR$^{17}$, OH, oxo, C$_1$-C$_6$alkyloxy, arylC$_1$-C$_6$alkyloxy, hetarylC$_1$-C$_6$alkyloxy, C$_1$-C$_6$alkyloxyC$_1$-C$_6$alkyl, C$_1$-C$_6$alkylcarboxy, arylcarboxy, hetarylcarboxy, arylC$_1$-C$_6$alkylcarboxy, and hetarylC$_1$-C$_6$alkylcarboxy, wherein each alkyl, and aryl/hetaryl group is substituted with 0-3 $R^{18}$; or $R^2$, $R^3$, $R^4$, $R^5$, $R^6$ and $R^8$ are each independently selected from H, halo, $C_2$-$C_{10}$alkenyl, $C_2$-$C_{10}$alkynyl, $NR^{10}R^{11}$, $C(O)R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, arylC$_1$-C$_6$alkyl, hetarylC$_1$-C$_6$alkyl, arylC$_1$-C$_6$alkyloxy, hetarylC$_1$-C$_6$alkyloxy, $C_3$-$C_{10}$cycloalkyl, $C_3$-$C_{10}$cycloalkyloxy, $C_3$-$C_{10}$cycloalkylC$_1$-C$_6$alkyloxy, $C_3$-$C_{10}$hetcycloalkyl, $C_3$-$C_{10}$hetcycloalkyloxy, aryloxyC$_1$-C$_6$alkyl, hetaryloxyC$_1$-C$_6$alkyl, $C_3$-$C_{10}$cycloalkyloxyC$_1$-C$_6$alkyl, and $C_3$-$C_{10}$-hetcycloalkyloxyC$_1$-C$_6$alkyl, wherein each alkyl, cykloalkyl, hetcycloalkyl, and aryl/hetaryl group is substituted with 0-3 $R^{18}$; and $R^1$ and $R^7$ together with the carbons to which they are attached form a 4-8 membered saturated, partially saturated or aromatic ring consisting of 2-8 carbon atoms, and 0-2 additional heteroatoms selected from nitrogen, oxygen, and $S(O)_n$, wherein this ring is substituted with 0-3 groups selected from fluoro, $C_1$-$C_6$alkyl, $C_3$-$C_{10}$-cycloalkyl, $C_3$-$C_{10}$hetcycloalkyl, $C_3$-$C_6$spirocycloalkyl, 3-6 membered spirohetcycloalkyl, aryl, hetaryl, arylC$_1$-C$_6$alkyl, hetarylC$_1$-C$_6$alkyl, —C(O)R$^{12}$, —S(O)$_n$R$^{12}$, —S(O)$_n$NR$^{14}$R$^{15}$, —N(R$^{14}$)S(O)$_n$R$^{12}$, —N(R$^{16}$)C(=Y)NR$^{14}$R$^{15}$, —C(=NR$^{17}$)NR$^{17}$, OH, oxo, C$_1$-C$_6$alkyloxy, arylC$_1$-C$_6$alkyloxy, hetarylC$_1$-C$_6$alkyloxy, C$_1$-C$_6$alkyloxyC$_1$-C$_6$alkyl, C$_1$-C$_6$alkylcarboxy, arylcarboxy, hetarylcarboxy, arylC$_1$-C$_6$alkylcarboxy, and hetarylC$_1$-C$_6$alkylcarboxy, wherein each alkyl, and aryl/hetaryl group is substituted with 0-3 R$^{18}$; or R$^1$, R$^2$, R$^3$, R$^6$, R$^7$ and R$^8$ are each independently selected from H, halo, C$_2$-C$_{10}$alkenyl, C$_2$-C$_{10}$alkynyl, NR$^{10}$R$^{11}$, C(O)R$^{12}$, R$^{13}$S(O)$_n$, R$^{13}$C(O)NR$^{10}$, R$^{10}$R$^{11}$NS(O)$_n$, R$^{13}$S(O)$_n$NR$^{10}$, aryl, hetaryl, aryloxy, hetaryloxy, arylC$_1$-C$_6$alkyl, hetarylC$_1$-C$_6$alkyl, arylC$_1$-C$_6$alkyloxy, hetarylC$_1$-C$_6$alkyloxy, C$_3$-C$_{10}$cycloalkyl, C$_3$-C$_{10}$cycloalkyloxy, C$_3$-C$_{10}$cycloalkylC$_1$-C$_6$alkyloxy, C$_3$-C$_{10}$hetcycloalkyl, C$_3$-C$_{10}$hetcycloalkyloxy, aryloxyC$_1$-C$_6$alkyl, hetaryloxyC$_1$-C$_6$alkyl, C$_3$-C$_{10}$cycloalkyloxyC$_1$-C$_6$alkyl, and C$_3$-C$_{10}$-hetcycloalkyloxyC$_1$-C$_6$alkyl, wherein each alkyl, cykloalkyl, hetcycloalkyl, and aryl/hetaryl group is substituted with 0-3 R$^{18}$; and R$^4$ and R$^5$ together with the carbons to which they are attached form a 4-8 membered saturated, partially saturated or aromatic ring consisting of 2-8 carbon atoms, and 0-2 additional heteroatoms selected from nitrogen, oxygen, and S(O)$_n$, wherein this ring is substituted with 0-3 groups selected from fluoro, C$_1$-C$_6$alkyl, C$_3$-C$_{10}$-cycloalkyl, C$_3$-C$_{10}$hetcycloalkyl, C$_3$-C$_6$spirocycloalkyl, 3-6 membered spirohetcycloalkyl, aryl, hetaryl, arylC$_1$-C$_6$alkyl, hetarylC$_1$-C$_6$alkyl, —C(O)R$^{12}$, —S(O)$_n$R$^{12}$, —S(O)$_n$NR$^{14}$R$^{15}$, —N(R$^{14}$)S(O)$_n$R$^{12}$, —N(R$^{16}$)C(=Y)NR$^{14}$R$^{15}$, —C(=NR$^{17}$)NR$^{17}$, OH, oxo, C$_1$-C$_6$alkyloxy, arylC$_1$-C$_6$alkyloxy, hetarylC$_1$-C$_6$alkyloxy, C$_1$-C$_6$alkyloxyC$_1$-C$_6$alkyl, C$_1$-C$_6$alkylcarboxy, arylcarboxy, hetarylcarboxy, arylC$_1$-C$_6$alkylcarboxy, and hetarylC$_1$-C$_6$alkylcarboxy, wherein each alkyl, and aryl/hetaryl group is substituted with 0-3 R$^{18}$;

R$^9$ is selected from H, halo, OH, cyano, C$_1$-C$_6$alkyl, C$_1$-C$_6$alkyloxy, trihalomethyloxy and C$_3$-C$_6$cycloalkyl;

R$^{10}$ and R$^{11}$ are each independently selected from H, C$_1$-C$_6$alkyl, C$_1$-C$_6$alkylcarbonyl, C(O)OC$_1$-C$_6$alkyl, aryl, hetaryl, arylC$_1$-C$_6$alkyl, hetarylC$_1$-C$_6$alkyl, C$_3$-C$_{10}$cycloalkyl, C$_3$-C$_{10}$hetcycloalkyl, arylcarbonyl, hetarylcarbonyl, arylC$_1$-C$_6$alkylcarbonyl, hetarylC$_1$-C$_6$alkylcarbonyl, C$_3$-C$_{10}$cycloalkylcarbonyl and C$_3$-C$_{10}$hetcycloalkylcarbonyl, wherein each alkyl, cykloalkyl, hetcycloalkyl, and aryl/hetaryl group is substituted with 0-3 R$^{18}$;

alternatively, R$^{10}$ and R$^{11}$, together with the nitrogen to which they are attached, form a 3-12 membered saturated or partially saturated monocyclic or bicyclic ring consisting of the shown nitrogen, 2-10 carbon atoms, and 0-2 additional heteroatoms selected from nitrogen, oxygen, and S(O)$_n$, wherein this ring is substituted with 0-3 groups selected from halo, C$_1$-C$_6$alkyl, C$_3$-C$_{10}$cycloalkyl, C$_3$-C$_{10}$hetcycloalkyl, C$_3$-C$_6$spirocycloalkyl, 3-6 membered spirohetcycloalkyl, aryl, hetaryl, arylC$_1$-C$_6$-alkyl, hetarylC$_1$-C$_6$alkyl, —C(O)R$^{12}$, —S(O)$_n$R$^{12}$, —S(O)$_n$NR$^{14}$R$^{15}$, —N(R$^{14}$)S(O)$_n$R$^{12}$, —N(R$^{16}$)C(=Y)NR$^{14}$R$^{15}$, —C(=NR$^{17}$)NR$^{17}$, OH, oxo, C$_1$-C$_6$alkyloxy, arylC$_1$-C$_6$alkyloxy, hetarylC$_1$-C$_6$alkyloxy, C$_1$-C$_6$alkyloxyC$_1$-C$_6$alkyl, C$_1$-C$_6$alkylcarboxy, arylcarboxy, hetarylcarboxy, arylC$_1$-C$_6$alkylcarboxy, and hetarylC$_1$-C$_6$alkylcarboxy, wherein each alkyl, and aryl/hetaryl group is substituted with 0-3 R$^{18}$;

R$^{12}$ is OH, NR$^{10}$R$^{11}$, C$_1$-C$_6$alkyloxy, C$_2$-C$_6$alkenyloxy, C$_2$-C$_6$alkynyloxy, C$_3$-C$_{10}$cycloalkyl, C$_3$-C$_{10}$cycloalkyloxy, C$_3$-C$_{10}$hetcycloalkyloxy, aryloxy, hetaryloxy, arylC$_1$-C$_6$alkyloxy, hetarylC$_1$-C$_6$alkyloxy;

R$^{13}$ is C$_1$-C$_6$alkyl, C$_2$-C$_6$alkenyl, C$_2$-C$_6$alkynyl, NR$^{10}$R$^{11}$, aryl, hetaryl, arylC$_1$-C$_6$alkyl, hetarylC$_1$-C$_6$alkyl, C$_3$-C$_{10}$cycloalkyl, C$_3$-C$_{10}$hetcycloalkyl, aryloxyC$_1$-C$_6$alkyl, hetaryloxyC$_1$-C$_6$alkyl, C$_3$-C$_{10}$cycloalkyloxyC$_1$-C$_6$alkyl, and C$_3$-C$_{10}$hetcycloalkyloxyC$_1$-C$_6$-alkyl, wherein each alkyl, cykloalkyl, hetcycloalkyl, and aryl/hetaryl group is substituted with 0-3 R$^{18}$;

R$^{14}$ and R$^{15}$ are independently selected from H, C$_1$-C$_6$alkyl, C$_1$-C$_6$alkyloxy, aryl, hetaryl, arylC$_1$-C$_6$alkylene, and hetarylC$_1$-C$_6$alkylene, wherein the alkyl/alkylene, aryl, and hetaryl groups are independently substituted with 0-3 R$^{20}$;

alternatively, R$^{14}$ and R$^{15}$, together with the nitrogen atom to which they are attached, form a saturated or partially saturated monocyclic, bicyclic, or tricyclic ring consisting of the shown nitrogen, 4-10 carbon atoms, and 0-2 additional heteroatoms selected from nitrogen, oxygen, and sulfur, wherein this ring is substituted with 0-3 C$_1$-C$_6$alkyl, aryl, hetaryl, arylC$_1$-C$_6$alkylene, hetarylC$_1$-C$_6$alkylene, hydroxy, oxo, C$_1$-C$_6$alkyloxy, arylC$_1$-C$_6$alkyloxy, hetarylC$_1$-C$_6$alkyloxy, C$_1$-C$_6$alkyloxyC$_1$-C$_6$alkyl, C$_1$-C$_6$alkylcarbonyl, arylcarbonyl, hetarylcarbonyl, arylC$_1$-C$_6$alkylcarbonyl, hetarylC$_1$-C$_6$alkylcarbonyl, C$_1$-C$_6$alkylcarboxy, arylcarboxy, hetarylcarboxy, arylC$_1$-C$_6$alkylcarboxy, and hetarylC$_1$-C$_6$alkylcarboxy;

R$^{16}$ is selected from H and C$_1$-C$_6$alkyl;

R$^{17}$ is selected from H, C$_1$-C$_6$alkyl, 3-10 membered cycloalkyl, halo, OH, cyano, —C(=O)R$^{12}$, —S(=O)$_n$R$^{12}$, S(=O)$_n$NR$^{14}$R$^{15}$, —N(R$^{14}$)S(=O)$_n$R$^{12}$, aryl, and hetaryl, wherein the alkyl and cycloalkyl groups are substituted with 0-3 R$^{20}$;

R$^{18}$ is selected from halo, OH, oxo, COOH, S(O)$_2$R$^{12}$, C(=O)OC$_1$-C$_6$alkyl, cyano, C$_1$-C$_1$-C$_6$alkyloxy, C$_3$-C$_{10}$cycloalkyloxy, aryloxy, hetaryloxy, hetarylthio, and arylC$_1$-C$_6$alkyloxy;

R$^{20}$ is selected from H, OH, oxo, halo, cyano, nitro, C$_1$-C$_6$alkyl, C$_1$-C$_6$alkyloxy, NR$^{21}$R$^{22}$, methylendioxo, dihalomethylendioxo, trihalomethyl, and trihalomethyloxy;

R$^{21}$ and R$^{22}$ are independently selected from H, C$_1$-C$_6$alkyl, and arylC$_1$-C$_6$alkyl;

Rn$^1$ and Rn$^2$ are each independently selected from H, C$_1$-C$_6$alkyl, arylC$_1$-C$_6$alkyl, hetarylC$_1$-C$_6$alkyl, C$_3$-C$_{12}$cycloalkyl, C$_3$-C$_{10}$hetcycloalkyl, wherein each alkyl, cycloalkyl, hetcycloalkyl, and aryl/hetaryl group is substituted with 0-3 R$^{18}$;

alternatively, Rn$^1$ and Rn$^2$, together with the nitrogen to which they are attached, form a 5-12 membered saturated or partially saturated monocyclic or bicyclic ring consisting of the shown nitrogen, 4-11 carbon atoms, and 0-2 additional heteroatoms selected from nitrogen, oxygen, and S(O)$_n$, wherein the ring is substituted with 0-3 groups selected from halo, trihalomethyl, trihalomethyloxy, cyano, C$_1$-C$_6$alkyl, C$_3$-C$_{10}$cycloalkyl, —C(O)R$^{12}$, —S(O)$_n$ R$^{12}$, —S(O)$_n$NR$^{14}$R$^{15}$, —N(R$^{14}$)S(O)$_n$R$^{12}$, OH, oxo, C$_1$-C$_6$alkyloxy, arylC$_1$-C$_6$alkyloxy, hetarylC$_1$-C$_6$alkyloxy, and C$_1$-C$_6$alkyloxyC$_1$-C$_6$alkyl, wherein each alkyl, and aryl/hetaryl group is substituted with 0-3 R$^{18}$;

n is selected from 0, 1 and 2; or a salt thereof with a pharmaceutically acceptable acid or base, or any optical isomer or mixture of optical isomers, including a racemic mixture, or any tautomeric forms.

In another embodiment, the present invention provides a compound of formula (I) wherein:

R$^1$, R$^2$, R$^3$, R$^4$, R$^5$, R$^6$, R$^7$ and R$^8$ are each independently selected from H, halo, C$_2$-C$_{10}$-alkenyl, C$_2$-C$_{10}$alkynyl, NR$^{10}$R$^{11}$, C(O)R$^{12}$, R$^{13}$S(O)$_n$, R$^{13}$C(O)NR$^{10}$, R$^{10}$R$^{11}$NS(O)$_n$, R$^{13}$S(O)$_n$NR$^{10}$, aryl, hetaryl, aryloxy, hetaryloxy, arylC$_1$-C$_6$alkyl, hetarylC$_1$-C$_6$alkyl, arylC$_1$-C$_6$alkyloxy, hetarylC$_1$-C$_6$alkyloxy, C$_3$-C$_{10}$cycloalkyl, C$_3$-C$_{10}$cycloalkyloxy, C$_3$-C$_{10}$cycloalkylC$_1$-C$_6$alkyloxy, C$_3$-C$_{10}$hetcycloalkyl, C$_3$-C$_{10}$hetcycloalkyloxy, aryloxyC$_1$-C$_6$alkyl, hetaryloxyC$_1$-C$_6$alkyl, C$_3$-C$_{10}$cycloalkyloxyC$_1$-C$_6$alkyl, and C$_3$-C$_{10}$-hetcycloalkyloxyC$_1$-C$_6$alkyl, wherein each alkyl, cykloalkyl, hetcycloalkyl, and aryl/hetaryl group is substituted with 0-3 R$^{18}$; or R$^1$, R$^2$, R$^3$, R$^6$, R$^7$ and R$^8$ are each independently selected from H, halo, C$_2$-C$_{10}$alkenyl, C$_2$-C$_{10}$alkynyl, NR$^{10}$R$^{11}$, C(O)R$^{12}$, R$^{13}$S(O)$_n$, R$^{13}$C(O)NR$^{10}$, R$^{10}$R$^{11}$NS(O)$_n$, R$^{13}$S(O)$_n$NR$^{10}$, aryl, hetaryl, aryloxy, hetaryloxy, arylC$_1$-C$_6$alkyl, hetarylC$_1$-C$_6$alkyl, arylC$_1$-C$_6$alkyloxy, hetarylC$_1$-C$_6$alkyloxy, C$_3$-C$_{10}$cycloalkyl, C$_3$-C$_{10}$cycloalkyloxy, C$_3$-C$_{10}$cycloalkylC$_1$-C$_6$alkyloxy, C$_3$-C$_{10}$hetcycloalkyl, C$_3$-C$_{10}$hetcycloalkyloxy, aryloxyC$_1$-C$_6$alkyl, hetaryloxyC$_1$-C$_6$alkyl, C$_3$-C$_{10}$cycloalkyloxyC$_1$-C$_6$alkyl, and C$_3$-C$_{10}$-hetcycloalkyloxyC$_1$-C$_6$alkyl, wherein each alkyl, cykloalkyl, hetcycloalkyl, and aryl/hetaryl group is substituted with 0-3 R$^{18}$; and R$^4$ and R$^5$ together with the carbons to which they are attached form a 4-8 membered saturated, partially saturated or aromatic ring consisting of 2-8 carbon atoms, and 0-2 additional heteroatoms selected from nitrogen, oxygen, and S(O)$_n$, wherein this ring is substituted with 0-3 groups selected from fluoro, C$_1$-C$_6$alkyl, C$_3$-C$_{10}$-cycloalkyl, C$_3$-C$_{10}$hetcycloalkyl, C$_3$-C$_6$spirocycloalkyl, 3-6 membered spirohetcycloalkyl, aryl, hetaryl, arylC$_1$-C$_6$alkyl, hetarylC$_1$-C$_6$alkyl, —C(O)R$^{12}$, —S(O)$_n$R$^{12}$, —S(O)$_n$NR$^{14}$R$^{15}$, —N(R$^{14}$)S(O)$_n$R$^{12}$, —N(R$^{16}$)C(=Y)NR$^{14}$R$^{15}$, —C(=NR$^{17}$)NR$^{17}$, OH, oxo, C$_1$-C$_6$alkyloxy, arylC$_1$-C$_6$alkyloxy, hetarylC$_1$-C$_6$alkyloxy, C$_1$-C$_6$alkyloxyC$_1$-C$_6$alkyl, C$_1$-C$_6$alkylcarboxy, arylcarboxy, hetarylcarboxy, arylC$_1$-C$_6$alkylcarboxy, and hetarylC$_1$-C$_6$alkylcarboxy, wherein each alkyl, and aryl/hetaryl group is substituted with 0-3 R$^{18}$;

R$^9$ is selected from H, halo, OH, cyano, C$_1$-C$_6$alkyl, C$_1$-C$_6$alkyloxy, trihalomethyloxy and C$_3$-C$_6$cycloalkyl;

R$^{10}$ and R$^{11}$ are each independently selected from H, C$_1$-C$_6$alkyl, C(O)O—C$_1$-C$_6$alkyl, aryl, hetaryl, arylC$_1$-C$_6$alkyl, hetarylC$_1$-C$_6$alkyl, C$_3$-C$_{10}$cycloalkyl, C$_3$-C$_{10}$hetcycloalkyl, wherein each alkyl, cykloalkyl, hetcycloalkyl, and aryl/hetaryl group is substituted with 0-3 R$^{18}$;

alternatively, R$^{10}$ and R$^{11}$, together with the nitrogen to which they are attached, form a 3-12 membered saturated or partially saturated monocyclic or bicyclic ring consisting of the shown nitrogen, 2-10 carbon atoms, and 0-2 additional heteroatoms selected from nitrogen, oxygen, and S(O)$_n$, wherein this ring is substituted with 0-3 groups selected from halo, C$_1$-C$_6$alkyl, C$_3$-C$_{10}$cycloalkyl, C$_3$-C$_{10}$hetcycloalkyl, C$_3$-C$_6$spirocycloalkyl, 3-6 membered spirohetcycloalkyl, aryl, hetaryl, arylC$_1$-C$_6$-alkyl, hetarylC$_1$-C$_6$alkyl, —C(O)R$^{12}$, —S(O)$_n$R$^{12}$, —S(O)$_n$NR$^{14}$R$^{15}$, —N(R$^{14}$)S(O)$_n$R$^{12}$, —N(R$^{16}$)C(=Y)NR$^{14}$R$^{15}$, —C(=NR$^{17}$)NR$^{17}$, OH, oxo, C$_1$-C$_6$alkyloxy, arylC$_1$-C$_6$alkyloxy, hetarylC$_1$-C$_6$alkyloxy, C$_1$-C$_6$alkyloxyC$_1$-C$_6$alkyl, C$_1$-C$_6$alkylcarboxy, arylcarboxy, hetarylcarboxy, arylC$_1$-C$_6$alkylcarboxy, and hetarylC$_1$-C$_6$alkylcarboxy, wherein each alkyl, and aryl/hetaryl group is substituted with 0-3 R$^{18}$;

R$^{12}$ is OH, NR$^{10}$R$^{11}$, C$_1$-C$_6$alkyloxy, C$_2$-C$_6$alkenyloxy, C$_2$-C$_6$alkynyloxy, C$_3$-C$_{10}$cycloalkyl, C$_3$-C$_{10}$cycloalkyloxy, C$_3$-C$_{10}$hetcycloalkyloxy, aryloxy, hetaryloxy, arylC$_1$-C$_6$alkyloxy, hetarylC$_1$-C$_6$alkyloxy, R$^{13}$ is C$_1$-C$_6$alkyl, C$_2$-C$_6$alkenyl, C$_2$-C$_6$alkynyl, NR$^{10}$R$^{11}$, aryl, hetaryl, arylC$_1$-C$_6$alkyl, hetarylC$_1$-C$_6$alkyl, C$_3$-C$_{10}$cycloalkyl, C$_3$-C$_{10}$hetcycloalkyl, aryloxyC$_1$-C$_6$alkyl, hetaryloxyC$_1$-C$_6$alkyl, C$_3$-C$_{10}$cycloalkyloxyC$_1$-C$_6$alkyl, and C$_3$-C$_{10}$hetcycloalkyloxyC$_1$-C$_6$-alkyl, wherein each alkyl, cykloalkyl, hetcycloalkyl, and aryl/hetaryl group is substituted with 0-3 R$^{18}$;

R$^{18}$ is selected from halo, OH, oxo, COOH, C(=O)OC$_1$-C$_6$alkyl cyano, C$_1$-C$_6$alkyl, C$_1$-C$_6$alkyloxy, C$_3$-C$_{10}$cycloalkyloxy, aryloxy, hetaryloxy, hetarylthio, and arylC$_1$-C$_6$alkyloxy;

R$^{14}$ and R$^{15}$ are independently selected from H, C$_1$-C$_6$alkyl, C$_1$-C$_6$alkyloxy, aryl, hetaryl, arylC$_1$-C$_6$alkylene, and hetarylC$_1$-C$_6$alkylene, wherein the alkyl/alkylene, aryl, and hetaryl groups are independently substituted with 0-3 R$^{20}$;

alternatively, R$^{14}$ and R$^{15}$, together with the nitrogen atom to which they are attached, form a saturated or partially saturated monocyclic, bicyclic, or tricyclic ring consisting of the shown nitrogen, 4-10 carbon atoms, and 0-2 additional heteroatoms selected from nitrogen, oxygen, and sulfur, wherein this ring is substituted with 0-3 C$_1$-C$_6$alkyl, aryl, hetaryl, arylC$_1$-C$_6$alkylene, hetarylC$_1$-C$_6$alkylene, hydroxy, oxo, C$_1$-C$_6$alkyloxy, arylC$_1$-C$_6$alkyloxy, hetarylC$_1$-C$_6$alkyloxy, C$_1$-C$_6$alkyloxyC$_1$-C$_6$alkyl, C$_1$-C$_6$alkylcarbonyl, arylcarbonyl, hetarylcarbonyl, arylC$_1$-C$_6$alkylcarbonyl, hetarylC$_1$-C$_6$alkylcarbonyl, C$_1$-C$_6$alkylcarboxy, arylcarboxy, hetarylcarboxy, arylC$_1$-C$_6$alkylcarboxy, and hetarylC$_1$-C$_6$alkylcarboxy;

R$^{17}$ is selected from H, C$_1$-C$_6$alkyl, 3-10 membered cycloalkyl, halo, OH, cyano, —C(=O)R$^{12}$, —S(=O)$_n$R$^{12}$, S(=O)$_n$NR$^{14}$R$^{15}$, —N(R$^{14}$)S(=O)$_n$R$^{12}$, aryl, and hetaryl, wherein the alkyl and cycloalkyl groups are substituted with 0-3 R$^{20}$;

R$^{20}$ is selected from H, OH, oxo, halo, cyano, nitro, C$_1$-C$_6$alkyl, C$_1$-C$_6$alkyloxy, NR$^{21}$R$^{22}$, methylendioxo, dihalomethylendioxo, trihalomethyl, and trihalomethyloxy;

R$^{21}$ and R$^{22}$ are independently selected from H, C$_1$-C$_6$alkyl, and arylC$_1$-C$_6$alkyl;

R$^{16}$ is selected from H and C$_1$-C$_6$alkyl;

Rn$^1$ and Rn$^2$ are each independently selected from H, C$_1$-C$_6$alkyl, arylC$_1$-C$_6$alkyl, hetarylC$_1$-C$_6$alkyl, C$_3$-C$_{12}$cycloalkyl, C$_3$-C$_{10}$hetcycloalkyl, wherein each alkyl, cycloalkyl, hetcycloalkyl, and aryl/hetaryl group is substituted with 0-3 R$^{18}$;

alternatively, Rn$^1$ and Rn$^2$, together with the nitrogen to which they are attached, form a 5-12 membered saturated or partially saturated monocyclic or bicyclic ring consisting of the shown nitrogen, 4-11 carbon atoms, and 0-2 additional heteroatoms selected from nitrogen, oxygen, and S(O)$_n$, wherein the ring is substituted with 0-3 groups selected from halo, trihalomethyl, trihalomethyloxy, cyano, C$_1$-C$_6$alkyl, C$_3$-C$_{10}$cycloalkyl, —C(O)R$^{12}$, —S(O)$_n$ R$^{12}$, —S(O)$_n$NR$^{14}$R$^{16}$, —N(R$^{14}$)S(O)$_n$R$^{12}$, OH, oxo, C$_1$-C$_6$alkyloxy, arylC$_1$-C$_6$alkyloxy, hetarylC$_1$-C$_6$alkyloxy, and C$_1$-C$_6$alkyloxyC$_1$-C$_6$alkyl, wherein each alkyl, and aryl/hetaryl group is substituted with 0-3 R$^{18}$;

n is selected from 0, 1 and 2;

or a salt thereof with a pharmaceutically acceptable acid or base, or any optical isomer or mixture of optical isomers, including a racemic mixture, or any tautomeric forms.

In another embodiment, the present invention provides a compound of formula I wherein:

R$^1$, R$^2$, R$^3$, R$^4$, R$^5$, R$^6$, R$^7$ and R$^8$ are each independently selected from H, halo, C$_2$-C$_{10}$-alkenyl, C$_2$-C$_{10}$alkynyl, NR$^{10}$R$^{11}$, C(O)R$^{12}$, R$^{13}$S(O)$_n$, R$^{13}$C(O)NR$^{10}$, R$^{10}$R$^{11}$NS(O)$_n$, R$^{13}$S(O)$_n$NR$^{10}$, aryl, hetaryl, aryloxy, hetaryloxy, arylC$_1$-C$_6$alkyl, hetarylC$_1$-C$_6$alkyl, arylC$_1$-C$_6$alkyloxy, hetarylC$_1$-C$_6$alkyloxy, C$_3$-C$_{10}$cycloalkyl, C$_3$-C$_{10}$cycloalkyloxy, C$_3$-C$_{10}$cycloalkylC$_1$-C$_6$alkyloxy, C$_3$-C$_{10}$hetcycloalkyl, C$_3$-C$_{10}$hetcycloalkyloxy, aryloxyC$_1$-C$_6$alkyl, hetaryloxyC$_1$-C$_6$alkyl, C$_3$-C$_{10}$cycloalkyloxyC$_1$-C$_6$alkyl, and C$_3$-C$_{10}$-hetcycloalkyloxyC$_1$-C$_6$alkyl, wherein each alkyl, cykloalkyl, hetcycloalkyl, and aryl/hetaryl group is substituted with 0-3 R$^{18}$;

with the proviso that when R$^1$, R$^2$, R$^3$, R$^4$, R$^5$, R$^6$, R$^7$ and R$^8$ each independently are aryl, hetaryl, arylC$_1$-C$_6$alkyl, hetarylC$_1$-C$_6$alkyl, arylC$_1$-C$_6$alkyloxy, and hetarylC$_1$-C$_6$alkyloxy then each group is substituted with 1-3 R$^{18}$;

or

R$^1$, R$^2$, R$^3$, R$^6$, R$^7$ and R$^8$ are each independently selected from H, halo, C$_2$-C$_{10}$alkenyl, C$_2$-C$_{10}$alkynyl, NR$^{10}$R$^{11}$, C(O)R$^{12}$, R$^{13}$S(O)$_n$, R$^{13}$C(O)NR$^{10}$, R$^{10}$R$^{11}$NS(O)$_n$, R$^{13}$S(O)$_n$NR$^{10}$, aryl, hetaryl, aryloxy, hetaryloxy, arylC$_1$-C$_6$alkyl, hetarylC$_1$-C$_6$alkyl, arylC$_1$-C$_6$alkyloxy, hetarylC$_1$-C$_6$alkyloxy, C$_3$-C$_{10}$cycloalkyl, C$_3$-C$_{10}$cycloalkyloxy, C$_3$-C$_{10}$cycloalkylC$_1$-C$_6$alkyloxy, C$_3$-C$_{10}$hetcycloalkyl, C$_3$-C$_{10}$hetcycloalkyloxy, aryloxyC$_1$-C$_6$alkyl, hetaryloxyC$_1$-C$_6$alkyl, C$_3$-C$_{10}$cycloalkyloxyC$_1$-C$_6$alkyl, and C$_3$-C$_{10}$-hetcycloalkyloxyC$_1$-C$_6$alkyl, wherein each alkyl, cykloalkyl, hetcycloalkyl, and aryl/hetaryl group is substituted with 0-3 R$^{18}$; and R$^4$ and R$^5$ together with the carbons to which they are attached form a 4-8 membered saturated, partially saturated or aromatic ring consisting of 2-8 carbon atoms, and 0-2 additional heteroatoms selected from nitrogen, oxygen, and S(O)$_n$, wherein this ring is substituted with 0-3 groups selected from fluoro, C$_1$-C$_6$alkyl, C$_3$-C$_{10}$-cycloalkyl, C$_3$-C$_{10}$hetcycloalkyl, C$_3$-C$_6$spirocycloalkyl, 3-6 membered spirohetcycloalkyl, aryl, hetaryl, arylC$_1$-C$_6$alkyl, hetarylC$_1$-C$_6$alkyl, —C(O)R$^{12}$, —S(O)$_n$R$^{12}$, —S(O)$_n$NR$^{14}$R$^{15}$, —N(R$^{14}$)S(O)$_n$R$^{12}$, —N(R$^{16}$)C(=Y)NR$^{14}$R$^{15}$, —C(=NR$^{17}$)NR$^{17}$, OH, oxo, C$_1$-C$_6$alkyloxy, arylC$_1$-C$_6$alkyloxy, hetarylC$_1$-C$_6$alkyloxy, C$_1$-C$_6$alkyloxyC$_1$-C$_6$alkyl, C$_1$-C$_6$alkylcarboxy, arylcarboxy, hetarylcarboxy, arylC$_1$-C$_6$alkylcarboxy, and hetarylC$_1$-C$_6$alkylcarboxy, wherein each alkyl, and aryl/hetaryl group is substituted with 0-3 R$^{18}$;

R$^9$ is selected from H, halo, OH, cyano, C$_1$-C$_6$alkyl, C$_1$-C$_6$alkyloxy, trihalomethyloxy and C$_3$-C$_6$cycloalkyl;

R$^{10}$ and R$^{11}$ are each independently selected from H, C$_1$-C$_6$alkyl, C(O)O—C$_1$-C$_6$alkyl, aryl, hetaryl, arylC$_1$-C$_6$alkyl, hetarylC$_1$-C$_6$alkyl, C$_3$-C$_{10}$cycloalkyl, C$_3$-C$_{10}$hetcycloalkyl, wherein each alkyl, cykloalkyl, hetcycloalkyl, and aryl/hetaryl group is substituted with 0-3 R$^{18}$;

alternatively, R$^{10}$ and R$^{11}$, together with the nitrogen to which they are attached, form a 3-12 membered saturated or partially saturated monocyclic or bicyclic ring consisting of the shown nitrogen, 2-10 carbon atoms, and 0-2 additional heteroatoms selected from nitrogen, oxygen, and S(O)$_n$, wherein this ring is substituted with 0-3 groups selected from halo, C$_1$-C$_6$alkyl, C$_3$-C$_{10}$cycloalkyl, C$_3$-C$_{10}$hetcycloalkyl, C$_3$-C$_6$spirocycloalkyl, 3-6 membered spirohetcycloalkyl, aryl, hetaryl, arylC$_1$-C$_6$-alkyl, hetarylC$_1$-C$_6$alkyl, —C(O)R$^{12}$, —S(O)$_n$R$^{12}$, —S(O)$_n$NR$^{14}$R$^{15}$, —N(R$^{14}$)S(O)$_n$R$^{12}$, —N(R$^{16}$)C(=Y)NR$^{14}$R$^{15}$, —C(=NR$^{17}$)NR$^{17}$, OH, oxo, C$_1$-C$_6$alkyloxy, arylC$_1$-C$_6$alkyloxy, hetarylC$_1$-C$_6$alkyloxy, C$_1$-C$_6$alkyloxyC$_1$-C$_6$alkyl, C$_1$-C$_6$alkylcarboxy, arylcarboxy, hetarylcarboxy, arylC$_1$-C$_6$alkylcarboxy, and hetarylC$_1$-C$_6$alkylcarboxy, wherein each alkyl, and aryl/hetaryl group is substituted with 0-3 R$^{18}$;

R$^{12}$ is OH, NR$^{10}$R$^{11}$, C$_1$-C$_6$alkyloxy, C$_2$-C$_6$alkenyloxy, C$_2$-C$_6$alkynyloxy, C$_3$-C$_{10}$cycloalkyl, C$_3$-C$_{10}$cycloalkyloxy, C$_3$-C$_{10}$hetcycloalkyloxy, aryloxy, hetaryloxy, arylC$_1$-C$_6$alkyloxy, hetarylC$_1$-C$_6$alkyloxy, R$^{13}$ is C$_1$-C$_6$alkyl, C$_2$-C$_6$alkenyl, C$_2$-C$_6$alkynyl, NR$^{10}$R$^{11}$, aryl, hetaryl, arylC$_1$-C$_6$alkyl, hetarylC$_1$-C$_6$alkyl, C$_3$-C$_{10}$cycloalkyl, C$_3$-C$_{10}$hetcycloalkyl, aryloxyC$_1$-C$_6$alkyl, hetaryloxyC$_1$-C$_6$alkyl, C$_3$-C$_{10}$cycloalkyloxyC$_1$-C$_6$alkyl, and C$_3$-C$_{10}$hetcycloalkyloxyC$_1$-C$_6$-alkyl, wherein each alkyl, cykloalkyl, hetcycloalkyl, and aryl/hetaryl group is substituted with 0-3 R$^{18}$;

R$^{18}$ is selected from halo, OH, oxo, COOH, C(=O)OC$_1$-C$_6$alkyl cyano, C$_1$-C$_6$alkyl, C$_1$-C$_6$alkyloxy, C$_3$-C$_{10}$cycloalkyloxy, aryloxy, hetaryloxy, hetarylthio, and arylC$_1$-C$_6$alkyloxy;

R$^{14}$ and R$^{15}$ are independently selected from H, C$_1$-C$_6$alkyl, C$_1$-C$_6$alkyloxy, aryl, hetaryl, arylC$_1$-C$_6$alkylene, and hetarylC$_1$-C$_6$alkylene, wherein the alkyl/alkylene, aryl, and hetaryl groups are independently substituted with 0-3 R$^{20}$;

alternatively, R$^{14}$ and R$^{15}$, together with the nitrogen atom to which they are attached, form a saturated or partially saturated monocyclic, bicyclic, or tricyclic ring consisting of the shown nitrogen, 4-10 carbon atoms, and 0-2 additional heteroatoms selected from nitrogen, oxygen, and sulfur, wherein this ring is substituted with 0-3 C$_1$-C$_6$alkyl, aryl, hetaryl, arylC$_1$-C$_6$alkylene, hetarylC$_1$-C$_6$alkylene, hydroxy, oxo, C$_1$-C$_6$alkyloxy, arylC$_1$-C$_6$alkyloxy, hetarylC$_1$-C$_6$alkyloxy, C$_1$-C$_6$alkyloxyC$_1$-C$_6$alkyl, C$_1$-C$_6$alkylcarbonyl, arylcarbonyl, hetarylcarbonyl, arylC$_1$-C$_6$alkylcarbonyl, hetarylC$_1$-C$_6$alkylcarbonyl, C$_1$-C$_6$alkylcarboxy, arylcarboxy, hetarylcarboxy, arylC$_1$-C$_6$alkylcarboxy, and hetarylC$_1$-C$_6$alkylcarboxy;

R$^{17}$ is selected from H, C$_1$-C$_6$alkyl, 3-10 membered cycloalkyl, halo, OH, cyano, —C(=O)R$^{12}$, —S(=O)$_n$R$^{12}$, S(=O)$_n$NR$^{14}$R$^{15}$, —N(R$^{14}$)S(=O)$_n$R$^{12}$, aryl, and hetaryl, wherein the alkyl and cycloalkyl groups are substituted with 0-3 R$^{20}$;

R$^{20}$ is selected from H, OH, oxo, halo, cyano, nitro, C$_1$-C$_6$alkyl, C$_1$-C$_6$alkyloxy, NR$^{21}$R$^{22}$, methylendioxo, dihalomethylendioxo, trihalomethyl, and trihalomethyloxy;

R$^{21}$ and R$^{22}$ are independently selected from H, C$_1$-C$_6$alkyl, and arylC$_1$-C$_6$alkyl;

R$^{16}$ is selected from H and C$_1$-C$_6$alkyl;

Rn$^1$ and Rn$^2$ are each independently selected from H, C$_1$-C$_6$alkyl, arylC$_1$-C$_6$alkyl, hetarylC$_1$-C$_6$alkyl, C$_3$-C$_{12}$cycloalkyl, C$_3$-C$_{10}$hetcycloalkyl, wherein each alkyl, cycloalkyl, hetcycloalkyl, and aryl/hetaryl group is substituted with 0-3 R$^{18}$;

alternatively, Rn$^1$ and Rn$^2$, together with the nitrogen to which they are attached, form a 5-12 membered saturated or partially saturated monocyclic or bicyclic ring consisting of the shown nitrogen, 4-11 carbon atoms, and 0-2 additional heteroatoms selected from nitrogen, oxygen, and S(O)$_n$, wherein the ring is substituted with 0-3 groups selected from halo, trihalomethyl, trihalomethyloxy, cyano, C$_1$-C$_6$alkyl, C$_3$-C$_{10}$cycloalkyl, —C(O)R$^{12}$, —S(O)$_n$R$^{12}$, —S(O)$_n$NR$^{14}$R$^{16}$, —N(R$^{14}$)S(O)$_n$R$^{12}$, OH, oxo, C$_1$-C$_6$alkyloxy, arylC$_1$-C$_6$alkyloxy, hetarylC$_1$-C$_6$alkyloxy, and C$_1$-C$_6$alkyloxyC$_1$-C$_6$alkyl, wherein each alkyl, and aryl/hetaryl group is substituted with 0-3 R$^{18}$;

n is selected from 0, 1 and 2;

or a salt thereof with a pharmaceutically acceptable acid or base, or any optical isomer or mixture of optical isomers, including a racemic mixture, or any tautomeric forms.

In another embodiment, the present invention provides a compound of formula I wherein:

R$^1$, R$^2$, R$^3$, R$^4$, R$^5$, R$^6$, R$^7$ and R$^8$ are each independently selected from H, halo, NR$^{10}$R$^{11}$, C(O)R$^{12}$, R$^{13}$S(O)$_n$, R$^{13}$C(O)NR$^{10}$, R$^{10}$R$^{11}$NS(O)$_n$, R$^{13}$S(O)$_n$NR$^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cyclo-alkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$;

$R^9$ is selected from H, halo, OH, cyano, $C_1$-$C_6$alkyl, $C_1$-$C_6$alkyloxy, and $C_3$-$C_6$cycloalkyl;

$R^{10}$ and $R^{11}$ are each independently selected from H, $C_1$-$C_6$alkyl, C(O)O—$C_1$-$C_6$alkyl, aryl, hetaryl, aryl-$C_1$-$C_6$alkyl, hetaryl$C_1$-$C_6$alkyl, $C_3$-$C_{10}$cycloalkyl, $C_3$-$C_{10}$hetcycloalkyl, wherein each alkyl, cykloalkyl, hetcycloalkyl, and aryl/hetaryl group is substituted with 0-3 $R^{18}$; alternatively, $R^{10}$ and $R^{11}$, together with the nitrogen to which they are attached, form a 5-12 membered saturated or partially saturated monocyclic or bicyclic ring consisting of the shown nitrogen, 2-10 carbon atoms, and 0-2 additional heteroatoms selected from nitrogen and oxygen, wherein this ring is substituted with 0-3 groups selected from halo, $C_1$-$C_6$alkyl, $C_3$-$C_{10}$cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, —C(O)$R^{12}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$-alkylcarboxy, arylcarboxy, hetarylcarboxy, aryl$C_1$-$C_6$alkylcarboxy, and hetaryl$C_1$-$C_6$-alkylcarboxy, $R^{12}$ is OH, $NR^{10}R^{11}$, $C_1$-$C_6$alkyloxy, $C_3$-$C_{10}$cycloalkyl, $C_3$-$C_{10}$cycloalkyloxy, $C_3$-$C_{10}$hetcycloalkyloxy, aryloxy, hetaryloxy, aryl$C_1$-$C_6$alkyloxy, hetaryl$C_1$-$C_6$alkyloxy, $R^{13}$ is $C_1$-$C_6$alkyl, $NR^{10}R^{11}$, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, aryloxy$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$;

$R^{18}$ is selected from halo, OH, COOH, C(=O)O$C_1$-$C_6$alkyl, cyano, $C_1$-$C_6$alkyl, $C_1$-$C_6$alkyloxy, $C_3$-$C_{10}$cycloalkyloxy, aryloxy and hetaryloxy;

one of $Rn^1$ and $Rn^2$ is H and the other one of $Rn^1$ and $Rn^2$ are selected from $C_1$-$C_6$alkyl, aryl$C_1$-$C_6$alkyl, hetaryl$C_1$-$C_6$alkyl, $C_6$-$C_{12}$cycloalkyl, $C_3$-$C_{10}$hetcycloalkyl, wherein each alkyl, cykloalkyl, hetcycloalkyl, and aryl/hetaryl group is substituted with 0-3 $R^{18}$;

alternatively, $Rn^1$ and $Rn^2$, together with the nitrogen to which they are attached, form a 6-12 membered saturated or partially saturated monocyclic or bicyclic ring consisting of the shown nitrogen, 4-11 carbon atoms, and 0-2 additional heteroatoms selected from nitrogen and oxygen wherein the ring is substituted with 0-3 groups selected from halo, trihalomethyl, $C_1$-$C_6$alkyl, $C_3$-$C_{10}$cycloalkyl, —C(O)$R^{12}$, OH, $C_1$-$C_6$alkyloxy, aryl$C_1$-$C_6$alkyloxy, and hetaryl$C_1$-$C_6$alkyloxy, and n is 2.

In another embodiment, the present invention provides a compound of formula I wherein:

$R^1$, $R^2$, $R^3$, $R^4$, $R^5$, $R^6$, $R^7$ and $R^8$ are each independently selected from H, halo, $NR^{10}R^{11}$, C(O)$R^{12}$, $R^{13}$C(O)$NR^{10}$, $R^{10}R^{11}NS(O)_n$, $R^{13}S(O)_nNR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cyclo-alkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$;

with the proviso that when $R^1$, $R^2$, $R^3$, $R^4$, $R^5$, $R^6$, $R^7$ and $R^8$ each independently are aryl, hetaryl, aryl$C_1$-$C_6$alkyl, hetaryl$C_1$-$C_6$alkyl, aryl$C_1$-$C_6$alkyloxy, and hetaryl$C_1$-$C_6$alkyloxy then each group is substituted with 1-3 $R^{18}$;

$R^9$ is selected from H, halo, OH, cyano, $C_1$-$C_6$alkyl, $C_1$-$C_6$alkyloxy, and $C_3$-$C_6$cycloalkyl;

$R^{10}$ and $R^{11}$ are each independently selected from H, $C_1$-$C_6$alkyl, C(O)O—$C_1$-$C_6$alkyl, aryl, hetaryl, aryl-$C_1$-$C_6$alkyl, hetaryl$C_1$-$C_6$alkyl, $C_3$-$C_{10}$cycloalkyl, $C_3$-$C_{10}$hetcycloalkyl, wherein each alkyl, cykloalkyl, hetcycloalkyl, and aryl/hetaryl group is substituted with 0-3 $R^{18}$;
alternatively, $R^{10}$ and $R^{11}$, together with the nitrogen to which they are attached, form a 5-12 membered saturated or partially saturated monocyclic or bicyclic ring consisting of the shown nitrogen, 2-10 carbon atoms, and 0-2 additional heteroatoms selected from nitrogen and oxygen, wherein this ring is substituted with 0-3 groups selected from halo, $C_1$-$C_6$alkyl, $C_3$-$C_{10}$cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, —C(O)$R^{12}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$-alkylcarboxy, arylcarboxy, hetarylcarboxy, aryl$C_1$-$C_6$alkylcarboxy, and hetaryl$C_1$-$C_6$-alkylcarboxy, $R^{12}$ is OH, $NR^{10}R^{11}$, $C_1$-$C_6$alkyloxy, $C_3$-$C_{10}$cycloalkyl, $C_3$-$C_{10}$cycloalkyloxy, $C_3$-$C_{10}$hetcycloalkyloxy, aryloxy, hetaryloxy, aryl$C_1$-$C_6$alkyloxy, hetaryl$C_1$-$C_6$alkyloxy, $R^{13}$ is $C_1$-$C_6$alkyl, $NR^{10}R^{11}$, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, aryloxy$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$;

$R^{18}$ is selected from halo, OH, COOH, C(=O)O$C_1$-$C_6$alkyl, cyano, $C_1$-$C_6$alkyl, $C_1$-$C_6$alkyloxy, $C_3$-$C_{10}$cycloalkyloxy, aryloxy and hetaryloxy;

one of $Rn^1$ and $Rn^2$ is H and the other one of $Rn^1$ and $Rn^2$ are selected from $C_1$-$C_6$alkyl, aryl$C_1$-$C_6$alkyl, hetaryl$C_1$-$C_6$alkyl, $C_6$-$C_{12}$cycloalkyl, $C_3$-$C_{10}$hetcycloalkyl, wherein each alkyl, cykloalkyl, hetcycloalkyl, and aryl/hetaryl group is substituted with 0-3 $R^{18}$;

alternatively, $Rn^1$ and $Rn^2$, together with the nitrogen to which they are attached, form a 6-12 membered saturated or partially saturated monocyclic or bicyclic ring consisting of the shown nitrogen, 4-11 carbon atoms, and 0-2 additional heteroatoms selected from nitrogen and oxygen wherein the ring is substituted with 0-3 groups selected from halo, trihalomethyl, $C_1$-$C_6$alkyl, $C_3$-$C_{10}$cycloalkyl, —C(O)$R^{12}$, OH, $C_1$-$C_6$alkyloxy, aryl$C_1$-$C_6$alkyloxy, and hetaryl$C_1$-$C_6$alkyloxy, and n is 2.

In another embodiment, the present invention provides a compound of formula I wherein:

$R^2$, $R^3$, $R^4$, $R^6$, $R^7$ and $R^8$ are each independently selected from H, halo, $C_2$-$C_{10}$alkenyl, $C_2$-$C_{10}$alkynyl, $NR^{10}R^{11}$, C(O)$R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cyclo-alkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$; and $R^1$ and $R^5$ together with the carbons to which they are attached form a 4-8 membered saturated, partially saturated or aromatic ring consisting of 2-8 carbon atoms, and 0-2 additional heteroatoms selected from nitrogen, oxygen, and $S(O)_n$, wherein this ring is substituted with 0-3 groups selected from fluoro, $C_1$-$C_6$alkyl, $C_3$-$C_{10}$cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, —C(O)$R^{12}$, —S(O)$_n R^{12}$, —S(O)$_n$N$R^{14}R^{15}$, —N($R^{14}$)S(O)$_n R^{12}$, —N($R^{16}$)C(=Y)N$R^{14}R^{15}$, —C(=N$R^{17}$)N$R^{17}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, and aryl/hetaryl group is substituted with 0-3 $R^{18}$.

In another embodiment, the present invention provides a compound of formula I wherein:
$R^2$, $R^3$, $R^4$, $R^5$, $R^6$ and $R^8$ are each independently selected from H, halo, $C_2$-$C_{10}$alkenyl, $C_2$-$C_{10}$alkynyl, N$R^{10}R^{11}$, C(O)$R^{12}$, $R^{13}$S(O)$_n$, $R^{13}$C(O)N$R^{10}$, $R^{10}R^{11}$NS(O)$_n$, $R^{13}$S(O)$_n$N$R^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cyclo-alkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$; and $R^1$ and $R^7$ together with the carbons to which they are attached form a 4-8 membered saturated, partially saturated or aromatic ring consisting of 2-8 carbon atoms, and 0-2 additional heteroatoms selected from nitrogen, oxygen, and $S(O)_n$, wherein this ring is substituted with 0-3 groups selected from fluoro, $C_1$-$C_6$alkyl, $C_3$-$C_{10}$cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, —C(O)$R^{12}$, —S(O)$_n R^{12}$, —S(O)$_n$N$R^{14}R^{15}$, —N($R^{14}$)S(O)$_n R^{12}$, —N($R^{16}$)C(=Y)N$R^{14}R^{15}$, —C(=N$R^{17}$)N$R^{17}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, and aryl/hetaryl group is substituted with 0-3 $R^{18}$.

In another embodiment, the present invention provides a compound of formula I, wherein $R^3$, $R^4$, $R^5$, $R^6$, are each independently selected from halo, N$R^{10}R^{11}$, C(O)$R^{12}$, $R^{13}$S(O)$_n$, $R^{13}$C(O)N$R^{10}$, $R^{10}R^{11}$NS(O)$_n$, $R^{13}$S(O)$_n$N$R^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cyclo-alkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$; and
$R^1$, $R^2$, $R^7$, and $R^8$ are H.

In another embodiment, the present invention provides a compound of formula I, wherein $R^3$, $R^4$, $R^5$, $R^6$, are each independently selected from N$R^{10}R^{11}$, C(O)$R^{12}$, $R^{13}$S(O)$_n$, $R^{13}$C(O)N$R^{10}$, $R^{13}$S(O)$_n$N$R^{10}$, aryl, hetaryl, aryloxy, hetaryloxy, hetaryloxy$C_1$-$C_6$alkyl, wherein each aryl/hetaryl group is substituted with 0-3 $R^{18}$.

In another embodiment, the present invention provides a compound of formula I, wherein $R^4$ and $R^5$ together with the carbons to which they are attached form a 4-8 membered saturated, partially saturated or aromatic ring consisting of 2-8 carbon atoms, and 0-2 additional heteroatoms selected from nitrogen, oxygen, and $S(O)_n$.

In another embodiment, the present invention provides a compound of formula I, wherein $R^9$ is selected from H, halo, OH, cyano and $C_1$-$C_6$alkyl.

In another embodiment, the present invention provides a compound of formula I, wherein $R^9$ is selected from H, OH, and $C_1$-$C_6$alkyl.

In another embodiment, the present invention provides a compound of formula I, wherein $R^9$ is H.

In another embodiment, the present invention provides a compound of formula I, wherein $R^{10}$ and $R^{11}$ are each independently selected from H, $C_1$-$C_6$alkyl, aryl, hetaryl, $C_3$-$C_{10}$cycloalkyl, $C_3$-$C_{10}$hetcycloalkyl, wherein each alkyl, cykloalkyl and hetcycloalkyl group is substituted with 0-3 $R^{18}$.

In another embodiment, the present invention provides a compound of formula I, wherein $R^{10}$ and $R^{11}$ are each independently selected from H, $C_1$-$C_6$alkyl, $C_3$-$C_{10}$cycloalkyl, $C_3$-$C_{10}$hetcycloalkyl, wherein each alkyl, cykloalkyl and hetcycloalkyl group is substituted with 0-3 $R^{18}$.

In another embodiment, the present invention provides a compound of formula I, wherein $R^{10}$ and $R^{11}$, together with the nitrogen to which they are attached, form a 5-12 membered saturated or partially saturated monocyclic or bicyclic ring consisting of the shown nitrogen, 2-10 carbon atoms, and 0-2 additional heteroatoms selected from nitrogen and oxygen, wherein this ring is substituted with 0-3 groups selected from halo, $C_1$-$C_6$alkyl, —C(O)$R^{12}$, OH, oxo, $C_1$-$C_6$alkyloxy, $C_1$-$C_6$alkyloxy$C_1$-$C_6$alkyl and $C_1$-$C_6$-alkylcarboxy.

In another embodiment, the present invention provides a compound of formula I, wherein $R^{10}$ and $R^{11}$, together with the nitrogen to which they are attached, form a 6-12 membered saturated or partially saturated monocyclic or bicyclic ring consisting of the shown nitrogen, 2-10 carbon atoms, and 0-1 additional heteroatoms selected from oxygen, wherein this ring is substituted with 0-3 groups selected from OH and $C_1$-$C_6$alkyloxy.

In another embodiment, the present invention provides a compound of formula I, wherein $R^{12}$ is OH, N$R^{10}R^{11}$, $C_1$-$C_6$alkyloxy, $C_3$-$C_{10}$cycloalkyloxy, $C_3$-$C_{10}$hetcycloalkyloxy, aryloxy and hetaryloxy.

In another embodiment, the present invention provides a compound of formula I, wherein $R^{12}$ is OH, N$R^{10}R^{11}$, and $C_1$-$C_6$alkyloxy, In another embodiment, the present invention provides a compound of formula I, wherein $R^{13}$ is $C_1$-$C_6$alkyl, N$R^{10}R^{11}$, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, wherein each alkyl, cykloalkyl, hetcycloalkyl, and aryl/hetaryl group is substituted with 0-3 $R^{18}$.

the present invention provides a compound of formula I, wherein $R^{13}$ is $C_1$-$C_6$alkyl, N$R^{10}R^{11}$, aryl, hetaryl, hetaryl$C_1$-$C_6$alkyl, $C_3$-$C_{10}$cycloalkyl, wherein each alkyl, and aryl/hetaryl group is substituted with 0-3 $R^{18}$.

In another embodiment, the present invention provides a compound of formula I, wherein $R^{18}$ is selected from halo, OH, COOH, C(=O)O$C_1$-$C_6$alkyl, cyano, $C_1$-$C_6$alkyl, $C_1$-$C_6$alkyloxy, $C_3$-$C_{10}$cycloalkyloxy, aryloxy and hetaryloxy.

In another embodiment, the present invention provides a compound of formula I, wherein $R^{18}$ is selected from halo, OH, COOH, C(=O)OC$_1$-C$_6$alkyl, cyano, and C$_1$-C$_6$alkyl.

In another embodiment, the present invention provides a compound of formula I, wherein n is 2.

In another embodiment, the present invention provides a compound of formula I, wherein one of $Rn^1$ and $Rn^2$ is H and the other one of $Rn^1$ and $Rn^2$ are selected from C$_1$-C$_6$alkyl, arylC$_1$-C$_6$alkyl, hetarylC$_1$-C$_6$alkyl, C$_6$-C$_{12}$cycloalkyl, C$_3$-C$_{10}$hetcycloalkyl, wherein each alkyl, cykloalkyl, hetcycloalkyl, and aryl/hetaryl group is substituted with 0-3 $R^{18}$;

In another embodiment, the present invention provides a compound of formula I, wherein one of $Rn^1$ and $Rn^2$ is H, and the other one of $Rn^1$ and $Rn^2$ is C$_6$-C$_{12}$cycloalkyl, substituted with 0-3 $R^{18}$.

In another embodiment, the present invention provides a compound of formula I, wherein $Rn^1$ and $Rn^2$, together with the nitrogen to which they are attached, form a 6-12 membered saturated or partially saturated monocyclic or bicyclic ring consisting of the shown nitrogen, 4-11 carbon atoms, and 0-2 additional heteroatoms selected from nitrogen and oxygen wherein the ring is substituted with 0-3 groups selected from halo, trihalomethyl, trihalomethyloxy, C$_1$-C$_6$alkyl, C$_3$-C$_{10}$cycloalkyl, —C(O)R$^{12}$, —S(O)$_n$R$^{12}$, oxo, C$_1$-C$_6$alkyloxy, arylC$_1$-C$_6$alkyloxy, hetarylC$_1$-C$_6$alkyloxy, and C$_1$-C$_6$alkyloxyC$_1$-C$_6$alkyl, wherein each alkyl, and aryl/hetaryl group is substituted with 0-3 $R^{18}$.

In another embodiment, the present invention provides a compound of formula I, wherein the ring formed by $Rn^1$ and $Rn^2$, together with the nitrogen to which they are attached is selected from:

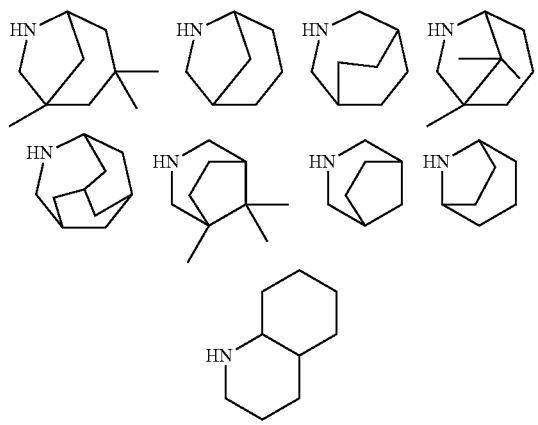

being substituted with 0-2 $R^{25}$; and,
$R^{25}$ is selected from C$_1$-C$_6$alkyl, halo, hydroxy, oxo, cyano, and C$_1$-C$_6$alkyloxy.

In another embodiment, the present invention provides a compound of formula I, wherein the ring formed by $Rn^1$ and $Rn^2$, together with the nitrogen to which they are attached is selected from:

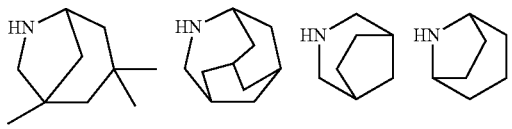

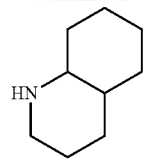

being substituted with 0-2 $R^{25}$; and,
$R^{25}$ is selected from C$_1$-C$_6$alkyl, halo, hydroxy, oxo, cyano, and C$_1$-C$_6$alkyloxy.

In another embodiment, the present invention provides a compound of formula I, wherein $Rn^1$ is hydrogen and N—$Rn^2$ is selected from:

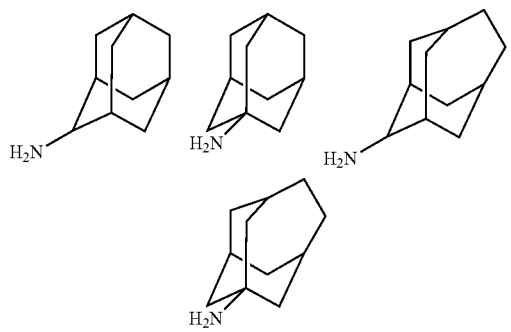

being substituted with 0-2 $R^{25}$; and,
$R^{25}$ is selected from C$_1$-C$_6$alkyl, halo, hydroxy, oxo, cyano, and C$_1$-C$_6$alkyloxy.

In another embodiment, the present invention provides a compound of formula Ia:

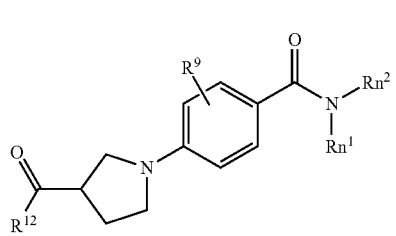

Ia wherein $R^{12}$, $R^9$, $Rn^1$, and $Rn^2$ are as defined above.

In another embodiment, the present invention provides a compound of formula Ib:

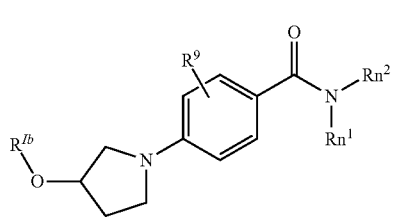

Ib wherein $R^{Ib}$ is hetaryl or arylC$_1$-C$_6$alkyl and $R^9$, $Rn^1$, and $Rn^2$ are as defined above.

In another embodiment, the present invention provides a compound of formula Ic:

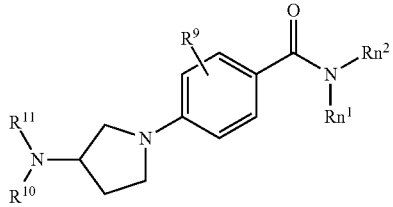

Ic wherein $R^{10}$, $R^{11}$, $R^9$, $Rn^1$, and $Rn^2$ are as defined above.

In another embodiment, the present invention provides a compound of formula Id:

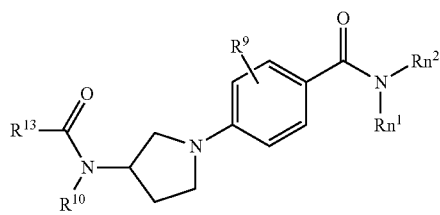

Id wherein $R^{10}$, $R^{13}$, $R^9$, $Rn^1$, and $Rn^2$ are as defined above.

In another embodiment, the present invention provides a compound of formula Ie:

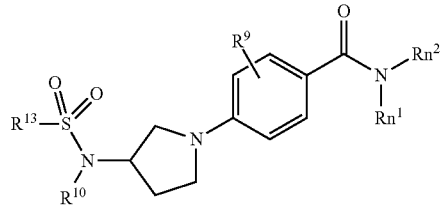

Ie wherein $R^{10}$, $R^{13}$, $R^9$, $Rn^1$, and $Rn^2$ are as defined above.

In another embodiment, the present invention provides a compound of formula If:

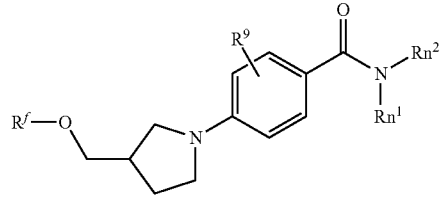

If wherein $R^f$ is hetaryl optionally substituted with $R^{18}$; and $R^9$, $Rn^1$, and $Rn^2$ are as defined above.

In another embodiment, the present invention provides a compound of formula Ig:

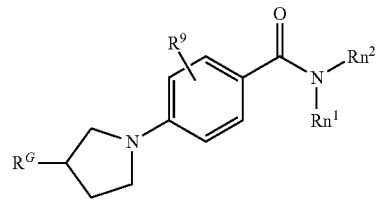

Ig wherein $R^G$ is aryl optionally substituted with $R^{18}$; and $R^9$, $Rn^1$, and $Rn^2$ are as defined above.

In another embodiment, the present invention provides a compound of formula Ih:

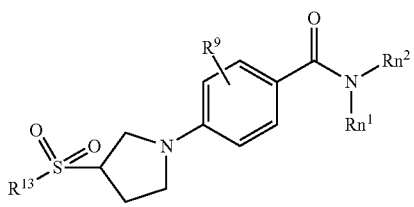

Ih wherein $R^{13}$, $R^9$, $Rn^1$, and $Rn^2$ are as defined above.

In another embodiment, the present invention provides a compound of formula Ij:

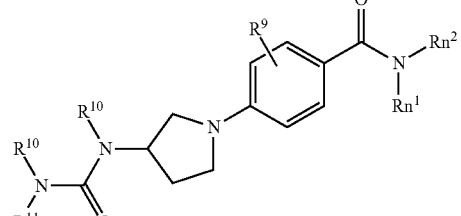

Ij wherein $R^9$, $R^{10}$, $R^{11}$, $Rn^1$ and $Rn^2$ are as defined above.

In another embodiment, the present invention provides a compound of formula Ik:

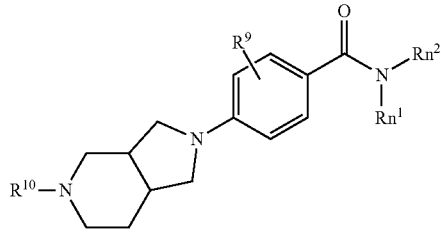

Ik wherein $R^9$, $R^{10}$, $Rn^1$ and $Rn^2$ are as defined above.

In another embodiment, the present invention provides a compound of formula Il:

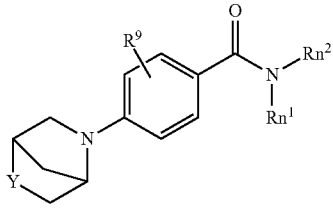

wherein R⁹, Rn¹ and Rn² are as defined above and Y is oxygen, $S(O)_n$ or $NR^{10}$.

In another embodiment, the present invention provides a compound of formula II':

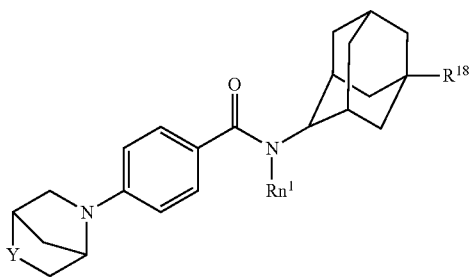

wherein Rn¹ and R¹⁸ are as defined above and Y is oxygen, $S(O)_n$ or $NR^{10}$.

In another embodiment, the present invention provides a compound of formula I, wherein the substituted amide or a prodrug thereof is selected from the group:

1-[4-(1,3,3-Trimethyl-6-aza-bicyclo[3.2.1]octane-6-carbonyl)-phenyl]-pyrrolidine-3-carboxylic acid methyl ester;
1-[4-(1,3,3-Trimethyl-6-aza-bicyclo[3.2.1]octane-6-carbonyl)-phenyl]-pyrrolidine-3-carboxylic acid;
{4-[3-(Morpholine-4-carbonyl)-pyrrolidin-1-yl]-phenyl}-(1,3,3-trimethyl-6-aza-bicyclo-3.2.1]oct-6-yl)-methanone;
1-[4-(1,3,3-Trimethyl-6-aza-bicyclo[3.2.1]octane-6-carbonyl)-phenyl]-pyrrolidine-3-carboxylic acid (3-hydroxy-adamantan-1-yl)-amide;
(Methyl-{1-[4-(1,3,3-trimethyl-6-aza-bicyclo[3.2.1]octane-6-carbonyl)-phenyl]-pyrrolidine-3-carbonyl}-amino)-acetic acid tert-butyl ester;
(Methyl-{1-[4-(1,3,3-trimethyl-6-aza-bicyclo[3.2.1]octane-6-carbonyl)-phenyl]-pyrrolidine-3-carbonyl}-amino)-acetic acid;
1-[4-(1,3,3-Trimethyl-6-aza-bicyclo[3.2.1]octane-6-carbonyl)-phenyl]-pyrrolidine-3-carboxylic acid (4-hydroxy-cyclohexyl)-amide;
{4-[3-(4-Hydroxy-piperidine-1-carbonyl)-pyrrolidin-1-yl]-phenyl}-(1,3,3-trimethyl-6-aza-bicyclo[3.2.1]oct-6-yl)-methanone;
{4-[3-(4-Hydroxymethyl-piperidine-1-carbonyl)-pyrrolidin-1-yl]-phenyl}-(1,3,3-trimethyl-6-aza-bicyclo[3.2.1]oct-6-yl)-methanone;
1-[4-(Octahydroquinoline-1-carbonyl)phenyl]-pyrrolidine-3-carboxylic acid;
{4-[3-(Morpholine-4-carbonyl)-pyrrolidin-1-yl]-phenyl} (octahydroquinolin-1-yl)methanone;
{4-[3-(4-Hydroxymethyl-piperidine-1-carbonyl)-pyrrolidin-1-yl]-phenyl}-(octahydroquinolin-1-yl)methanone;
1-[4-(Adamantan-1-ylcarbamoyl)-phenyl]-pyrrolidine-3-carboxylic acid;
{4-[3-(4-Hydroxy-piperidine-1-carbonyl)-pyrrolidin-1-yl]-phenyl}-(octahydro-quinolin-1-yl)-methanone;
1-[4-(Octahydro-quinoline-1-carbonyl)-phenyl]-pyrrolidine-3-carboxylic acid (tetrahydro-pyran-4-yl)-amide;
(Octahydro-quinolin-1-yl)-{4-[3-(2-oxa-5-aza-bicyclo[2.2.1]heptane-5-carbonyl)-pyrrolidin-1-yl]-phenyl}-methanone;
4-(3-Acetylamino-pyrrolidin-1-yl)-N-adamantan-2-yl-benzamide;
N-{1-[4-(Octahydro-quinoline-1-carbonyl)-phenyl]-pyrrolidin-3-yl}-acetamide;
N-{1-[4-(3-Aza-bicyclo[3.2.2]nonane-3-carbonyl)-phenyl]-pyrrolidin-3-yl}-acetamide;
{1-[4-(3-Aza-bicyclo[3.2.2]nonane-3-carbonyl)-phenyl]-pyrrolidin-3-yl}-methyl-carbamic acid tert-butyl ester;
(3-Aza-bicyclo[3.2.2]non-3-yl)-[4-(3-methylamino-pyrrolidin-1-yl)-phenyl]-methanone;
N-{1-[4-(3-Aza-bicyclo[3.2.2]nonane-3-carbonyl)-phenyl]-pyrrolidin-3-yl}-N-methyl-acetamide;
Cyclopropanecarboxylic acid {1-[4-(3-aza-bicyclo[3.2.2]nonane-3-carbonyl)-phenyl]-pyrrolidin-3-yl}-methyl-amide;
5-Methyl-isoxazole-3-carboxylic acid {1-[4-(3-aza-bicyclo[3.2.2]nonane-3-carbonyl)-phenyl]-pyrrolidin-3-yl}-methyl-amide;
N-{1-[4-(3-Aza-bicyclo[3.2.2]nonane-3-carbonyl)-phenyl]-pyrrolidin-3-yl}-N-methyl-phenyl-methanesulfonamide;
N-{1-[4-(3-Aza-bicyclo[3.2.2]nonane-3-carbonyl)-phenyl]-pyrrolidin-3-yl}-4-chloro-N-methyl-benzenesulfonamide;
Pyridine-2-carboxylic acid {1-[4-(3-aza-bicyclo[3.2.2]nonane-3-carbonyl)-phenyl]-pyrrolidin-3-yl}-methyl-amide;
1-{1-[4-(3-Aza-bicyclo[3.2.2]nonane-3-carbonyl)-phenyl]-pyrrolidin-3-yl}-3-cyclohexyl-1-methyl-urea;
(3-Aza-bicyclo[3.2.2]non-3-yl)-{4-[3-(pyridin-2-yloxy)-pyrrolidin-1-yl]-phenyl}-methanone;
4-(2-Oxa-5-aza-bicyclo[2.2.1]hept-5-yl)-N-adamantan-2-yl-benzamide;
4-[3-(4-Chloro-phenyl)-pyrrolidin-1-yl]-N-adamantan-2-yl-benzamide;
4-[3-(Pyridin-2-yloxymethyl)-pyrrolidin-1-yl]-N-adamantan-2-yl-benzamide;
(3-Aza-bicyclo[3.2.2]non-3-yl)-{4-[3-(pyridin-2-yloxymethyl)-pyrrolidin-1-yl]-phenyl}-methanone;
4-(3-Methanesulfonyl-pyrrolidin-1-yl)-N-adamantan-2-yl-benzamide;
(3-Aza-bicyclo[3.2.2]non-3-yl)-[4-(3-morpholin-4-yl-pyrrolidin-1-yl)-phenyl]-methanone;
[4-(3-Morpholin-4-yl-pyrrolidin-1-yl)-phenyl]-(1,3,3-trimethyl-6-aza-bicyclo[3.2.1]oct-6-yl)-methanone;
(3-Aza-bicyclo[3.2.2]non-3-yl)-{4-[3-(6-methyl-pyridin-3-yloxymethyl)-pyrrolidin-1-yl]-phenyl}-methanone;
(3-Aza-bicyclo[3.2.2]non-3-yl)-[4-((R)-3-benzyloxy-pyrrolidin-1-yl)-phenyl]-methanone;
N-{(R)-1-[4-(3-Aza-bicyclo[3.2.2]nonane-3-carbonyl)-phenyl]-pyrrolidin-3-yl}-acetamide;
1-{(R)-1-[4-(3-Aza-bicyclo[3.2.2]nonane-3-carbonyl)-phenyl]-pyrrolidin-3-yl}-3-isopropyl-urea;
1-{(R)-1-[4-(3-Aza-bicyclo[3.2.2]nonane-3-carbonyl)-phenyl]-pyrrolidin-3-yl}-3-N,N-dimethyl-sulfamide;
4-[(R)-3-(3-Isopropyl-ureido)-pyrrolidin-1-yl]-N-adamantan-2-yl-benzamide;

Morpholine-4-carboxylic acid {(R)-1-[4-(3-aza-bicyclo[3.2.2]nonane-3-carbonyl)-phenyl]-pyrrolidin-3-yl}-amide;
Morpholine-4-carboxylic acid {(R)-1-[4-(adamantan-2-yl-carbamoyl)-phenyl]-pyrrolidin-3-yl}-amide;
1-{(R)-1-[4-(adamantan-2-yl-phenyl]-pyrrolidin-3-yl}-3-N,N-dimethyl-sulfamide;
6-Chloro-N-{(R)-1-[4-(octahydro-quinoline-1-carbonyl)-phenyl]-pyrrolidin-3-yl}-nicotinamide;
1,1-Dimethyl-3-{(R)-1-[4-(octahydro-quinoline-1-carbonyl)-phenyl]-pyrrolidin-3-yl}-urea; or a salt thereof with a pharmaceutically acceptable acid or base, or any optical isomer or mixture of optical isomers, including a racemic mixture, or any tautomeric forms.

In another embodiment, the present invention provides a compound of formula I, wherein the substituted amide or a prodrug thereof is selected from the group:
N-{1-[4-(1,3,3-Trimethyl-6-aza-bicyclo[3.2.1]octane-6-carbonyl)-phenyl]-pyrrolidin-3-yl}-acetamide;
N-{1-[4-(8-Hydroxy-3-aza-bicyclo[3.2.1]octane-3-carbonyl)-phenyl]-pyrrolidin-3-yl}-acetamide;
4-(3-Acetylamino-pyrrolidin-1-yl)-N-(3-hydroxymethyl-adamantan-1-yl)-benzamide;
4-(3-Acetylamino-pyrrolidin-1-yl)-N-(5-hydroxy-adamantan-2-yl)-benzamide;
4-(3-Acetylamino-pyrrolidin-1-yl)-N-(5-hydroxy-adamantan-2-yl)-N-methyl-benzamide;
5-[4-(3-Aza-bicyclo[3.2.2]-nonane-3-carbonyl)-phenyl]-2,5-diaza-bicyclo[2.2.1]-heptane-2-carboxylic acid tert-butyl ester;
N-Adamantan-2-yl-4-((R)-3-benzyloxy-pyrrolidin-1-yl)-benzamide;
[4-((R)-3-Benzyloxy-pyrrolidin-1-yl)-phenyl]-(octahydro-quinolin-1-yl)-methanone;
4-((R)-3-Benzyloxy-pyrrolidin-1-yl)-N-(1-hydroxy-adamantan-2-yl)-benzamide;
4-((S)-3-Acetylamino-pyrrolidin-1-yl)-N-adamantan-2-yl-benzamide;
4-(3-Acetylamino-pyrrolidin-1-yl)-N-(3-hydroxy-adamantan-1-yl)-benzamide;
N-{(S)-1-[4-(Adamantan-2-ylcarbamoyl)-phenyl]-pyrrolidin-3-yl}-6-chloro-nicotin-amide;
1-Isopropyl-3-{(S)-1-[4-(octahydro-quinoline-1-carbonyl)-phenyl]-pyrrolidin-3-yl}-urea;
(Octahydro-quinolin-1-yl)-{4-[(1S,5R)-3-(pyridin-2-yloxy)-8-aza-bicyclo[3.2.1]oct-8-yl]-phenyl}-methanone;
N-Adamantan-2-yl-4-[(1S,5R)-3-(pyridin-2-yloxy)-8-aza-bicyclo[3.2.1]oct-8-yl]-benzamide;
2-[4-(Adamantan-2-yl-carbamoyl)-phenyl]-octahydro-pyrrolo[3,4-c]pyridine-5-carboxylic acid isopropylamide;
or a salt thereof with a pharmaceutically acceptable acid or base, or any optical isomer or mixture of optical isomers, including a racemic mixture, or any tautomeric forms.

In another embodiment, the present invention provides a compound of formula I, selected from the group:
[4-(3-Benzyloxy-pyrrolidin-1-yl)-phenyl]-(octahydro-quinolin-1-yl)-methanone;
4-(3-Benzyloxy-pyrrolidin-1-yl)-N-tricyclo[3.3.1.13,7]decan-2-yl-benzamide;
(3-Aza-bicyclo[3.2.2]non-3-yl)-[4-(3-benzyloxy-pyrrolidin-1-yl)-phenyl]-methanone;
(S)-(3-Aza-bicyclo[3.2.2]non-3-yl)-[4-(3-benzyloxy-pyrrolidin-1-yl)-phenyl]-methanone;
or a salt thereof with a pharmaceutically acceptable acid or base, or any optical isomer or mixture of optical isomers, including a racemic mixture, or any tautomeric forms.

In another embodiment, the present invention provides for the use of a substituted amide, a prodrug thereof, or a salt thereof with a pharmaceutically acceptable acid or base, or any optical isomer or mixture of optical isomers, including a racemic mixture or any tautomeric forms, wherein the substituted amide or a prodrug thereof is of formula I:

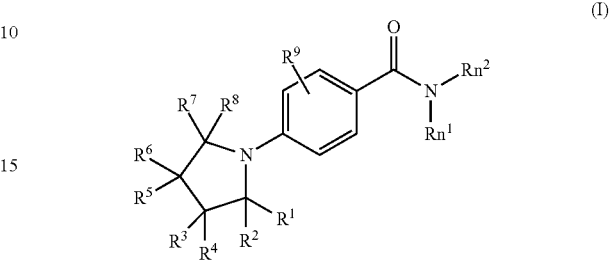

wherein:
$R^1$, $R^2$, $R^3$, $R^4$, $R^5$, $R^6$, $R^7$ and $R^8$ are each independently selected from H, halo, $C_2$-$C_{10}$-alkenyl, $C_2$-$C_{10}$alkynyl, $NR^{10}R^{11}$, $C(O)R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, arylC_1-C_6alkyl, hetarylC_1-C_6alkyl, arylC_1-C_6alkyloxy, hetarylC_1-C_6alkyloxy, $C_3$-$C_{10}$cycloalkyl, $C_3$-$C_{10}$cycloalkyloxy, $C_3$-$C_{10}$cycloalkylC_1-C_6alkyloxy, $C_3$-$C_{10}$hetcycloalkyl, $C_3$-$C_{10}$hetcycloalkyloxy, aryloxyC_1-C_6alkyl, hetaryloxyC_1-C_6alkyl, $C_3$-$C_{10}$cycloalkyloxyC_1-C_6alkyl, and $C_3$-$C_{10}$hetcycloalkyloxyC_1-C_6alkyl, wherein each alkyl, cykloalkyl, hetcycloalkyl, and aryl/hetaryl group is substituted with 0-3 $R^{18}$; or $R^2$, $R^3$, $R^4$, $R^6$, $R^7$ and $R^8$ are each independently selected from H, halo, $C_2$-$C_{10}$alkenyl, $C_2$-$C_{10}$alkynyl, $NR^{10}R^{11}$, $C(O)R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, arylC_1-C_6alkyl, hetarylC_1-C_6alkyl, arylC_1-C_6alkyloxy, hetarylC_1-C_6alkyloxy, $C_3$-$C_{10}$cycloalkyl, $C_3$-$C_{10}$cycloalkyloxy, $C_3$-$C_{10}$cycloalkylC_1-C_6alkyloxy, $C_3$-$C_{10}$hetcycloalkyl, $C_3$-$C_{10}$hetcycloalkyloxy, aryloxyC_1-C_6alkyl, hetaryloxyC_1-C_6alkyl, $C_3$-$C_{10}$cycloalkyloxyC_1-C_6alkyl, and $C_3$-$C_{10}$-hetcycloalkyloxyC_1-C_6alkyl, wherein each alkyl, cykloalkyl, hetcycloalkyl, and aryl/hetaryl group is substituted with 0-3 $R^{18}$; and $R^1$ and $R^5$ together with the carbons to which they are attached form a 4-8 membered saturated, partially saturated or aromatic ring consisting of 2-8 carbon atoms, and 0-2 additional heteroatoms selected from nitrogen, oxygen, and $S(O)_n$, wherein this ring is substituted with 0-3 groups selected from fluoro, $C_1$-$C_6$alkyl, $C_3$-$C_{10}$-cycloalkyl, $C_3$-$C_{10}$hetcycloalkyl, $C_3$-$C_6$spirocycloalkyl, 3-6 membered spirohetcycloalkyl, aryl, hetaryl, arylC_1-C_6alkyl, hetarylC_1-C_6alkyl, —C(O)$R^{12}$, —S(O)_n$R^{12}$, —S(O)_nNR^{14}R^{15}$, —N(R^{14})S(O)_n$R^{12}$, —N(R^{16})C(=Y)NR^{14}R^{15}$, —C(=NR^{17})NR^{17}$, OH, oxo, $C_1$-$C_6$alkyloxy, arylC_1-C_6alkyloxy, hetarylC_1-C_6alkyloxy, $C_1$-$C_6$alkyloxyC_1-C_6alkyl, $C_1$-$C_6$alkylcarboxy, arylcarboxy, hetarylcarboxy, arylC_1-C_6alkylcarboxy, and hetarylC_1-C_6alkylcarboxy, wherein each alkyl, and aryl/hetaryl group is substituted with 0-3 $R^{18}$; or $R^2$, $R^3$, $R^4$, $R^5$, $R^6$ and $R^8$ are each independently selected from H, halo, $C_2$-$C_{10}$alkenyl, $C_2$-$C_{10}$alkynyl, $NR^{10}R^{11}$, $C(O)R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, arylC_1-C_6alkyl, hetarylC_1-C_6alkyl, arylC_1-C_6alkyloxy, hetarylC$_1$-C$_6$alkyloxy, C$_3$-C$_{10}$cycloalkyl, C$_3$-C$_{10}$cycloalkyloxy, C$_3$-C$_{10}$cycloalkylC$_1$-C$_6$alkyloxy, C$_3$-C$_{10}$hetcycloalkyl, C$_3$-C$_{10}$hetcycloalkyloxy, aryloxyC$_1$-C$_6$alkyl, hetaryloxyC$_1$-C$_6$alkyl, C$_3$-C$_{10}$cyclo-alkyloxyC$_1$-C$_6$alkyl, and C$_3$-C$_{10}$-hetcycloalkyloxyC$_1$-C$_6$alkyl, wherein each alkyl, cykloalkyl, hetcycloalkyl, and aryl/hetaryl group is substituted with 0-3 R$^{18}$; and R$^1$ and R$^7$ together with the carbons to which they are attached form a 4-8 membered saturated, partially saturated or aromatic ring consisting of 2-8 carbon atoms, and 0-2 additional heteroatoms selected from nitrogen, oxygen, and S(O)$_n$, wherein this ring is substituted with 0-3 groups selected from fluoro, C$_1$-C$_6$alkyl, C$_3$-C$_{10}$cycloalkyl, C$_3$-C$_{10}$hetcycloalkyl, C$_3$-C$_6$spirocycloalkyl, 3-6 membered spirohetcycloalkyl, aryl, hetaryl, arylC$_1$-C$_6$alkyl, hetarylC$_1$-C$_6$alkyl, —C(O)R$^{12}$, —S(O)$_n$R$^{12}$, —S(O)$_n$NR$^{14}$R$^{15}$, —N(R$^{14}$)S(O)$_n$R$^{12}$, —N(R$^{16}$)C(=Y)NR$^{14}$R$^{15}$, —C(=NR$^{17}$)NR$^{17}$, OH, oxo, C$_1$-C$_6$alkyloxy, arylC$_1$-C$_6$alkyloxy, hetarylC$_1$-C$_6$alkyloxy, C$_1$-C$_6$alkyloxyC$_1$-C$_6$alkyl, C$_1$-C$_6$alkylcarboxy, arylcarboxy, hetarylcarboxy, arylC$_1$-C$_6$alkylcarboxy, and hetarylC$_1$-C$_6$alkylcarboxy, wherein each alkyl, and aryl/hetaryl group is substituted with 0-3 R$^{18}$; or R$^1$, R$^2$, R$^3$, R$^6$, R$^7$ and R$^8$ are each independently selected from H, halo, C$_2$-C$_{10}$alkenyl, C$_2$-C$_{10}$alkynyl, NR$^{10}$R$^{11}$, C(O)R$^{12}$, R$^{13}$S(O)$_n$, R$^{13}$C(O)NR$^{10}$, R$^{10}$R$^{11}$NS(O)$_n$, R$^{13}$S(O)$_n$NR$^{10}$, aryl, hetaryl, aryloxy, hetaryloxy, arylC$_1$-C$_6$alkyl, hetarylC$_1$-C$_6$alkyl, arylC$_1$-C$_6$alkyloxy, hetarylC$_1$-C$_6$alkyloxy, C$_3$-C$_{10}$cycloalkyl, C$_3$-C$_{10}$cycloalkyloxy, C$_3$-C$_{10}$cycloalkylC$_1$-C$_6$alkyloxy, C$_3$-C$_{10}$hetcycloalkyl, C$_3$-C$_{10}$hetcycloalkyloxy, aryloxyC$_1$-C$_6$alkyl, hetaryloxyC$_1$-C$_6$alkyl, C$_3$-C$_{10}$cyclo-alkyloxyC$_1$-C$_6$alkyl, and C$_3$-C$_{10}$-hetcycloalkyloxyC$_1$-C$_6$alkyl, wherein each alkyl, cykloalkyl, hetcycloalkyl, and aryl/hetaryl group is substituted with 0-3 R$^{18}$; and R$^4$ and R$^5$ together with the carbons to which they are attached form a 4-8 membered saturated, partially saturated or aromatic ring consisting of 2-8 carbon atoms, and 0-2 additional heteroatoms selected from nitrogen, oxygen, and S(O)$_n$, wherein this ring is substituted with 0-3 groups selected from fluoro, C$_1$-C$_6$alkyl, C$_3$-C$_{10}$cycloalkyl, C$_3$-C$_{10}$hetcycloalkyl, C$_3$-C$_6$spirocycloalkyl, 3-6 membered spirohetcycloalkyl, aryl, hetaryl, arylC$_1$-C$_6$alkyl, hetarylC$_1$-C$_6$alkyl, —C(O)R$^{12}$, —S(O)$_n$R$^{12}$, —S(O)$_n$NR$^{14}$R$^{15}$, —N(R$^{14}$)S(O)$_n$R$^{12}$, —N(R$^{16}$)C(=Y) NR$^{14}$R$^{15}$, —C(=NR$^{17}$)NR$^{17}$, OH, oxo, C$_1$-C$_6$alkyloxy, arylC$_1$-C$_6$alkyloxy, hetarylC$_1$-C$_6$alkyloxy, C$_1$-C$_6$alkyloxyC$_1$-C$_6$alkyl, C$_1$-C$_6$alkylcarboxy, arylcarboxy, hetarylcarboxy, arylC$_1$-C$_6$alkylcarboxy, and hetarylC$_1$-C$_6$alkylcarboxy, wherein each alkyl, and aryl/hetaryl group is substituted with 0-3 R$^{18}$;

R$^9$ is selected from H, halo, OH, cyano, C$_1$-C$_6$alkyl, C$_1$-C$_6$alkyloxy, trihalomethyloxy and C$_3$-C$_6$cycloalkyl;

R$^{10}$ and R$^{11}$ are each independently selected from H, C$_1$-C$_6$alkyl, C$_1$-C$_6$alkylcarbonyl, C(O)OC$_1$-C$_6$alkyl, aryl, hetaryl, arylC$_1$-C$_6$alkyl, hetarylC$_1$-C$_6$alkyl, C$_3$-C$_{10}$cycloalkyl, C$_3$-C$_{10}$hetcycloalkyl, arylcarbonyl, hetarylcarbonyl, arylC$_1$-C$_6$alkylcarbonyl, hetarylC$_1$-C$_6$alkylcarbonyl, C$_3$-C$_{10}$cycloalkylcarbonyl and C$_3$-C$_{10}$hetcycloalkyl-carbonyl, wherein each alkyl, cykloalkyl, hetcycloalkyl, and aryl/hetaryl group is substituted with 0-3 R$^{18}$;

alternatively, R$^{10}$ and R$^{11}$, together with the nitrogen to which they are attached, form a 3-12 membered saturated or partially saturated monocyclic or bicyclic ring consisting of the shown nitrogen, 2-10 carbon atoms, and 0-2 additional heteroatoms selected from nitrogen, oxygen, and S(O)$_n$, wherein this ring is substituted with 0-3 groups selected from halo, C$_1$-C$_6$alkyl, C$_3$-C$_{10}$cycloalkyl, C$_3$-C$_{10}$hetcycloalkyl, C$_3$-C$_6$spirocycloalkyl, 3-6 membered spirohetcycloalkyl, aryl, hetaryl, arylC$_1$-C$_6$-alkyl, hetarylC$_1$-C$_6$alkyl, —C(O)R$^{12}$, —S(O)$_n$R$^{12}$, —S(O)$_n$NR$^{14}$R$^{15}$, —N(R$^{14}$)S(O)$_n$R$^{12}$, —N(R$^{16}$)C(=Y)NR$^{14}$R$^{15}$, —C(=NR$^{17}$)NR$^{17}$, OH, oxo, C$_1$-C$_6$alkyloxy, arylC$_1$-C$_6$alkyloxy, hetarylC$_1$-C$_6$alkyloxy, C$_1$-C$_6$alkyloxyC$_1$-C$_6$alkyl, C$_1$-C$_6$alkylcarboxy, arylcarboxy, hetarylcarboxy, arylC$_1$-C$_6$alkylcarboxy, and hetarylC$_1$-C$_6$alkylcarboxy, wherein each alkyl, and aryl/hetaryl group is substituted with 0-3 R$^{18}$;

R$^{12}$ is OH, NR$^{10}$R$^{11}$, C$_1$-C$_6$alkyloxy, C$_2$-C$_6$alkenyloxy, C$_2$-C$_6$alkynyloxy, C$_3$-C$_{10}$cycloalkyl, C$_3$-C$_{10}$cycloalkyloxy, C$_3$-C$_{10}$hetcycloalkyloxy, aryloxy, hetaryloxy, arylC$_1$-C$_6$alkyloxy, hetarylC$_1$-C$_6$alkyloxy;

R$^{13}$ is C$_1$-C$_6$alkyl, C$_2$-C$_6$alkenyl, C$_2$-C$_6$alkynyl, NR$^{10}$R$^{11}$, aryl, hetaryl, arylC$_1$-C$_6$alkyl, hetarylC$_1$-C$_6$alkyl, C$_3$-C$_{10}$cycloalkyl, C$_3$-C$_{10}$hetcycloalkyl, aryloxyC$_1$-C$_6$alkyl, hetaryloxyC$_1$-C$_6$alkyl, C$_3$-C$_{10}$cycloalkyloxyC$_1$-C$_6$alkyl, and C$_3$-C$_{10}$hetcycloalkyloxyC$_1$-C$_6$-alkyl, wherein each alkyl, cykloalkyl, hetcycloalkyl, and aryl/hetaryl group is substituted with 0-3 R$^{18}$;

R$^{14}$ and R$^{15}$ are independently selected from H, C$_1$-C$_6$alkyl, C$_1$-C$_6$alkyloxy, aryl, hetaryl, arylC$_1$-C$_6$alkylene, and hetarylC$_1$-C$_6$alkylene, wherein the alkyl/alkylene, aryl, and hetaryl groups are independently substituted with 0-3 R$^{20}$;

alternatively, R$^{14}$ and R$^{15}$, together with the nitrogen atom to which they are attached, form a saturated or partially saturated monocyclic, bicyclic, or tricyclic ring consisting of the shown nitrogen, 4-10 carbon atoms, and 0-2 additional heteroatoms selected from nitrogen, oxygen, and sulfur, wherein this ring is substituted with 0-3 C$_1$-C$_6$alkyl, aryl, hetaryl, arylC$_1$-C$_6$alkylene, hetarylC$_1$-C$_6$alkylene, hydroxy, oxo, C$_1$-C$_6$alkyloxy, arylC$_1$-C$_6$alkyloxy, hetarylC$_1$-C$_6$alkyloxy, C$_1$-C$_6$alkyloxyC$_1$-C$_6$alkyl, C$_1$-C$_6$alkylcarbonyl, arylcarbonyl, hetarylcarbonyl, arylC$_1$-C$_6$alkylcarbonyl, hetarylC$_1$-C$_6$alkylcarbonyl, C$_1$-C$_6$alkylcarboxy, arylcarboxy, hetarylcarboxy, arylC$_1$-C$_6$alkyl-carboxy, and hetarylC$_1$-C$_6$alkylcarboxy;

R$^{16}$ is selected from H and C$_1$-C$_6$alkyl;

R$^{17}$ is selected from H, C$_1$-C$_6$alkyl, 3-10 membered cycloalkyl, halo, OH, cyano, —C(=O)R$^{12}$, —S(=O)$_n$R$^{12}$, S(=O)$_n$NR$^{14}$R$^{15}$, —N(R$^{14}$)S(=O)$_n$R$^{12}$, aryl, and hetaryl, wherein the alkyl and cycloalkyl groups are substituted with 0-3 R$^{20}$;

R$^{18}$ is selected from halo, OH, oxo, COOH, S(O)$_2$R$^{12}$, C(=O)OC$_1$-C$_6$alkyl, cyano, C$_1$-C$_6$alkyl, C$_1$-C$_6$alkyloxy, C$_3$-C$_{10}$cycloalkyloxy, aryloxy, hetaryloxy, hetarylthio, and arylC$_1$-C$_6$alkyloxy;

R$^{20}$ is selected from H, OH, oxo, halo, cyano, nitro, C$_1$-C$_6$alkyl, C$_1$-C$_6$alkyloxy, NR$^{21}$R$^{22}$, methylendioxo, dihalomethylendioxo, trihalomethyl, and trihalomethyloxy;

R$^{21}$ and R$^{22}$ are independently selected from H, C$_1$-C$_6$alkyl, and arylC$_1$-C$_6$alkyl;

Rn$^1$ and Rn$^2$ are each independently selected from H, C$_1$-C$_6$alkyl, arylC$_1$-C$_6$alkyl, hetaryl-C$_1$-C$_6$alkyl, C$_3$-C$_{12}$cycloalkyl, C$_3$-C$_{10}$hetcycloalkyl, wherein each alkyl, cycloalkyl, hetcycloalkyl, and aryl/hetaryl group is substituted with 0-3 R$^{18}$;

alternatively, Rn$^1$ and Rn$^2$, together with the nitrogen to which they are attached, form a 5-12 membered saturated or partially saturated monocyclic or bicyclic ring consisting of the shown nitrogen, 4-11 carbon atoms, and 0-2 additional heteroatoms selected from nitrogen, oxygen, and $S(O)_n$, wherein the ring is substituted with 0-3 groups selected from halo, trihalomethyl, trihalomethyloxy, cyano, $C_1$-$C_6$alkyl, $C_3$-$C_{10}$cycloalkyl, —$C(O)R^{12}$, —$S(O)_n R^{12}$, —$S(O)_n NR^{14}R^{15}$, —$N(R^{14})S(O)_n R^{12}$, OH, oxo, $C_1$-$C_6$alkyloxy, aryl$C_1$-$C_6$alkyloxy, hetaryl$C_1$-$C_6$alkyloxy, and $C_1$-$C_6$alkyloxy-$C_1$-$C_6$alkyl, wherein each alkyl, and aryl/hetaryl group is substituted with 0-3 $R^{18}$;

n is selected from 0, 1 and 2; or a salt thereof with a pharmaceutically acceptable acid or base, or any optical isomer or mixture of optical isomers, including a racemic mixture, or any tautomeric forms.

In another embodiment, the present invention provides for the use of a substituted amide, a prodrug thereof, or a salt thereof with a pharmaceutically acceptable acid or base, or any optical isomer or mixture of optical isomers, including a racemic mixture or any tautomeric forms, wherein the substituted amide or a prodrug thereof is of formula I:

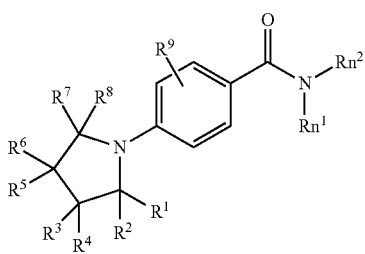

I wherein:

$R^1$, $R^2$, $R^3$, $R^4$, $R^5$, $R^6$, $R^7$ and $R^8$ are each independently selected from H, halo, $C_2$-$C_{10}$-alkenyl, $C_2$-$C_{10}$alkynyl, $NR^{10}R^{11}$, $C(O)R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cyclo-alkyloxy$C_1$-$C_6$alkyl, and $C_3$-$C_{10}$-hetcycloalkyloxy$C_1$-$C_6$alkyl, wherein each alkyl, cykloalkyl, hetcycloalkyl, and aryl/hetaryl group is substituted with 0-3 $R^{18}$; or $R^1$, $R^2$, $R^3$, $R^6$, $R^7$ and $R^8$ are each independently selected from H, halo, $C_2$-$C_{10}$alkenyl, $C_2$-$C_{10}$alkynyl, $NR^{10}R^{11}$, $C(O)R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cyclo-alkyloxy$C_1$-$C_6$alkyl, and $C_3$-$C_{10}$-hetcycloalkyloxy$C_1$-$C_6$alkyl, wherein each alkyl, cykloalkyl, hetcycloalkyl, and aryl/hetaryl group is substituted with 0-3 $R^{18}$; and $R^4$ and $R^5$ together with the carbons to which they are attached form a 4-8 membered saturated, partially saturated or aromatic ring consisting of 2-8 carbon atoms, and 0-2 additional heteroatoms selected from nitrogen, oxygen, and $S(O)_n$, wherein this ring is substituted with 0-3 groups selected from fluoro, $C_1$-$C_6$alkyl, $C_3$-$C_{10}$-cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, —$C(O)R^{12}$, —$S(O)_n R^{12}$, —$S(O)_n NR^{14}R^{15}$, —$N(R^{14})S(O)_n R^{12}$, —$N(R^{16})C(=Y)NR^{14}R^{15}$, —$C(=NR^{17})NR^{17}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, and aryl/hetaryl group is substituted with 0-3 $R^{18}$;

$R^9$ is selected from H, halo, OH, cyano, $C_1$-$C_6$alkyl, $C_1$-$C_6$alkyloxy, trihalomethyloxy and $C_3$-$C_6$cycloalkyl;

$R^{10}$ and $R^{11}$ are each independently selected from H, $C_1$-$C_6$alkyl, $C(O)O$—$C_1$-$C_6$alkyl, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, wherein each alkyl, cykloalkyl, hetcycloalkyl, and aryl/hetaryl group is substituted with 0-3 $R^{18}$;

alternatively, $R^{10}$ and $R^{11}$, together with the nitrogen to which they are attached, form a 3-12 membered saturated or partially saturated monocyclic or bicyclic ring consisting of the shown nitrogen, 2-10 carbon atoms, and 0-2 additional heteroatoms selected from nitrogen, oxygen, and $S(O)_n$, wherein this ring is substituted with 0-3 groups selected from halo, $C_1$-$C_6$alkyl, $C_3$-$C_{10}$cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$-alkyl, hetaryl$C_1$-$C_6$alkyl, —$C(O)R^{12}$, —$S(O)_nNR^{14}R^{15}$, —$N(R^{14})S(O)_nR^{12}$, —$N(R^{16})C(=Y)NR^{14}R^{15}$, —$C(=NR^{17})NR^{17}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, and aryl/hetaryl group is substituted with 0-3 $R^{18}$;

$R^{12}$ is OH, $NR^{10}R^{11}$, $C_1$-$C_6$alkyloxy, $C_2$-$C_6$alkenyloxy, $C_2$-$C_6$alkynyloxy, $C_3$-$C_{10}$cycloalkyl, $C_3$-$C_{10}$cycloalkyloxy, $C_3$-$C_{10}$hetcycloalkyloxy, aryloxy, hetaryloxy, aryl$C_1$-$C_6$alkyloxy, hetaryl$C_1$-$C_6$alkyloxy, $R^{13}$ is $C_1$-$C_6$alkyl, $C_2$-$C_6$alkenyl, $C_2$-$C_6$alkynyl, $NR^{10}R^{11}$, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, aryloxy$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$hetcycloalkyloxy$C_1$-$C_6$-alkyl, wherein each alkyl, cykloalkyl, hetcycloalkyl, and aryl/hetaryl group is substituted with 0-3 $R^{18}$;

$R^{18}$ is selected from halo, OH, oxo, COOH, $C(=O)OC_1$-$C_6$alkyl cyano, $C_1$-$C_6$alkyl, $C_1$-$C_6$alkyloxy, $C_3$-$C_{10}$cycloalkyloxy, aryloxy, hetaryloxy, hetarylthio, and aryl$C_1$-$C_6$alkyloxy;

$R^{14}$ and $R^{15}$ are independently selected from H, $C_1$-$C_6$alkyl, $C_1$-$C_6$alkyloxy, aryl, hetaryl, aryl$C_1$-$C_6$alkylene, and hetaryl$C_1$-$C_6$alkylene, wherein the alkyl/alkylene, aryl, and hetaryl groups are independently substituted with 0-3 $R^{20}$;

alternatively, $R^{14}$ and $R^{15}$, together with the nitrogen atom to which they are attached, form a saturated or partially saturated monocyclic, bicyclic, or tricyclic ring consisting of the shown nitrogen, 4-10 carbon atoms, and 0-2 additional heteroatoms selected from nitrogen, oxygen, and sulfur, wherein this ring is substituted with 0-3 $C_1$-$C_6$alkyl, aryl, hetaryl, aryl$C_1$-$C_6$alkylene, hetaryl$C_1$-$C_6$alkylene, hydroxy, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarbonyl, arylcarbonyl, hetarylcarbonyl, aryl$C_1$-$C_6$alkylcarbonyl, hetaryl$C_1$-$C_6$alkylcarbonyl, $C_1$-$C_6$alkylcarboxy, arylcarboxy, hetarylcarboxy, aryl$C_1$-$C_6$alkyl-carboxy, and hetaryl$C_1$-$C_6$alkylcarboxy;

$R^{17}$ is selected from H, $C_1$-$C_6$alkyl, 3-10 membered cycloalkyl, halo, OH, cyano, —$C(=O)R^{12}$, —$S(=O)_n$ $R^{12}$, $S(=O)_nNR^{14}R^{15}$, $-N(R^{14})S(=O)_nR^{12}$, aryl, and hetaryl, wherein the alkyl and cycloalkyl groups are substituted with 0-3 $R^{20}$;

$R^{20}$ is selected from H, OH, oxo, halo, cyano, nitro, $C_1$-$C_6$alkyl, $C_1$-$C_6$alkyloxy, $NR^{21}R^{22}$, methylendioxo, dihalomethylendioxo, trihalomethyl, and trihalomethyloxy;

$R^{21}$ and $R^{22}$ are independently selected from H, $C_1$-$C_6$alkyl, and aryl$C_1$-$C_6$alkyl;

$R^{16}$ is selected from H and $C_1$-$C_6$alkyl;

$Rn^1$ and $Rn^2$ are each independently selected from H, $C_1$-$C_6$alkyl, aryl$C_1$-$C_6$alkyl, hetaryl-$C_1$-$C_6$alkyl, $C_3$-$C_{12}$cycloalkyl, $C_3$-$C_{10}$hetcycloalkyl, wherein each alkyl, cycloalkyl, hetcycloalkyl, and aryl/hetaryl group is substituted with 0-3 $R^{18}$;

alternatively, $Rn^1$ and $Rn^2$, together with the nitrogen to which they are attached, form a 5-12 membered saturated or partially saturated monocyclic or bicyclic ring consisting of the shown nitrogen, 4-11 carbon atoms, and 0-2 additional heteroatoms selected from nitrogen, oxygen, and $S(O)_n$, wherein the ring is substituted with 0-3 groups selected from halo, trihalomethyl, trihalomethyloxy, cyano, $C_1$-$C_6$alkyl, $C_3$-$C_{10}$cycloalkyl, $-C(O)R^{12}$, $-S(O)_n R^{12}$, $-S(O)_nNR^{14}R^{16}$, $-N(R^{14})S(O)_nR^{12}$, OH, oxo, $C_1$-$C_6$alkyloxy, aryl$C_1$-$C_6$alkyloxy, hetaryl$C_1$-$C_6$alkyloxy, and $C_1$-$C_6$alkyloxy-$C_1$-$C_6$alkyl, wherein each alkyl, and aryl/hetaryl group is substituted with 0-3 $R^{18}$;

n is selected from 0, 1 and 2;

or a salt thereof with a pharmaceutically acceptable acid or base, or any optical isomer or mixture of optical isomers, including a racemic mixture, or any tautomeric forms.

In another embodiment, the present invention provides the use of a compound of formula I, wherein $R^1$, $R^2$, $R^3$, $R^4$, $R^5$, $R^6$, $R^7$ and $R^8$ are each independently selected from H, halo, $C_2$-$C_{10}$-alkenyl, $C_2$-$C_{10}$alkynyl, $NR^{10}R^{11}$, $C(O)R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cyclo-alkyloxy$C_1$-$C_6$alkyl, and $C_3$-$C_{10}$-hetcycloalkyloxy$C_1$-$C_6$alkyl, wherein each alkyl, cykloalkyl, hetcycloalkyl, and aryl/hetaryl group is substituted with 0-3 $R^{18}$;

with the proviso that when $R^1$, $R^2$, $R^3$, $R^4$, $R^5$, $R^6$, $R^7$ and $R^8$ each independently are aryl, hetaryl, aryl$C_1$-$C_6$alkyl, hetaryl$C_1$-$C_6$alkyl, aryl$C_1$-$C_6$alkyloxy, and hetaryl$C_1$-$C_6$alkyloxy then each group is substituted with 1-3 $R^{18}$;

or $R^1$, $R^2$, $R^3$, $R^6$, $R^7$ and $R^8$ are each independently selected from H, halo, $C_2$-$C_{10}$alkenyl, $C_2$-$C_{10}$alkynyl, $NR^{10}R^{11}$, $C(O)R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cyclo-alkyloxy$C_1$-$C_6$alkyl, and $C_3$-$C_{10}$-hetcycloalkyloxy$C_1$-$C_6$alkyl, wherein each alkyl, cykloalkyl, hetcycloalkyl, and aryl/hetaryl group is substituted with 0-3 $R^{18}$; and $R^4$ and $R^5$ together with the carbons to which they are attached form a 4-8 membered saturated, partially saturated or aromatic ring consisting of 2-8 carbon atoms, and 0-2 additional heteroatoms selected from nitrogen, oxygen, and $S(O)_n$, wherein this ring is substituted with 0-3 groups selected from fluoro, $C_1$-$C_6$alkyl, $C_3$-$C_{10}$-cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, $-C(O)R^{12}$, $-S(O)_nR^{12}$, $-S(O)_nNR^{14}R^{15}$, $-N(R^{14})S(O)_nR^{12}$, $-N(R^{16})C(=Y)NR^{14}R^{15}$, $-C(=NR^{17})NR^{17}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, and aryl/hetaryl group is substituted with 0-3 $R^{18}$;

$R^9$ is selected from H, halo, OH, cyano, $C_1$-$C_6$alkyl, $C_1$-$C_6$alkyloxy, trihalomethyloxy and $C_3$-$C_6$cycloalkyl;

$R^{10}$ and $R^{11}$ are each independently selected from H, $C_1$-$C_6$alkyl, $C(O)O$—$C_1$-$C_6$alkyl, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, wherein each alkyl, cykloalkyl, hetcycloalkyl, and aryl/hetaryl group is substituted with 0-3 $R^{18}$;

alternatively, $R^{10}$ and $R^{11}$, together with the nitrogen to which they are attached, form a 3-12 membered saturated or partially saturated monocyclic or bicyclic ring consisting of the shown nitrogen, 2-10 carbon atoms, and 0-2 additional heteroatoms selected from nitrogen, oxygen, and $S(O)_n$, wherein this ring is substituted with 0-3 groups selected from halo, $C_1$-$C_6$alkyl, $C_3$-$C_{10}$cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$-alkyl, hetaryl$C_1$-$C_6$alkyl, $-C(O)R^{12}$, $-S(O)_nR^{12}$, $-S(O)_nNR^{14}R^{15}$, $-N(R^{14})S(O)_nR^{12}$, $-N(R^{16})C(=Y)NR^{14}R^{15}$, $-C(=NR^{17})NR^{17}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, and aryl/hetaryl group is substituted with 0-3 $R^{18}$;

$R^{12}$ is OH, $NR^{10}R^{11}$, $C_1$-$C_6$alkyloxy, $C_2$-$C_6$alkenyloxy, $C_2$-$C_6$alkynyloxy, $C_3$-$C_{10}$cycloalkyl, $C_3$-$C_{10}$cycloalkyloxy, $C_3$-$C_{10}$hetcycloalkyloxy, aryloxy, hetaryloxy, aryl$C_1$-$C_6$alkyloxy, hetaryl$C_1$-$C_6$alkyloxy, $R^{13}$ is $C_1$-$C_6$alkyl, $C_2$-$C_6$alkenyl, $C_2$-$C_6$alkynyl, $NR^{10}R^{11}$, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, aryloxy$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$hetcycloalkyloxy$C_1$-$C_6$-alkyl, wherein each alkyl, cykloalkyl, hetcycloalkyl, and aryl/hetaryl group is substituted with 0-3 $R^{18}$;

$R^{18}$ is selected from halo, OH, oxo, COOH, $C(=O)OC_1$-$C_6$alkyl cyano, $C_1$-$C_6$alkyl, $C_1$-$C_6$alkyloxy, $C_3$-$C_{10}$cycloalkyloxy, aryloxy, hetaryloxy, hetarylthio, and aryl$C_1$-$C_6$alkyloxy;

$R^{14}$ and $R^{15}$ are independently selected from H, $C_1$-$C_6$alkyl, $C_1$-$C_6$alkyloxy, aryl, hetaryl, aryl$C_1$-$C_6$alkylene, and hetaryl$C_1$-$C_6$alkylene, wherein the alkyl/alkylene, aryl, and hetaryl groups are independently substituted with 0-3 $R^{20}$;

alternatively, $R^{14}$ and $R^{15}$, together with the nitrogen atom to which they are attached, form a saturated or partially saturated monocyclic, bicyclic, or tricyclic ring consisting of the shown nitrogen, 4-10 carbon atoms, and 0-2 additional heteroatoms selected from nitrogen, oxygen, and sulfur, wherein this ring is substituted with 0-3 $C_1$-$C_6$alkyl, aryl, hetaryl, aryl$C_1$-$C_6$alkylene, hetaryl$C_1$-$C_6$alkylene, hydroxy, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarbonyl, arylcarbonyl, hetarylcarbonyl, aryl$C_1$-$C_6$alkylcarbonyl, hetaryl$C_1$-$C_6$alkylcarbonyl, $C_1$-$C_6$alkylcarboxy, arylcarboxy, hetarylcarboxy, aryl$C_1$-$C_6$alkyl-carboxy, and hetaryl$C_1$-$C_6$alkylcarboxy;

$R^{17}$ is selected from H, $C_1$-$C_6$alkyl, 3-10 membered cycloalkyl, halo, OH, cyano, —C(=O)$R^{12}$, —S(=O)$_n$ $R^{12}$, S(=O)$_n$N$R^{14}R^{15}$, —N($R^{14}$)S(=O)$_n$$R^{12}$, aryl, and hetaryl, wherein the alkyl and cycloalkyl groups are substituted with 0-3 $R^{20}$;

$R^{20}$ is selected from H, OH, oxo, halo, cyano, nitro, $C_1$-$C_6$alkyl, $C_1$-$C_6$alkyloxy, N$R^{21}R^{22}$, methylendioxo, dihalomethylendioxo, trihalomethyl, and trihalomethyloxy;

$R^{21}$ and $R^{22}$ are independently selected from H, $C_1$-$C_6$alkyl, and aryl$C_1$-$C_6$alkyl;

$R^{16}$ is selected from H and $C_1$-$C_6$alkyl;

$Rn^1$ and $Rn^2$ are each independently selected from H, $C_1$-$C_6$alkyl, aryl$C_1$-$C_6$alkyl, hetaryl-$C_1$-$C_6$alkyl, $C_3$-$C_{12}$cycloalkyl, $C_3$-$C_{10}$hetcycloalkyl, wherein each alkyl, cycloalkyl, hetcycloalkyl, and aryl/hetaryl group is substituted with 0-3 $R^{18}$;

alternatively, $Rn^1$ and $Rn^2$, together with the nitrogen to which they are attached, form a 5-12 membered saturated or partially saturated monocyclic or bicyclic ring consisting of the shown nitrogen, 4-11 carbon atoms, and 0-2 additional heteroatoms selected from nitrogen, oxygen, and S(O)$_n$, wherein the ring is substituted with 0-3 groups selected from halo, trihalomethyl, trihalomethyloxy, cyano, $C_1$-$C_6$alkyl, $C_3$-$C_{10}$cycloalkyl, —C(O)$R^{12}$, —S(O)$_n$ $R^{12}$, —S(O)$_n$N$R^{14}R^{16}$, —N($R^{14}$)S(O)$_n$$R^{12}$, OH, oxo, $C_1$-$C_6$alkyloxy, aryl$C_1$-$C_6$alkyloxy, hetaryl$C_1$-$C_6$alkyloxy, and $C_1$-$C_6$alkyloxy-$C_1$-$C_6$alkyl, wherein each alkyl, and aryl/hetaryl group is substituted with 0-3 $R^{18}$;

n is selected from 0, 1 and 2;

or a salt thereof with a pharmaceutically acceptable acid or base, or any optical isomer or mixture of optical isomers, including a racemic mixture, or any tautomeric forms.

In another embodiment, the present invention provides the use of a compound of formula I wherein:

$R^1$, $R^2$, $R^3$, $R^4$, $R^5$, $R^6$, $R^7$ and $R^8$ are each independently selected from H, halo, N$R^{10}R^{11}$, C(O)$R^{12}$, $R^{13}$S(O)$_n$, $R^{13}$C(O)N$R^{10}$, $R^{10}R^{11}$NS(O)$_n$, $R^{13}$S(O)$_n$N$R^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cyclo-alkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$;

$R^9$ is selected from H, halo, OH, cyano, $C_1$-$C_6$alkyl, $C_1$-$C_6$alkyloxy, and $C_3$-$C_6$cycloalkyl;

$R^{10}$ and $R^{11}$ are each independently selected from H, $C_1$-$C_6$alkyl, C(O)O—$C_1$-$C_6$alkyl, aryl, hetaryl, aryl-$C_1$-$C_6$alkyl, hetaryl$C_1$-$C_6$alkyl, $C_3$-$C_{10}$cycloalkyl, $C_3$-$C_{10}$hetcycloalkyl, wherein each alkyl, cykloalkyl, hetcycloalkyl, and aryl/hetaryl group is substituted with 0-3 $R^{18}$;

alternatively, $R^{10}$ and $R^{11}$, together with the nitrogen to which they are attached, form a 5-12 membered saturated or partially saturated monocyclic or bicyclic ring consisting of the shown nitrogen, 2-10 carbon atoms, and 0-2 additional heteroatoms selected from nitrogen and oxygen, wherein this ring is substituted with 0-3 groups selected from halo, $C_1$-$C_6$alkyl, $C_3$-$C_{10}$cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, —C(O)$R^{12}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$-alkylcarboxy, arylcarboxy, hetarylcarboxy, aryl$C_1$-$C_6$alkylcarboxy, and hetaryl$C_1$-$C_6$-alkylcarboxy, $R^{12}$ is OH, N$R^{10}R^{11}$, $C_1$-$C_6$alkyloxy, $C_3$-$C_{10}$cycloalkyl, $C_3$-$C_{10}$cycloalkyloxy, $C_3$-$C_{10}$hetcycloalkyloxy, aryloxy, hetaryloxy, aryl$C_1$-$C_6$alkyloxy, hetaryl$C_1$-$C_6$alkyloxy, $R^{13}$ is $C_1$-$C_6$alkyl, N$R^{10}R^{11}$, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, aryloxy$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$;

$R^{18}$ is selected from halo, OH, COOH, C(=O)O$C_1$-$C_6$alkyl, cyano, $C_1$-$C_6$alkyl, $C_1$-$C_6$alkyloxy, $C_3$-$C_{10}$cycloalkyloxy, aryloxy and hetaryloxy;

one of $Rn^1$ and $Rn^2$ is H and the other one of $Rn^1$ and $Rn^2$ are selected from $C_1$-$C_6$alkyl, aryl$C_1$-$C_6$alkyl, hetaryl$C_1$-$C_6$alkyl, $C_6$-$C_{12}$cycloalkyl, $C_3$-$C_{10}$hetcycloalkyl, wherein each alkyl, cykloalkyl, hetcycloalkyl, and aryl/hetaryl group is substituted with 0-3 $R^{18}$;

alternatively, $Rn^1$ and $Rn^2$, together with the nitrogen to which they are attached, form a 6-12 membered saturated or partially saturated monocyclic or bicyclic ring consisting of the shown nitrogen, 4-11 carbon atoms, and 0-2 additional heteroatoms selected from nitrogen and oxygen wherein the ring is substituted with 0-3 groups selected from halo, trihalomethyl, $C_1$-$C_6$alkyl, $C_3$-$C_{10}$cycloalkyl, —C(O)$R^{12}$, OH, $C_1$-$C_6$alkyloxy, aryl$C_1$-$C_6$alkyloxy, and hetaryl$C_1$-$C_6$alkyloxy, and n is 2.

In another embodiment, the present invention provides the use of a compound of formula I wherein:

$R^1$, $R^2$, $R^3$, $R^4$, $R^5$, $R^6$, $R^7$ and $R^8$ are each independently selected from H, halo, N$R^{10}R^{11}$, C(O)$R^{12}$, $R^{13}$S(O)$_n$, $R^{13}$C(O)N$R^{10}$, $R^{10}R^{11}$NS(O)$_n$, $R^{13}$S(O)$_n$N$R^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cyclo-alkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$;

with the proviso that when $R^1$, $R^2$, $R^3$, $R^4$, $R^5$, $R^6$, $R^7$ and $R^8$ each independently are aryl, hetaryl, aryl$C_1$-$C_6$alkyl, hetaryl$C_1$-$C_6$alkyl, aryl$C_1$-$C_6$alkyloxy, and hetaryl$C_1$-$C_6$alkyloxy then each group is substituted with 1-3 $R^{18}$;

$R^9$ is selected from H, halo, OH, cyano, $C_1$-$C_6$alkyl, $C_1$-$C_6$alkyloxy, and $C_3$-$C_6$cycloalkyl;

$R^{10}$ and $R^{11}$ are each independently selected from H, $C_1$-$C_6$alkyl, C(O)O—$C_1$-$C_6$alkyl, aryl, hetaryl, aryl-$C_1$-$C_6$alkyl, hetaryl$C_1$-$C_6$alkyl, $C_3$-$C_{10}$cycloalkyl, $C_3$-$C_{10}$hetcycloalkyl, wherein each alkyl, cykloalkyl, hetcycloalkyl, and aryl/hetaryl group is substituted with 0-3 $R^{18}$;

alternatively, $R^{10}$ and $R^{11}$, together with the nitrogen to which they are attached, form a 5-12 membered saturated or partially saturated monocyclic or bicyclic ring consisting of the shown nitrogen, 2-10 carbon atoms, and 0-2 additional heteroatoms selected from nitrogen and oxygen, wherein this ring is substituted with 0-3 groups selected from halo, $C_1$-$C_6$alkyl, $C_3$-$C_{10}$cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, —C(O)$R^{12}$, OH, oxo, $C_1$-$C_6$alkyloxy, aryl$C_1$-$C_6$alkyloxy, hetaryl$C_1$-

$C_6$alkyloxy, $C_1$-$C_6$alkyloxy$C_1$-$C_6$alkyl, $C_1$-$C_6$-alkylcarboxy, arylcarboxy, hetarylcarboxy, aryl$C_1$-$C_6$alkylcarboxy, and hetaryl$C_1$-$C_6$-alkylcarboxy, $R^{12}$ is OH, $NR^{10}R^{11}$, $C_1$-$C_6$alkyloxy, $C_3$-$C_{10}$cycloalkyl, $C_3$-$C_{10}$cycloalkyloxy, $C_3$-$C_{10}$hetcycloalkyloxy, aryloxy, hetaryloxy, aryl$C_1$-$C_6$alkyloxy, hetaryl$C_1$-$C_6$alkyloxy, $R^{13}$ is $C_1$-$C_6$alkyl, $NR^{10}R^{11}$, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, aryloxy$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$;

$R^{18}$ is selected from halo, OH, COOH, C(=O)O$C_1$-$C_6$alkyl, cyano, $C_1$-$C_6$alkyl, $C_1$-$C_6$alkyloxy, $C_3$-$C_{10}$cycloalkyloxy, aryloxy and hetaryloxy;

one of $Rn^1$ and $Rn^2$ is H and the other one of $Rn^1$ and $Rn^2$ are selected from $C_1$-$C_6$alkyl, aryl$C_1$-$C_6$alkyl, hetaryl$C_1$-$C_6$alkyl, $C_6$-$C_{12}$cycloalkyl, $C_3$-$C_{10}$hetcycloalkyl, wherein each alkyl, cykloalkyl, hetcycloalkyl, and aryl/hetaryl group is substituted with 0-3 $R^{18}$;

alternatively, $Rn^1$ and $Rn^2$, together with the nitrogen to which they are attached, form a 6-12 membered saturated or partially saturated monocyclic or bicyclic ring consisting of the shown nitrogen, 4-11 carbon atoms, and 0-2 additional heteroatoms selected from nitrogen and oxygen wherein the ring is substituted with 0-3 groups selected from halo, trihalomethyl, $C_1$-$C_6$alkyl, $C_3$-$C_{10}$cycloalkyl, —C(O)$R^{12}$, OH, $C_1$-$C_6$alkyloxy, aryl$C_1$-$C_6$alkyloxy, and hetaryl$C_1$-$C_6$alkyloxy, and n is 2.

In another embodiment, the present invention provides the use of a compound of formula I, wherein:

$R^2$, $R^3$, $R^4$, $R^6$, $R^7$ and $R^8$ are each independently selected from H, halo, $C_2$-$C_{10}$alkenyl, $C_2$-$C_{10}$alkynyl, $NR^{10}R^{11}$, C(O)$R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cyclo-alkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$; and $R^1$ and $R^5$ together with the carbons to which they are attached form a 4-8 membered saturated, partially saturated or aromatic ring consisting of 2-8 carbon atoms, and 0-2 additional heteroatoms selected from nitrogen, oxygen, and $S(O)_n$, wherein this ring is substituted with 0-3 groups selected from fluoro, $C_1$-$C_6$alkyl, $C_3$-$C_{10}$cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, —C(O)$R^{12}$, —S(O)$_n R^{12}$, —S(O)$_n NR^{14}R^{15}$, —N($R^{14}$)S(O)$_n R^{12}$, —N($R^{16}$)C(=Y)$NR^{14}R^{15}$, —C(=$NR^{17}$)$NR^{17}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarboxy, arylcarboxy, hetaryl-carboxy, aryl$C_1$-$C_6$alkylcarboxy, and hetaryl$C_1$-$C_6$alkylcarboxy, wherein each alkyl, and aryl/hetaryl group is substituted with 0-3 $R^{18}$.

In another embodiment, the present invention provides the use of a compound of formula I, wherein $R^2$, $R^3$, $R^4$, $R^5$, $R^6$ and $R^8$ are each independently selected from H, halo, $C_2$-$C_{10}$alkenyl, $C_2$-$C_{10}$alkynyl, $NR^{10}R^{11}$, C(O)$R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cyclo-alkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$; and $R^1$ and $R^7$ together with the carbons to which they are attached form a 4-8 membered saturated, partially saturated or aromatic ring consisting of 2-8 carbon atoms, and 0-2 additional heteroatoms selected from nitrogen, oxygen, and $S(O)_n$, wherein this ring is substituted with 0-3 groups selected from fluoro, $C_1$-$C_6$alkyl, $C_3$-$C_{10}$cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, —C(O)$R^{12}$, —S(O)$_n R^{12}$, —S(O)$_n NR^{14}R^{15}$, —N($R^{14}$)S(O)$_n R^{12}$, —N($R^{16}$)C(=Y)$NR^{14}R^{15}$, —C(=$NR^{17}$)$NR^{17}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarboxy, arylcarboxy, hetaryl-carboxy, aryl$C_1$-$C_6$alkylcarboxy, and hetaryl$C_1$-$C_6$alkylcarboxy, wherein each alkyl, and aryl/hetaryl group is substituted with 0-3 $R^{18}$.

In another embodiment, the present invention provides the use of a compound of formula I, wherein $R^3$, $R^4$, $R^5$, $R^6$, are each independently selected from halo, $NR^{10}R^{11}$, C(O)$R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cyclo-alkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$; and $R^1$, $R^2$, $R^7$, and $R^8$ are H.

In another embodiment, the present invention provides the use of a compound of formula I, wherein $R^3$, $R^4$, $R^5$, $R^6$, are each independently selected from $NR^{10}R^{11}$, C(O)$R^{12}$, $R^{13}S(O)_n$, $R^{13}C(O)NR^{10}$, $R^{13}S(O)_nNR^{10}$, aryl, hetaryl, aryloxy, hetaryloxy, hetaryl$C_1$-$C_6$alkyl, wherein each aryl/hetaryl group is substituted with 0-3 $R^{18}$.

In another embodiment, the present invention provides the use of a compound of formula I, wherein $R^4$ and $R^5$ together with the carbons to which they are attached form a 4-8 membered saturated, partially saturated or aromatic ring consisting of 2-8 carbon atoms, and 0-2 additional heteroatoms selected from nitrogen, oxygen, and $S(O)_n$.

In another embodiment, the present invention provides the use of a compound of formula I, wherein $R^9$ is selected from H, halo, OH, cyano and $C_1$-$C_6$alkyl.

In another embodiment, the present invention provides the use of a compound of formula I, wherein $R^9$ is selected from H, OH, and $C_1$-$C_6$alkyl.

In another embodiment, the present invention provides the use of a compound of formula I, wherein $R^9$ is H.

In another embodiment, the present invention provides the use of a compound of formula I, wherein $R^{10}$ and $R^{11}$ are each independently selected from H, $C_1$-$C_6$alkyl, aryl, hetaryl, $C_3$-$C_{10}$cycloalkyl, $C_3$-$C_{10}$hetcycloalkyl, wherein each alkyl, cykloalkyl and hetcycloalkyl group is substituted with 0-3 $R^{18}$.

In another embodiment, the present invention provides the use of a compound of formula I, wherein $R^{10}$ and $R^{11}$ are each independently selected from H, $C_1$-$C_6$alkyl, $C_3$-$C_{10}$cycloalkyl, $C_3$-$C_{10}$hetcycloalkyl, wherein each alkyl, cykloalkyl and hetcycloalkyl group is substituted with 0-3 $R^{18}$.

In another embodiment, the present invention provides the use of a compound of formula I, wherein $R^{10}$ and $R^{11}$, together with the nitrogen to which they are attached, form a 5-12 membered saturated or partially saturated monocyclic or bicyclic ring consisting of the shown nitrogen, 2-10 carbon atoms, and 0-2 additional heteroatoms selected from nitrogen and oxygen, wherein this ring is substituted with 0-3 groups selected from halo, $C_1$-$C_6$alkyl, —C(O)$R^{12}$, OH, oxo, $C_1$-$C_6$alkyloxy, $C_1$-$C_6$alkyloxy$C_1$-$C_6$alkyl and $C_1$-$C_6$alkyl-carboxy.

In another embodiment, the present invention provides the use of a compound of formula I, wherein $R^{10}$ and $R^{11}$, together with the nitrogen to which they are attached, form a 6-12 membered saturated or partially saturated monocyclic or bicyclic ring consisting of the shown nitrogen, 2-10 carbon atoms, and 0-1 additional heteroatoms selected from oxygen, wherein this ring is substituted with 0-3 groups selected from OH and $C_1$-$C_6$alkyloxy.

In another embodiment, the present invention provides the use of a compound of formula I, wherein $R^{12}$ is OH, $NR^{10}R^{11}$, $C_1$-$C_6$alkyloxy, $C_3$-$C_{10}$cycloalkyloxy, $C_3$-$C_{10}$hetcycloalkyloxy, aryloxy and hetaryloxy.

In another embodiment, the present invention provides the use of a compound of formula I, wherein $R^{12}$ is OH, $NR^{10}R^{11}$, and $C_1$-$C_6$alkyloxy, In another embodiment, the present invention provides the use of a compound of formula I, wherein $R^{13}$ is $C_1$-$C_6$alkyl, $NR^{10}R^{11}$, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, wherein each alkyl, cykloalkyl, hetcycloalkyl, and aryl/hetaryl group is substituted with 0-3 $R^{18}$.

In another embodiment, the present invention provides the use of a compound of formula I, wherein $R^{13}$ is $C_1$-$C_6$alkyl, $NR^{10}R^{11}$, aryl, hetaryl, hetaryl$C_1$-$C_6$alkyl, $C_3$-$C_{10}$cycloalkyl, wherein each alkyl, and aryl/hetaryl group is substituted with 0-3 $R^{18}$.

In another embodiment, the present invention provides the use of a compound of formula I, wherein $R^{18}$ is selected from halo, OH, COOH, C(=O)O$C_1$-$C_6$alkyl, cyano, $C_1$-$C_6$alkyl, $C_1$-$C_6$alkyloxy, $C_3$-$C_{10}$cycloalkyloxy, aryloxy and hetaryloxy.

In another embodiment, the present invention provides the use of a compound of formula I, wherein $R^{18}$ is selected from halo, OH, COOH, C(=O)O$C_1$-$C_6$alkyl, cyano, and $C_1$-$C_6$alkyl.

In another embodiment, the present invention provides the use of a compound of formula I, wherein n is 2.

In another embodiment, the present invention provides the use of a compound of formula I, wherein one of $Rn^1$ and $Rn^2$ is H and the other one of $Rn^1$ and $Rn^2$ are selected from $C_1$-$C_6$alkyl, aryl$C_1$-$C_6$alkyl, hetaryl$C_1$-$C_6$alkyl, $C_6$-$C_{12}$cycloalkyl, $C_3$-$C_{10}$hetcycloalkyl, wherein each alkyl, cykloalkyl, hetcycloalkyl, and aryl/hetaryl group is substituted with 0-3 $R^{18}$;

In another embodiment, the present invention provides the use of a compound of formula I, wherein one of $Rn^1$ and $Rn^2$ is H, and the other one of $Rn^1$ and $Rn^2$ is $C_6$-$C_{12}$-cycloalkyl, substituted with 0-3 $R^{18}$.

In another embodiment, the present invention provides the use of a compound of formula I, wherein $Rn^1$ and $Rn^2$, together with the nitrogen to which they are attached, form a 6-12 membered saturated or partially saturated monocyclic or bicyclic ring consisting of the shown nitrogen, 4-11 carbon atoms, and 0-2 additional heteroatoms selected from nitrogen and oxygen wherein the ring is substituted with 0-3 groups selected from halo, trihalomethyl, trihalomethyloxy, $C_1$-$C_6$alkyl, $C_3$-$C_{10}$cycloalkyl, —C(O)$R^{12}$, —S(O)$_n R^{12}$, oxo, $C_1$-$C_6$alkyloxy, aryl$C_1$-$C_6$alkyloxy, hetaryl$C_1$-$C_6$alkyloxy, and $C_1$-$C_6$alkyloxy$C_1$-$C_6$alkyl, wherein each alkyl, and aryl/hetaryl group is substituted with 0-3 $R^{18}$.

In another embodiment, the present invention provides the use of a compound of formula I, wherein the ring formed by $Rn^1$ and $Rn^2$, together with the nitrogen to which they are attached is selected from:

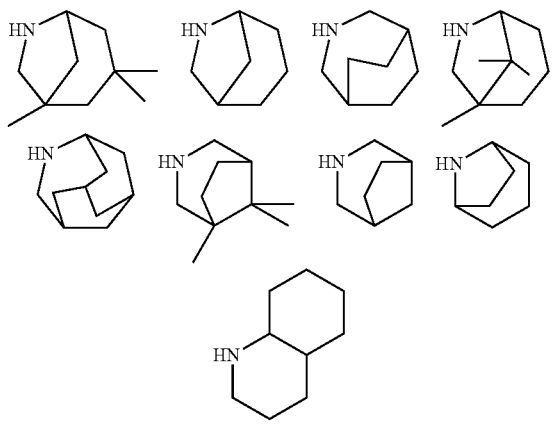

being substituted with 0-2 $R^{25}$; and $R^{25}$ is selected from $C_1$-$C_6$alkyl, halo, hydroxy, oxo, cyano, and $C_1$-$C_6$alkyloxy.

In another embodiment, the present invention provides the use of a compound of formula I, wherein the ring formed by $Rn^1$ and $Rn^2$, together with the nitrogen to which they are attached is selected from:

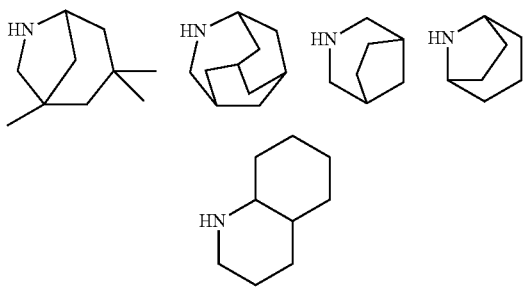

being substituted with 0-2 $R^{25}$; and $R^{25}$ is selected from $C_1$-$C_6$alkyl, halo, hydroxy, oxo, cyano, and $C_1$-$C_6$alkyloxy.

In another embodiment, the present invention provides the use of a compound of formula I, wherein $Rn^1$ is hydrogen and N—$Rn^2$ is selected from:

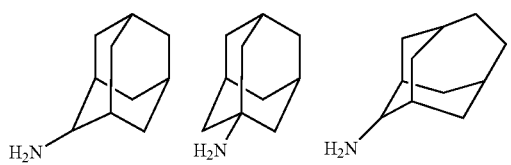

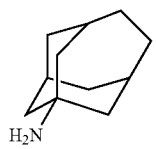

being substituted with 0-2 $R^{25}$; and
$R^{25}$ is selected from $C_1$-$C_6$alkyl, halo, hydroxy, oxo, cyano, and $C_1$-$C_6$alkyloxy.

In another embodiment, the present invention provides the use of a compound of formula Ia:

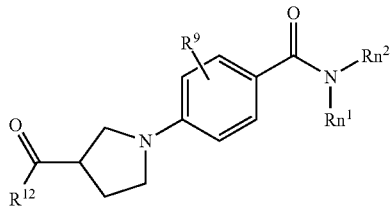

Ia wherein $R^{12}$, $R^9$, $Rn^1$, and $Rn^2$ are as defined above.

In another embodiment, the present invention provides the use of a compound of formula Ib:

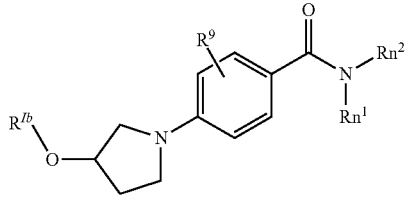

Ib wherein $R^{Ib}$ is hetaryl or aryl$C_1$-$C_6$alkyl and $R^9$, $Rn^1$, and $Rn^2$ are as defined above.

In another embodiment, the present invention provides the use of a compound of formula Ic:

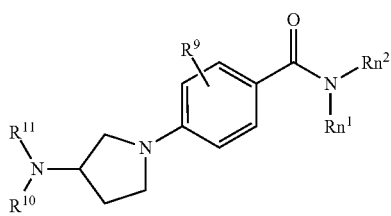

Ic wherein $R^{10}$, $R^{11}$, $R^9$, $Rn^1$, and $Rn^2$ are as defined above.

In another embodiment, the present invention provides the use of a compound of formula Id:

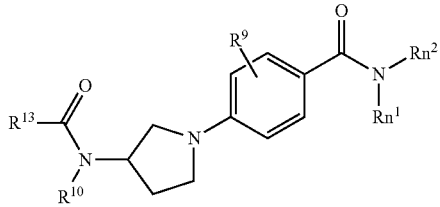

Id wherein $R^{10}$, $R^{13}$, $R^9$, $Rn^1$, and $Rn^2$ are as defined above.

In another embodiment, the present invention provides the use of a compound of formula Ie:

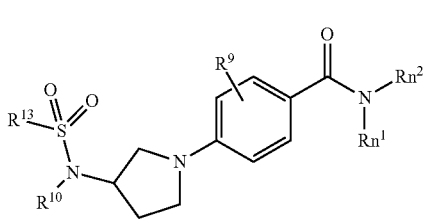

Ie wherein $R^{10}$, $R^{13}$, $R^9$, $Rn^1$, and $Rn^2$ are as defined above.

In another embodiment, the present invention provides the use of a compound of formula If:

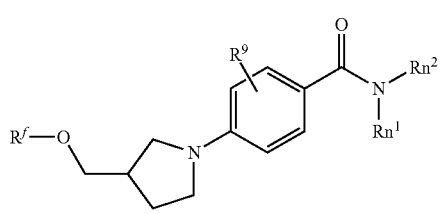

If wherein $R^f$ is hetaryl optionally substituted with $R^{18}$; and $R^9$, $Rn^1$, and $Rn^2$ are as defined above.

In another embodiment, the present invention provides the use of a compound of formula Ig:

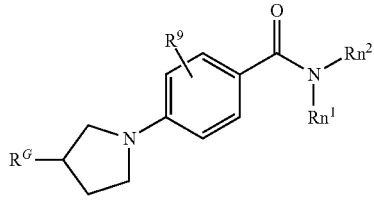

Ig wherein $R^G$ is aryl optionally substituted with $R^{18}$; and $R^9$, $Rn^1$, and $Rn^2$ are as defined above.

In another embodiment, the present invention provides the use of a compound of formula Ih:

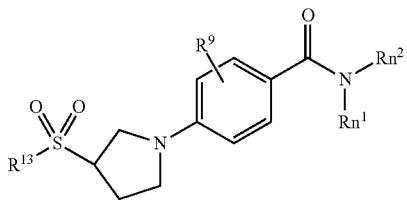

wherein $R^{13}$, $R^9$, $Rn^1$, and $Rn^2$ are as defined above.

In another embodiment, the present invention provides the use of a compound of formula Ij:

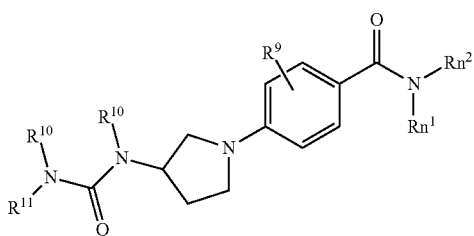

wherein $R^9$, $R^{10}$, $R^{11}$, $Rn^1$ and $Rn^2$ are as defined above.

In another embodiment, the present invention provides the use of a compound of formula Ik:

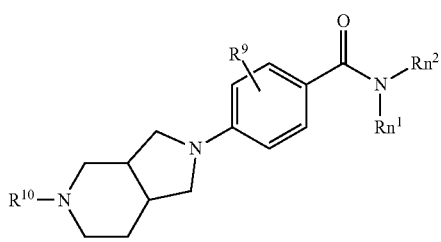

wherein $R^9$, $R^{10}$, $Rn^1$ and $Rn^2$ are as defined above.

In another embodiment, the present invention provides the use of a compound of formula Il:

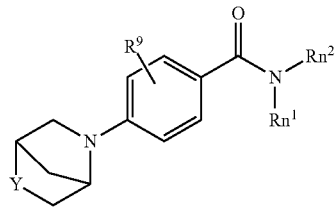

wherein $R^9$, $Rn^1$ and $Rn^2$ are as defined above and Y is oxygen, $S(O)_n$ or $NR^{10}$.

In another embodiment, the present invention provides the use of a compound of formula Ij: Il'

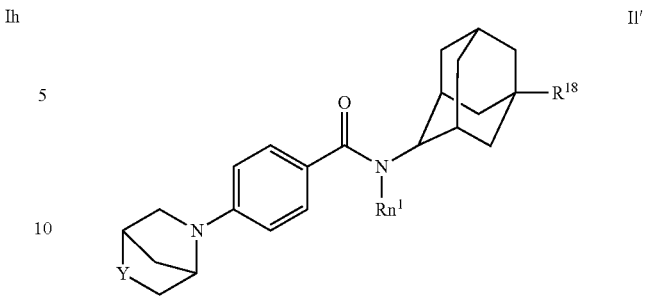

wherein $Rn^1$ and $R^{18}$ are as defined above and Y is oxygen, $S(O)_n$ or $NR^{10}$.

In another embodiment, the present invention provides the use of a compound of formula I, which is selected from the group:

1-[4-(1,3,3-Trimethyl-6-aza-bicyclo[3.2.1]octane-6-carbonyl)-phenyl]-pyrrolidine-3-carboxylic acid methyl ester;
1-[4-(1,3,3-Trimethyl-6-aza-bicyclo[3.2.1]octane-6-carbonyl)-phenyl]-pyrrolidine-3-carboxylic acid;
{4-[3-(Morpholine-4-carbonyl)-pyrrolidin-1-yl]-phenyl}-(1,3,3-trimethyl-6-aza-bicyclo-3.2.1]oct-6-yl)-methanone;
1-[4-(1,3,3-Trimethyl-6-aza-bicyclo[3.2.1]octane-6-carbonyl)-phenyl]-pyrrolidine-3-carboxylic acid (3-hydroxy-adamantan-1-yl)-amide;
(Methyl-{1-[4-(1,3,3-trimethyl-6-aza-bicyclo[3.2.1]octane-6-carbonyl)-phenyl]-pyrrolidine-3-carbonyl}-amino)-acetic acid tert-butyl ester;
(Methyl-{1-[4-(1,3,3-trimethyl-6-aza-bicyclo[3.2.1]octane-6-carbonyl)-phenyl]-pyrrolidine-3-carbonyl}-amino)-acetic acid;
1-[4-(1,3,3-Trimethyl-6-aza-bicyclo[3.2.1]octane-6-carbonyl)-phenyl]-pyrrolidine-3-carboxylic acid (4-hydroxy-cyclohexyl)-amide;
{4-[3-(4-Hydroxy-piperidine-1-carbonyl)-pyrrolidin-1-yl]-phenyl}-(1,3,3-trimethyl-6-aza-bicyclo[3.2.1]oct-6-yl)-methanone;
{4-[3-(4-Hydroxymethyl-piperidine-1-carbonyl)-pyrrolidin-1-yl]-phenyl}-(1,3,3-trimethyl-6-aza-bicyclo[3.2.1]oct-6-yl)-methanone;
1-[4-(Octahydroquinoline-1-carbonyl)phenyl]-pyrrolidine-3-carboxylic acid;
{4-[3-(Morpholine-4-carbonyl)-pyrrolidin-1-yl]-phenyl}(octahydroquinolin-1-yl)methanone;
{4-[3-(4-Hydroxymethyl-piperidine-1-carbonyl)-pyrrolidin-1-yl]-phenyl}-(octahydroquinolin-1-yl)methanone;
1-[4-(Adamantan-1-ylcarbamoyl)-phenyl]-pyrrolidine-3-carboxylic acid;
{4-[3-(4-Hydroxy-piperidine-1-carbonyl)-pyrrolidin-1-yl]-phenyl}-octahydro-quinolin-1-yl)-methanone;
1-[4-(Octahydro-quinoline-1-carbonyl)-phenyl]-pyrrolidine-3-carboxylic acid (tetrahydropyran-4-yl)-amide;
(Octahydro-quinolin-1-yl)-{4-[3-(2-oxa-5-aza-bicyclo[2.2.1]heptane-5-carbonyl)-pyrrolidin-1-yl]-phenyl}-methanone;
4-(3-Acetylamino-pyrrolidin-1-yl)-N-adamantan-2-yl-benzamide;
N-{1-[4-(Octahydro-quinoline-1-carbonyl)-phenyl]-pyrrolidin-3-yl}-acetamide;
N-{1-[4-(3-Aza-bicyclo[3.2.2]nonane-3-carbonyl)-phenyl]-pyrrolidin-3-yl}-acetamide;
{1-[4-(3-Aza-bicyclo[3.2.2]nonane-3-carbonyl)-phenyl]-pyrrolidin-3-yl}-methyl-carbamic acid tert-butyl ester;

(3-Aza-bicyclo[3.2.2]non-3-yl)-[4-(3-methylamino-pyrrolidin-1-yl)-phenyl]-methanone;
N-{1-[4-(3-Aza-bicyclo[3.2.2]nonane-3-carbonyl)-phenyl]-pyrrolidin-3-yl}-N-methyl-acetamide;
Cyclopropanecarboxylic acid {1-[4-(3-aza-bicyclo[3.2.2]nonane-3-carbonyl)-phenyl]-pyrrolidin-3-yl}-methyl-amide;
5-Methyl-isoxazole-3-carboxylic acid {1-[4-(3-aza-bicyclo[3.2.2]nonane-3-carbonyl)-phenyl]-pyrrolidin-3-yl}-methyl-amide;
N-{1-[4-(3-Aza-bicyclo[3.2.2]nonane-3-carbonyl)-phenyl]-pyrrolidin-3-yl}-N-methyl-phenyl-methanesulfonamide;
N-{1-[4-(3-Aza-bicyclo[3.2.2]nonane-3-carbonyl)-phenyl]-pyrrolidin-3-yl}-4-chloro-N-methyl-benzenesulfonamide;
Pyridine-2-carboxylic acid {1-[4-(3-aza-bicyclo[3.2.2]nonane-3-carbonyl)-phenyl]-pyrrolidin-3-yl}-methyl-amide;
1-{1-[4-(3-Aza-bicyclo[3.2.2]nonane-3-carbonyl)-phenyl]-pyrrolidin-3-yl}-3-cyclohexyl-1-methyl-urea;
(3-Aza-bicyclo[3.2.2]non-3-yl)-{4-[3-(pyridin-2-yloxy)-pyrrolidin-1-yl]-phenyl}-methanone;
4-(2-Oxa-5-aza-bicyclo[2.2.1]hept-5-yl)-N-adamantan-2-yl-benzamide;
4-[3-(4-Chloro-phenyl)-pyrrolidin-1-yl]-N-adamantan-2-yl-benzamide;
4-[3-(Pyridin-2-yloxymethyl)-pyrrolidin-1-yl]-N-adamantan-2-yl-benzamide;
(3-Aza-bicyclo[3.2.2]non-3-yl)-{4-[3-(pyridin-2-yloxymethyl)-pyrrolidin-1-yl]-phenyl}-methanone;
4-(3-Methanesulfonyl-pyrrolidin-1-yl)-N-adamantan-2-yl-benzamide;
(3-Aza-bicyclo[3.2.2]non-3-yl)-[4-(3-morpholin-4-yl-pyrrolidin-1-yl)-phenyl]-methanone;
[4-(3-Morpholin-4-yl-pyrrolidin-1-yl)-phenyl]-(1,3,3-trimethyl-6-aza-bicyclo[3.2.1]oct-6-yl)-methanone;
(3-Aza-bicyclo[3.2.2]non-3-yl)-{4-[3-(6-methyl-pyridin-3-yloxymethyl)-pyrrolidin-1-yl]-phenyl}methanone;
(3-Aza-bicyclo[3.2.2]non-3-yl)-[4-((R)-3-benzyloxy-pyrrolidin-1-yl)-phenyl]-methanone;
N-{(R)-1-[4-(3-Aza-bicyclo[3.2.2]nonane-3-carbonyl)-phenyl]-pyrrolidin-3-yl}-acetamide;
1-{(R)-1-[4-(3-Aza-bicyclo[3.2.2]nonane-3-carbonyl)-phenyl]-pyrrolidin-3-yl}-3-isopropyl-urea;
1-{(R)-1-[4-(3-Aza-bicyclo[3.2.2]nonane-3-carbonyl)-phenyl]-pyrrolidin-3-yl}-3-N,N-dimethyl-sulfamide;
4-[(R)-3-(3-Isopropyl-ureido)-pyrrolidin-1-yl]-N-adamantan-2-yl-benzamide;
Morpholine-4-carboxylic acid {(R)-1-[4-(3-aza-bicyclo[3.2.2]nonane-3-carbonyl)-phenyl]-pyrrolidin-3-yl}-amide;
Morpholine-4-carboxylic acid {(R)-1-[4-(adamantan-2-yl-carbamoyl)-phenyl]-pyrrolidin-3-yl}-amide;
1-{(R)-[4-(adamantan-2-yl-phenyl)-pyrrolidin-3-yl}-3-N,N-dimethyl-sulfamide;
6-Chloro-N-{(R)-1-[4-(octahydro-quinoline-1-carbonyl)-phenyl]-pyrrolidin-3-yl}-nicotin-amide;
1,1-Dimethyl-3-{(R)-1-[4-(octahydro-quinoline-1-carbonyl)-phenyl]-pyrrolidin-3-yl}-urea;
or a salt thereof with a pharmaceutically acceptable acid or base, or any optical isomer or mixture of optical isomers, including a racemic mixture, or any tautomeric forms.

In another embodiment, the present invention provides the use of a compound of formula I, which is selected from the group:
N-{1-[4-(1,3,3-Trimethyl-6-aza-bicyclo[3.2.1]octane-6-carbonyl)-phenyl]-pyrrolidin-3-yl}-acetamide;
N-{1-[4-(8-Hydroxy-3-aza-bicyclo[3.2.1]octane-3-carbonyl)-phenyl]-pyrrolidin-3-yl}-acetamide;
4-(3-Acetylamino-pyrrolidin-1-yl)-N-(3-hydroxymethyl-adamantan-1-yl)-benzamide;
4-(3-Acetylamino-pyrrolidin-1-yl)-N-(5-hydroxy-adamantan-2-yl)-benzamide;
4-(3-Acetylamino-pyrrolidin-1-yl)-N-(5-hydroxy-adamantan-2-yl)-N-methyl-benzamide;
5-[4-(3-Aza-bicyclo[3.2.2]-nonane-3-carbonyl)-phenyl]-2,5-diaza-bicyclo[2.2.1]-heptane-2-carboxylic acid tert-butyl ester;
N-Adamantan-2-yl-4-((R)-3-benzyloxy-pyrrolidin-1-yl)-benzamide;
[4-((R)-3-Benzyloxy-pyrrolidin-1-yl)-phenyl]-(octahydro-quinolin-1-yl)-methanone;
4-((R)-3-Benzyloxy-pyrrolidin-1-yl)-N-(1-hydroxy-adamantan-2-yl)-benzamide;
4-((S)-3-Acetylamino-pyrrolidin-1-yl)-N-adamantan-2-yl-benzamide;
4-(3-Acetylamino-pyrrolidin-1-yl)-N-(3-hydroxy-adamantan-1-yl)-benzamide;
N-{(S)-1-[4-(Adamantan-2-ylcarbamoyl)-phenyl]-pyrrolidin-3-yl}-6-chloro-nicotin-amide;
1-Isopropyl-3-{(S)-1-[4-(octahydro-quinoline-1-carbonyl)-phenyl]-pyrrolidin-3-yl}-urea;
(Octahydro-quinolin-1-yl)-{4-[(1S,5R)-3-(pyridin-2-yloxy)-8-aza-bicyclo[3.2.1]oct-8-yl]-phenyl}-methanone;
N-Adamantan-2-yl-4-[(1S,5R)-3-(pyridin-2-yloxy)-8-aza-bicyclo[3.2.1]oct-8-yl]-benzamide;
2-[4-(Adamantan-2-yl-carbamoyl)-phenyl]-octahydro-pyrrolo[3,4-c]pyridine-5-carboxylic acid isopropylamide;
or a salt thereof with a pharmaceutically acceptable acid or base, or any optical isomer or mixture of optical isomers, including a racemic mixture, or any tautomeric forms.

In another embodiment, the present invention provides the use of a compound selected from the group:
[4-(3-Benzyloxy-pyrrolidin-1-yl)-phenyl]-(octahydro-quinolin-1-yl)-methanone;
4-(3-Benzyloxy-pyrrolidin-1-yl)-N-tricyclo[3.3.1.13,7]decan-2-yl-benzamide;
(3-Aza-bicyclo[3.2.2]non-3-yl)-[4-(3-benzyloxy-pyrrolidin-1-yl)-phenyl]-methanone;
(S)-(3-Aza-bicyclo[3.2.2]non-3-yl)-[4-(3-benzyloxy-pyrrolidin-1-yl)-phenyl]-methanone;
or a salt thereof with a pharmaceutically acceptable acid or base, or any optical isomer or mixture of optical isomers, including a racemic mixture, or any tautomeric forms.

In another embodiment, the present invention provides for the preparation of a pharmaceutical composition for the treatment of conditions, disorders, or diseases wherein a modulation or an inhibition of the activity of 11βHSD1 is beneficial.

In another embodiment, the present invention provides for the preparation of a pharmaceutical composition, wherein: the conditions, disorders, and diseases that are influenced by intracellular glucocorticoid levels.

In another embodiment, the present invention provides for the preparation of a pharmaceutical composition, wherein: the conditions, disorders, or diseases are selected from metabolic syndrome, insulin resistance, dyslipidemia, hypertension, obesity, type 2 diabetes, impaired glucose tolerance (IGT), impaired fasting glucose (IFG), the progression from IGT to type 2 diabetes, the progression of the metabolic syndrome into type 2 diabetes, diabetic late complications, neurodegenerative and psychiatric disorders, and the adverse effects of glucocorticoid receptor agonist treatment or therapy.

In another embodiment, the present invention provides for the preparation of a pharmaceutical composition, wherein: the pharmaceutical composition is suitable for a route of administration selected from oral, nasal, buccal, transdermal, pulmonal, and parenteral.

In another embodiment, the present invention provides a method for the treatment of conditions, disorders, or diseases wherein a modulation or an inhibition of the activity of 11βHSD1 is beneficial, the method comprising administering to a subject in need thereof an effective amount of a compound of the present invention.

In another embodiment, the present invention provides a method wherein the conditions, disorders, and diseases that are influenced by intracellular glucocorticoid levels.

In another embodiment, the present invention provides a method wherein the conditions, disorders, or diseases are selected from metabolic syndrome, insulin resistance, dyslipidemia, hypertension, obesity, type 2 diabetes, impaired glucose tolerance (IGT), impaired fasting glucose (IFG), progression from IGT to type 2 diabetes, progression of metabolic syndrome into type 2 diabetes, diabetic late complications, neurodegenerative and psychiatric disorders, and the adverse effects of glucocorticoid receptor agonist treatment or therapy.

In another embodiment, the present invention provides a method wherein the administering is via a route selected from oral, nasal, buccal, transdermal, pulmonal, and parenteral.

In another embodiment, the present invention provides a compound, which is an agent useful for the treatment of conditions, disorders, or diseases wherein a modulation or an inhibition of the activity of 11βHSD1 is beneficial.

In another embodiment, the present invention provides a method wherein the conditions, disorders, and diseases that are influenced by intracellular glucocorticoid levels.

In another embodiment, the present invention provides a method wherein the conditions, disorders, or diseases are selected from metabolic syndrome, insulin resistance, dyslipidemia, hypertension, obesity, type 2 diabetes, impaired glucose tolerance (IGT), impaired fasting glucose (IFG), progression from IGT to type 2 diabetes, progression of metabolic syndrome into type 2 diabetes, diabetic late complications, neurodegenerative and psychiatric disorders, and the adverse effects of glucocorticoid receptor agonist treatment or therapy.

In another embodiment, the present invention provides a method pharmaceutical composition comprising, as an active ingredient, at least one compound according of the present invention together with one or more pharmaceutically acceptable carriers or excipients.

In another embodiment, the present invention provides a pharmaceutical composition, which is suitable for oral, nasal, buccal, transdermal, pulmonal, or parenteral administration.

The compounds of the present invention have asymmetric centers and may occur as racemates, racemic mixtures, and as individual enantiomers or diastereoisomers, with all isomeric forms being included in the present invention as well as mixtures thereof.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, and nitric acids. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, and ketoglutarates. Further examples of pharmaceutically acceptable inorganic or organic acid addition salts include the pharmaceutically acceptable salts listed in J. Pharm. Sci., 66, 2 (1977), which is incorporated herein by reference. Examples of metal salts include lithium, sodium, potassium, barium, calcium, magnesium, zinc, and calcium salts. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylenediamine, N-benzylphenylethylamine, N-methyl-D-glucamine, and guanidine. Examples of cationic amino acids include lysine, arginine, and histidine.

Further, some of the compounds of the present invention may form solvates with water or common organic solvents. Such solvates are encompassed within the scope of the invention.

The pharmaceutically acceptable salts are prepared by reacting a compound of the present invention with 1 to 4 equivalents of a base such as sodium hydroxide, sodium methoxide, sodium hydride, potassium tert-butoxide, calcium hydroxide, and magnesium hydroxide, in solvents such as ether, THF, methanol, tert-butanol, dioxane, and isopropanol, ethanol. Mixtures of solvents may be used. Organic bases such as lysine, arginine, diethanolamine, choline, guanidine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, and tartaric acid in solvents such as ethyl acetate, ether, alcohols, acetone, THF, and dioxane. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, enzymatic resolution, resolving the diastereomeric salts formed with chiral acids such as mandelic acid, camphorsulfonic acid, tartaric acid, and lactic acid, wherever applicable or chiral bases such as brucine, (R)- or (S)-phenylethylamine, cinchona alkaloids and their derivatives. Commonly used methods are compiled by Jaques et al. in "Enantiomers, Racemates and Resolution" (Wiley Interscience, 1981). More specifically the compound of the present invention may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula I may be prepared by hydrolysing the pure diastereomeric amide.

Various polymorphs of the compounds forming part of this invention may be pre-pared by crystallization of said compounds under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, it spectroscopy, differential scanning calorimetry, powder X-ray diffraction or such other techniques.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the present invention. Conventional procedures for the selection and preparation of suitable prodrug derivatives are described, for example, in "Design of Prodrugs", ed. H. Bundgaard, Elsevier, 1985.

It is a well known problem in drug discovery that compounds, such as enzyme inhibitors, may be very potent and selective in biochemical assays, yet be inactive in vivo. This lack of so-called bioavailability may be ascribed to a number of different factors such as lack of or poor absorption in the gut, first pass metabolism in the liver and/or poor up-take in cells. Although the factors determining bioavailability are not completely understood, there are many examples in the scientific literature—well known to those skilled in the art—of how to modify compounds, which are potent and selective in biochemical assays but show low or no activity in vivo, into drugs that are biologically active.

It is within the scope of the invention to modify the compounds of the present invention, termed the 'original compound', by attaching chemical groups that will improve the bioavailability of said compounds in such a way that the uptake in cells or mammals is facilitated.

Examples of said modifications, which are not intended in any way to limit the scope of the invention, include changing of one or more carboxy groups to esters (for instance methyl esters, ethyl esters, tert-butyl, acetoxymethyl, pivaloyloxymethyl esters or other acyloxymethyl esters). Compounds of the invention, original compounds, such modified by attaching chemical groups are termed 'modified compounds'.

The invention also encompasses active metabolites of the present compounds.

The compounds according to the invention alter, and more specifically, reduce the level of active intracellular glucocorticoid and are accordingly useful for the treatment of conditions, disorders, and diseases in which such a modulation or reduction is beneficial.

Accordingly, the present compounds may be applicable for the treatment of the metabolic syndrome, insulin resistance, dyslipidemia, hypertension, obesity, type 2 diabetes, impaired glucose tolerance (IGT), impaired fasting glucose (IFG), Latent Autoimmune Diabetes in the Adult (LADA), type 1 diabetes, diabetic late complications including cardiovascular diseases, cardiovascular disorders, disorders of lipid metabolism, neurodegenerative and psychiatric disorders, dysregulation of intraocular pressure including glaucoma, immune disorders, inappropriate immune responses, musculo-skeletal disorders, gastrointestinal disorders, polycystic ovarie syndrome (PCOS), reduced hair growth or other diseases, disorders or conditions that are influenced by intracellular glucocorticoid levels, adverse effects of increased blood levels of active endogenous or exogenous glucocorticoid, and any combination thereof, adverse effects of increased plasma levels of endogenous active glucocorticoid, Cushing's disease, Cushing's syndrome, adverse effects of glucocorticoid receptor agonist treatment of autoimmune diseases, adverse effects of glucocorticoid receptor agonist treatment of inflammatory diseases, adverse effects of glucocorticoid receptor agonist treatment of diseases with an inflammatory component, adverse effects of glucocorticoid receptor agonist treatment as a part of cancer chemotherapy, adverse effects of glucocorticoid receptor agonist treatment for surgical/post-surgical or other trauma, adverse effects of glucocorticoid receptor agonist therapy in the context of organ or tissue transplantation or adverse effects of glucocorticoid receptor agonist treatment in other diseases, disorders or conditions where glucocorticoid receptor agonists provide clinically beneficial effects.

More specifically the present compounds may be applicable for the treatment of the metabolic syndrome, type 2 diabetes, diabetes as a consequence of obesity, insulin resistance, hyperglycemia, prandial hyperglycemia, hyperinsulinemia, inappropriately low insulin secretion, impaired glucose tolerance (IGT), impaired fasting glucose (IFG), increased hepatic glucose production, type 1 diabetes, LADA, pediatric diabetes, dyslipidemia, diabetic dyslipidemia, hyperlipidemia, hypertriglyceridemia, hyperlipoproteinemia, hypercholesterolemia, decreased HDL cholesterol, impaired LDL/HDL ratio, other disorders of lipid metabolism, obesity, visceral obesity, obesity as a consequence of diabetes, increased food intake, hypertension, diabetic late complications, micro-/macroalbuminuria, nephropathy, retinopathy, neuropathy, diabetic ulcers, cardiovascular diseases, arteriosclerosis, atherosclerosis, coronary artery disease, cardiac hypertrophy, myocardial ischemia, heart insufficiency, congestional heart failure, stroke, myocardial infarction, arrythmia, decreased blood flow, erectile dysfunction (male or female), myopathy, loss of muscle tissue, muscle wasting, muscle catabolism, osteoporosis, decreased linear growth, neurodegenerative and psychiatric disorders, Alzheimers disease, neuronal death, impaired cognitive function, depression, anxiety, eating disorders, appetite regulation, migraine, epilepsia, addiction to chemical substances, disorders of intraocular pressure, glaucoma, polycystic ovary syndrome (PCOS), inappropriate immune responses, inappropriate T helper-1/T helper-2 polarisation, bacterial infections, mycobacterial infections, fungal infections, viral infections, parasitic infestations, suboptimal responses to immunizations, immune dysfunction, partial or complete baldness, or other diseases, disorders or conditions that are influenced by intracellular glucocorticoid levels and any combination thereof, adverse effects of glucocorticoid receptor agonist treatment of allergic-inflammatory diseases such as asthma and atopic dermatitis, adverse effects of glucocorticoid receptor agonist treatment of disorders of the respiratory system e.g., asthma, cystic fibrosis, emphysema, bronchitis, hypersensitivity, pneumonitis, eosinophilic pneumonias, pulmonary fibrosis, adverse effects of glucocorticoid receptor agonist treatment of inflammatory bowel disease such as Crohn's disease and ulcerative colitis; adverse effects of glucocorticoid receptor agonist treatment of disorders of the immune system, connective tissue and joints e.g., reactive arthritis, rheumatoid arthritis, Sjögren's syndrome, systemic lupus erythematosus, lupus nephritis, Henoch-Schönlein purpura, Wegener's granulomatosis, temporal arteritis, systemic sclerosis, vasculitis, sarcoidosis, dermatomyositis-polymyositis, pemphigus vulgaris; adverse effects of glucocorticoid receptor agonist treatment of endocrinological diseases such as hyperthyroidism, hypoaldosteronism, hypopituitarism; adverse effects of glucocorticoid receptor agonist treatment of hematological diseases e.g., hemolytic anemia, thrombocytopenia, paroxysmal nocturnal hemoglobinuria; adverse effects of glucocorticoid receptor agonist treatment of cancer such as spinal cord diseases, neoplastic compression of the spinal cord, brain tumours, acute lymphoblastic leukemia, Hodgkin's disease, chemotherapy-induced nausea, adverse effects of glucocorticoid receptor agonist treatment of diseases of muscle and at the neuro-muscular joint e.g., myasthenia gravis and hereditary myopathies (e.g., Duchenne muscular dystrophy), adverse effects of glucocorticoid receptor agonist treatment in the context of surgery & transplantation e.g., trauma, post-surgical stress, surgical stress, renal transplantation, liver transplantation, lung transplantation, pancreatic islet transplantation, blood stem cell transplantation, bone marrow transplantation, heart transplantation, adrenal gland transplantation, tracheal transplantation, intestinal transplantation, corneal transplantation, skin grafting, keratoplasty, lens implantation and other procedures where immunosuppression with glucocorticoid receptor agonists is beneficial; adverse effects of glucocorticoid receptor agonist treatment of brain absess, nausea/vomiting, infections, hypercalcemia, adrenal hyperplasia, autoimmune hepatitis, spinal cord diseases, saccular aneurysms or adverse effects to glucocorticoid receptor agonist treatment in other diseases, disorders and conditions where glucocorticoid receptor agonists provide clinically beneficial effects.

Accordingly, in a further aspect the invention relates to a compound according to the invention for use as a pharmaceutical composition.

The invention also relates to pharmaceutical compositions comprising, as an active ingredient, at least one compound according to the invention together with one or more pharmaceutically acceptable carriers or diluents.

The pharmaceutical composition is preferably in unit dosage form, comprising from about 0.05 mg/day to about 2000 mg/day, preferably from about 0.1 mg/day to about 1000 mg/day, and more preferably from about 0.5 mg/day to about 500 mg/day of a compound according to the invention.

In another embodiment, the patient is treated with a compound according to the invention for at least about 1 week, for at least about 2 weeks, for at least about 4 weeks, for at least about 2 months or for at least about 4 months.

In yet another embodiment, the pharmaceutical composition is for oral, nasal, buccal, transdermal, pulmonal or parenteral administration.

Furthermore, the invention relates to the use of a compound according to the invention for the preparation of a pharmaceutical composition for the treatment of disorders and diseases wherein a modulation or an inhibition of the activity of 11βHSD1 is beneficial.

The invention also relates to a method for the treatment of disorders and diseases wherein a modulation or an inhibition of the activity of 11βHSD1 is beneficial, the method comprising administering to a subject in need thereof an effective amount of a compound according to the invention.

In a preferred embodiment of the invention the present compounds are used for the preparation of a medicament for the treatment of any diseases and conditions that are influenced by intracellular glucocorticoid levels as mentioned above.

Thus, in a preferred embodiment of the invention the present compounds are used for the preparation of a medicament for the treatment of conditions and disorders where a decreased level of active intracellular glucocorticoid is desirable, such as the conditions and diseases mentioned above.

In yet a preferred embodiment of the invention the present compounds are used for the preparation of a medicament for the treatment of metabolic syndrome, insulin resistance, dyslipidemia, hypertension obesity, type 2 diabetes, impaired glucose tolerance (IGT), impaired fasting glucose (IFG), progression from IGT to type 2 diabetes, progression of the metabolic syndrome into type 2 diabetes, diabetic late complications (e.g., cardiovascular diseases, arteriosclerosis, and atherosclerosis), neurodegenerative and psychiatric disorders, and, the adverse effects of glucocorticoid receptor agonist treatment or therapy.

In another embodiment of the present invention, the route of administration may be any route which effectively transports a compound according to the invention to the appropriate or desired site of action, such as oral, nasal, buccal, transdermal, pulmonal, or parenteral.

In still a further aspect of the invention the present compounds are administered in combination with one or more further active substances in any suitable ratios. Such further active substances may e.g., be selected from antiobesity agents, antidiabetics, agents modifying the lipid metabolism, antihypertensive agents, glucocorticoid receptor agonists, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, H3 histamine antagonists, opioid antagonists (such as naltrexone), exendin-4, GLP-1 and ciliary neurotrophic factor.

In one embodiment of the invention the antiobesity agent is leptin; dexamphetamine or amphetamine; fenfluramine or dexfenfluramine; sibutramine; orlistat; mazindol or phentermine.

Suitable antidiabetic agents include insulin, insulin analogues and derivatives such as those disclosed in EP 792 290 (Novo Nordisk A/S), e.g., $N^{\epsilon B29}$-tetradecanoyl des (B30) human insulin, EP 214 826 and EP 705 275 (Novo Nordisk NS), e.g., $Asp^{B28}$ human insulin, U.S. Pat. No. 5,504,188 (Eli Lilly), e.g., $Lys^{B28}$ $Pro^{B29}$ human insulin, EP 368 187 (Aventis), eg Lantus, which are all incorporated herein by reference, GLP-1 (glucagon like peptide-1) and GLP-1 derivatives such as those disclosed in WO 98/08871 to Novo Nordisk A/S, which is incorporated herein by reference as well as orally active hypoglycaemic agents.

The orally active hypoglycaemic agents preferably comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as PPARα modulators, PPARδ modulators, cholesterol absorption inhibitors, HSL (hormone-sensitive lipase) inhibitors and HMG CoA inhibitors (statins), nicotinic acid, fibrates, anion exchangers, compounds lowering food intake, bile acid resins, RXR agonists and agents acting on the ATP-dependent potassium channel of the β-cells.

In one embodiment, the present compounds are administered in combination with insulin or an insulin analogue or derivative, such as $N^{\epsilon B29}$-tetradecanoyl des (B30) human insulin, $Asp^{B28}$ human insulin, $Lys^{B28} Pro^{B29}$ human insulin, Lantus®, or a mix-preparation comprising one or more of these.

In a further embodiment the present compounds are administered in combination with a sulphonylurea e.g., tolbutamide, glibenclamide, glipizide or glicazide.

In another embodiment the present compounds are administered in combination with a biguanide e.g., metformin.

In yet another embodiment the present compounds are administered in combination with a meglitinide e.g., repaglinide or senaglinide.

In still another embodiment the present compounds are administered in combination with a thiazolidinedione e.g., troglitazone, ciglitazone, pioglitazone, rosiglitazone or compounds disclosed in WO 97/41097 such as 5-[[4-[3-Methyl-4-oxo-3,4-dihydro-2-quinazolinyl]methoxy]phenyl-methyl] thiazolidine-2,4-dione or a pharmaceutically acceptable salt thereof, preferably the potassium salt.

In yet another embodiment the present compounds may be administered in combination with the insulin sensitizers disclosed in WO 99/19313 such as (−)3-[4-[2-phen-oxazin-10-yl)ethoxy]phenyl]-2-ethoxypropanoic acid or a pharmaceutically acceptable salts thereof, preferably the arginine salt.

In a further embodiment the present compounds are administered in combination with an α-glucosidase inhibitor e.g., miglitol or acarbose.

In another embodiment the present compounds are administered in combination with an agent acting on the ATP-dependent potassium channel of the β-cells e.g., tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent e.g., cholestyramine, colestipol, clofibrate, gemfibrozil, fenofibrate, bezafibrate, tesaglitazar, EML-4156, LY-818, MK-767, atorvastatin, fluvastatin, lovastatin, pravastatin, simvastatin, acipimox, probucol, ezetimibe or dextrothyroxine.

In a further embodiment the present compounds are administered in combination with more than one of the above-mentioned compounds e.g., in combination with a sulphonylurea and metformin, a sulphonylurea and acarbose, repaglinide and metformin, insulin and a sulphonylurea, insulin and metformin, insulin, insulin and lovastatin, etc.

Further, the present compounds may be administered in combination with one or more antihypertensive agents. Examples of antihypertensive agents are β-blockers such as alprenolol, atenolol, timolol, pindolol, propranolol, metoprolol, bisoprololfumerate, esmolol, acebutelol, metoprolol, acebutolol, betaxolol, celiprolol, nebivolol, tertatolol, oxprenolol, amusolalul, carvedilol, labetalol, β2-receptor blockers e.g., S-atenolol, OPC-1085, ACE (angiotensin converting enzyme) inhibitors such as quinapril, lisinopril, enalapril, captopril, benazepril, perindopril, trandolapril, fosinopril, ramipril, cilazapril, delapril, imidapril, moexipril, spirapril, temocapril, zofenopril, S-5590, fasidotril, Hoechst-Marion Roussel: 100240 (EP 00481522), omapatrilat, gemopatrilat and GW-660511, calcium channel blockers such as nifedipine, felodipine, nicardipine, isradipine, nimodipine, diltiazem, amlodipine, nitrendipine, verapamil, lacidipine, lercanidipine, aranidipine, cilnidipine, clevidipine, azelnidipine, barnidipine, efonodipine, iasidipine, iemildipine, iercanidipine, manidipine, nilvadipine, pranidipine, furnidipine, α-blockers such as doxazosin, urapidil, prazosin, terazosin, bunazosin and OPC-28326, diuretics such as thiazides/sulphonamides (e.g., bendroflumetazide, chlorothalidone, hydrochlorothiazide and clopamide), loop-diuretics (e.g., bumetanide, furosemide and torasemide) and potassium sparing diuretics (e.g., amiloride, spironolactone), endothelin ET-A antagonists such as ABT-546, ambrisetan, atrasentan, SB-234551, CI-1034, S-0139 and YM-598, endothelin antagonists e.g., bosentan and J-104133, renin inhibitors such as aliskiren, vasopressin V1 antagonists e.g., OPC-21268, vasopressin V2 antagonists such as tolvaptan, SR-121463 and OPC-31260, B-type natriuretic peptide agonists e.g., Nesiritide, angiotensin II antagonists such as irbesartan, candesartancilexetil, losartan, valsartan, telmisartan, eprosartan, candesartan, CL-329167, eprosartan, iosartan, olmesartan, pratosartan, TA-606, and YM-358, 5-HT2 agonists e.g., fenoldopam and ketanserin, adenosine A1 antagonists such as naftopidil, N-0861 and FK-352, thromboxane A2 antagonists such as KT2-962, endopeptidase inhibitors e.g., ecadotril, nitric oxide agonists such as LP-805, dopamine D1 antagonists e.g., MYD-37, dopamine D2 agonists such as nolomirole, n-3 fatty acids e.g., omacor, prostacyclin agonists such as treprostinil, beraprost, PGE1 agonists e.g., ecraprost, Na+/K+ATPase modulators e.g., PST-2238, Potassium channel activators e.g., KR-30450, vaccines such as PMD-3117, Indapamides, CGRP-unigene, guanylate cyclase stimulators, hydralazines, methyldopa, docarpamine, moxonidine, CoAprovel, MondoBiotech-811.

Further reference can be made to Remington: The Science and Practice of Pharmacy, 19th Edition, Gennaro, Ed., Mack Publishing Co., Easton, Pa., 1995.

Furthermore, the present compounds may be administered in combination with one or more glucocorticoid receptor agonists. Examples of such glucocorticoid receptor agonists are betametasone, dexamethasone, hydrocortisone, methylprednisolone, prednisolone, prednisone, beclomethasone, butixicort, clobetasol, flunisolide, flucatisone (and analogues), mometasone, triamcinolonacetonide, triamcinolonhexacetonide GW-685698, NXC-1015, NXC-1020, NXC-1021, NS-126, P-4112, P-4114, RU-24858 and T-25 series.

It should be understood that any suitable combination of the compounds according to the invention with one or more of the above-mentioned compounds and optionally one or more further pharmacologically active substances are considered to be within the scope of the present invention.

Pharmaceutical Compositions

The compounds of the present invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well-known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, crèmes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 2000 mg, e.g., from about 0.1 to about 1000 mg, from about 0.5 mg to about 500 mg, from about 1 mg to about 200 mg, e.g., about 100 mg.

For parenteral routes, such as intravenous, intrathecal, intramuscular and similar administration, typically doses are in the order of about half the dose employed for oral administration.

The compounds of this invention are generally utilized as the free substance or as a pharmaceutically acceptable salt thereof. Examples are an acid addition salt of a compound having the utility of a free base and a base addition salt of a compound having the utility of a free acid. The term "pharmaceutically acceptable salts" refers to non-toxic salts of the compounds for use according to the present invention which are generally prepared by reacting the free base with a suitable organic or inorganic acid or by reacting the acid with a suitable organic or inorganic base. When a compound for use according to the present invention, contains a free base such salts are prepared in a conventional manner by treating a solution or suspension of the compound with a chemical equivalent of a pharmaceutically acceptable acid. When a compounds for use according to the present invention, contains a free acid such salts are prepared in a conventional manner by treating a solution or suspension of the compound with a chemical equivalent of a pharmaceutically acceptable base. Physiologically acceptable salts of a compound with a hydroxy group include the anion of said compound in combination with a suitable cation such as sodium or ammonium ion. Other salts which are not pharmaceutically acceptable may be useful in the preparation of compounds for use according to the present invention and these form a further aspect of the present invention.

For parenteral administration, solutions of the present compounds in sterile aqueous solution, aqueous propylene glycol or sesame or peanut oil may be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of suitable carriers are water, salt solutions, alcohols, polyethylene glycols, polyhydroxyethoxylated castor oil, peanut oil, olive oil, syrup, phospholipids, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents.

The pharmaceutical compositions formed by combining the compounds of the invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

Compositions intended for oral use may be prepared according to any known method, and such compositions may contain one or more agents selected from the group consisting of sweetening agents, flavouring agents, colouring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatine or acacia; and lubricating agents, for ex-ample magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for con-trolled release.

Formulations for oral use may also be presented as hard gelatine capsules where the active ingredient is mixed with an inert solid diluent, for example, calcium carbonate, calcium phosphate or kaolin, or a soft gelatine capsule wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkyl oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavouring, and colouring agents may also be present.

The pharmaceutical compositions comprising a compound for use according to the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, preservative and flavouring and colouring agent. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the present invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the present invention are contemplated. For the purpose of this application, topical applications shall include mouth washes and gargles.

The compounds for use according to the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In addition, some of the compounds for use according to the present invention may form solvates with water or common organic solvents. Such solvates are also encompassed within the scope of the present invention.

Thus, in a further embodiment, there is provided a pharmaceutical composition comprising a compound for use according to the present invention, or a pharmaceutically acceptable salt, solvate, or prodrug thereof, and one or more pharmaceutically acceptable carriers, excipients, or diluents.

If a solid carrier is used for oral administration, the preparation may be tableted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet which may be prepared by conventional tabletting techniques may contain:

Core:

| | |
|---|---|
| Active compound (as free compound or salt thereof) | 5.0 mg |
| Lactosum PH. Eur. | 67.8 mg |
| Cellulose, microcryst. (Avicel) | 31.4 mg |
| Amberlite ® IRP88* | 1.0 mg |
| Magnesii stearas PH. Eur. | q.s. |

Coating:

| | |
|---|---|
| Hydroxypropyl methylcellulose | approx. 9 mg |
| Mywacett 9-40 T** | approx. 0.9 mg |

Polacrillin potassium NF, tablet disintegrant, Rohm and Haas.
**Acylated monoglyceride used as plasticizer for film coating.

The compounds of the invention may be administered to a patient which is a mammal, especially a human in need thereof. Such mammals include also animals, both domestic animals, e.g., household pets, and non-domestic animals such as wildlife.

Any novel feature or combination of features described herein is considered essential to this invention.

The present invention also relate to the below methods of preparing the compounds of the invention.

The present invention is further illustrated in the following representative examples which are, however, not intended to limit the scope of the invention in any way.

EXAMPLES

Compounds of General Formula (I)

The following examples and general procedures refer to intermediate compounds and final products for general formula (I) identified in the specification and in the synthesis schemes. The preparation of the compounds of general formula (I) of the present invention is described in detail using the following examples. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, which is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. The structures of the compounds are confirmed by either elemental analysis or nuclear magnetic resonance (NMR), where peaks assigned to characteristic protons in the title compounds are presented where appropriate. $^1$H NMR shifts ($\delta_H$) are given in parts per million (ppm) down field from tetramethylsilane as internal reference standard. M.p.: is melting point and is given in ° C. and is not corrected. Column chromatography was carried out using the technique described by W. C. Still et al., *J. Org. Chem.* 43: 2923 (1978) on Merck silica gel 60 (Art. 9385). HPLC analyses are performed using 5 μm C18 4×250 mm column eluted with various mixtures of water and acetonitrile, flow=1 ml/min, as described in the experimental section.

Microwave oven synthesis: The reaction was heated by microwave irradiation in sealed microwave vessels in a single mode Emrys Optimizer EXP from PersonalChemistry®.

Preparative HPLC: Column: 1.9×15 cm Waters XTerra RP-18. Buffer: linear gradient 5-95% in 15 min, MeCN, 0.1% TFA, flow rate of 15 ml/min. The pooled fractions are either evaporated to dryness in vacuo, or evaporated in vacuo until the MeCN is removed, and then frozen and freeze dried.

The abbreviations as used in the examples have the following meaning:

TLC: Thin layer chromatography
CDCl$_3$: Deuterio chloroform
CD$_3$OD: Tetradeuterio methanol
DCM: Dichloromethane
DMF: N,N-dimethylformamide
DMSO-d$_6$: Hexadeuterio dimethylsulfoxide
DMSO: Dimethylsulfoxide
DIPEA: Diisopropylethylamine
EDAC: 1-(3-Dimethylaminopropyl)-3-ethylcarbodiimide hydrochloride
EtOAc: Ethyl acetate
THF: Tetrahydrofuran
HOBT: 1-Hydroxy-benzotriazole
MeCN: Acetonitrile
NMP: N-Methylpyrrolidinone
TFA: Trifluoroacetic acid
min: minutes
hrs: hours General Method A

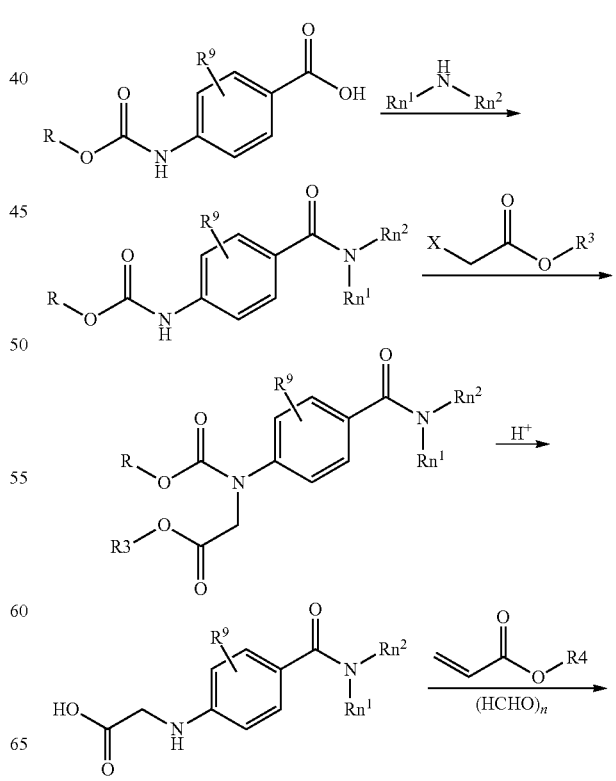

-continued
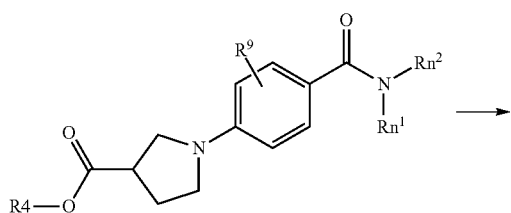
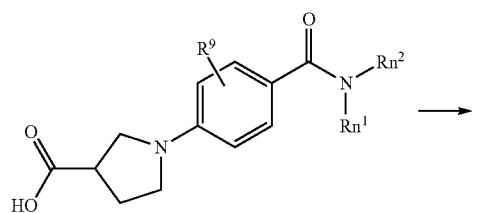
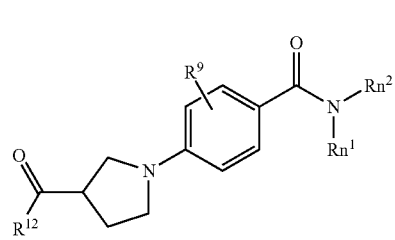
General Method B
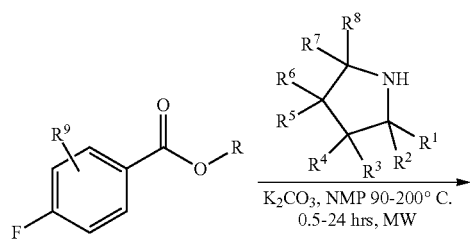
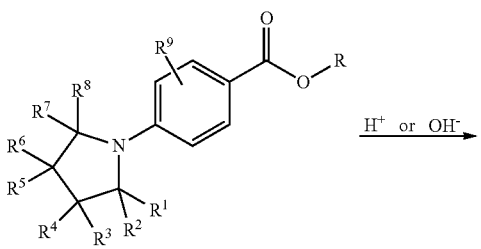
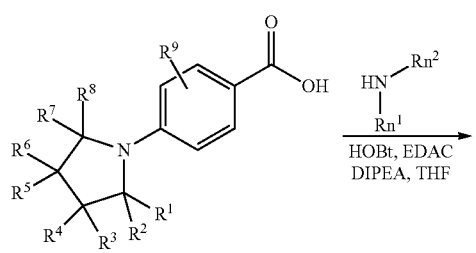
-continued
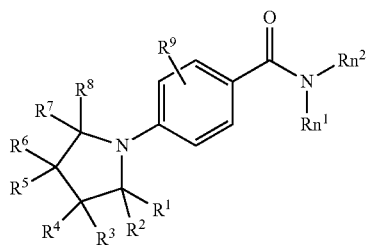
General Method C
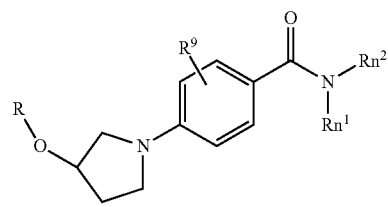
General Method D
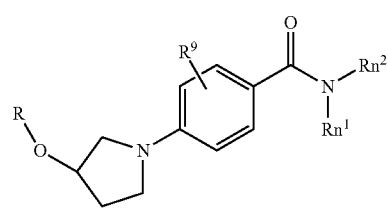

General Method E
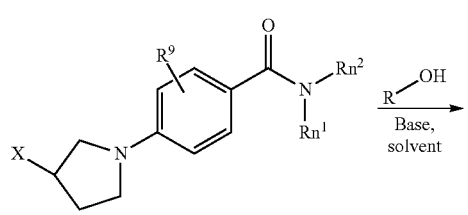
General Method F
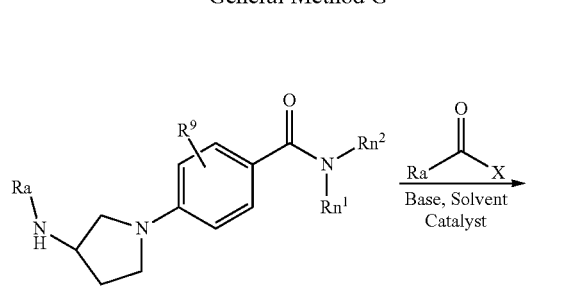
General Method G
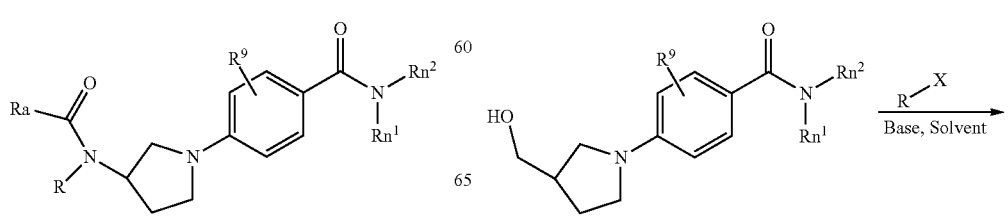
General Method H
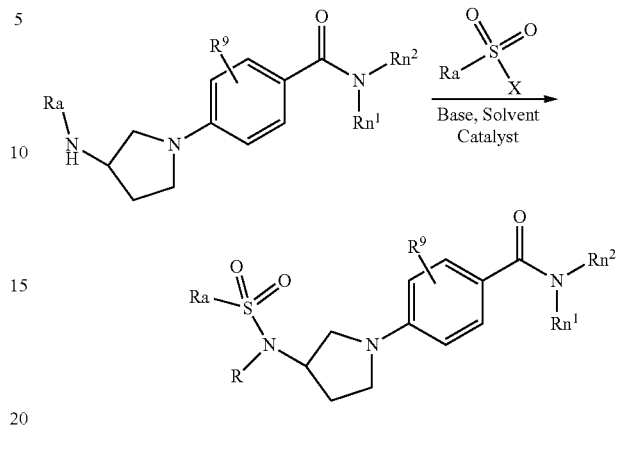
General Method I
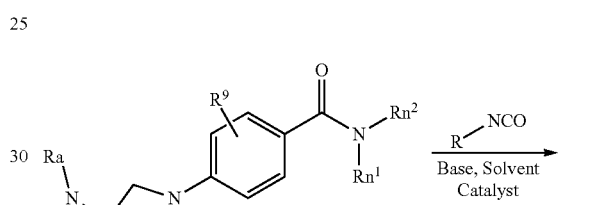
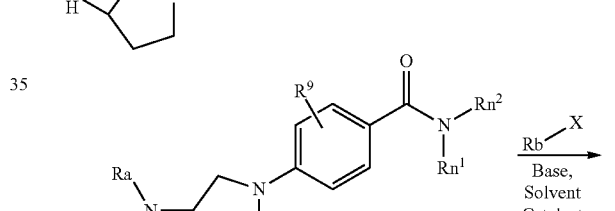
General Method J
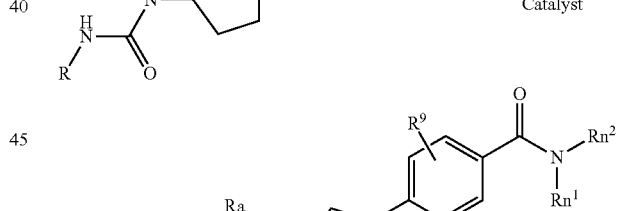

General Method K

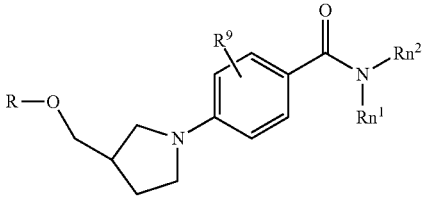

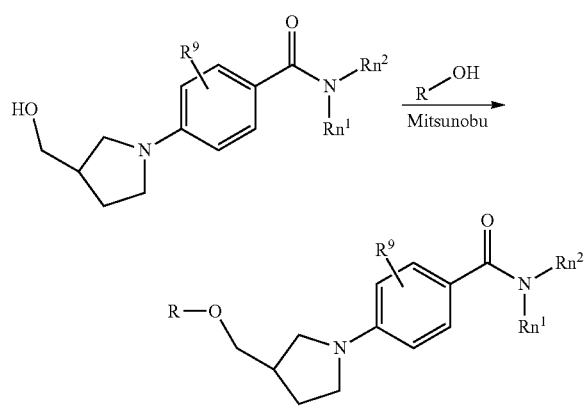

Example 1

General Method (A)

1-[4-(1,3,3-Trimethyl-6-aza-bicyclo[3.2.1]octane-6-carbonyl)-phenyl]-pyrrolidine-3-carboxylic acid

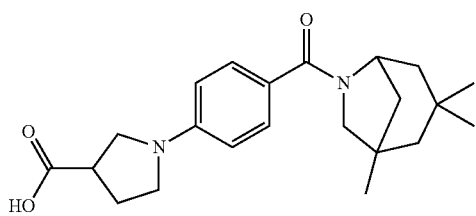 [SMILES: CC1(C)CC2CC(C)(CN2C(=O)c2ccc(N3CCC(C(=O)O)C3)cc2)C1]

To a mixture of 4-tert-butoxycarbonylamino-benzoic acid (50 g, 0.21 mol) and HOBT (31.33 g, 0.231 mol) in dry THF (0.5 L) was added EDAC (44.44 g, 0.231 mol). The resulting mixture was stirred for 10 min followed by addition of a mixture of DIPEA (40.4 ml, 0.231 mol) and 1,3,3-trimethyl-6-aza-bicyclo[3.2.1]octane (39.4 ml, 0.231 mol). The reaction mixture was stirred for an additional 16 hrs. and evaporated to dryness. To the residue was added water (600 ml) and the resulting mixture was extracted with EtOAc (3×500 ml). The combined organic phases were dried (Na$_2$SO$_4$), filtered and evaporated in vacuo. The resulting residue was purified by column chromatography (silica gel) using a mixture of EtOAc-Heptane (1:2) as eluent. Pure fractions were collected and evaporated to dryness. To the solid residue was added diethyl ether (100 ml) and the precipitate was filtered off, washed with diethyl ether and dried in vacuo at 50° C. affording 60.5 g (77%) of [4-(1,3,3-trimethyl-6-aza-bicyclo[3.2.1]octane-6-carbonyl)-phenyl]carbamic acid tert-butyl ester as a solid.

$^1$H-NMR (300 MHz, CDCl$_3$) δ 0.92 (d, 3H), 1.02 (d, 3H), 1.11 (s, 3H), 1.2-1.4 (m, 3.5H), 1.52 (s, 9H), 1.55-2.27 (m, 2.5H), 3.17-3.29 (m, 1.5H), 3.57 (d, 0.5H), 4.01 and 4.58 (2xt, 1H), 6.72 (s, 1H), 7.36-7.44 (m, 4H).

To a solution of [4-(1,3,3-trimethyl-6-aza-bicyclo[3.2.1]octane-6-carbonyl)-phenyl]carbamic acid tert-butyl ester (5.0 g, 13.42 mmol) in dry DMF (75 ml) was added sodium hydride (750 mg, 33.3 mmol in 60% mineral oil) and the mixture was stirred for 30 min. Bromo-acetic acid tert-butyl ester (3.14 g, 16.11 mmol) was added and the stirring was continued for an additional 1 hr. at 50° C. The reaction was quenched by addition of water (50 ml) and extracted with diethyl ether (2×50 ml). The combined organic phases were dried (Na$_2$SO$_4$), filtered and evaporated in vacuo. The residue was dissolved in DCM (75 ml) and TFA (40 ml) was added. The resulting mixture was stirred for 16 hrs. at room temperature and evaporated in vacuo. To the residue was added water (75 ml) and diethyl ether (25 ml) and the precipitate was filtered off, washed with diethyl ether and dried in vacuo at 50° C. affording 3.3 g (74%) of [4-(1,3,3-trimethyl-6-aza-bicyclo[3.2.1]-octane-6-carbonyl)-phenylamino]-acetic acid an solid.

$^1$H-NMR (400 MHz, DMSO$_{d6}$) δ 0.94 (s, 3H), 1.02 (d, 3H), 1.11 (d, 3H), 1.21-1.75 (m, 5.5H), 2.25 (d, 0.5H), 3.27 (t, 1H), 3.35 (d, 0.5H), 3.47-3.55 (m, 2.5H), 3.71 (m, 6H), 3.89 (s, 2H), 4.11 (m, 0.5H), 4.57 (m, 0.5H), 6.58 (t, 2H), 7.37 (dd, 2H).

[4-(1,3,3-Trimethyl-6-aza-bicyclo[3.2.1]octane-6-carbonyl)-phenylamino]-acetic acid (1.3 g, 3.93 mmol), methyl acrylate (275 μl, 3.03 mmol) and paraformaldehyde (636 mg, 21.18 mmol) were dissolved in toluene (180 ml) in a three necked reaction flask equipped with a water separator. The mixture was stirred at reflux temp. for 3 hrs at which time a small portion of methyl acrylate (40 μl) was added. The resulting mixture was stirred at reflux temp. for an additional 16 hrs. and evaporated. The residue was dissolved in EtOAc (50 ml) and washed with water (2×25 ml), dried (Na$_2$SO$_4$), filtered and evaporated in vacuo. The resulting residue was purified by column chromatography (silica gel) using first pure heptane (300 ml) followed by a mixture of EtOAc-Heptane (1:1) as eluents. Pure fractions were collected and evaporated to dryness affording 603 mg (52%) of 1-[4-(1,3,3-trimethyl-6-aza-bicyclo[3.2.1]octane-6-carbonyl)-phenyl]-pyrrolidine-3-carboxylic acid methyl ester as an oil.

$^1$H-NMR (400 MHz, DMSO$_{d6}$) δ 0.94 (s, 3H), 1.02 (d, 3H), 1.11 (d, 3H), 1.21-1.75 (m, 5.5H), 2.25 (d, 0.5H), 3.27 (t, 1H), 3.35 (d, 0.5H), 3.47-3.55 (m, 2.5H), 3.71 (m, 6H), 3.89 (s, 2H), 4.11 (m, 0.5H), 4.57 (m, 0.5H), 6.58 (t, 2H), 7.37 (dd, 2H).

To a solution of the above methyl ester (603 mg, 1.57 mmol) in EtOH (25 ml) was added 1 N NaOH (2.35 ml) and the resulting mixture was stirred for 4 hrs. The volatiles were evaporated and to the residue was added water (15 ml) followed by washing with diethyl ether (2×10 ml). The pH of the aqueous phase was adjusted to 3 by addition of 3 N HCl. The precipitate was filtered off and washed with water and dried in vacuo at 50° C. affording 423 mg (73%) of the title compound as a solid.

$^1$H-NMR (400 MHz, DMSO$_{d6}$) δ 0.94 (s, 3H), 1.02 (d, 3H), 1.11 (d, 3H), 1.21-1.75 (m, 5.5H), 2.25 (d, 0.5H), 3.27 (t, 1H), 3.35 (d, 0.5H), 3.47-3.55 (m, 2.5H), 3.71 (m, 6H), 3.89 (s, 2H), 4.11 (m, 0.5H), 4.57 (m, 0.5H), 6.58 (t, 2H), 7.37 (dd, 2H).

Example 2

General Method (A)

{4-[3-(Morpholine-4-carbonyl)-pyrrolidin-1-yl]-phenyl}-(1,3,3-trimethyl-6-aza-bicyclo-[3.2.1]oct-6-yl)-methanone

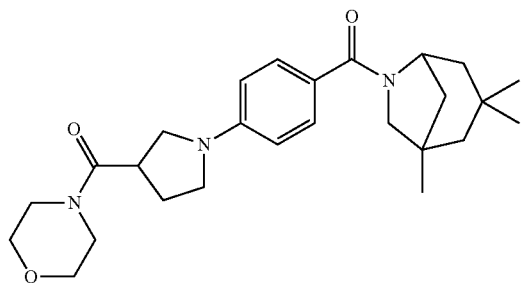 [SMILES: CC1(C)CC2CC(C)(CN2C(=O)c2ccc(N3CCC(C(=O)N4CCOCC4)C3)cc2)C1]

To a mixture of 1-[4-(1,3,3-trimethyl-6-aza-bicyclo[3.2.1]octane-6-carbonyl)-phenyl]-pyrrolidine-3-carboxylic acid (300 mg, 0.81 mmol, prepared as described in ex-ample 1) and HOBT (131 mg, 0.97 mmol) in dry THF (20 ml) was added EDAC (186 mg, 0.97 mmol). The resulting mixture was stirred for 10 min followed by addition of a mixture of DIPEA (219 µl, 1.22 mmol) and morpholine (85 µl, 0.97 mmol). The reaction mixture was stirred for an additional 16 hrs. and evaporated to dryness. The resulting residue was purified by preparative HPLC (Gilson) and pure fractions were collected and evaporated to dryness and dried in vacuo at 50° C. affording 250 mg (70%) of the title compound as a solid.

$^1$H-NMR (300 MHz, CDCl$_3$) δ 0.92 (d, 3H), 1.02 (d, 3H), 1.11 (s, 3H), 1.2-1.4 (m, 3.5H), 1.52 (s, 9H), 1.55-2.27 (m, 2.5H), 3.17-3.29 (m, 1.5H), 3.57 (d, 0.5H), 4.01 and 4.58 (2xt, 1H), 6.72 (s, 1H), 7.36-7.44 (m, 4H).

The following compounds were made as outlined in general method A-K above:

| Ex. | Structure | LC/MS [M + 1]+ | IUPAC Name |
|---|---|---|---|
| 1-1 | 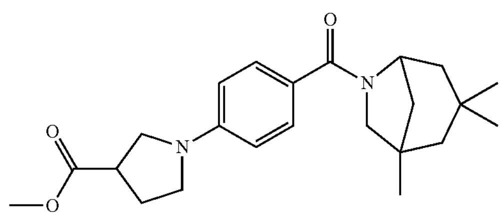 | 384.5 | 1-[4-(1,3,3-Trimethyl-6-aza-bicyclo[3.2.1]octane-6-carbonyl)-phenyl]-pyrrolidine-3-carboxylic acid methyl ester |
| 1-2 | 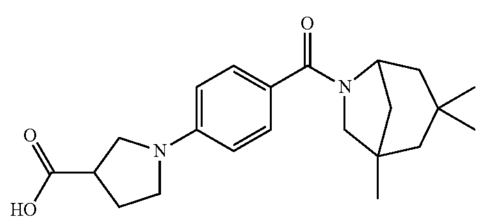 [SMILES: CC1(C)CC2CC(C)(CN2C(=O)c2ccc(N3CCC(C(=O)O)C3)cc2)C1] | 370.5 | 1-[4-(1,3,3-Trimethyl-6-aza-bicyclo[3.2.1]octane-6-carbonyl)-phenyl]-pyrrolidine-3-carboxylic acid |
| 1-3 | 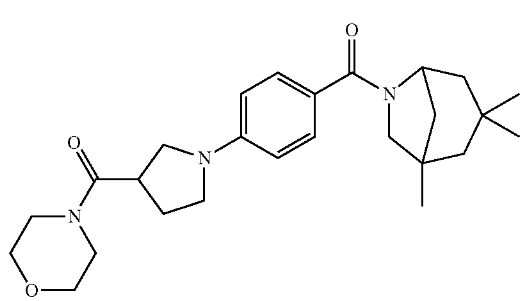 [SMILES: CC1(C)CC2CC(C)(CN2C(=O)c2ccc(N3CCC(C(=O)N4CCOCC4)C3)cc2)C1] | 439.6 | {4-[3-(Morpholine-4-carbonyl)-pyrrolidin-1-yl]-phenyl}-(1,3,3-trimethyl-6-aza-bicyclo[3.2.1]-oct-6-yl)-methanone |

-continued

| Ex. | Structure | LC/MS [M + 1]+ | IUPAC Name |
|---|---|---|---|
| 1-4 | 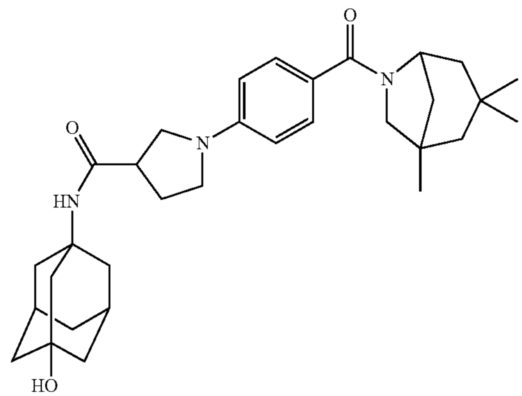 [SMILES: CC1(C)CC2CC(C)(CN2C(=O)c2ccc(N3CCC(C(=O)NC45CC6CC(CC(O)(C6)C4)C5)C3)cc2)C1] | 519.7 | 1-[4-(1,3,3-Trimethyl-6-aza-bicyclo[3.2.1]octane-6-carbonyl)-phenyl]-pyrrolidine-3-carboxylic acid (3-hydroxy-adamantan-1-yl)-amide |
| 1-5 | 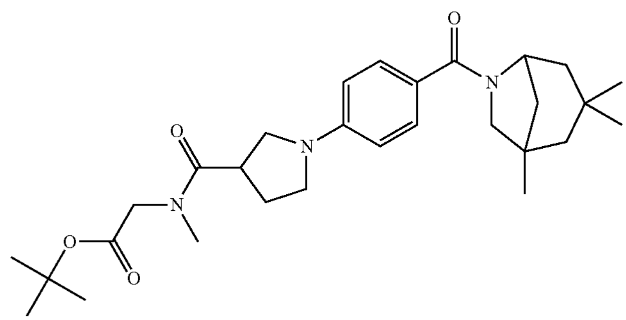 [SMILES: CN(CC(=O)OC(C)(C)C)C(=O)C1CCN(c2ccc(C(=O)N3CC4(C)CC3CC(C)(C)C4)cc2)C1] | 497.7 | (Methyl-{1-[4-(1,3,3-trimethyl-6-aza-bicyclo[3.2.1]octane-6-carbonyl)-phenyl]-pyrrolidine-3-carbonyl}-amino)-acetic acid tert-butyl ester |
| 1-6 | 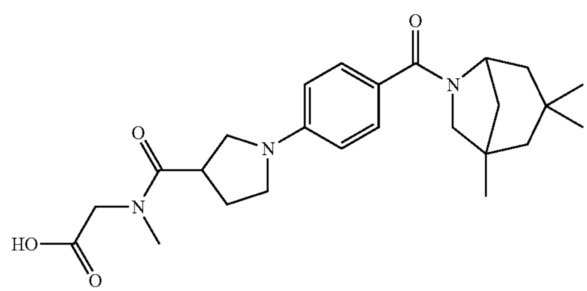 [SMILES: CN(CC(=O)O)C(=O)C1CCN(c2ccc(C(=O)N3CC4(C)CC3CC(C)(C)C4)cc2)C1] | 441.6 | (Methyl-{1-[4-(1,3,3-trimethyl-6-aza-bicyclo[3.2.1]octane-6-carbonyl)-phenyl]-pyrrolidine-3-carbonyl}-amino)-acetic acid |
| 1-7 | 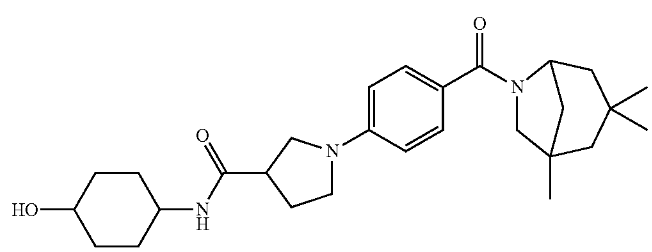 [SMILES: CC1(C)CC2CC(C)(CN2C(=O)c2ccc(N3CCC(C(=O)NC4CCC(O)CC4)C3)cc2)C1] | 467.7 | 1-[4-(1,3,3-Trimethyl-6-aza-bicyclo[3.2.1]octane-6-carbonyl)-phenyl]-pyrrolidine-3-carboxylic acid (4-hydroxy-cyclohexyl)-amide |
| 1-8 | 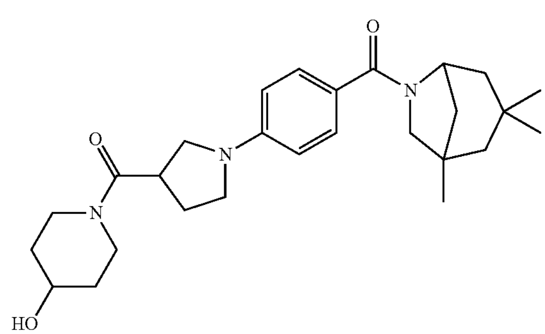 [SMILES: CC1(C)CC2CC(C)(CN2C(=O)c2ccc(N3CCC(C(=O)N4CCC(O)CC4)C3)cc2)C1] | 453.6 | {4-[3-(4-Hydroxy-piperidine-1-carbonyl)-pyrrolidin-1-yl]-phenyl}-(1,3,3-trimethyl-6-aza-bicyclo[3.2.1]oct-6-yl)-methanone |

| Ex. | Structure | LC/MS [M + 1]+ | IUPAC Name |
|---|---|---|---|
| 1-9 | 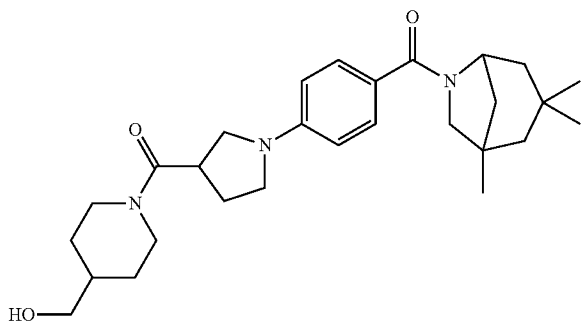 [SMILES: CC1(C)CC2CC(C)(CN2C(=O)c2ccc(N3CCC(C(=O)N4CCC(CO)CC4)C3)cc2)C1] | 467.7 | {4-[3-(4-Hydroxymethyl-piperidine-1-carbonyl)-pyrrolidin-1-yl]-phenyl}-(1,3,3-trimethyl-6-aza-bicyclo[3.2.1]oct-6-yl)-methanone |
| 1-10 | 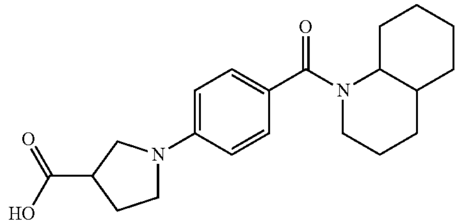 [SMILES: O=C(O)C1CCN(c2ccc(C(=O)N3CCCC4CCCCC43)cc2)C1] | 356.5 | 1-[4-(Octahydroquinoline-1-carbonyl)phenyl]-pyrrolidine-3-carboxylic acid |
| 1-11 | 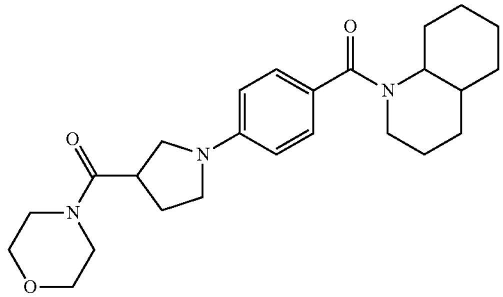 [SMILES: O=C(C1CCN(c2ccc(C(=O)N3CCCC4CCCCC43)cc2)C1)N1CCOCC1] | 425.6 | {4-[3-(Morpholine-4-carbonyl)-pyrrolidin-1-yl]-phenyl}(octahydroquinolin-1-yl)methanone |
| 1-12 | 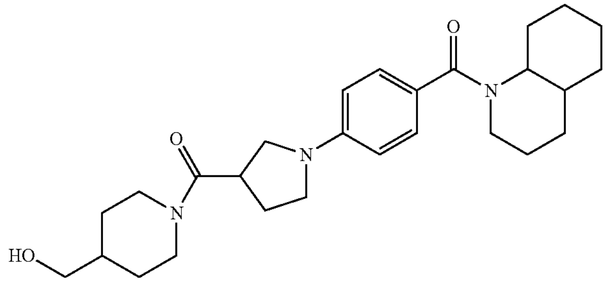 [SMILES: O=C(C1CCN(c2ccc(C(=O)N3CCCC4CCCCC43)cc2)C1)N1CCC(CO)CC1] | 453.6 | {4-[3-(4-Hydroxymethyl-piperidine-1-carbonyl)-pyrrolidin-1-yl]-phenyl}-(octahydroquinolin-1-yl)methanone |
| 1-13 | 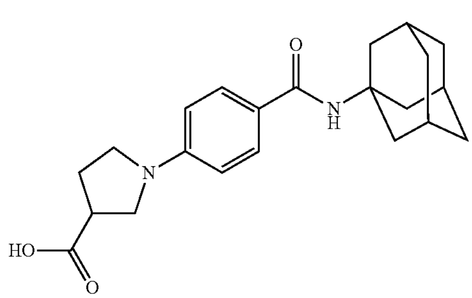 [SMILES: O=C(NC12CC3CC(CC(C3)C1)C2)c1ccc(N2CCC(C(=O)O)C2)cc1] | 368.5 | 1-[4-(Adamantan-1-ylcarbamoyl)-phenyl]-pyrrolidine-3-carboxylic acid |

-continued

| Ex. | Structure | LC/MS [M + 1]+ | IUPAC Name |
|---|---|---|---|
| 1-14 | 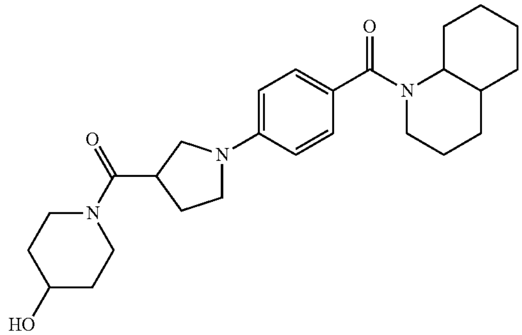 [SMILES: O=C(C1CCN(c2ccc(C(=O)N3CCCC4CCCCC43)cc2)C1)N1CCC(O)CC1] | 439.6 | {4-[3-(4-Hydroxy-piperidine-1-carbonyl)-pyrrolidin-1-yl]-phenyl}-octahydro-quinolin-1-yl)-methanone |
| 1-15 | 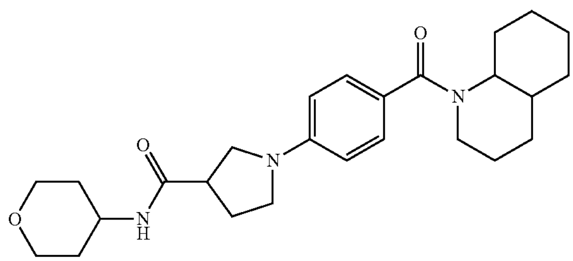 [SMILES: O=C(NC1CCOCC1)C1CCN(c2ccc(C(=O)N3CCCC4CCCCC43)cc2)C1] | 439.6 | 1-[4-(Octahydro-quinoline-1-carbonyl)-phenyl]-pyrrolidine-3-carboxylic acid (tetrahydro-pyran-4-yl)-amide |
| 1-16 | 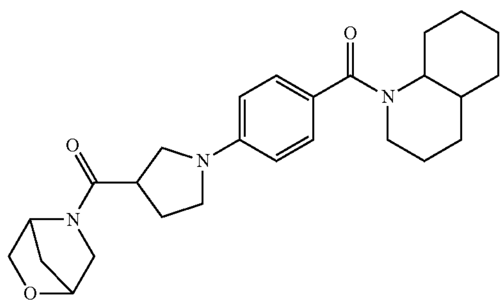 [SMILES: O=C(C1CCN(c2ccc(C(=O)N3CCCC4CCCCC43)cc2)C1)N1CC2CC1CO2] | 437.6 | (Octahydro-quinolin-1-yl)-{4-[3-(2-oxa-5-aza-bicyclo[2.2.1]-heptane-5-carbonyl)-pyrrolidin-1-yl]-phenyl}-methanone |
| 1-17 | 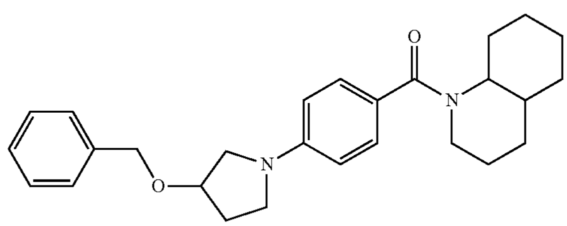 [SMILES: O=C(c1ccc(N2CCC(OCc3ccccc3)C2)cc1)N1CCCC2CCCCC21] | 418.6 | [4-(3-Benzyloxy-pyrrolidin-1-yl)-phenyl]-(octahydro-quinolin-1-yl)-methanone |
| 1-18 | 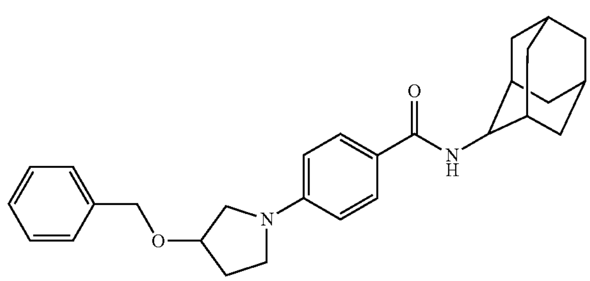 [SMILES: O=C(NC1C2CC3CC(C2)CC1C3)c1ccc(N2CCC(OCc3ccccc3)C2)cc1] | 430.6 | 4-(3-Benzyloxy-pyrrolidin-1-yl)-N-tricyclo[3.3.1.13,7]-decan-2-yl-benzamide |

-continued

| Ex. | Structure | LC/MS [M + 1]+ | IUPAC Name |
|---|---|---|---|
| 1-19 | 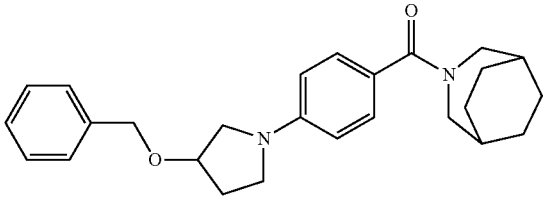 [SMILES: O=C(c1ccc(N2CCC(OCc3ccccc3)C2)cc1)N1CC2CCC(CC2)C1] | 404.6 | (3-Aza-bicyclo[3.2.2]non-3-yl)-[4-(3-benzyloxy-pyrrolidin-1-yl)-phenyl]-methanone |
| 1-20 | 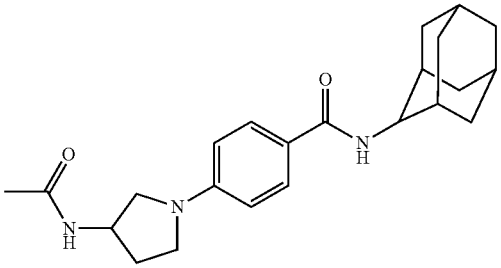 | 381.5 | 4-(3-Acetylamino-pyrrolidin-1-yl)-N-adamantan-2-yl-benzamide |
| 1-21 | 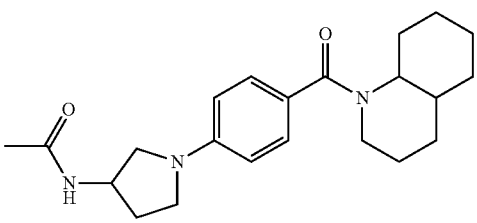 [SMILES: CC(=O)NC1CCN(c2ccc(C(=O)N3CCCC4CCCCC43)cc2)C1] | 369.5 | N-{1-[4-(Octahydro-quinoline-1-carbonyl)-phenyl]-pyrrolidin-3-yl}-acetamide |
| 1-22 | 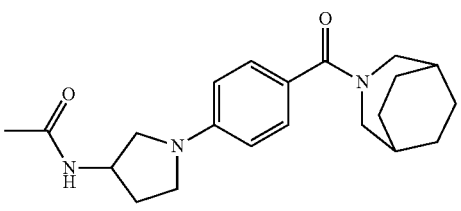 [SMILES: CC(=O)NC1CCN(c2ccc(C(=O)N3CC4CCC(CC4)C3)cc2)C1] | 355.5 | N-{1-[4-(3-Aza-bicyclo[3.2.2]-nonane-3-carbonyl)-phenyl]-pyrrolidin-3-yl}-acetamide |
| 1-23 | 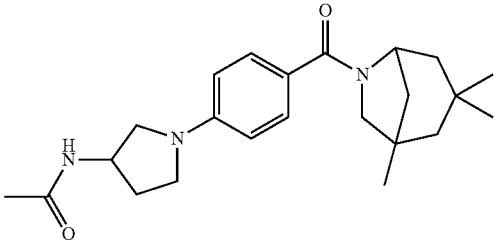 [SMILES: CC(=O)NC1CCN(c2ccc(C(=O)N3CC4(C)CC3CC(C)(C)C4)cc2)C1] | 385 | N-{1-[4-(1,3,3-Trimethyl-6-aza-bicyclo[3.2.1]octane-6-carbonyl)-phenyl]-pyrrolidin-3-yl}-acetamide |
| 1-24 | 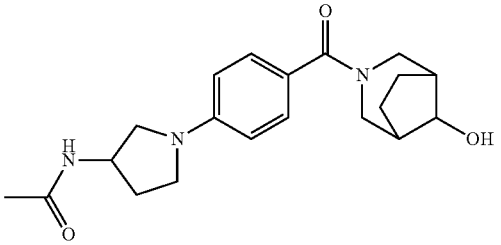 [SMILES: CC(=O)NC1CCN(c2ccc(C(=O)N3CC4CCC(C3)C4O)cc2)C1] | 358 | N-{1-[4-(8-Hydroxy-3-aza-bicyclo[3.2.1]octane-3-carbonyl)-phenyl]-pyrrolidin-3-yl}-acetamide |

-continued

| Ex. | Structure | LC/MS [M + 1]+ | IUPAC Name |
|---|---|---|---|
| 1-25 | 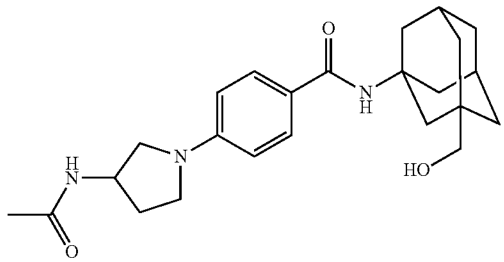 [SMILES: CC(=O)NC1CCN(c2ccc(C(=O)NC34CC5CC(CC(CO)(C5)C3)C4)cc2)C1] | 413 | 4-(3-Acetylamino-pyrrolidin-1-yl)-N-(3-hydroxymethyl-adamantan-1-yl)-benzamide |
| 1-26 | 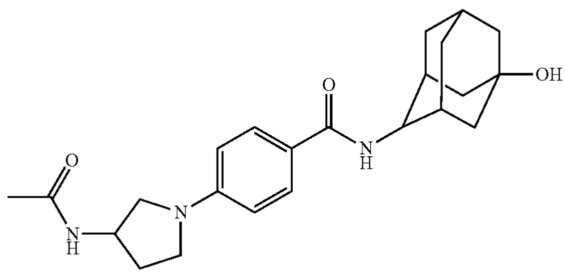 | 399 | 4-(3-Acetylamino-pyrrolidin-1-yl)-N-(5-hydroxy-adamantan-2-yl)-benzamide |
| 1-27 | 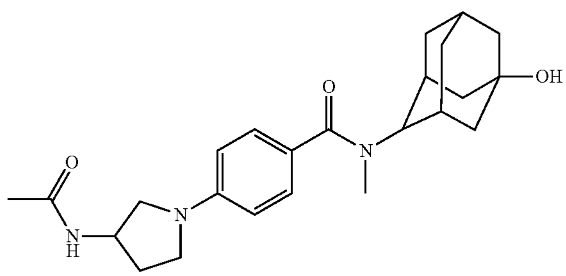 [SMILES: CC(=O)NC1CCN(c2ccc(C(=O)N(C)C3C4CC5CC3CC(O)(C5)C4)cc2)C1] | 413 | 4-(3-Acetylamino-pyrrolidin-1-yl)-N-(5-hydroxy-adamantan-2-yl)-N-methyl-benzamide |
| 1-28 | 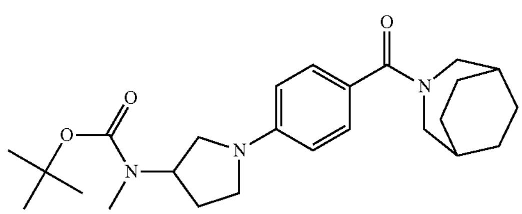 [SMILES: CN(C(=O)OC(C)(C)C)C1CCN(c2ccc(C(=O)N3CC4CCC(CC4)C3)cc2)C1] | 427.6 | {1-[4-(3-Aza-bicyclo[3.2.2]-nonane-3-carbonyl)-phenyl]-pyrrolidin-3-yl}-methyl-carbamic acid tert-butyl ester |
| 1-29 | 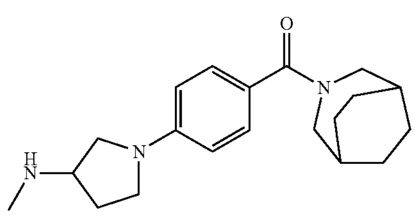 [SMILES: CNC1CCN(c2ccc(C(=O)N3CC4CCC(CC4)C3)cc2)C1] | 327.5 | (3-Aza-bicyclo[3.2.2]non-3-yl)-[4-(3-methylamino-pyrrolidin-1-yl)-phenyl]-methanone |
| 1-30 | 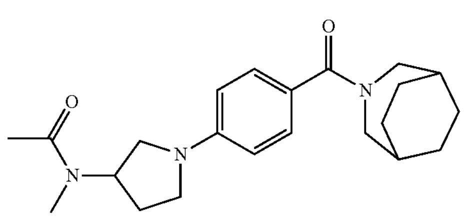 [SMILES: CC(=O)N(C)C1CCN(c2ccc(C(=O)N3CC4CCC(CC4)C3)cc2)C1] | 369.5 | N-{1-[4-(3-Aza-bicyclo[3.2.2]-nonane-3-carbonyl)-phenyl]-pyrrolidin-3-yl}-N-methyl-acetamide |

-continued

| Ex. | Structure | LC/MS [M + 1]+ | IUPAC Name |
|---|---|---|---|
| 1-31 | 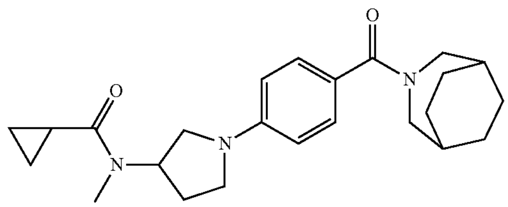 [SMILES: CN(C(=O)C1CC1)C1CCN(c2ccc(C(=O)N3CC4CCC(CC4)C3)cc2)C1] | 395.5 | Cyclopropanecarboxylic acid {1-[4-(3-aza-bicyclo[3.2.2]-nonane-3-carbonyl)-phenyl]-pyrrolidin-3-yl}-methyl-amide |
| 1-32 | 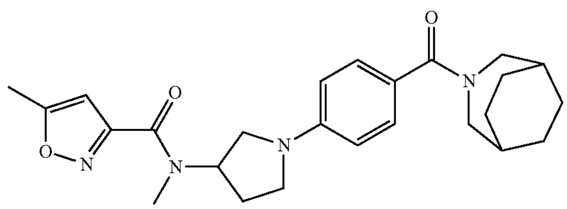 [SMILES: Cc1cc(C(=O)N(C)C2CCN(c3ccc(C(=O)N4CC5CCC(CC5)C4)cc3)C2)no1] | 436.6 | 5-Methyl-isoxazole-3-carboxylic acid {1-[4-(3-aza-bicyclo-[3.2.2]nonane-3-carbonyl)-phenyl]-pyrrolidin-3-yl}-methyl-amide |
| 1-33 | 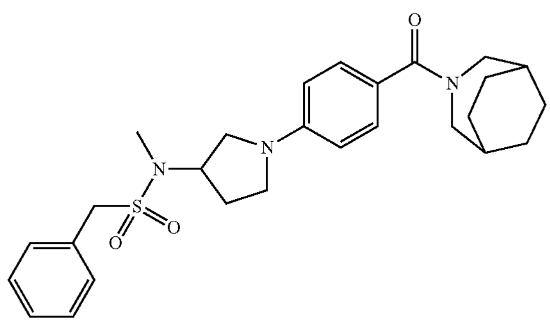 [SMILES: CN(C1CCN(c2ccc(C(=O)N3CC4CCC(CC4)C3)cc2)C1)S(=O)(=O)Cc1ccccc1] | 481.7 | N-{1-[4-(3-Aza-bicyclo[3.2.2]-nonane-3-carbonyl)-phenyl]-pyrrolidin-3-yl}-N-methyl-phenyl-methanesulfonamide |
| 1-34 | 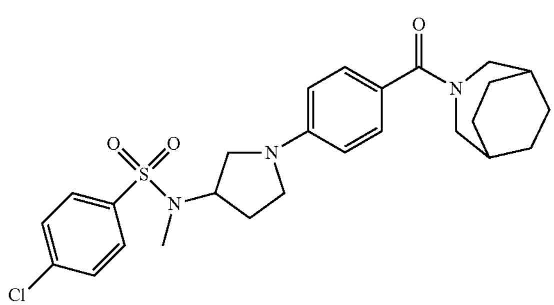 [SMILES: CN(C1CCN(c2ccc(C(=O)N3CC4CCC(CC4)C3)cc2)C1)S(=O)(=O)c1ccc(Cl)cc1] | 502.1 | N-{1-[4-(3-Aza-bicyclo[3.2.2]-nonane-3-carbonyl)-phenyl]-pyrrolidin-3-yl}-4-chloro-N-methyl-benzenesulfonamide |
| 1-35 | 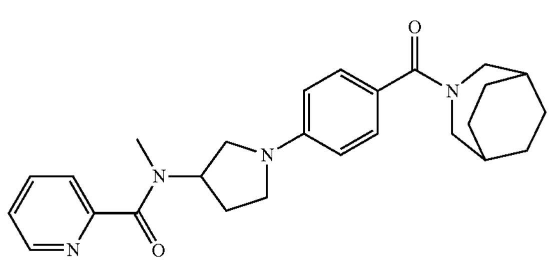 [SMILES: CN(C(=O)c1ccccn1)C1CCN(c2ccc(C(=O)N3CC4CCC(CC4)C3)cc2)C1] | 432.6 | Pyridine-2-carboxylic acid {1-[4-(3-aza-bicyclo[3.2.2]nonane-3-carbonyl)-phenyl]-pyrrolidin-3-yl}-methyl-amide |

-continued

| Ex. | Structure | LC/MS [M + 1]+ | IUPAC Name |
|---|---|---|---|
| 1-36 | 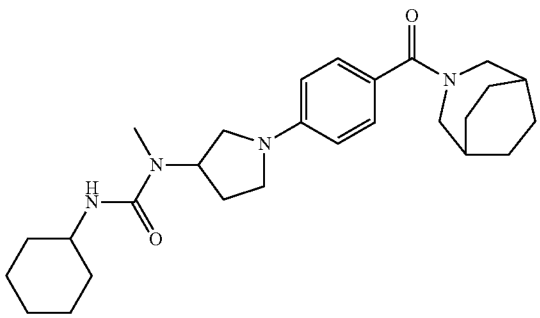 [SMILES: CN(C(=O)NC1CCCCC1)C1CCN(c2ccc(C(=O)N3CC4CCC(CC4)C3)cc2)C1] | 452.6 | 1-{1-[4-(3-Aza-bicyclo[3.2.2]-nonane-3-carbonyl)-phenyl]-pyrrolidin-3-yl}-3-cyclohexyl-1-methyl-urea |
| 1-37 | 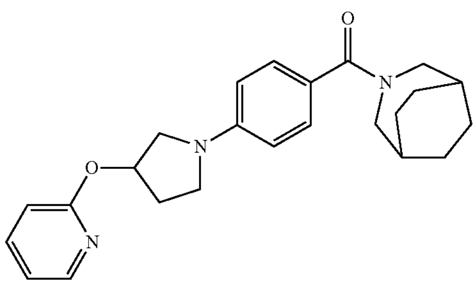 [SMILES: O=C(c1ccc(N2CCC(Oc3ccccn3)C2)cc1)N1CC2CCC(CC2)C1] | 391.5 | (3-Aza-bicyclo[3.2.2]non-3-yl)-{4-[3-(pyridin-2-yloxy)-pyrrolidin-1-yl]-phenyl}-methanone |
| 1-38 | 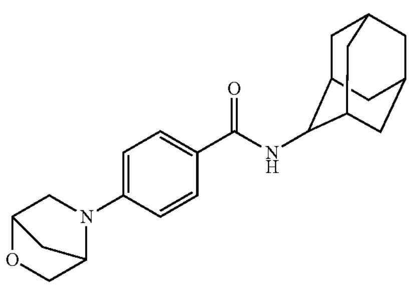 [SMILES: O=C(NC1C2CC3CC(C2)CC1C3)c1ccc(N2CC3CC2CO3)cc1] | 352.5 | 4-(2-Oxa-5-aza-bicyclo[2.2.1]-hept-5-yl)-N-adamantan-2-yl-benzamide |
| 1-39 | 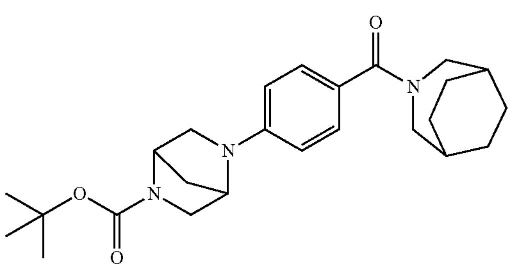 [SMILES: CC(C)(C)OC(=O)N1CC2CC1CN2c1ccc(C(=O)N2CC3CCC(CC3)C2)cc1] | 427 | 5-[4-(3-Aza-bicyclo[3.2.2]-nonane-3-carbonyl)-phenyl]-2,5-diaza-bicyclo[2.2.1]-heptane-2-carboxylic acid tert-butyl ester |
| 1-40 | 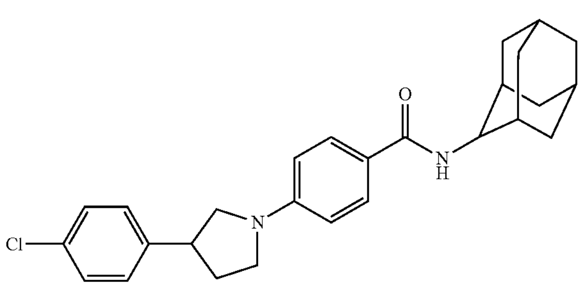 [SMILES: O=C(NC1C2CC3CC(C2)CC1C3)c1ccc(N2CCC(c3ccc(Cl)cc3)C2)cc1] | 435 | 4-[3-(4-Chloro-phenyl)-pyrrolidin-1-yl]-N-adamantan-2-yl-benzamide |

-continued

| Ex. | Structure | LC/MS [M + 1]+ | IUPAC Name |
|---|---|---|---|
| 1-41 | 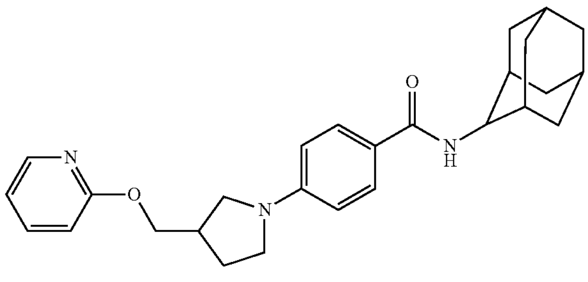 | 431.6 | 4-[3-(Pyridin-2-yloxymethyl)-pyrrolidin-1-yl]-N-adamantan-2-yl-benzamide |
| 1-42 | 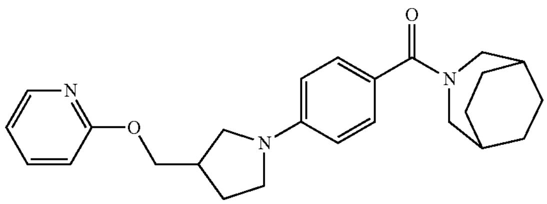 [SMILES: O=C(c1ccc(N2CCC(COc3ccccn3)C2)cc1)N1CC2CCC(CC2)C1] | 405.5 | (3-Aza-bicyclo[3.2.2]non-3-yl)-{4-[3-(pyridin-2-yloxymethyl)-pyrrolidin-1-yl]-phenyl}-methanone |
| 1-43 | 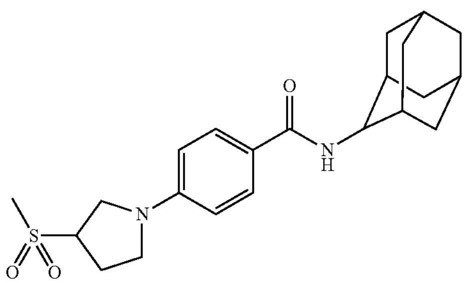 [SMILES: CS(=O)(=O)C1CCN(c2ccc(C(=O)NC3C4CC5CC(C4)CC3C5)cc2)C1] | 402.6 | 4-(3-Methanesulfonyl-pyrrolidin-1-yl)-N-adamantan-2-yl-benzamide |
| 1-44 | 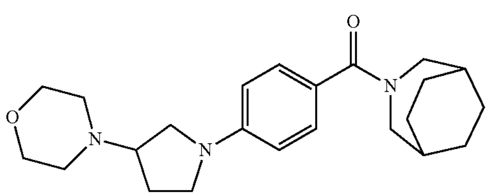 [SMILES: O=C(c1ccc(N2CCC(N3CCOCC3)C2)cc1)N1CC2CCC(CC2)C1] | 383.5 | (3-Aza-bicyclo[3.2.2]non-3-yl)-[4-(3-morpholin-4-yl-pyrrolidin-1-yl)-phenyl]-methanone |
| 1-45 | 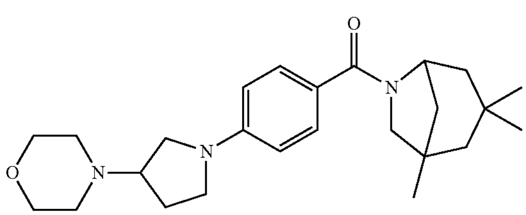 [SMILES: CC1(C)CC2CC(C)(CN2C(=O)c2ccc(N3CCC(N4CCOCC4)C3)cc2)C1] | 411.6 | [4-(3-Morpholin-4-yl-pyrrolidin-1-yl)-phenyl]-(1,3,3-trimethyl-6-aza-bicyclo[3.2.1]oct-6-yl)-methanone |
| 1-46 | 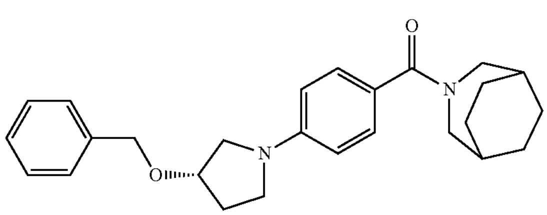 [SMILES: O=C(c1ccc(N2CC[C@H](OCc3ccccc3)C2)cc1)N1CC2CCC(CC2)C1] | 404.6 | (S)-(3-Aza-bicyclo[3.2.2]non-3-yl)-[4-(3-benzyloxy-pyrrolidin-1-yl)-phenyl]-methanone |

-continued

| Ex. | Structure | LC/MS [M + 1]+ | IUPAC Name |
|---|---|---|---|
| 1-47 | 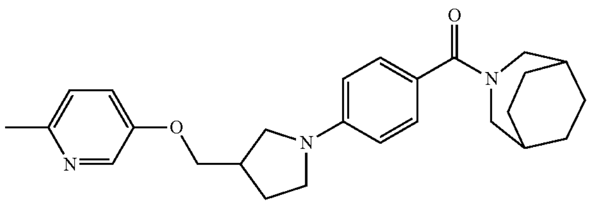 [SMILES: Cc1ccc(OCC2CCN(c3ccc(C(=O)N4CC5CCC(CC5)C4)cc3)C2)cn1] | 419.6 | (3-Aza-bicyclo[3.2.2]non-3-yl)-{4-[3-(6-methyl-pyridin-3-yloxymethyl)-pyrrolidin-1-yl]-phenyl}-methanone |
| 1-48 | 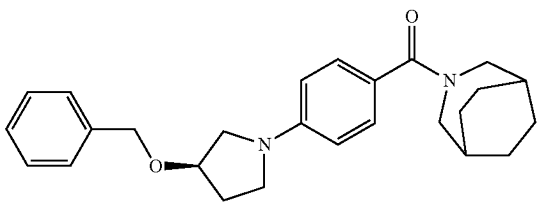 [SMILES: O=C(c1ccc(N2CC[C@@H](OCc3ccccc3)C2)cc1)N1CC2CCC(CC2)C1] | 404.6 | (3-Aza-bicyclo[3.2.2]non-3-yl)-[4-((R)-3-benzyloxy-pyrrolidin-1-yl)-phenyl]-methanone |
| 1-49 | 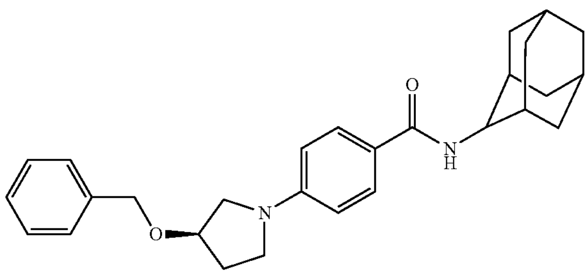 [SMILES: O=C(NC1C2CC3CC(C2)CC1C3)c1ccc(N2CC[C@@H](OCc3ccccc3)C2)cc1] | 432 | N-Adamantan-2-yl-4-((R)-3-benzyloxy-pyrrolidin-1-yl)-benzamide |
| 1-50 | 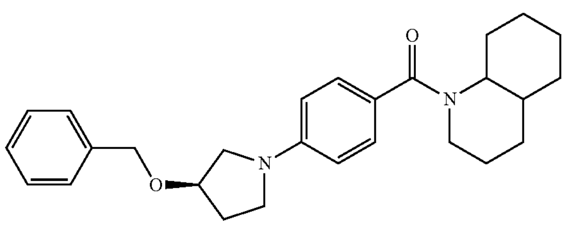 [SMILES: O=C(c1ccc(N2CC[C@@H](OCc3ccccc3)C2)cc1)N1CCCC2CCCCC21] | 420 | [4-((R)-3-Benzyloxy-pyrrolidin-1-yl)-phenyl]-(octahydro-quinolin-1-yl)-methanone |
| 1-51 | 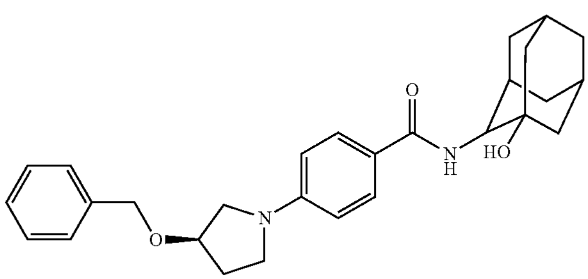 [SMILES: O=C(NC1C2CC3CC(C2)CC1(O)C3)c1ccc(N2CC[C@@H](OCc3ccccc3)C2)cc1] | 448 | 4-((R)-3-Benzyloxy-pyrrolidin-1-yl)-N-(1-hydroxy-adamantan-2-yl)-benzamide |
| 1-52 | 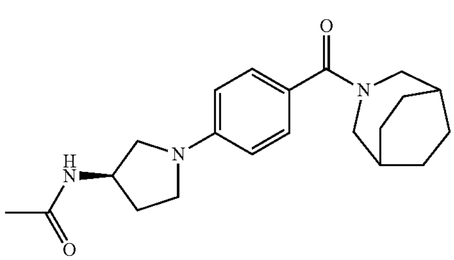 [SMILES: CC(=O)N[C@@H]1CCN(c2ccc(C(=O)N3CC4CCC(CC4)C3)cc2)C1] | 355.5 | N-{(R)-1-[4-(3-Aza-bicyclo-[3.2.2]nonane-3-carbonyl)-phenyl]-pyrrolidin-3-yl}-acetamide |

-continued

| Ex. | Structure | LC/MS [M + 1]+ | IUPAC Name |
|---|---|---|---|
| 1-53 | 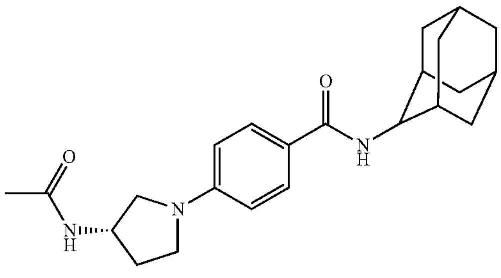 [SMILES: CC(=O)N[C@H]1CCN(c2ccc(C(=O)NC3C4CC5CC(C4)CC3C5)cc2)C1] | 383 | 4-((S)-3-Acetylamino-pyrrolidin-1-yl)-N-adamantan-2-yl-benzamide |
| 1-54 | 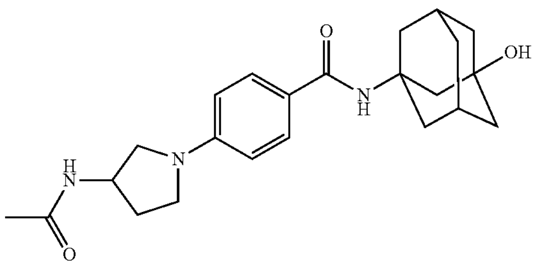 [SMILES: CC(=O)NC1CCN(c2ccc(C(=O)NC34CC5CC(CC(O)(C5)C3)C4)cc2)C1] | 399 | 4-(3-Acetylamino-pyrrolidin-1-yl)-N-(3-hydroxy-adamantan-1-yl)-benzamide |
| 1-55 | 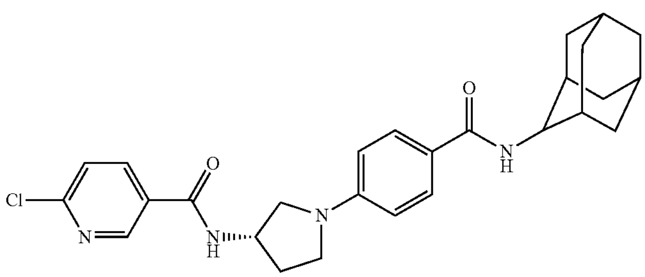 [SMILES: O=C(NC1C2CC3CC(C2)CC1C3)c1ccc(N2CC[C@H](NC(=O)c3ccc(Cl)nc3)C2)cc1] | 480 | N-{(S)-1-[4-(Adamantan-2-ylcarbamoyl)-phenyl]-pyrrolidin-3-yl}-6-chloro-nicotinamide |
| 1-56 | 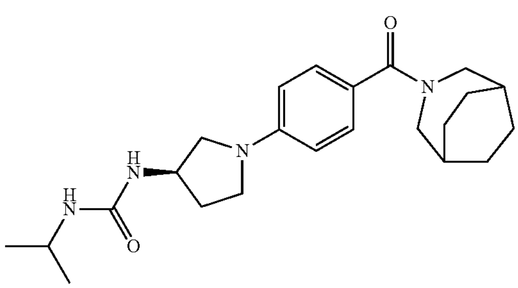 [SMILES: CC(C)NC(=O)N[C@@H]1CCN(c2ccc(C(=O)N3CC4CCC(CC4)C3)cc2)C1] | 398.6 | 1-{(R)-1-[4-(3-Aza-bicyclo-[3.2.2]nonane-3-carbonyl)-phenyl]-pyrrolidin-3-yl}-3-isopropyl-urea |
| 1-57 | 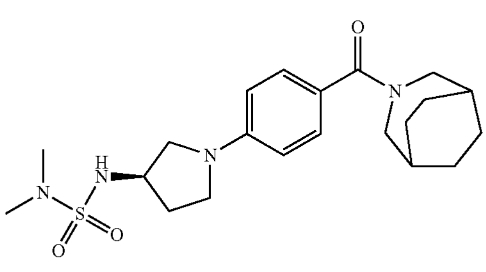 [SMILES: CN(C)S(=O)(=O)N[C@@H]1CCN(c2ccc(C(=O)N3CC4CCC(CC4)C3)cc2)C1] | 420.6 | 1-{(R)-1-[4-(3-Aza-bicyclo-[3.2.2]nonane-3-carbonyl)-phenyl]-pyrrolidin-3-yl}-3-N,N-dimethyl-sulfamide |

-continued

| Ex. | Structure | LC/MS [M + 1]+ | IUPAC Name |
|---|---|---|---|
| 1-58 | 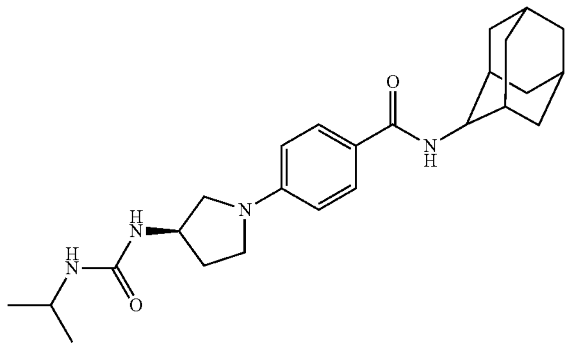 [SMILES: CC(C)NC(=O)N[C@@H]1CCN(c2ccc(C(=O)NC3C4CC5CC(C4)CC3C5)cc2)C1] | 424.6 | 4-[(R)-3-(3-Isopropyl-ureido)-pyrrolidin-1-yl]-N-adamantan-2-yl-benzamide |
| 1-59 | 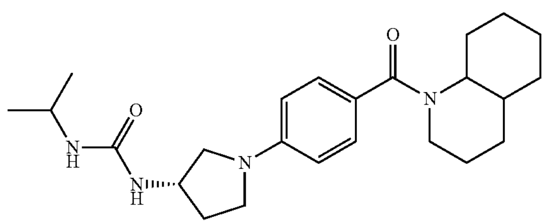 [SMILES: CC(C)NC(=O)N[C@H]1CCN(c2ccc(C(=O)N3CCCC4CCCCC43)cc2)C1] | 414 | 1-Isopropyl-3-{(S)-1-[4-(octahydro-quinoline-1-carbonyl)-phenyl]-pyrrolidin-3-yl}-urea |
| 1-60 | 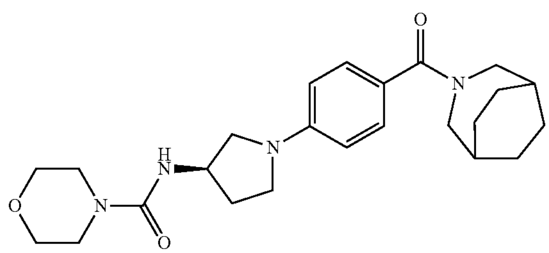 [SMILES: O=C(N[C@@H]1CCN(c2ccc(C(=O)N3CC4CCC(CC4)C3)cc2)C1)N1CCOCC1] | 426.6 | Morpholine-4-carboxylic acid {(R)-1-[4-(3-aza-bicyclo[3.2.2]-nonane-3-carbonyl)-phenyl]-pyrrolidin-3-yl}-amide |
| 1-61 | 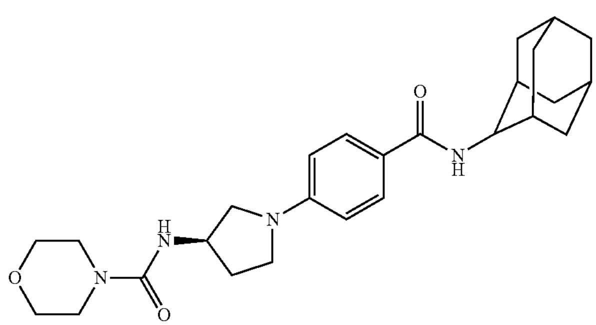 [SMILES: O=C(NC1C2CC3CC(C2)CC1C3)c1ccc(N2CC[C@@H](NC(=O)N3CCOCC3)C2)cc1] | 452.6 | Morpholine-4-carboxylic acid {(R)-1-[4-(adamantan-2-ylcarbamoyl)-phenyl]-pyrrolidin-3-yl}-amide |
| 1-62 | 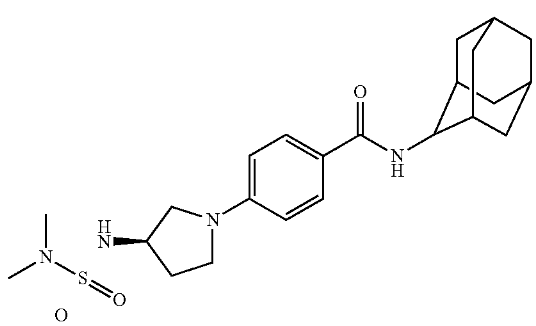 | 446.6 | 1-{(R)-1-[4-(adamantan-2-yl-phenyl]-pyrrolidin-3-yl}-3-N,N-dimethyl-sulfamide |

| Ex. | Structure | LC/MS [M + 1]+ | IUPAC Name |
|---|---|---|---|
| 1-63 | 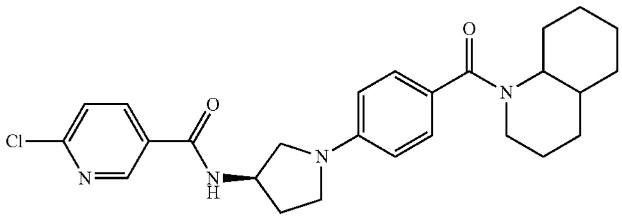 [SMILES: O=C(N[C@@H]1CCN(c2ccc(C(=O)N3CCCC4CCCCC43)cc2)C1)c1ccc(Cl)nc1] | 467.0 | 6-Chloro-N-{(R)-1-[4-(octa-hydro-quinoline-1-carbonyl)-phenyl]-pyrrolidin-3-yl}-nicotinamide |
| 1-64 | 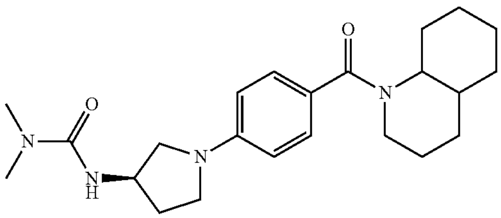 [SMILES: CN(C)C(=O)N[C@@H]1CCN(c2ccc(C(=O)N3CCCC4CCCCC43)cc2)C1] | 398.6 | 1,1-Dimethyl-3-{(R)-1-[4-(octa-hydro-quinoline-1-carbonyl)-phenyl]pyrrolidin-3-yl}-urea |
| 1-65 | 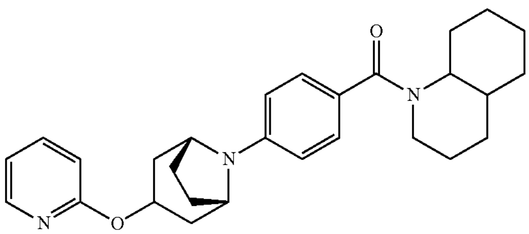 [SMILES: O=C(c1ccc(N2[C@@H]3CC[C@H]2CC(Oc2ccccn2)C3)cc1)N1CCCC2CCCCC21] | 447 | (Octahydro-quinolin-1-yl)-{4-[(1S,5R)-3-(pyridin-2-yloxy)-8-aza-bicyclo[3.2.1]oct-8-yl]-phenyl}-methanone |
| 1-66 | 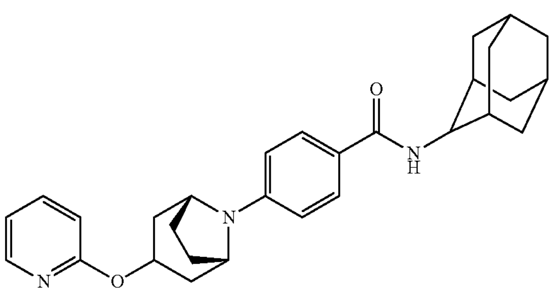 [SMILES: O=C(NC1C2CC3CC(C2)CC1C3)c1ccc(N2[C@@H]3CC[C@H]2CC(Oc2ccccn2)C3)cc1] | 459 | N-Adamantan-2-yl-4-[(1S,5R)-3-(pyridin-2-yloxy)-8-aza-bicyclo[3.2.1]oct-8-yl]-benzamide |
| 1-67 | 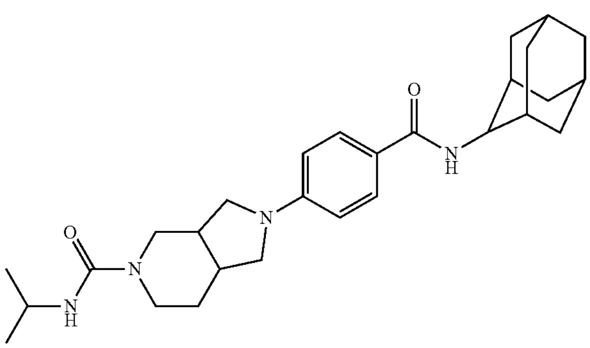 [SMILES: CC(C)NC(=O)N1CCC2CN(c3ccc(C(=O)NC4C5CC6CC(C5)CC4C6)cc3)CC2C1] | 466 | 2-[4-(Adamantan-2-yl-carbamoyl)-phenyl]-octahydro-pyrrolo[3,4-c]pyridine-5-carboxylic acid isopropylamide |

Pharmacological Methods

11βHSD1 Enzyme Assay

Materials

³H-cortisone and anti-rabbit Ig coated scintillation proximity assay (SPA) beads were purchased from Amersham Pharmacia Biotech, β-NADPH was from Sigma and rabbit anti-cortisol antibodies were from Fitzgerald. An extract of yeast transformed with h-11βHSD1 (Hutt et al., FEBS Lett., 441, 25 (1998)) was used as the source of enzyme. The test compounds were dissolved in DMSO (10 mM). All dilutions were performed in a buffer containing 50 mM TRIS-HCl (Sigma Chemical Co), 4 mM EDTA (Sigma Chemical Co), 0.1% BSA (Sigma Chemical Co), 0.01% Tween-20 (Sigma Chemical Co) and 0.005% bacitracin (Novo Nordisk A/S), pH=7.4. Optiplate 96 wells plates were supplied by Packard. The amount of $^3$H-cortisol bound to the SPA beads was measured on Top-Count NXT, Packard.

Methods h-11βHSD1, 120 nM $^3$H-cortisone, 4 mM (3-NADPH, antibody (1:200), serial dilutions of test compound and SPA particles (2 mg/well) were added to the wells. The reaction was initiated by mixing the different components and was allowed to proceed under shaking for 60 min at 30° C. The reaction was stopped be the addition of 10 fold excess of a stopping buffer containing 500 μM carbenoxolone and 1 μM cortisone. Data was analysed using GraphPad Prism software.

TABLE 1

Inhibition of h-11βHSD1 by compounds of the invention

| Example No. | h-11βHSD1 IC$_{50}$ values (nM) |
|---|---|
| 1-7 | 125 |
| 1-31 | 128 |
| 1-33 | 43 |

While the invention has been described and illustrated with reference to certain preferred embodiments thereof, those skilled in the art will appreciate that various changes, modifications, and substitutions can be made therein without departing from the spirit and scope of the present invention. For example, effective dosages other than the preferred dosages as set forth herein may be applicable as a consequence of variations in the responsiveness of the mammal being treated. Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention. Accordingly, the invention is not to be limited as by the appended claims.

The features disclosed in the foregoing description and/or in the claims may both separately and in any combination thereof be material for realising the invention in diverse forms thereof.

Preferred Features of the Invention:
1. A compound of the general formula I:

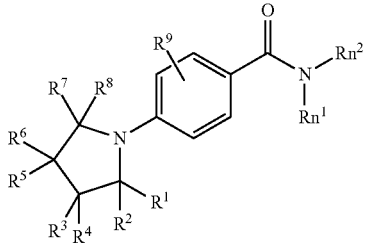

I wherein:
$R^1$, $R^2$, $R^3$, $R^4$, $R^5$, $R^6$, $R^7$ and $R^8$ are each independently selected from H, halo, $C_2$-$C_{10}$-alkenyl, $C_2$-$C_{10}$alkynyl, $NR^{10}R^{11}$, $C(O)R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy-$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$; or $R^2$, $R^3$, $R^4$, $R^6$, $R^7$ and $R^8$ are each independently selected from H, halo, $C_2$-$C_{10}$alkenyl, $C_2$-$C_{10}$alkynyl, $NR^{10}R^{11}$, $C(O)R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cyclo-alkyloxy$C_1$-$C_6$alkyl, and $C_3$-$C_{10}$-hetcycloalkyloxy$C_1$-$C_6$alkyl, wherein each alkyl, cykloalkyl, hetcycloalkyl, and aryl/hetaryl group is substituted with 0-3 $R^{18}$; and $R^1$ and $R^5$ together with the carbons to which they are attached form a 4-8 membered saturated, partially saturated or aromatic ring consisting of 2-8 carbon atoms, and 0-2 additional heteroatoms selected from nitrogen, oxygen, and $S(O)_n$, wherein this ring is substituted with 0-3 groups selected from fluoro, $C_1$-$C_6$alkyl, $C_3$-$C_{10}$-cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, —$C(O)R^{12}$, —$S(O)_nR^{12}$, —$S(O)_nNR^{14}R^{15}$, —$N(R^{14})S(O)_nR^{12}$, —$N(R^{16})C(=Y)NR^{14}R^{15}$, —$C(=NR^{17})NR^{17}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, and aryl/hetaryl group is substituted with 0-3 $R^{18}$; or $R^2$, $R^3$, $R^4$, $R^5$, $R^6$ and $R^8$ are each independently selected from H, halo, $C_2$-$C_{10}$alkenyl, $C_2$-$C_{10}$alkynyl, $NR^{10}R^{11}$, $C(O)R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cyclo-alkyloxy$C_1$-$C_6$alkyl, and $C_3$-$C_{10}$-hetcycloalkyloxy$C_1$-$C_6$alkyl, wherein each alkyl, cykloalkyl, hetcycloalkyl, and aryl/hetaryl group is substituted with 0-3 $R^{18}$; and $R^1$ and $R^7$ together with the carbons to which they are attached form a 4-8 membered saturated, partially saturated or aromatic ring consisting of 2-8 carbon atoms, and 0-2 additional heteroatoms selected from nitrogen, oxygen, and $S(O)_n$, wherein this ring is substituted with 0-3 groups selected from fluoro, $C_1$-$C_6$alkyl, $C_3$-$C_{10}$-cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, —$C(O)R^{12}$, —$S(O)_nR^{12}$, —$S(O)_nNR^{14}R^{15}$, —$N(R^{14})S(O)_nR^{12}$, —$N(R^{16})C(=Y)NR^{14}R^{15}$, —$C(=NR^{17})NR^{17}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, and aryl/hetaryl group is substituted with 0-3 $R^{18}$; or $R^1$, $R^2$, $R^3$, $R^6$, $R^7$ and $R^8$ are each independently selected from H, halo, $C_2$-$C_{10}$alkenyl, $C_2$-$C_{10}$alkynyl, $NR^{10}R^{11}$, $C(O)R^{12}$, $R^{13}S(O)_n$, $R^{13}C(O)NR^{10}$, $R^{10}R^{11}NS(O)_n$, $R^{13}S$ $(O)_n NR^{10}$, aryl, hetaryl, aryloxy, hetaryloxy, arylC$_1$-C$_6$alkyl, hetarylC$_1$-C$_6$alkyl, arylC$_1$-C$_6$alkyloxy, hetarylC$_1$-C$_6$alkyloxy, C$_3$-C$_{10}$cycloalkyl, C$_3$-C$_{10}$cycloalkyloxy, C$_3$-C$_{10}$cycloalkylC$_1$-C$_6$alkyloxy, C$_3$-C$_{10}$hetcycloalkyl, C$_3$-C$_{10}$hetcycloalkyloxy, aryloxyC$_1$-C$_6$alkyl, hetaryloxyC$_1$-C$_6$alkyl, C$_3$-C$_{10}$cyclo-alkyloxyC$_1$-C$_6$alkyl, and C$_3$-C$_{10}$-hetcycloalkyloxyC$_1$-C$_6$alkyl, wherein each alkyl, cykloalkyl, hetcycloalkyl, and aryl/hetaryl group is substituted with 0-3 R$^{18}$; and R$^4$ and R$^5$ together with the carbons to which they are attached form a 4-8 membered saturated, partially saturated or aromatic ring consisting of 2-8 carbon atoms, and 0-2 additional heteroatoms selected from nitrogen, oxygen, and S(O)$_n$, wherein this ring is substituted with 0-3 groups selected from fluoro, C$_1$-C$_6$alkyl, C$_3$-C$_{10}$cycloalkyl, C$_3$-C$_{10}$hetcycloalkyl, C$_3$-C$_6$spirocycloalkyl, 3-6 membered spirohetcycloalkyl, aryl, hetaryl, arylC$_1$-C$_6$alkyl, hetarylC$_1$-C$_6$alkyl, —C(O)R$^{12}$, —S(O)$_n$R$^{12}$, —S(O)$_n$NR$^{14}$R$^{15}$, —N(R$^{14}$)S(O)$_n$R$^{12}$, —N(R$^{16}$)C(=Y)NR$^{14}$R$^{15}$, —C(=NR$^{17}$)NR$^{17}$, OH, oxo, C$_1$-C$_6$alkyloxy, arylC$_1$-C$_6$alkyloxy, hetarylC$_1$-C$_6$alkyloxy, C$_1$-C$_6$alkyloxyC$_1$-C$_6$alkyl, C$_1$-C$_6$alkylcarboxy, arylcarboxy, hetarylcarboxy, arylC$_1$-C$_6$alkylcarboxy, and hetarylC$_1$-C$_6$alkylcarboxy, wherein each alkyl, and aryl/hetaryl group is substituted with 0-3 R$^{18}$;

R$^9$ is selected from H, halo, OH, cyano, C$_1$-C$_6$alkyl, C$_1$-C$_6$alkyloxy, trihalomethyloxy and C$_3$-C$_6$cycloalkyl;

R$^{10}$ and R$^{11}$ are each independently selected from H, C$_1$-C$_6$alkyl, C$_1$-C$_6$alkylcarbonyl, C(O)OC$_1$-C$_6$alkyl, aryl, hetaryl, arylC$_1$-C$_6$alkyl, hetarylC$_1$-C$_6$alkyl, C$_3$-C$_{10}$cycloalkyl, C$_3$-C$_{10}$hetcycloalkyl, arylcarbonyl, hetarylcarbonyl, arylC$_1$-C$_6$alkylcarbonyl, hetarylC$_1$-C$_6$alkylcarbonyl, C$_3$-C$_{10}$cycloalkylcarbonyl and C$_3$-C$_{10}$hetcycloalkyl-carbonyl, wherein each alkyl, cykloalkyl, hetcycloalkyl, and aryl/hetaryl group is substituted with 0-3 R$^{18}$;

alternatively, R$^{10}$ and R$^{11}$, together with the nitrogen to which they are attached, form a 3-12 membered saturated or partially saturated monocyclic or bicyclic ring consisting of the shown nitrogen, 2-10 carbon atoms, and 0-2 additional heteroatoms selected from nitrogen, oxygen, and S(O)$_n$, wherein this ring is substituted with 0-3 groups selected from halo, C$_1$-C$_6$alkyl, C$_3$-C$_{10}$cycloalkyl, C$_3$-C$_{10}$hetcycloalkyl, C$_3$-C$_6$spirocycloalkyl, 3-6 membered spirohetcycloalkyl, aryl, hetaryl, arylC$_1$-C$_6$-alkyl, hetarylC$_1$-C$_6$alkyl, —C(O)R$^{12}$, —S(O)$_n$R$^{12}$, —S(O)$_n$NR$^{14}$R$^{15}$, —N(R$^{14}$)S(O)$_n$R$^{12}$, —N(R$^{16}$)C(=Y)NR$^{14}$R$^{15}$, —C(=NR$^{17}$)NR$^{17}$, OH, oxo, C$_1$-C$_6$alkyloxy, arylC$_1$-C$_6$alkyloxy, hetarylC$_1$-C$_6$alkyloxy, C$_1$-C$_6$alkyloxyC$_1$-C$_6$alkyl, C$_1$-C$_6$alkylcarboxy, arylcarboxy, hetarylcarboxy, arylC$_1$-C$_6$alkylcarboxy, and hetarylC$_1$-C$_6$alkylcarboxy, wherein each alkyl, and aryl/hetaryl group is substituted with 0-3 R$^{18}$;

R$^{12}$ is OH, NR$^{10}$R$^{11}$, C$_1$-C$_6$alkyloxy, C$_2$-C$_6$alkenyloxy, C$_2$-C$_6$alkynyloxy, C$_3$-C$_{10}$cycloalkyl, C$_3$-C$_{10}$cycloalkyloxy, C$_3$-C$_{10}$hetcycloalkyloxy, aryloxy, hetaryloxy, arylC$_1$-C$_6$alkyloxy, hetarylC$_1$-C$_6$alkyloxy;

R$^{13}$ is C$_1$-C$_6$alkyl, C$_2$-C$_6$alkenyl, C$_2$-C$_6$alkynyl, NR$^{10}$R$^{11}$, aryl, hetaryl, arylC$_1$-C$_6$alkyl, hetarylC$_1$-C$_6$alkyl, C$_3$-C$_{10}$cycloalkyl, C$_3$-C$_{10}$hetcycloalkyl, aryloxyC$_1$-C$_6$alkyl, hetaryloxyC$_1$-C$_6$alkyl, C$_3$-C$_{10}$cycloalkyloxyC$_1$-C$_6$alkyl, and C$_3$-C$_{10}$hetcycloalkyloxyC$_1$-C$_6$-alkyl, wherein each alkyl, cykloalkyl, hetcycloalkyl, and aryl/hetaryl group is substituted with 0-3 R$^{18}$;

R$^{14}$ and R$^{15}$ are independently selected from H, C$_1$-C$_6$alkyl, C$_1$-C$_6$alkyloxy, aryl, hetaryl, arylC$_1$-C$_6$alkylene, and hetarylC$_1$-C$_6$alkylene, wherein the alkyl/alkylene, aryl, and hetaryl groups are independently substituted with 0-3 R$^{20}$;

alternatively, R$^{14}$ and R$^{15}$, together with the nitrogen atom to which they are attached, form a saturated or partially saturated monocyclic, bicyclic, or tricyclic ring consisting of the shown nitrogen, 4-10 carbon atoms, and 0-2 additional heteroatoms selected from nitrogen, oxygen, and sulfur, wherein this ring is substituted with 0-3 C$_1$-C$_6$alkyl, aryl, hetaryl, arylC$_1$-C$_6$alkylene, hetarylC$_1$-C$_6$alkylene, hydroxy, oxo, C$_1$-C$_6$alkyloxy, arylC$_1$-C$_6$alkyloxy, hetarylC$_1$-C$_6$alkyloxy, C$_1$-C$_6$alkyloxyC$_1$-C$_6$alkyl, C$_1$-C$_6$alkylcarbonyl, arylcarbonyl, hetarylcarbonyl, arylC$_1$-C$_6$alkylcarbonyl, hetarylC$_1$-C$_6$alkylcarbonyl, C$_1$-C$_6$alkylcarboxy, arylcarboxy, hetarylcarboxy, arylC$_1$-C$_6$alkyl-carboxy, and hetarylC$_1$-C$_6$alkylcarboxy;

R$^{16}$ is selected from H and C$_1$-C$_6$alkyl;

R$^{17}$ is selected from H, C$_1$-C$_6$alkyl, 3-10 membered cycloalkyl, halo, OH, cyano, —C(=O)R$^{12}$, —S(=O)$_n$R$^{12}$, S(=O)$_n$NR$^{14}$R$^{15}$, —N(R$^{14}$)S(=O)$_n$R$^{12}$, aryl, and hetaryl, wherein the alkyl and cycloalkyl groups are substituted with 0-3 R$^{20}$;

R$^{18}$ is selected from halo, OH, oxo, COOH, S(O)$_2$R$^{12}$, C(=O)OC$_1$-C$_6$alkyl, cyano, C$_1$-C$_1$-C$_6$alkyloxy, C$_3$-C$_{10}$cycloalkyloxy, aryloxy, hetaryloxy, hetarylthio, and arylC$_1$-C$_6$alkyloxy;

R$^{20}$ is selected from H, OH, oxo, halo, cyano, nitro, C$_1$-C$_6$alkyl, C$_1$-C$_6$alkyloxy, NR$^{21}$R$^{22}$, methylendioxo, dihalomethylendioxo, trihalomethyl, and trihalomethyloxy;

R$^{21}$ and R$^{22}$ are independently selected from H, C$_1$-C$_6$alkyl, and arylC$_1$-C$_6$alkyl;

Rn$^1$ and Rn$^2$ are each independently selected from H, C$_1$-C$_6$alkyl, arylC$_1$-C$_6$alkyl, hetaryl-C$_1$-C$_6$alkyl, C$_3$-C$_{12}$cycloalkyl, C$_3$-C$_{10}$hetcycloalkyl, wherein each alkyl, cycloalkyl, hetcycloalkyl, and aryl/hetaryl group is substituted with 0-3 R$^{18}$;

alternatively, Rn$^1$ and Rn$^2$, together with the nitrogen to which they are attached, form a 5-12 membered saturated or partially saturated monocyclic or bicyclic ring consisting of the shown nitrogen, 4-11 carbon atoms, and 0-2 additional heteroatoms selected from nitrogen, oxygen, and S(O)$_n$, wherein the ring is substituted with 0-3 groups selected from halo, trihalomethyl, trihalomethyloxy, cyano, C$_1$-C$_6$alkyl, C$_3$-C$_{10}$cycloalkyl, —C(O)R$^{12}$, —S(O)$_n$R$^{12}$, —S(O)$_n$NR$^{14}$R$^{16}$, —N(R$^{14}$)S(O)$_n$R$^{12}$, OH, oxo, C$_1$-C$_6$alkyloxy, arylC$_1$-C$_6$alkyloxy, hetarylC$_1$-C$_6$alkyloxy, and C$_1$-C$_6$alkyloxy-C$_1$-C$_6$alkyl, wherein each alkyl, and aryl/hetaryl group is substituted with 0-3 R$^{18}$;

n is selected from 0, 1 and 2; or a salt thereof with a pharmaceutically acceptable acid or base, or any optical isomer or mixture of optical isomers, including a racemic mixture, or any tautomeric forms.

2. A compound according to clause 1:

wherein:

R$^1$, R$^2$, R$^3$, R$^4$, R$^5$, R$^6$, R$^7$ and R$^8$ are each independently selected from H, halo, C$_2$-C$_{10}$-alkenyl, C$_2$-C$_{10}$alkynyl, NR$^{10}$R$^{11}$, C(O)R$^{12}$, R$^{13}$S(O)$_n$, R$^{13}$C(O)NR$^{10}$, R$^{10}$R$^{11}$NS(O)$_n$, R$^{13}$S(O)$_n$NR$^{10}$, aryl, hetaryl, aryloxy, hetaryloxy, arylC$_1$-C$_6$alkyl, hetarylC$_1$-C$_6$alkyl, arylC$_1$-C$_6$alkyloxy, hetarylC$_1$-C$_6$alkyloxy, C$_3$-C$_{10}$cycloalkyl, C$_3$-C$_{10}$cycloalkyloxy, C$_3$-C$_{10}$cycloalkylC$_1$-C$_6$alkyloxy, C$_3$-C$_{10}$hetcycloalkyl, C$_3$-C$_{10}$hetcycloalkyloxy, aryloxy-C$_1$-C$_6$alkyl, hetaryloxyC$_1$-C$_6$alkyl, C$_3$-C$_{10}$cycloalkyloxyC$_1$-C$_6$alkyl, and C$_3$-C$_{10}$ hetcycloalkyloxy$C_1$-$C_6$alkyl, wherein each alkyl, cykloalkyl, hetcycloalkyl, and aryl/hetaryl group is substituted with 0-3 $R^{18}$; or $R^1$, $R^2$, $R^3$, $R^6$, $R^7$ and $R^8$ are each independently selected from H, halo, $C_2$-$C_{10}$alkenyl, $C_2$-$C_{10}$alkynyl, $NR^{10}R^{11}$, $C(O)R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cyclo-alkyloxy$C_1$-$C_6$alkyl, and $C_3$-$C_{10}$-hetcycloalkyloxy$C_1$-$C_6$alkyl, wherein each alkyl, cykloalkyl, hetcycloalkyl, and aryl/hetaryl group is substituted with 0-3 $R^{18}$; and $R^4$ and $R^5$ together with the carbons to which they are attached form a 4-8 membered saturated, partially saturated or aromatic ring consisting of 2-8 carbon atoms, and 0-2 additional heteroatoms selected from nitrogen, oxygen, and $S(O)_n$, wherein this ring is substituted with 0-3 groups selected from fluoro, $C_1$-$C_6$alkyl, $C_3$-$C_{10}$-cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, —$C(O)R^{12}$, —$S(O)_nR^{12}$, —$S(O)_nNR^{14}R^{15}$, —$N(R^{14})S(O)_nR^{12}$, —$N(R^{16})C(=Y)NR^{14}R^{15}$, —$C(=NR^{17})NR^{17}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, and aryl/hetaryl group is substituted with 0-3 $R^{18}$;

$R^9$ is selected from H, halo, OH, cyano, $C_1$-$C_6$alkyl, $C_1$-$C_6$alkyloxy, trihalomethyloxy and $C_3$-$C_6$cycloalkyl;

$R^{10}$ and $R^{11}$ are each independently selected from H, $C_1$-$C_6$alkyl, $C(O)OC_1$-$C_6$alkyl, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, wherein each alkyl, cykloalkyl, hetcycloalkyl, and aryl/hetaryl group is substituted with 0-3 $R^{18}$;

alternatively, $R^{10}$ and $R^{11}$, together with the nitrogen to which they are attached, form a 3-12 membered saturated or partially saturated monocyclic or bicyclic ring consisting of the shown nitrogen, 2-10 carbon atoms, and 0-2 additional heteroatoms selected from nitrogen, oxygen, and $S(O)_n$, wherein this ring is substituted with 0-3 groups selected from halo, $C_1$-$C_6$alkyl, $C_3$-$C_{10}$cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$-alkyl, hetaryl$C_1$-$C_6$alkyl, —$C(O)R^{12}$, —$S(O)_nR^{12}$, —$S(O)_nNR^{14}R^{15}$, —$N(R^{14})S(O)_nR^{12}$, —$N(R^{16})C(=Y)NR^{14}R^{15}$, —$C(=NR^{17})NR^{17}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, and aryl/hetaryl group is substituted with 0-3 $R^{18}$;

$R^{12}$ is OH, $NR^{10}R^{11}$, $C_1$-$C_6$alkyloxy, $C_2$-$C_6$alkenyloxy, $C_2$-$C_6$alkynyloxy, $C_3$-$C_{10}$cycloalkyl, $C_3$-$C_{10}$cycloalkyloxy, $C_3$-$C_{10}$hetcycloalkyloxy, aryloxy, hetaryloxy, aryl$C_1$-$C_6$alkyloxy, hetaryl$C_1$-$C_6$alkyloxy;

$R^{13}$ is $C_1$-$C_6$alkyl, $C_2$-$C_6$alkenyl, $C_2$-$C_6$alkynyl, $NR^{10}R^{11}$, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, aryloxy$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$hetcycloalkyloxy$C_1$-$C_6$-alkyl, wherein each alkyl, cykloalkyl, hetcycloalkyl, and aryl/hetaryl group is substituted with 0-3 $R^{18}$;

$R^{14}$ and $R^{15}$ are independently selected from H, $C_1$-$C_6$alkyl, $C_1$-$C_6$alkyloxy, aryl, hetaryl, aryl$C_1$-$C_6$alkylene, and hetaryl$C_1$-$C_6$alkylene, wherein the alkyl/alkylene, aryl, and hetaryl groups are independently substituted with 0-3 $R^{19}$;

alternatively, $R^{14}$ and $R^{15}$, together with the nitrogen atom to which they are attached, form a saturated or partially saturated monocyclic, bicyclic, or tricyclic ring consisting of the shown nitrogen, 4-10 carbon atoms, and 0-2 additional heteroatoms selected from nitrogen, oxygen, and sulfur, wherein this ring is substituted with 0-3 $C_1$-$C_6$alkyl, aryl, hetaryl, aryl$C_1$-$C_6$alkylene, hetaryl$C_1$-$C_6$alkylene, hydroxy, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarbonyl, arylcarbonyl, hetarylcarbonyl, aryl$C_1$-$C_6$alkylcarbonyl, hetaryl$C_1$-$C_6$alkylcarbonyl, $C_1$-$C_6$alkylcarboxy, arylcarboxy, hetarylcarboxy, aryl$C_1$-$C_6$alkyl-carboxy, and hetaryl$C_1$-$C_6$alkylcarboxy;

$R^{16}$ is selected from H and $C_1$-$C_6$alkyl;

$R^{17}$ is selected from H, $C_1$-$C_6$alkyl, 3-10 membered cycloalkyl, halo, OH, cyano, —$C(=O)R^{12}$, —$S(=O)_nR^{12}$, $S(=O)_nNR^{14}R^{15}$, —$N(R^{14})S(=O)_nR^{12}$, aryl, and hetaryl, wherein the alkyl and cycloalkyl groups are substituted with 0-3 $R^{19}$;

$R^{18}$ is selected from halo, OH, oxo, COOH, $S(O)_2R^{12}$, $C(=O)OC_1$-$C_6$alkyl, cyano, $C_1$-$C_1$-$C_6$alkyloxy, $C_3$-$C_{10}$cycloalkyloxy, aryloxy, hetaryloxy, hetarylthio, and aryl$C_1$-$C_6$alkyloxy;

$R^{19}$ is selected from H, OH, oxo, halo, cyano, nitro, $C_1$-$C_6$alkyl, $C_1$-$C_6$alkyloxy, $NR^{20}R^{21}$, methylendioxo, dihalomethylendioxo, trihalomethyl, and trihalomethyloxy;

$R^{20}$ and $R^{21}$ are independently selected from H, $C_1$-$C_6$alkyl, and aryl$C_1$-$C_6$alkyl;

$Rn^1$ and $Rn^2$ are each independently selected from H, $C_1$-$C_6$alkyl, aryl$C_1$-$C_6$alkyl, hetaryl-$C_1$-$C_6$alkyl, $C_3$-$C_{12}$cycloalkyl, $C_3$-$C_{10}$hetcycloalkyl, wherein each alkyl, cycloalkyl, hetcycloalkyl, and aryl/hetaryl group is substituted with 0-3 $R^{18}$;

alternatively, $Rn^1$ and $Rn^2$, together with the nitrogen to which they are attached, form a 5-12 membered saturated or partially saturated monocyclic or bicyclic ring consisting of the shown nitrogen, 4-11 carbon atoms, and 0-2 additional heteroatoms selected from nitrogen, oxygen, and $S(O)_n$, wherein the ring is substituted with 0-3 groups selected from halo, trihalomethyl, trihalomethyloxy, cyano, $C_1$-$C_6$alkyl, $C_3$-$C_{10}$cycloalkyl, —$C(O)R^{12}$, —$S(O)_nR^{12}$, —$S(O)_nNR^{14}R^{16}$, —$N(R^{14})S(O)_nR^{12}$, OH, oxo, $C_1$-$C_6$alkyloxy, aryl$C_1$-$C_6$alkyloxy, hetaryl$C_1$-$C_6$alkyloxy, and $C_1$-$C_6$alkyloxy-$C_1$-$C_6$alkyl, wherein each alkyl, and aryl/hetaryl group is substituted with 0-3 $R^{18}$; and n is selected from 0, 1 and 2.

3. The compound according to clause 1 wherein:

$R^1$, $R^2$, $R^3$, $R^4$, $R^5$, $R^6$, $R^7$ and $R^8$ are each independently selected from H, halo, $C_2$-$C_{10}$-alkenyl, $C_2$-$C_{10}$alkynyl, $NR^{10}R^{11}$, $C(O)R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cycloalkyl$C_1$-$C_6$alkyl, and $C_3$-$C_{10}$-hetcycloalkyloxy$C_1$-$C_6$alkyl, wherein each alkyl, cykloalkyl, hetcycloalkyl, and aryl/hetaryl group is substituted with 0-3 $R^{18}$;

with the proviso that when $R^1$, $R^2$, $R^3$, $R^4$, $R^5$, $R^6$, $R^7$ and $R^8$ each independently are aryl, hetaryl, aryl$C_1$-$C_6$alkyl, hetaryl$C_1$-$C_6$alkyl, aryl$C_1$-$C_6$alkyloxy, and hetaryl$C_1$-$C_6$alkyloxy then each group is substituted with 1-3 $R^{18}$;

or $R^1$, $R^2$, $R^3$, $R^6$, $R^7$ and $R^8$ are each independently selected from H, halo, $C_2$-$C_{10}$alkenyl, $C_2$-$C_{10}$alkynyl, $NR^{10}R^{11}$, $C(O)R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$-hetcycloalkyloxy$C_1$-$C_6$alkyl, wherein each alkyl, cykloalkyl, hetcycloalkyl, and aryl/hetaryl group is substituted with 0-3 $R^{18}$; and $R^4$ and $R^5$ together with the carbons to which they are attached form a 4-8 membered saturated, partially saturated or aromatic ring consisting of 2-8 carbon atoms, and 0-2 additional heteroatoms selected from nitrogen, oxygen, and $S(O)_n$, wherein this ring is substituted with 0-3 groups selected from fluoro, $C_1$-$C_6$alkyl, $C_3$-$C_{10}$-cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, —$C(O)R^{12}$, —$S(O)_nR^{12}$, —$S(O)_nNR^{14}R^{15}$, —$N(R^{14})S(O)_nR^{12}$, —$N(R^{16})C(=Y)NR^{14}R^{15}$, —$C(=NR^{17})NR^{17}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, and aryl/hetaryl group is substituted with 0-3 $R^{18}$;

$R^9$ is selected from H, halo, OH, cyano, $C_1$-$C_6$alkyl, $C_1$-$C_6$alkyloxy, trihalomethyloxy and $C_3$-$C_6$cycloalkyl;

$R^{10}$ and $R^{11}$ are each independently selected from H, $C_1$-$C_6$alkyl, $C_1$-$C_6$alkylcarbonyl, $C(O)OC_1$-$C_6$alkyl, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, arylcarbonyl, hetarylcarbonyl, aryl$C_1$-$C_6$alkylcarbonyl, hetaryl$C_1$-$C_6$alkylcarbonyl, $C_3$-$C_{10}$cycloalkylcarbonyl and $C_3$-$C_{10}$hetcycloalkylcarbonyl, wherein each alkyl, cykloalkyl, hetcycloalkyl, and aryl/hetaryl group is substituted with 0-3 $R^{18}$;

alternatively, $R^{10}$ and $R^{11}$, together with the nitrogen to which they are attached, form a 3-12 membered saturated or partially saturated monocyclic or bicyclic ring consisting of the shown nitrogen, 2-10 carbon atoms, and 0-2 additional heteroatoms selected from nitrogen, oxygen, and $S(O)_n$, wherein this ring is substituted with 0-3 groups selected from halo, $C_1$-$C_6$alkyl, $C_3$-$C_{10}$cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$-alkyl, hetaryl$C_1$-$C_6$alkyl, —$C(O)R^{12}$, —$S(O)_nR^{12}$, —$S(O)_nNR^{14}R^{15}$, —$N(R^{14})S(O)_nR^{12}$, —$N(R^{16})C(=Y)NR^{14}R^{15}$, —$C(=NR^{17})NR^{17}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, and aryl/hetaryl group is substituted with 0-3 $R^{18}$;

$R^{12}$ is OH, $NR^{10}R^{11}$, $C_1$-$C_6$alkyloxy, $C_2$-$C_6$alkenyloxy, $C_2$-$C_6$alkynyloxy, $C_3$-$C_{10}$cycloalkyl, $C_3$-$C_{10}$cycloalkyloxy, $C_3$-$C_{10}$hetcycloalkyloxy, aryloxy, hetaryloxy, aryl$C_1$-$C_6$alkyloxy, hetaryl$C_1$-$C_6$alkyloxy, $R^{13}$ is $C_1$-$C_6$alkyl, $C_2$-$C_6$alkenyl, $C_2$-$C_6$alkynyl, $NR^{10}R^{11}$, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, aryloxy$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$hetcycloalkyloxy$C_1$-$C_6$-alkyl, wherein each alkyl, cykloalkyl, hetcycloalkyl, and aryl/hetaryl group is substituted with 0-3 $R^{18}$;

$R^{14}$ and $R^{15}$ are independently selected from H, $C_1$-$C_6$alkyl, $C_1$-$C_6$alkyloxy, aryl, hetaryl, aryl$C_1$-$C_6$alkylene, and hetaryl$C_1$-$C_6$alkylene, wherein the alkyl/alkylene, aryl, and hetaryl groups are independently substituted with 0-3 $R^{20}$;

alternatively, $R^{14}$ and $R^{15}$, together with the nitrogen atom to which they are attached, form a saturated or partially saturated monocyclic, bicyclic, or tricyclic ring consisting of the shown nitrogen, 4-10 carbon atoms, and 0-2 additional heteroatoms selected from nitrogen, oxygen, and sulfur, wherein this ring is substituted with 0-3 $C_1$-$C_6$alkyl, aryl, hetaryl, aryl$C_1$-$C_6$alkylene, hetaryl$C_1$-$C_6$alkylene, hydroxy, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarbonyl, arylcarbonyl, hetarylcarbonyl, aryl$C_1$-$C_6$alkylcarbonyl, hetaryl$C_1$-$C_6$alkylcarbonyl, $C_1$-$C_6$alkylcarboxy, arylcarboxy, hetarylcarboxy, aryl$C_1$-$C_6$alkyl-carboxy, and hetaryl$C_1$-$C_6$alkylcarboxy;

$R^{16}$ is selected from H and $C_1$-$C_6$alkyl;

$R^{17}$ is selected from H, $C_1$-$C_6$alkyl, 3-10 membered cycloalkyl, halo, OH, cyano, —$C(=O)R^{12}$, —$S(=O)_nR^{12}$, $S(=O)_nNR^{14}R^{15}$, —$N(R^{14})S(=O)_nR^{12}$, aryl, and hetaryl, wherein the alkyl and cycloalkyl groups are substituted with 0-3 $R^{20}$;

$R^{18}$ is selected from halo, OH, oxo, $S(O)_2R^{12}$, COOH, $C(=O)OC_1$-$C_6$alkyl, cyano, $C_1$-$C_6$alkyl, $C_1$-$C_6$alkyloxy, $C_3$-$C_{10}$cycloalkyloxy, aryloxy, hetaryloxy, hetarylthio, and aryl$C_1$-$C_6$alkyloxy;

$R^{20}$ is selected from H, OH, oxo, halo, cyano, nitro, $C_1$-$C_6$alkyl, $C_1$-$C_6$alkyloxy, $NR^{21}R^{22}$, methylendioxo, dihalomethylendioxo, trihalomethyl, and trihalomethyloxy;

$R^{21}$ and $R^{22}$ are independently selected from H, $C_1$-$C_6$alkyl, and aryl$C_1$-$C_6$alkyl;

$Rn^1$ and $Rn^2$ are each independently selected from H, $C_1$-$C_6$alkyl, aryl$C_1$-$C_6$alkyl, hetaryl-$C_1$-$C_6$alkyl, $C_3$-$C_{12}$cycloalkyl, $C_3$-$C_{10}$hetcycloalkyl, wherein each alkyl, cycloalkyl, hetcycloalkyl, and aryl/hetaryl group is substituted with 0-3 $R^{18}$;

alternatively, $Rn^1$ and $Rn^2$, together with the nitrogen to which they are attached, form a 5-12 membered saturated or partially saturated monocyclic or bicyclic ring consisting of the shown nitrogen, 4-11 carbon atoms, and 0-2 additional heteroatoms selected from nitrogen, oxygen, and $S(O)_n$, wherein the ring is substituted with 0-3 groups selected from halo, trihalomethyl, trihalomethyloxy, cyano, $C_1$-$C_6$alkyl, $C_3$-$C_{10}$cycloalkyl, —$C(O)R^{12}$, —$S(O)_nR^{12}$, —$S(O)_nNR^{14}R^{16}$, —$N(R^{14})S(O)_nR^{12}$, OH, oxo, $C_1$-$C_6$alkyloxy, aryl$C_1$-$C_6$alkyloxy, hetaryl$C_1$-$C_6$alkyloxy, and $C_1$-$C_6$alkyloxy-$C_1$-$C_6$alkyl, wherein each alkyl, and aryl/hetaryl group is substituted with 0-3 $R^{18}$; and n is selected from 0, 1 and 2.

4. The compound according to clause 1 wherein:

$R^1$, $R^2$, $R^3$, $R^4$, $R^5$, $R^6$, $R^7$ and $R^8$ are each independently selected from H, halo, $C_2$-$C_{10}$-alkenyl, $C_2$-$C_{10}$alkynyl, $NR^{10}R^{11}$, $C(O)R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$-hetcycloalkyloxy$C_1$-$C_6$alkyl, wherein each alkyl, cykloalkyl, hetcycloalkyl, and aryl/hetaryl group is substituted with 0-3 $R^{18}$;

with the proviso that when $R^1$, $R^2$, $R^3$, $R^4$, $R^5$, $R^6$, $R^7$ and $R^8$ each independently are aryl, hetaryl, aryl$C_1$-$C_6$alkyl, hetaryl$C_1$-$C_6$alkyl, aryl$C_1$-$C_6$alkyloxy, and hetaryl$C_1$-$C_6$alkyloxy then each group is substituted with 1-3 $R^{18}$; or $R^1$, $R^2$, $R^3$, $R^6$, $R^7$ and $R^8$ are each independently selected from H, halo, $C_2$-$C_{10}$alkenyl, $C_2$-$C_{10}$alkynyl, $NR^{10}R^{11}$, $C(O)R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$-hetcycloalkyloxy$C_1$-$C_6$alkyl, wherein each alkyl, cykloalkyl, hetcycloalkyl, and aryl/hetaryl group is substituted with 0-3 $R^{18}$; and $R^4$ and $R^5$ together with the carbons to which they are attached form a 4-8 membered saturated, partially saturated or aromatic ring consisting of 2-8 carbon atoms, and 0-2 additional heteroatoms selected from nitrogen, oxygen, and $S(O)_n$, wherein this ring is substituted with 0-3 groups selected from fluoro, $C_1$-$C_6$alkyl, $C_3$-$C_{10}$-cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, —$C(O)R^{12}$, —$S(O)_nR^{12}$, —$S(O)_nNR^{14}R^{15}$, —$N(R^{14})S(O)_nR^{12}$, —$N(R^{16})C(=Y)NR^{14}R^{15}$, —$C(=NR^{17})NR^{17}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, and aryl/hetaryl group is substituted with 0-3 $R^{18}$;

$R^9$ is selected from H, halo, OH, cyano, $C_1$-$C_6$alkyl, $C_1$-$C_6$alkyloxy, trihalomethyloxy and $C_3$-$C_6$cycloalkyl;

$R^{10}$ and $R^{11}$ are each independently selected from H, $C_1$-$C_6$alkyl, $C(O)O$—$C_1$-$C_6$alkyl, aryl, hetaryl, aryl-$C_1$-$C_6$alkyl, hetaryl$C_1$-$C_6$alkyl, $C_3$-$C_{10}$cycloalkyl, $C_3$-$C_{10}$hetcycloalkyl, wherein each alkyl, cykloalkyl, hetcycloalkyl, and aryl/hetaryl group is substituted with 0-3 $R^{18}$;

alternatively, $R^{10}$ and $R^{11}$, together with the nitrogen to which they are attached, form a 3-12 membered saturated or partially saturated monocyclic or bicyclic ring consisting of the shown nitrogen, 2-10 carbon atoms, and 0-2 additional heteroatoms selected from nitrogen, oxygen, and $S(O)_n$, wherein this ring is substituted with 0-3 groups selected from halo, $C_1$-$C_6$alkyl, $C_3$-$C_{10}$cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$-alkyl, hetaryl$C_1$-$C_6$alkyl, —$C(O)R^{12}$, —$S(O)_nR^{12}$, —$S(O)_nNR^{14}R^{15}$, —$N(R^{14})S(O)_nR^{12}$, —$N(R^{16})C(=Y)NR^{14}R^{15}$, —$C(=NR^{17})NR^{17}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, and aryl/hetaryl group is substituted with 0-3 $R^{18}$;

$R^{12}$ is OH, $NR^{10}R^{11}$, $C_1$-$C_6$alkyloxy, $C_2$-$C_6$alkenyloxy, $C_2$-$C_6$alkynyloxy, $C_3$-$C_{10}$cycloalkyl, $C_3$-$C_{10}$cycloalkyloxy, $C_3$-$C_{10}$hetcycloalkyloxy, aryloxy, hetaryloxy, aryl$C_1$-$C_6$alkyloxy, hetaryl$C_1$-$C_6$alkyloxy;

$R^{13}$ is $C_1$-$C_6$alkyl, $C_2$-$C_6$alkenyl, $C_2$-$C_6$alkynyl, $NR^{10}R^{11}$, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, aryloxy$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$hetcycloalkyloxy$C_1$-$C_6$-alkyl, wherein each alkyl, cykloalkyl, hetcycloalkyl, and aryl/hetaryl group is substituted with 0-3 $R^{18}$;

$R^{18}$ is selected from halo, OH, oxo, COOH, $C(=O)OC_1$-$C_6$alkyl cyano, $C_1$-$C_6$alkyl, $C_1$-$C_6$alkyloxy, $C_3$-$C_{10}$cycloalkyloxy, aryloxy, hetaryloxy, hetarylthio, and aryl$C_1$-$C_6$alkyloxy;

$R^{14}$ and $R^{15}$ are independently selected from H, $C_1$-$C_6$alkyl, $C_1$-$C_6$alkyloxy, aryl, hetaryl, aryl$C_1$-$C_6$alkylene, and hetaryl$C_1$-$C_6$alkylene, wherein the alkyl/alkylene, aryl, and hetaryl groups are independently substituted with 0-3 $R^{20}$;

alternatively, $R^{14}$ and $R^{15}$, together with the nitrogen atom to which they are attached, form a saturated or partially saturated monocyclic, bicyclic, or tricyclic ring consisting of the shown nitrogen, 4-10 carbon atoms, and 0-2 additional heteroatoms selected from nitrogen, oxygen, and sulfur, wherein this ring is substituted with 0-3 $C_1$-$C_6$alkyl, aryl, hetaryl, aryl$C_1$-$C_6$alkylene, hetaryl$C_1$-$C_6$alkylene, hydroxy, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarbonyl, arylcarbonyl, hetarylcarbonyl, aryl$C_1$-$C_6$alkylcarbonyl, hetaryl$C_1$-$C_6$alkylcarbonyl, $C_1$-$C_6$alkylcarboxy, arylcarboxy, hetarylcarboxy, aryl$C_1$-$C_6$alkyl-carboxy, and hetaryl$C_1$-$C_6$alkylcarboxy;

$R^{17}$ is selected from H, $C_1$-$C_6$alkyl, 3-10 membered cycloalkyl, halo, OH, cyano, —$C(=O)R^{12}$, —$S(=O)_nR^{12}$, $S(=O)_nNR^{14}R^{15}$, —$N(R^{14})S(=O)_nR^{12}$, aryl, and hetaryl, wherein the alkyl and cycloalkyl groups are substituted with 0-3 $R^{20}$;

$R^{20}$ is selected from H, OH, oxo, halo, cyano, nitro, $C_1$-$C_6$alkyl, $C_1$-$C_6$alkyloxy, $NR^{21}R^{22}$, methylendioxo, dihalomethylendioxo, trihalomethyl, and trihalomethyloxy;

$R^{21}$ and $R^{22}$ are independently selected from H, $C_1$-$C_6$alkyl, and aryl$C_1$-$C_6$alkyl;

$R^{16}$ is selected from H and $C_1$-$C_6$alkyl;

$Rn^1$ and $Rn^2$ are each independently selected from H, $C_1$-$C_6$alkyl, aryl$C_1$-$C_6$alkyl, hetaryl-$C_1$-$C_6$alkyl, $C_3$-$C_{12}$cycloalkyl, $C_3$-$C_{10}$hetcycloalkyl, wherein each alkyl, cycloalkyl, hetcycloalkyl, and aryl/hetaryl group is substituted with 0-3 $R^{18}$;

alternatively, $Rn^1$ and $Rn^2$, together with the nitrogen to which they are attached, form a 5-12 membered saturated or partially saturated monocyclic or bicyclic ring consisting of the shown nitrogen, 4-11 carbon atoms, and 0-2 additional heteroatoms selected from nitrogen, oxygen, and $S(O)_n$, wherein the ring is substituted with 0-3 groups selected from halo, trihalomethyl, trihalomethyloxy, cyano, $C_1$-$C_6$alkyl, $C_3$-$C_{10}$cycloalkyl, —$C(O)R^{12}$, —$S(O)_nR^{12}$, —$S(O)_nNR^{14}R^{16}$, —$N(R^{14})S(O)_nR^{12}$, OH, oxo, $C_1$-$C_6$alkyloxy, aryl$C_1$-$C_6$alkyloxy, hetaryl$C_1$-$C_6$alkyloxy, and $C_1$-$C_6$alkyloxy-$C_1$-$C_6$alkyl, wherein each alkyl, and aryl/hetaryl group is substituted with 0-3 $R^{18}$; and n is selected from 0, 1 and 2.

5. The compound according to clause 1 wherein:

$R^1$, $R^2$, $R^3$, $R^4$, $R^5$, $R^6$, $R^7$ and $R^8$ are each independently selected from H, halo, $NR^{10}R^{11}$, $C(O)R^{12}$, $R^{13}S(O)_n$, $R^{13}C(O)NR^{10}$, $R^{10}R^{11}NS(O)_n$, $R^{13}S(O)_nNR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$;

$R^9$ is selected from H, halo, OH, cyano, $C_1$-$C_6$alkyl, $C_1$-$C_6$alkyloxy, and $C_3$-$C_6$cycloalkyl;

$R^{10}$ and $R^{11}$ are each independently selected from H, $C_1$-$C_6$alkyl, $C_1$-$C_6$alkylcarbonyl, C(O)O$C_1$-$C_6$alkyl, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, arylcarbonyl, hetarylcarbonyl, aryl$C_1$-$C_6$alkylcarbonyl, hetaryl$C_1$-$C_6$alkyl-carbonyl, $C_3$-$C_{10}$cycloalkylcarbonyl and $C_3$-$C_{10}$hetcycloalkylcarbonyl, wherein each alkyl, cykloalkyl, hetcycloalkyl, and aryl/hetaryl group is substituted with 0-3 $R^{18}$;

alternatively, $R^{10}$ and $R^{11}$, together with the nitrogen to which they are attached, form a 5-12 membered saturated or partially saturated monocyclic or bicyclic ring consisting of the shown nitrogen, 2-10 carbon atoms, and 0-2 additional heteroatoms selected from nitrogen and oxygen, wherein this ring is substituted with 0-3 groups selected from halo, $C_1$-$C_6$alkyl, $C_3$-$C_{10}$cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, —C(O)$R^{12}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$-alkylcarboxy, arylcarboxy, hetarylcarboxy, aryl$C_1$-$C_6$alkylcarboxy, and hetaryl$C_1$-$C_6$-alkylcarboxy, $R^{12}$ is OH, $NR^{10}R^{11}$, $C_1$-$C_6$alkyloxy, $C_3$-$C_{10}$cycloalkyl, $C_3$-$C_{10}$cycloalkyloxy, $C_3$-$C_{10}$hetcycloalkyloxy, aryloxy, hetaryloxy, aryl$C_1$-$C_6$alkyloxy, hetaryl$C_1$-$C_6$alkyloxy, $R^{13}$ is $C_1$-$C_6$alkyl, $NR^{10}R^{11}$, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, aryloxy$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$;

$R^{18}$ is selected from halo, OH, $S(O)_2R^{12}$, COOH, C(=O)O$C_1$-$C_6$alkyl, cyano, $C_1$-$C_6$alkyl, $C_1$-$C_6$alkyloxy, $C_3$-$C_{10}$cycloalkyloxy, aryloxy and hetaryloxy;

one of $Rn^1$ and $Rn^2$ is H and the other one of $Rn^1$ and $Rn^2$ are selected from $C_1$-$C_6$alkyl, aryl$C_1$-$C_6$alkyl, hetaryl$C_1$-$C_6$alkyl, $C_6$-$C_{12}$cycloalkyl, $C_3$-$C_{10}$hetcycloalkyl, wherein each alkyl, cykloalkyl, hetcycloalkyl, and aryl/hetaryl group is substituted with 0-3 $R^{18}$;

alternatively, $Rn^1$ and $Rn^2$, together with the nitrogen to which they are attached, form a 6-12 membered saturated or partially saturated monocyclic or bicyclic ring consisting of the shown nitrogen, 4-11 carbon atoms, and 0-2 additional heteroatoms selected from nitrogen and oxygen wherein the ring is substituted with 0-3 groups selected from halo, trihalomethyl, $C_1$-$C_6$alkyl, $C_3$-$C_{10}$cycloalkyl, —C(O)$R^{12}$, OH, $C_1$-$C_6$alkyloxy, aryl$C_1$-$C_6$alkyloxy, and hetaryl$C_1$-$C_6$alkyloxy, and n is 2.

6. The compound according to clause 1 wherein:

$R^1$, $R^2$, $R^3$, $R^4$, $R^5$, $R^6$, $R^7$ and $R^8$ are each independently selected from H, halo, $NR^{10}R^{11}$, C(O)$R^{12}$, $R^{13}S(O)_n$, $R^{13}$C(O)$NR^{10}$, $R^{10}R^{11}NS(O)_n$, $R^{13}S(O)_nNR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$;

$R^9$ is selected from H, halo, OH, cyano, $C_1$-$C_6$alkyl, $C_1$-$C_6$alkyloxy, and $C_3$-$C_6$cycloalkyl;

$R^{10}$ and $R^{11}$ are each independently selected from H, $C_1$-$C_6$alkyl, C(O)O—$C_1$-$C_6$alkyl, aryl, hetaryl, aryl-$C_1$-$C_6$alkyl, hetaryl$C_1$-$C_6$alkyl, $C_3$-$C_{10}$cycloalkyl, $C_3$-$C_{10}$hetcycloalkyl, wherein each alkyl, cykloalkyl, hetcycloalkyl, and aryl/hetaryl group is substituted with 0-3 $R^{18}$;

alternatively, $R^{10}$ and $R^{11}$, together with the nitrogen to which they are attached, form a 5-12 membered saturated or partially saturated monocyclic or bicyclic ring consisting of the shown nitrogen, 2-10 carbon atoms, and 0-2 additional heteroatoms selected from nitrogen and oxygen, wherein this ring is substituted with 0-3 groups selected from halo, $C_1$-$C_6$alkyl, $C_3$-$C_{10}$cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, —C(O)$R^{12}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$-alkylcarboxy, arylcarboxy, hetarylcarboxy, aryl$C_1$-$C_6$alkylcarboxy, and hetaryl$C_1$-$C_6$-alkylcarboxy, $R^{12}$ is OH, $NR^{10}R^{11}$, $C_1$-$C_6$alkyloxy, $C_3$-$C_{10}$cycloalkyl, $C_3$-$C_{10}$cycloalkyloxy, $C_3$-$C_{10}$hetcycloalkyloxy, aryloxy, hetaryloxy, aryl$C_1$-$C_6$alkyloxy, hetaryl$C_1$-$C_6$alkyloxy, $R^{13}$ is $C_1$-$C_6$alkyl, $NR^{10}R^{11}$, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, aryloxy$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$;

$R^{18}$ is selected from halo, OH, COOH, C(=O)O$C_1$-$C_6$alkyl, cyano, $C_1$-$C_6$alkyl, $C_1$-$C_6$alkyloxy, $C_3$-$C_{10}$cycloalkyloxy, aryloxy and hetaryloxy;

one of $Rn^1$ and $Rn^2$ is H and the other one of $Rn^1$ and $Rn^2$ are selected from $C_1$-$C_6$alkyl, aryl$C_1$-$C_6$alkyl, hetaryl$C_1$-$C_6$alkyl, $C_6$-$C_{12}$cycloalkyl, $C_3$-$C_{10}$hetcycloalkyl, wherein each alkyl, cykloalkyl, hetcycloalkyl, and aryl/hetaryl group is substituted with 0-3 $R^{18}$;

alternatively, $Rn^1$ and $Rn^2$, together with the nitrogen to which they are attached, form a 6-12 membered saturated or partially saturated monocyclic or bicyclic ring consisting of the shown nitrogen, 4-11 carbon atoms, and 0-2 additional heteroatoms selected from nitrogen and oxygen wherein the ring is substituted with 0-3 groups selected from halo, trihalomethyl, $C_1$-$C_6$alkyl, $C_3$-$C_{10}$cycloalkyl, —C(O)$R^{12}$, OH, $C_1$-$C_6$alkyloxy, aryl$C_1$-$C_6$alkyloxy, and hetaryl$C_1$-$C_6$alkyloxy, and n is 2.

7. The compound according to clause 1 wherein:

$R^1$, $R^2$, $R^3$, $R^4$, $R^5$, $R^6$, $R^7$ and $R^8$ are each independently selected from H, halo, $NR^{10}R^{11}$, C(O)$R^{12}$, $R^{13}S(O)_n$, $R^{13}$C(O)$NR^{10}$, $R^{10}R^{11}NS(O)_n$, $R^{13}S(O)_nNR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$;

with the proviso that when $R^1$, $R^2$, $R^3$, $R^4$, $R^5$, $R^6$, $R^7$ and $R^8$ each independently are aryl, hetaryl, aryl$C_1$-$C_6$alkyl, hetaryl$C_1$-$C_6$alkyl, aryl$C_1$-$C_6$alkyloxy, and hetaryl$C_1$-$C_6$alkyloxy then each group is substituted with 1-3 $R^{18}$;

$R^9$ is selected from H, halo, OH, cyano, $C_1$-$C_6$alkyl, $C_1$-$C_6$alkyloxy, and $C_3$-$C_6$cycloalkyl;

$R^{10}$ and $R^{11}$ are each independently selected from H, $C_1$-$C_6$alkyl, $C_1$-$C_6$alkylcarbonyl, C(O)O$C_1$-$C_6$alkyl, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, arylcarbonyl, hetarylcarbonyl, aryl$C_1$-$C_6$alkylcarbonyl, hetaryl$C_1$-$C_6$alkyl-carbonyl, $C_3$-$C_{10}$cycloalkylcarbonyl and $C_3$-$C_{10}$hetcycloalkylcarbonyl, wherein each alkyl, cykloalkyl, hetcycloalkyl, and aryl/hetaryl group is substituted with 0-3 $R^{18}$;

alternatively, $R^{10}$ and $R^{11}$, together with the nitrogen to which they are attached, form a 5-12 membered saturated or partially saturated monocyclic or bicyclic ring consisting of the shown nitrogen, 2-10 carbon atoms, and 0-2 additional heteroatoms selected from nitrogen and oxygen, wherein this ring is substituted with 0-3 groups selected from halo, $C_1$-$C_6$alkyl, $C_3$-$C_{10}$cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, —C(O)$R^{12}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$-alkylcarboxy, arylcarboxy, hetarylcarboxy, aryl$C_1$-$C_6$alkylcarboxy, and hetaryl$C_1$-$C_6$-alkylcarboxy;

$R^{12}$ is OH, $NR^{10}R^{11}$, $C_1$-$C_6$alkyl, $C_1$-$C_6$alkyloxy, $C_3$-$C_{10}$cycloalkyl, $C_3$-$C_{10}$cycloalkyloxy, $C_3$-$C_{10}$hetcycloalkyloxy, aryloxy, hetaryloxy, aryl$C_1$-$C_6$alkyloxy, hetaryl$C_1$-$C_6$alkyloxy;

$R^{13}$ is $C_1$-$C_6$alkyl, $NR^{10}R^{11}$, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, aryloxy$C_1$-$C_6$alkyl, hetaryloxy$C_1$-$C_6$alkyl, $C_3$-$C_{10}$cycloalkyloxy$C_1$-$C_6$-alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$;

$R^{18}$ is selected from halo, OH, S(O)$_2R^{12}$, COOH, C(=O)O$C_1$-$C_6$alkyl, cyano, $C_1$-$C_6$alkyl, $C_1$-$C_6$alkyloxy, $C_3$-$C_{10}$cycloalkyloxy, aryloxy and hetaryloxy;

one of $Rn^1$ and $Rn^2$ is H and the other one of $Rn^1$ and $Rn^2$ are selected from $C_1$-$C_6$alkyl, aryl$C_1$-$C_6$alkyl, hetaryl$C_1$-$C_6$alkyl, $C_6$-$C_{12}$cycloalkyl, $C_3$-$C_{10}$hetcycloalkyl, wherein each alkyl, cykloalkyl, hetcycloalkyl, and aryl/hetaryl group is substituted with 0-3 $R^{18}$;

alternatively, $Rn^1$ and $Rn^2$, together with the nitrogen to which they are attached, form a 6-12 membered saturated or partially saturated monocyclic or bicyclic ring consisting of the shown nitrogen, 4-11 carbon atoms, and 0-2 additional heteroatoms selected from nitrogen and oxygen wherein the ring is substituted with 0-3 groups selected from halo, trihalomethyl, $C_1$-$C_6$alkyl, $C_3$-$C_{10}$cycloalkyl, —C(O)$R^{12}$, OH, $C_1$-$C_6$alkyloxy, aryl$C_1$-$C_6$alkyloxy, and hetaryl$C_1$-$C_6$alkyloxy, and n is 2.

8. The compound according to clause 1 wherein:

$R^1$, $R^2$, $R^3$, $R^4$, $R^5$, $R^6$, $R^7$ and $R^8$ are each independently selected from H, halo, $NR^{10}R^{11}$, C(O)$R^{12}$, $R^{13}$S(O)$_n$, $R^{13}$C(O)$NR^{10}$, $R^{10}R^{11}$NS(O)$_n$, $R^{13}$S(O)$_n NR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$;

with the proviso that when $R^1$, $R^2$, $R^3$, $R^4$, $R^5$, $R^6$, $R^7$ and $R^8$ each independently are aryl, hetaryl, aryl$C_1$-$C_6$alkyl, hetaryl$C_1$-$C_6$alkyl, aryl$C_1$-$C_6$alkyloxy, and hetaryl$C_1$-$C_6$alkyloxy then each group is substituted with 1-3 $R^{18}$;

$R^9$ is selected from H, halo, OH, cyano, $C_1$-$C_6$alkyl, $C_1$-$C_6$alkyloxy, and $C_3$-$C_6$cycloalkyl;

$R^{10}$ and $R^{11}$ are each independently selected from H, $C_1$-$C_6$alkyl, C(O)O—$C_1$-$C_6$alkyl, aryl, hetaryl, aryl-$C_1$-$C_6$alkyl, hetaryl$C_1$-$C_6$alkyl, $C_3$-$C_{10}$cycloalkyl, $C_3$-$C_{10}$hetcycloalkyl, wherein each alkyl, cykloalkyl, hetcycloalkyl, and aryl/hetaryl group is substituted with 0-3 $R^{18}$;

alternatively, $R^{10}$ and $R^{11}$, together with the nitrogen to which they are attached, form a 5-12 membered saturated or partially saturated monocyclic or bicyclic ring consisting of the shown nitrogen, 2-10 carbon atoms, and 0-2 additional heteroatoms selected from nitrogen and oxygen, wherein this ring is substituted with 0-3 groups selected from halo, $C_1$-$C_6$alkyl, $C_3$-$C_{10}$cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, —C(O)$R^{12}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$-alkylcarboxy, arylcarboxy, hetarylcarboxy, aryl$C_1$-$C_6$alkylcarboxy, and hetaryl$C_1$-$C_6$-alkylcarboxy, $R^{12}$ is OH, $NR^{10}R^{11}$, $C_1$-$C_6$alkyloxy, $C_3$-$C_{10}$cycloalkyl, $C_3$-$C_{10}$cycloalkyloxy, $C_3$-$C_{10}$hetcycloalkyloxy, aryloxy, hetaryloxy, aryl$C_1$-$C_6$alkyloxy, hetaryl$C_1$-$C_6$alkyloxy, $R^{13}$ is $C_1$-$C_6$alkyl, $NR^{10}R^{11}$, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, aryloxy$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$;

$R^{18}$ is selected from halo, OH, COOH, C(=O)O$C_1$-$C_6$alkyl, cyano, $C_1$-$C_6$alkyl, $C_1$-$C_6$alkyl-$C_3$-$C_{10}$cycloalkyloxy, aryloxy and hetaryloxy;

one of $Rn^1$ and $Rn^2$ is H and the other one of $Rn^1$ and $Rn^2$ are selected from $C_1$-$C_6$alkyl, aryl$C_1$-$C_6$alkyl, hetaryl$C_1$-$C_6$alkyl, $C_6$-$C_{12}$cycloalkyl, $C_3$-$C_{10}$hetcycloalkyl, wherein each alkyl, cykloalkyl, hetcycloalkyl, and aryl/hetaryl group is substituted with 0-3 $R^{18}$;

alternatively, $Rn^1$ and $Rn^2$, together with the nitrogen to which they are attached, form a 6-12 membered saturated or partially saturated monocyclic or bicyclic ring consisting of the shown nitrogen, 4-11 carbon atoms, and 0-2 additional heteroatoms selected from nitrogen and oxygen wherein the ring is substituted with 0-3 groups selected from halo, trihalomethyl, $C_1$-$C_6$alkyl, $C_3$-$C_{10}$cycloalkyl, —C(O)$R^{12}$, OH, $C_1$-$C_6$alkyloxy, aryl$C_1$-$C_6$alkyloxy, and hetaryl$C_1$-$C_6$alkyloxy, and n is 2.

9. The compound according to clause 1 wherein $R^2$, $R^3$, $R^4$, $R^6$, $R^7$ and $R^8$ are each independently selected from H, halo, $C_2$-$C_{10}$alkenyl, $C_2$-$C_{10}$alkynyl, $NR^{10}R^{11}$, C(O)$R^{12}$, $R^{13}$S(O)$_n$, $R^{13}$C(O)$NR^{10}$, $R^{10}R^{11}$NS(O)$_n$, $R^{13}$S(O)$_n NR^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy-$C_1$-$C_6$alkyl, hetaryloxy$C_1$-$C_6$alkyl, $C_3$-$C_{10}$cyclo-alkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$; and $R^1$ and $R^5$ together with the carbons to which they are attached form a 4-8 membered saturated, partially saturated or aromatic ring consisting of 2-8 carbon atoms, and 0-2 additional heteroatoms selected from nitrogen, oxygen, and $S(O)_n$, wherein this ring is substituted with 0-3 groups selected from fluoro, $C_1$-$C_6$alkyl, $C_3$-$C_{10}$cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, —C(O)$R^{12}$, —S(O)$_n R^{12}$, —S(O)$_n$N$R^{14}R^{15}$, —N($R^{14}$)S(O)$_n R^{12}$, —N($R^{16}$)C(=Y)N$R^{14}R^{15}$, —C(=N$R^{17}$)N$R^{17}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, and aryl/hetaryl group is substituted with 0-3 $R^{18}$.

10. The compound according to clause 1 wherein
$R^2$, $R^3$, $R^4$, $R^5$, $R^6$ and $R^8$ are each independently selected from H, halo, $C_2$-$C_{10}$alkenyl, $C_2$-$C_{10}$alkynyl, N$R^{10}R^{11}$, C(O)$R^{12}$, $R^{13}$S(O)$_n$, $R^{13}$C(O)N$R^{10}$, $R^{10}R^{11}$NS(O)$_n$, $R^{13}$S(O)$_n$N$R^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$-hetcycloalkyloxy$C_1$-$C_6$alkyl, wherein each alkyl, cykloalkyl, hetcycloalkyl, and aryl/hetaryl group is substituted with 0-3 $R^{18}$; and
$R^1$ and $R^7$ together with the carbons to which they are attached form a 4-8 membered saturated, partially saturated or aromatic ring consisting of 2-8 carbon atoms, and 0-2 additional heteroatoms selected from nitrogen, oxygen, and $S(O)_n$, wherein this ring is substituted with 0-3 groups selected from fluoro, $C_1$-$C_6$alkyl, $C_3$-$C_{10}$cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, —C(O)$R^{12}$, —S(O)$_n R^{12}$, —S(O)$_n$N$R^{14}R^{15}$, —N($R^{14}$)S(O)$_n R^{12}$, —N($R^{16}$)C(=Y)N$R^{14}R^{15}$, —C(=N$R^{17}$)N$R^{17}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, and aryl/hetaryl group is substituted with 0-3 $R^{18}$.

11. The compound according to clause 1 wherein $R^3$, $R^4$, $R^5$, $R^6$, are each independently selected from halo, N$R^{10}R^{11}$, C(O)$R^{12}$, $R^{13}$S(O)$_n$, $R^{13}$C(O)N$R^{10}$, $R^{10}R^{11}$NS(O)$_n$, $R^{13}$S(O)$_n$N$R^{10}$, aryl, hetaryl, aryloxy, hetaryloxy, aryl$C_1$-$C_6$alkyl, hetaryl$C_1$-$C_6$alkyl, aryl$C_1$-$C_6$alkyloxy, hetaryl$C_1$-$C_6$alkyloxy, $C_3$-$C_{10}$cycloalkyl, $C_3$-$C_{10}$cycloalkyloxy, $C_3$-$C_{10}$cycloalkyl$C_1$-$C_6$alkyloxy, $C_3$-$C_{10}$hetcycloalkyl, $C_3$-$C_{10}$hetcycloalkyloxy, aryloxy$C_1$-$C_6$alkyl, hetaryloxy$C_1$-$C_6$alkyl, $C_3$-$C_{10}$cycloalkyloxy$C_1$-$C_6$alkyl, and $C_3$-$C_{10}$hetcycloalkyloxy$C_1$-$C_6$alkyl, wherein each alkyl, cykloalkyl, hetcycloalkyl, and aryl/hetaryl group is substituted with 0-3 $R^{18}$; and
$R^1$, $R^2$, $R^7$, and $R^8$ are H.

12. The compound according to clause 1 wherein $R^3$, $R^4$, $R^5$, $R^6$, are each independently selected from N$R^{10}R^{11}$, C(O)$R^{12}$, $R^{13}$S(O)$_n$, $R^{13}$C(O)N$R^{10}$, $R^{13}$S(O)$_n$N$R^{10}$, aryl, hetaryl, aryloxy, hetaryloxy, hetaryloxy$C_1$-$C_6$alkyl, wherein each aryl/hetaryl group is substituted with 0-3 $R^{18}$.

13. The compound according to clause 1 wherein $R^4$ and $R^5$ together with the carbons to which they are attached form a 4-8 membered saturated, partially saturated or aromatic ring consisting of 2-8 carbon atoms, and 0-2 additional heteroatoms selected from nitrogen, oxygen, and $S(O)_n$.

14. The compound according to clause 1 wherein $R^9$ is selected from H, halo, OH, cyano and $C_1$-$C_6$alkyl.

15. The compound according to clause 1 wherein $R^9$ is selected from H, OH, and $C_1$-$C_6$alkyl.

16. The compound according to clause 1 wherein $R^9$ is H.

17. The compound according to clause 1 wherein $R^{10}$ and $R^{11}$ are each independently selected from H, $C_1$-$C_6$alkyl, aryl, hetaryl, $C_3$-$C_{10}$cycloalkyl, $C_3$-$C_{10}$hetcycloalkyl, wherein each alkyl, cykloalkyl and hetcycloalkyl group is substituted with 0-3 $R^{18}$.

18. The compound according to clause 1 wherein $R^{10}$ and $R^{11}$ are each independently selected from H, $C_1$-$C_6$alkyl, $C_3$-$C_{10}$cycloalkyl, $C_3$-$C_{10}$hetcycloalkyl, wherein each alkyl, cykloalkyl and hetcycloalkyl group is substituted with 0-3 $R^{18}$.

19. The compound according to clause 1 wherein $R^{10}$ and $R^{11}$, together with the nitrogen to which they are attached, form a 5-12 membered saturated or partially saturated monocyclic or bicyclic ring consisting of the shown nitrogen, 2-10 carbon atoms, and 0-2 additional heteroatoms selected from nitrogen and oxygen, wherein this ring is substituted with 0-3 groups selected from halo, $C_1$-$C_6$alkyl, —C(O)$R^{12}$, OH, oxo, $C_1$-$C_6$alkyloxy, $C_1$-$C_6$alkyloxy$C_1$-$C_6$alkyl and $C_1$-$C_6$alkylcarboxy.

20. The compound according to clause 1 wherein $R^{10}$ and $R^{11}$, together with the nitrogen to which they are attached, form a 6-12 membered saturated or partially saturated monocyclic or bicyclic ring consisting of the shown nitrogen, 2-10 carbon atoms, and 0-1 additional heteroatoms selected from oxygen, wherein this ring is substituted with 0-3 groups selected from OH and $C_1$-$C_6$alkyloxy.

21. The compound according to clause 1 wherein $R^{12}$ is OH, N$R^{10}R^{11}$, $C_1$-$C_6$alkyl, $C_1$-$C_6$alkyloxy, $C_3$-$C_{10}$cycloalkyloxy, $C_3$-$C_{10}$hetcycloalkyloxy, aryloxy and hetaryloxy.

22. The compound according to clause 1 wherein $R^{12}$ is OH, N$R^{10}R^{11}$, $C_1$-$C_6$alkyloxy, $C_3$-$C_{10}$cycloalkyloxy, $C_3$-$C_{10}$hetcycloalkyloxy, aryloxy and hetaryloxy.

23. The compound according to clause 1 wherein $R^{12}$ is OH, N$R^{10}R^{11}$, and $C_1$-$C_6$alkyloxy, 24. The compound according to clause 1 wherein $R^{13}$ is $C_1$-$C_6$alkyl, N$R^{10}R^{11}$, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, wherein each alkyl, cykloalkyl, hetcycloalkyl, and aryl/hetaryl group is substituted with 0-3 $R^{18}$.

25. The compound according to clause 1 wherein $R^{13}$ is $C_1$-$C_6$alkyl, N$R^{10}R^{11}$, aryl, hetaryl, hetaryl$C_1$-$C_6$alkyl, $C_3$-$C_{10}$cycloalkyl, wherein each alkyl, and aryl/hetaryl group is substituted with 0-3 $R^{18}$.

26. The compound according to clause 1 wherein $R^{18}$ is selected from halo, OH, COOH, C(=O)O$C_1$-$C_6$alkyl, cyano, $C_1$-$C_6$alkyl, $C_1$-$C_6$alkyloxy, $C_3$-$C_{10}$cycloalkyloxy, aryloxy and hetaryloxy.

27. The compound according to clause 1 wherein $R^{18}$ is selected from halo, OH, COOH, C(=O)O$C_1$-$C_6$alkyl, cyano, and $C_1$-$C_6$alkyl.

28. The compound according to clause 1 wherein n is 2.

29. The compound according to clause 1 wherein one of $Rn^1$ and $Rn^2$ is H and the other one of $Rn^1$ and $Rn^2$ are selected from $C_1$-$C_6$alkyl, aryl$C_1$-$C_6$alkyl, hetaryl$C_1$-$C_6$alkyl, $C_6$-$C_{12}$cycloalkyl, $C_3$-$C_{10}$hetcycloalkyl, wherein each alkyl, cykloalkyl, hetcycloalkyl, and aryl/hetaryl group is substituted with 0-3 $R^{18}$;

30. The compound according to clause 1 wherein one of $Rn^1$ and $Rn^2$ is H, and the other one of $Rn^1$ and $Rn^2$ is $C_6$-$C_{12}$cycloalkyl, substituted with 0-3 $R^{18}$.

31. The compound according to clause 1 wherein $Rn^1$ and $Rn^2$, together with the nitrogen to which they are attached, form a 6-12 membered saturated or partially saturated monocyclic or bicyclic ring consisting of the shown nitrogen, 4-11 carbon atoms, and 0-2 additional heteroatoms selected from nitrogen and oxygen wherein the ring is substituted with 0-3 groups selected from halo, trihalomethyl, trihalomethyloxy, $C_1$-$C_6$alkyl, $C_3$-$C_{10}$-cycloalkyl, —C(O)$R^{12}$, —S(O)$_n$$R^{12}$, oxo, hydroxy, $C_1$-$C_6$alkyloxy, aryl$C_1$-$C_6$alkyloxy, hetaryl$C_1$-$C_6$alkyloxy, and $C_1$-$C_6$alkyloxy$C_1$-$C_6$alkyl, wherein each alkyl, and aryl/hetaryl group is substituted with 0-3 $R^{18}$.

32. The compound according to clause 1 wherein $Rn^1$ and $Rn^2$, together with the nitrogen to which they are attached, form a 6-12 membered saturated or partially saturated monocyclic or bicyclic ring consisting of the shown nitrogen, 4-11 carbon atoms, and 0-2 additional heteroatoms selected from nitrogen and oxygen wherein the ring is substituted with 0-3 groups selected from halo, trihalomethyl, trihalomethyloxy, $C_1$-$C_6$alkyl, $C_3$-$C_{10}$-cycloalkyl, —C(O)$R^{12}$, —S(O)$_n$$R^{12}$, oxo, $C_1$-$C_6$alkyloxy, aryl$C_1$-$C_6$alkyloxy, hetaryl$C_1$-$C_6$alkyloxy, and $C_1$-$C_6$alkyloxy$C_1$-$C_6$alkyl, wherein each alkyl, and aryl/hetaryl group is substituted with 0-3 $R^{18}$.

33. The compound according to clause 1 wherein the ring formed by $Rn^1$ and $Rn^2$, together with the nitrogen to which they are attached is selected from:

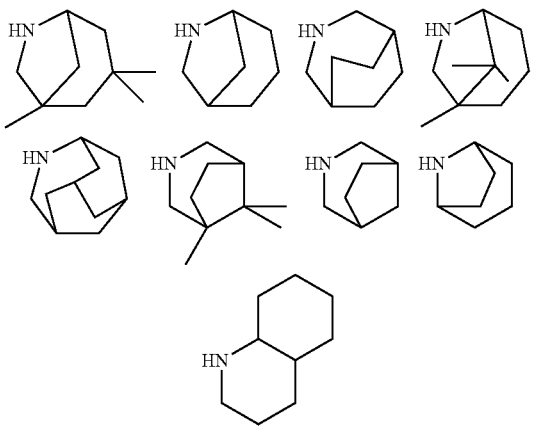

being substituted with 0-2 $R^{25}$; and,
$R^{25}$ is selected from $C_1$-$C_6$alkyl, S(O)$_2$$R^{12}$, halo, hydroxy, oxo, cyano, and $C_1$-$C_6$alkyloxy.

34. The compound according to clause 1 wherein the ring formed by $Rn^1$ and $Rn^2$, together with the nitrogen to which they are attached is selected from:

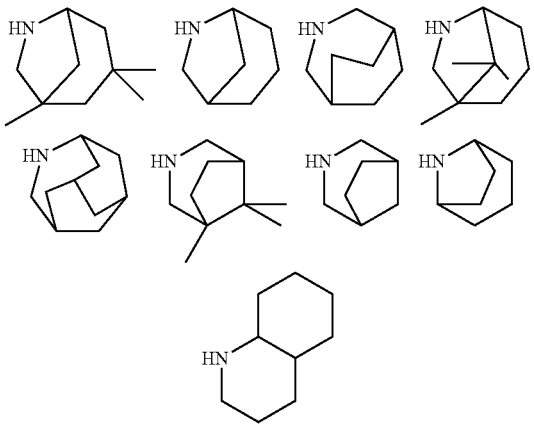

being substituted with 0-2 $R^{25}$; and,
$R^{25}$ is selected from $C_1$-$C_6$alkyl, halo, hydroxy, oxo, cyano, and $C_1$-$C_6$alkyloxy.

35. The compound according to clause 1 wherein the ring formed by $Rn^1$ and $Rn^2$, together with the nitrogen to which they are attached is selected from:

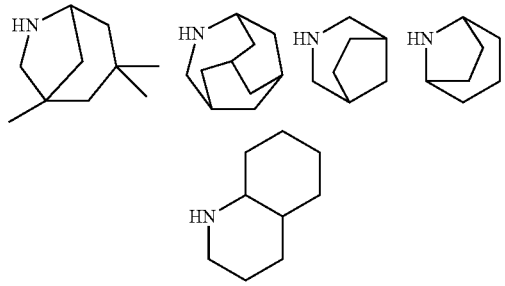

being substituted with 0-2 $R^{25}$; and,
$R^{25}$ is selected from $C_1$-$C_6$alkyl, S(O)$_2$$R^{12}$, halo, hydroxy, oxo, cyano, and $C_1$-$C_6$alkyloxy.

36. The compound according to clause 1 wherein the ring formed by $Rn^1$ and $Rn^2$, together with the nitrogen to which they are attached is selected from:

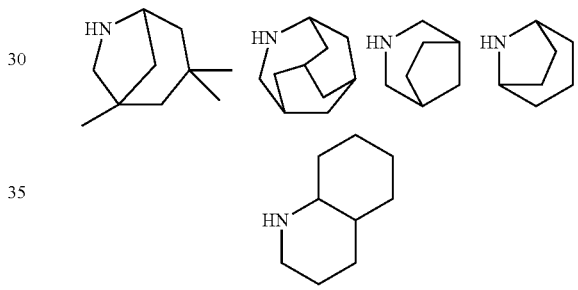

being substituted with 0-2 $R^{25}$; and,
$R^{25}$ is selected from $C_1$-$C_6$alkyl, halo, hydroxy, oxo, cyano, and $C_1$-$C_6$alkyloxy.

37. The compound according to clause 1 wherein $Rn^1$ is selected from hydrogen, cyclopropyl or $C_1$-$C_6$alkyl and N—$Rn^2$ is selected from:

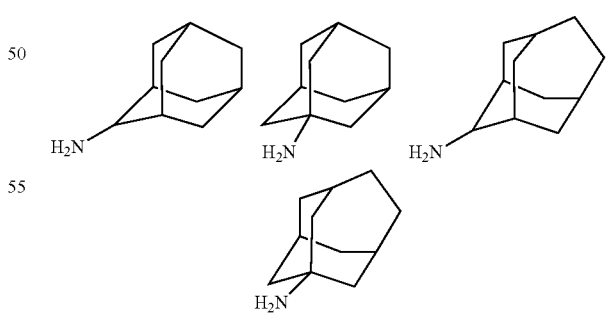

being substituted with 0-2 $R^{25}$; and $R^{25}$ is selected from $C_1$-$C_6$alkyl, S(O)$_2$$R^{12}$, halo, hydroxy, oxo, cyano, and $C_1$-$C_6$alkyloxy.

38. The compound according to clause 1 wherein $Rn^1$ is selected from cyclopropyl or $C_1$-$C_6$alkyl and N—$Rn^2$ is selected from:

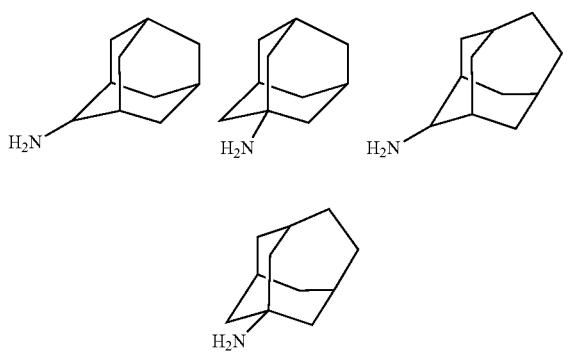

being substituted with 0-2 $R^{25}$; and, $R^{25}$ is selected from $C_1$-$C_6$alkyl, $S(O)_2R^{12}$, halo, hydroxy, oxo, cyano, and $C_1$-$C_6$alkyloxy.

39. The compound according to clause 1 wherein $Rn^1$ is $C_1$-$C_6$alkyl and N—$Rn^2$ is selected from:

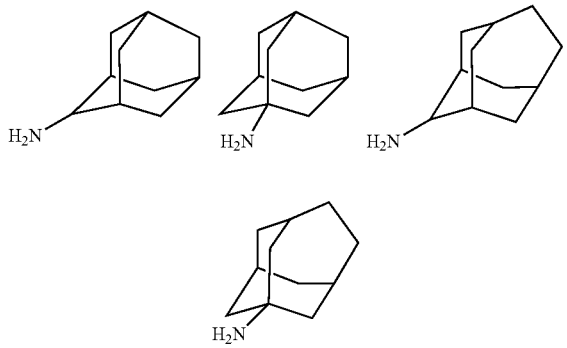

being substituted with 0-2 $R^{25}$; and, $R^{25}$ is selected from $C_1$-$C_6$alkyl, $S(O)_2R^{12}$, halo, hydroxy, oxo, cyano, and $C_1$-$C_6$alkyloxy.

40. The compound according to clause 1 wherein $Rn^1$ is hydrogen and N—$Rn^2$ is selected from:

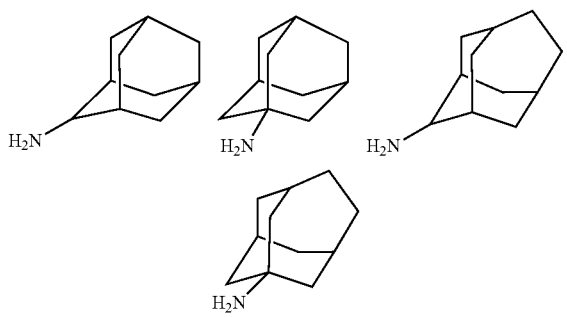

being substituted with 0-2 $R^{25}$; and, $R^{25}$ is selected from $C_1$-$C_6$alkyl, $S(O)_2R^{12}$, halo, hydroxy, oxo, cyano, and $C_1$-$C_6$alkyloxy.

41. The compound according to clause 1 wherein $Rn^1$ is hydrogen and N—$Rn^2$ is selected from:

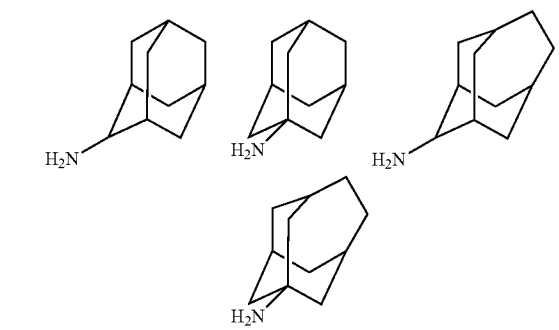

being substituted with 0-2 $R^{25}$; and, $R^{25}$ is selected from $C_1$-$C_6$alkyl, halo, hydroxy, oxo, cyano, and $C_1$-$C_6$alkyloxy.

42. The compound according to clause 1 wherein the compound is of formula Ia:

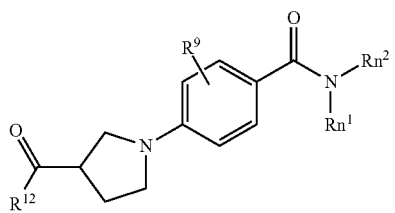

Ia wherein $R^{12}$, $R^9$, $Rn^1$, and $Rn^2$ are as defined above.

43. The compound according to clause 42 wherein in the compound of formula Ia $R^{12}$ is OH, $NR^{10}R^{11}$, $C_1$-$C_6$alkyloxy, $C_3$-$C_{10}$cycloalkyloxy, $C_3$-$C_{10}$hetcycloalkyloxy, aryloxy, hetaryloxy, aryl$C_1$-$C_6$alkyloxy, hetaryl$C_1$-$C_6$alkyloxy, $R^9$ is H and $Rn^1$ and $Rn^2$ are as defined above.

44. The compound according to clause 43 wherein in the compound of formula Ia $R^{12}$ is OH, $C_1$-$C_6$alkyloxy, $C_3$-$C_{10}$cycloalkyloxy, aryl$C_1$-$C_6$alkyloxy, hetaryl$C_1$-$C_6$alkyloxy, $R^9$ is H and $Rn^1$ and $Rn^2$ are as defined above.

45. The compound according to clause 44 wherein in the compound of formula Ia $R^{12}$ is OH, $C_1$-$C_6$alkyloxy, $C_3$-$C_{10}$cycloalkyloxy, $R^9$ is H and $Rn^1$ and $Rn^2$ are as defined above.

46. The compound according to clause 45 wherein in the compound of formula Ia $R^{12}$ is OH, $R^9$ is H and $Rn^1$ and $Rn^2$ are as defined above.

47. The compound according to clause 1 wherein the compound is of formula Ib:

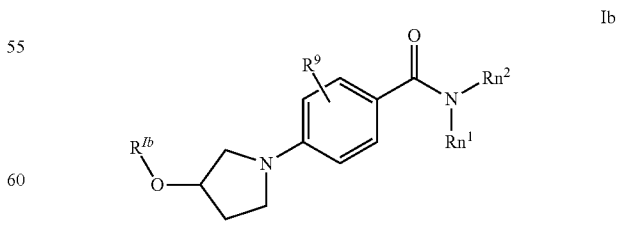

Ib wherein $R^{Ib}$ is hetaryl or aryl$C_1$-$C_6$alkyl and $R^9$, $Rn^1$, and $Rn^2$ are as defined above.

48. The compound according to clause 1 wherein the compound is of formula Ic:

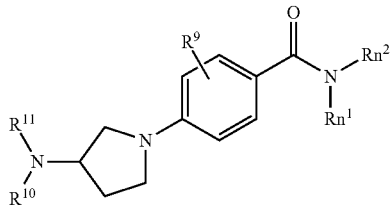

Ic wherein $R^{10}$, $R^{11}$, $R^9$, $Rn^1$, and $Rn^2$ are as defined above.

49. The compound according to clause 1 wherein the compound is of formula Id:

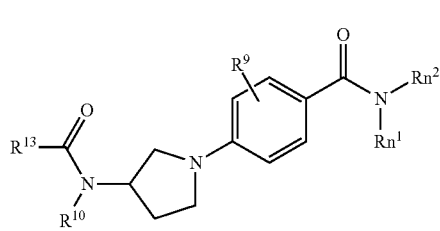

Id wherein $R^{10}$, $R^{13}$, $R^9$, $Rn^1$, and $Rn^2$ are as defined above.

50. The compound according to clause 49 wherein in the compound of formula Id, $R^9$ and $R^{10}$ are H and $R^{13}$, $Rn^1$, and $Rn^2$ are as defined above.

51. The compound according to clause 49 and 50 wherein the compound of formula Id have the following formula Id'

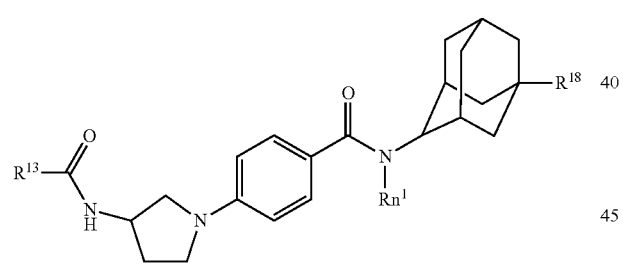

Id' wherein $R^{13}$, $Rn^1$, and $R^{18}$ are as defined above.

52. The compound according to clause 1 wherein the compound is of formula Ie:

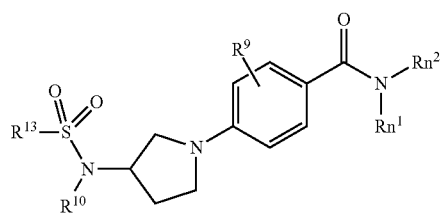

Ie wherein $R^{10}$, $R^{13}$, $R^9$, $Rn^1$, and $Rn^2$ are as defined above.

53. The compound according to clause 1 wherein the compound is of formula If:

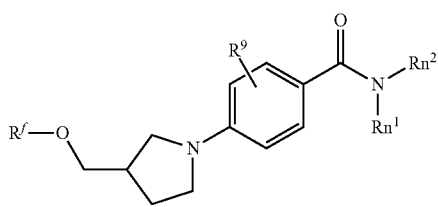

If wherein $R^f$ is hetaryl optionally substituted with $R^{18}$; and $R^9$, $Rn^1$, and $Rn^2$ are as defined above.

54. The compound according to clause 1 wherein the compound is of formula Ig:

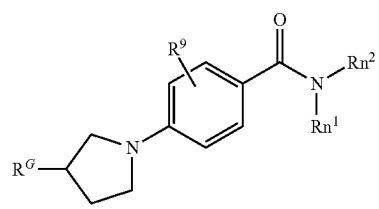

Ig wherein $R^G$ is aryl optionally substituted with $R^{18}$; and $R^9$, $Rn^1$, and $Rn^2$ are as defined above.

55. The compound according to clause 1 wherein the compound is of formula Ih:

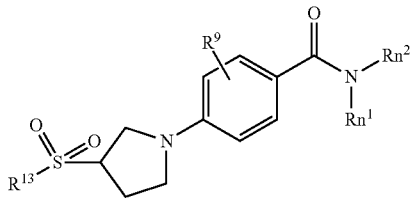

Ih wherein $R^{13}$, $R^9$, $Rn^1$, and $Rn^2$ are as defined above.

56. The compound according to clause 1 wherein the compound is of formula Ij:

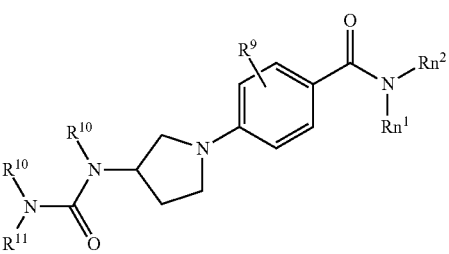

Ij wherein $R^9$, $R^{10}$, $R^{11}$, $Rn^1$ and $Rn^2$ are as defined above.

57. The compound according to clause 1 wherein the compound is of formular Ik:

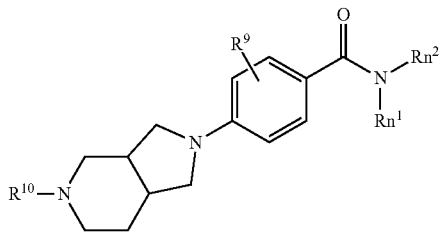

wherein $R^9$, $R^{10}$, $Rn^1$ and $Rn^2$ are as defined above.

58. The compound according to clause 1 wherein the compound is of formular Il

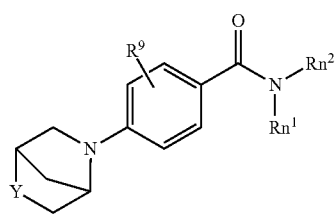

wherein $R^9$, $Rn^1$ and $Rn^2$ are as defined above and Y is oxygen, $S(O)_n$ or $NR^{10}$.

59. The compound according to clause 58 wherein the compound is of formular Il'

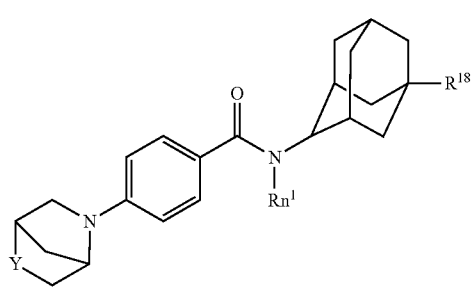

wherein $Rn^1$ and $R^{18}$ are as defined above and Y is oxygen, $S(O)_n$ or $NR^{10}$.

60. The compound according to clause 1 wherein the compound is selected from the group:

1-[4-(1,3,3-Trimethyl-6-aza-bicyclo[3.2.1]octane-6-carbonyl)-phenyl]-pyrrolidine-3-carboxylic acid methyl ester;
1-[4-(1,3,3-Trimethyl-6-aza-bicyclo[3.2.1]octane-6-carbonyl)-phenyl]-pyrrolidine-3-carboxylic acid;
{4-[3-(Morpholine-4-carbonyl)-pyrrolidin-1-yl]-phenyl}-(1,3,3-trimethyl-6-aza-bicyclo-3.2.1]oct-6-yl)-methanone;
1-[4-(1,3,3-Trimethyl-6-aza-bicyclo[3.2.1]octane-6-carbonyl)-phenyl]-pyrrolidine-3-carboxylic acid (3-hydroxy-adamantan-1-yl)-amide;
(Methyl-{1-[4-(1,3,3-trimethyl-6-aza-bicyclo[3.2.1]octane-6-carbonyl)-phenyl]-pyrrolidine-3-carbonyl}-amino)-acetic acid tert-butyl ester;
(Methyl-{1-[4-(1,3,3-trimethyl-6-aza-bicyclo[3.2.1]octane-6-carbonyl)-phenyl]-pyrrolidine-3-carbonyl}-amino)-acetic acid;
1-[4-(1,3,3-Trimethyl-6-aza-bicyclo[3.2.1]octane-6-carbonyl)-phenyl]-pyrrolidine-3-carboxylic acid (4-hydroxy-cyclohexyl)-amide;
{4-[3-(4-Hydroxy-piperidine-1-carbonyl)-pyrrolidin-1-yl]-phenyl}-(1,3,3-trimethyl-6-aza-bicyclo[3.2.1]oct-6-yl)-methanone;
{4-[3-(4-Hydroxymethyl-piperidine-1-carbonyl)-pyrrolidin-1-yl]-phenyl}-(1,3,3-trimethyl-6-aza-bicyclo[3.2.1]oct-6-yl)-methanone;
1-[4-(Octahydroquinoline-1-carbonyl)phenyl]-pyrrolidine-3-carboxylic acid;
{4-[3-(Morpholine-4-carbonyl)-pyrrolidin-1-yl]-phenyl}(octahydroquinolin-1-yl)methanone;
{4-[3-(4-Hydroxymethyl-piperidine-1-carbonyl)-pyrrolidin-1-yl]-phenyl}-(octahydroquinolin-1-yl)methanone;
1-[4-(Adamantan-1-ylcarbamoyl)-phenyl]-pyrrolidine-3-carboxylic acid;
{4-[3-(4-Hydroxy-piperidine-1-carbonyl)-pyrrolidin-1-yl]-phenyl}-(octahydro-quinolin-1-yl)-methanone;
1-[4-(Octahydro-quinoline-1-carbonyl)-phenyl]-pyrrolidine-3-carboxylic acid (tetrahydro-pyran-4-yl)-amide;
(Octahydro-quinolin-1-yl)-{4-[3-(2-oxa-5-aza-bicyclo[2.2.1]heptane-5-carbonyl)-pyrrolidin-1-yl]-phenyl}-methanone;
4-(3-Acetylamino-pyrrolidin-1-yl)-N-adamantan-2-yl-benzamide;
N-{1-[4-(Octahydro-quinoline-1-carbonyl)-phenyl]-pyrrolidin-3-yl}-acetamide;
N-{1-[4-(3-Aza-bicyclo[3.2.2]nonane-3-carbonyl)-phenyl]-pyrrolidin-3-yl}-acetamide;
{1-[4-(3-Aza-bicyclo[3.2.2]nonane-3-carbonyl)-phenyl]-pyrrolidin-3-yl}-methyl-carbamic acid tert-butyl ester;
(3-Aza-bicyclo[3.2.2]non-3-yl)-[4-(3-methylamino-pyrrolidin-1-yl)-phenyl]-methanone;
N-{1-[4-(3-Aza-bicyclo[3.2.2]nonane-3-carbonyl)-phenyl]-pyrrolidin-3-yl}-N-methyl-acetamide; Cyclopropanecarboxylic acid {1-[4-(3-aza-bicyclo[3.2.2]nonane-3-carbonyl)-phenyl]-pyrrolidin-3-yl}-methyl-amide;
5-Methyl-isoxazole-3-carboxylic acid {1-[4-(3-aza-bicyclo[3.2.2]nonane-3-carbonyl)-phenyl]-pyrrolidin-3-yl}-methyl-amide;
N-{1-[4-(3-Aza-bicyclo[3.2.2]nonane-3-carbonyl)-phenyl]-pyrrolidin-3-yl}-N-methyl-phenyl-methanesulfonamide;
N-{1-[4-(3-Aza-bicyclo[3.2.2]nonane-3-carbonyl)-phenyl]-pyrrolidin-3-yl}-4-chloro-N-methyl-benzenesulfonamide;
Pyridine-2-carboxylic acid {1-[4-(3-aza-bicyclo[3.2.2]nonane-3-carbonyl)-phenyl]-pyrrolidin-3-yl}-methyl-amide;
1-{1-[4-(3-Aza-bicyclo[3.2.2]nonane-3-carbonyl)-phenyl]-pyrrolidin-3-yl}-3-cyclohexyl-1-methyl-urea;
(3-Aza-bicyclo[3.2.2]non-3-yl)-{4-[3-(pyridin-2-yloxy)-pyrrolidin-1-yl]-phenyl}-methanone;
4-(2-Oxa-5-aza-bicyclo[2.2.1]hept-5-yl)-N-adamantan-2-yl-benzamide;
4-[3-(4-Chloro-phenyl)-pyrrolidin-1-yl]-N-adamantan-2-yl-benzamide;
4-[3-(Pyridin-2-yloxymethyl)-pyrrolidin-1-yl]-N-adamantan-2-yl-benzamide;
(3-Aza-bicyclo[3.2.2]non-3-yl)-{4-[3-(pyridin-2-yloxymethyl)-pyrrolidin-1-yl]-phenyl}-methanone;
4-(3-Methanesulfonyl-pyrrolidin-1-yl)-N-adamantan-2-yl-benzamide;
(3-Aza-bicyclo[3.2.2]non-3-yl)-[4-(3-morpholin-4-yl-pyrrolidin-1-yl)-phenyl]-methanone;
[4-(3-Morpholin-4-yl-pyrrolidin-1-yl)-phenyl]-(1,3,3-trimethyl-6-aza-bicyclo[3.2.1]oct-6-yl)-methanone;

(3-Aza-bicyclo[3.2.2]non-3-yl)-{4-[3-(6-methyl-pyridin-3-yloxymethyl)-pyrrolidin-1-yl]-phenyl}-methanone;

(3-Aza-bicyclo[3.2.2]non-3-yl)-[4-((R)-3-benzyloxy-pyrrolidin-1-yl)-phenyl]-methanone;

N-{(R)-1-[4-(3-Aza-bicyclo[3.2.2]nonane-3-carbonyl)-phenyl]-pyrrolidin-3-yl}-acetamide;

1-{(R)-1-[4-(3-Aza-bicyclo[3.2.2]nonane-3-carbonyl)-phenyl]-pyrrolidin-3-yl}-3-isopropyl-urea;

1-{(R)-1-[4-(3-Aza-bicyclo[3.2.2]nonane-3-carbonyl)-phenyl]-pyrrolidin-3-yl}-3-N,N-dimethyl-sulfamide;

4-[(R)-3-(3-Isopropyl-ureido)-pyrrolidin-1-yl]-N-adamantan-2-yl-benzamide;

Morpholine-4-carboxylic acid {(R)-1-[4-(3-aza-bicyclo[3.2.2]nonane-3-carbonyl)-phenyl]-pyrrolidin-3-yl}-amide;

Morpholine-4-carboxylic acid {(R)-1-[4-(adamantan-2-yl-carbamoyl)-phenyl]-pyrrolidin-3-yl}-amide;

1-{(R)-[4-(adamantan-2-yl-phenyl)-pyrrolidin-3-yl]-3-N,N-dimethyl-sulfamide;

6-Chloro-N-{(R)-1-[4-(octahydro-quinoline-1-carbonyl)-phenyl]-pyrrolidin-3-yl}-nicotin-amide;

1,1-Dimethyl-3-{(R)-1-[4-(octahydro-quinoline-1-carbonyl)-phenyl]-pyrrolidin-3-yl}-urea; or a salt thereof with a pharmaceutically acceptable acid or base, or any optical isomer or mixture of optical isomers, including a racemic mixture, or any tautomeric forms.

61. The compound according to clause 1 wherein the compound is selected from the group:

N-{1-[4-(1,3,3-Trimethyl-6-aza-bicyclo[3.2.1]octane-6-carbonyl)-phenyl]-pyrrolidin-3-yl}-acetamide;

N-{1-[4-(8-Hydroxy-3-aza-bicyclo[3.2.1]octane-3-carbonyl)-phenyl]-pyrrolidin-3-yl}-acetamide;

4-(3-Acetylamino-pyrrolidin-1-yl)-N-(3-hydroxymethyl-adamantan-1-yl)-benzamide;

4-(3-Acetylamino-pyrrolidin-1-yl)-N-(5-hydroxy-adamantan-2-yl)-benzamide;

4-(3-Acetylamino-pyrrolidin-1-yl)-N-(5-hydroxy-adamantan-2-yl)-N-methyl-benzamide;

5-[4-(3-Aza-bicyclo[3.2.2]-nonane-3-carbonyl)-phenyl]-2,5-diaza-bicyclo[2.2.1]-heptane-2-carboxylic acid tert-butyl ester;

N-Adamantan-2-yl-4-((R)-3-benzyloxy-pyrrolidin-1-yl)-benzamide;

[4-((R)-3-Benzyloxy-pyrrolidin-1-yl)-phenyl]-(octahydro-quinolin-1-yl)-methanone;

4-((R)-3-Benzyloxy-pyrrolidin-1-yl)-N-(1-hydroxy-adamantan-2-yl)-benzamide;

4-((S)-3-Acetylamino-pyrrolidin-1-yl)-N-adamantan-2-yl-benzamide;

4-(3-Acetylamino-pyrrolidin-1-yl)-N-(3-hydroxy-adamantan-1-yl)-benzamide;

N-{(S)-1-[4-(Adamantan-2-ylcarbamoyl)-phenyl]-pyrrolidin-3-yl}-6-chloro-nicotin-amide;

1-Isopropyl-3-{(S)-1-[4-(octahydro-quinoline-1-carbonyl)-phenyl]-pyrrolidin-3-yl}-urea;

(Octahydro-quinolin-1-yl)-{4-[(1S,5R)-3-(pyridin-2-yloxy)-8-aza-bicyclo[3.2.1]oct-8-yl]-phenyl}-methanone;

N-Adamantan-2-yl-4-[(1S,5R)-3-(pyridin-2-yloxy)-8-aza-bicyclo[3.2.1]oct-8-yl]-benzamide;

2-[4-(Adamantan-2-yl-carbamoyl)-phenyl]-octahydro-pyrrolo[3,4-c]pyridine-5-carboxylic acid isopropylamide;

or a salt thereof with a pharmaceutically acceptable acid or base, or any optical isomer or mixture of optical isomers, including a racemic mixture, or any tautomeric forms.

62. A compound selected from the group:

[4-(3-Benzyloxy-pyrrolidin-1-yl)-phenyl]-(octahydroquinolin-1-yl)-methanone;

4-(3-Benzyloxy-pyrrolidin-1-yl)-N-tricyclo[3.3.1.13,7]decan-2-yl-benzamide;

(3-Aza-bicyclo[3.2.2]non-3-yl)-[4-(3-benzyloxy-pyrrolidin-1-yl)-phenyl]-methanone;

(S)-(3-Aza-bicyclo[3.2.2]non-3-yl)-[4-(3-benzyloxy-pyrrolidin-1-yl)-phenyl]-methanone;

or a salt thereof with a pharmaceutically acceptable acid or base, or any optical isomer or mixture of optical isomers, including a racemic mixture, or any tautomeric forms.

63. The compound according to any one of the preceding clauses, which is an agent useful for the treatment, prevention and/or prophylaxis of any conditions, disorders and diseases wherein a modulation or an inhibition of the activity of 11βHSD1 is beneficial.

64. The compound according to any one of the clauses 1-62, which is an agent useful for the treatment, prevention and/or prophylaxis of any conditions, disorders and diseases that are influenced by intracellular glucocorticoid levels.

65. The compound according to any one of the clauses 1-62 which is an agent useful for the treatment, prevention and/or prophylaxis of conditions, disorders or diseases selected from the group consisting of the metabolic syndrome, insulin resistance, dyslipidemia, hypertension and obesity.

66. The compound according to any one of the clauses 1-62 which is an agent useful for the treatment, prevention and/or prophylaxis of type 2 diabetes, impaired glucose tolerance (IGT), impaired fasting glucose (IFG).

67. The compound according to any one of the clauses 1-62 which is an agent useful for the delaying or prevention of the progression from IGT into type 2 diabetes.

68. The compound according to any one of the clauses 1-62 which is an agent useful for delaying or prevention of the progression of the metabolic syndrome into type 2 diabetes.

69. The compound according to any one of the clauses 1-62 which is an agent useful for the treatment, prevention and/or prophylaxis of adverse effects of glucocorticoid receptor agonist treatment or therapy.

70. A pharmaceutical composition comprising, as an active ingredient, at least one compound according to any one of the clauses 1-62 together with one or more pharmaceutically acceptable carriers or excipients.

71. The pharmaceutical composition according to clause 70 which is for oral, nasal, buccal, transdermal, pulmonal or parenteral administration.

72. The pharmaceutical composition according to clause 70 or 71 in unit dosage form, comprising from 0.05 mg to 2000 mg/day, from 0.1 mg to 1000 mg or from 0.5 mg to 500 mg per day of the compound according to anyone of the clauses 1-62.

73. Use of a compound according to any of the clauses 1-62, for the preparation of a pharmaceutical composition for the treatment, prevention and/or prophylaxis of any conditions, disorders and diseases wherein a modulation or an inhibition of the activity of 11βHSD1 is beneficial.

74. Use of a compound according to any of the clauses 1-62, for the preparation of a pharmaceutical composition for the treatment, prevention and/or prophylaxis of any conditions, disorders and diseases that are influenced by intracellular glucocorticoid levels.

75. Use of a compound according to any of the clauses 1-62, for the preparation of a pharmaceutical composition for the treatment, prevention and/or prophylaxis of conditions, disorders or diseases selected from the group consisting of the metabolic syndrome, insulin resistance, dyslipidemia, hypertension and obesity.

76. Use of a compound according to any of the clauses 1-62, for the preparation of a pharmaceutical composition for the treatment, prevention and/or prophylaxis of type 2 diabetes, impaired glucose tolerance (IGT), impaired fasting glucose (IFG).

77. Use of a compound according to any of the clauses 1-62, for the preparation of a pharmaceutical composition for the delaying or prevention of the progression from IGT to type 2 diabetes.

78. Use of a compound according to any of the clauses 1-62, for the preparation of a pharmaceutical composition for the delaying or prevention of the progression of the metabolic syndrome into type 2 diabetes.

79. Use of a compound according to any of the clauses 1-62, for the preparation of a pharmaceutical composition for the treatment, prevention and/or prophylaxis of adverse effects of glucocorticoid receptor agonist treatment or therapy.

80. A method for the treatment, prevention and/or prophylaxis of any conditions, disorders or diseases wherein a modulation or an inhibition of the activity of 11βHSD1 is beneficial, the method comprising administering to a subject in need thereof an effective amount of a compound according to the invention.

81. The method according to clause 80 wherein the conditions, disorders or diseases are selected from the group consisting of the metabolic syndrome, insulin resistance, dyslipidemia, hypertension and obesity.

The invention claimed is:

1. A method of lowering intracellular glucocorticoid levels in a subject, the method comprising administering to a subject a compound of formula I or a pharmaceutically acceptable salt thereof:

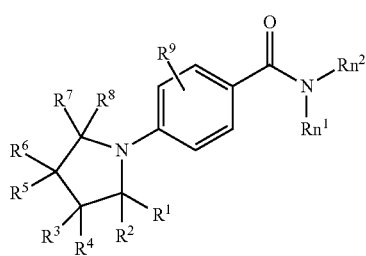

I wherein:
$R^1$, $R^2$, $R^3$, $R^4$, $R^7$ and $R^8$ are each H;
one of $R^5$ and $R^6$ is H, and the other is selected from the group consisting of —C(=O)—$R^{12}$, —O—$R^{Ib}$, and —$NR^{10}R^{11}$;
$R^{Ib}$ is hetaryl or aryl$C_1$-$C_6$alkyl;
$R^9$ is selected from the group consisting of H, halo, OH, cyano, $C_1$-$C_6$alkyl, $C_1$-$C_6$alkyloxy, trihalomethyloxy and $C_3$-$C_6$cycloalkyl;
$R^{10}$ and $R^{11}$ are each independently selected from the group consisting of H, $C_1$-$C_6$alkyl, $C_1$-$C_6$alkylcarbonyl, C(O)O$C_1$-$C_6$alkyl, aryl, hetaryl, aryl$C_1$-$C_6$alkyl, hetaryl$C_1$-$C_6$alkyl, $C_3$-$C_{10}$cycloalkyl, $C_3$-$C_{10}$hetcycloalkyl, arylcarbonyl, hetarylcarbonyl, aryl$C_1$-$C_6$alkylcarbonyl, hetaryl$C_1$-$C_6$alkylcarbonyl, $C_3$-$C_{10}$cycloalkylcarbonyl and $C_3$-$C_{10}$hetcycloalkylcarbonyl, wherein each alkyl, cykloalkyl, hetcycloalkyl, aryl, and hetaryl group is substituted with 0-3 $R^{18}$;
alternatively, $R^{10}$ and $R^{11}$, together with the nitrogen to which they are attached, form a 3-12 membered saturated or partially saturated monocyclic or bicyclic ring consisting of the shown nitrogen, 2-10 carbon atoms, and 0-2 additional heteroatoms selected from nitrogen, oxygen, and S(O)$_n$, wherein this ring is substituted with 0-3 groups selected from the group consisting of halo, $C_1$-$C_6$alkyl, $C_3$-$C_{10}$cycloalkyl, $C_3$-$C_{10}$hetcycloalkyl, $C_3$-$C_6$spirocycloalkyl, 3-6 membered spirohetcycloalkyl, aryl, hetaryl, aryl$C_1$-$C_6$alkyl, hetaryl$C_1$-$C_6$alkyl, —C(O)$R^{12}$, —S(O)$_n R^{12}$, —S(O)$_n NR^{14}R^{15}$, —N($R^{14}$)S(O)$_n R^{12}$, —N($R^{16}$)C(=Y)N$R^{14}R^{15}$, —C(=N$R^{17}$)N$R^{17}$, OH, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarboxy, arylcarboxy, hetarylcarboxy, aryl$C_1$-$C_6$alkylcarboxy, and hetaryl$C_1$-$C_6$alkylcarboxy, wherein each alkyl, aryl, and hetaryl group is substituted with 0-3 $R^{18}$;
$R^{12}$ is OH, $NR^{10}R^{11}$, $C_1$-$C_6$alkyloxy, $C_2$-$C_6$alkenyloxy, $C_2$-$C_6$alkynyloxy, $C_3$-$C_{10}$cycloalkyl, $C_3$-$C_{10}$cycloalkyloxy, $C_3$-$C_{10}$hetcycloalkyloxy, aryloxy, hetaryloxy, aryl$C_1$-$C_6$alkyloxy, or hetaryl$C_1$-$C_6$alkyloxy;
$R^{14}$ and $R^{15}$ are independently selected from the group consisting of H, $C_1$-$C_6$alkyl, $C_1$-$C_6$alkyloxy, aryl, hetaryl, aryl$C_1$-$C_6$alkylene, and hetaryl$C_1$-$C_6$alkylene, wherein the alkyl, alkylene, aryl, and hetaryl groups are independently substituted with 0-3 $R^{20}$;
alternatively, $R^{14}$ and $R^{15}$, together with the nitrogen atom to which they are attached, form a saturated or partially saturated monocyclic, bicyclic, or tricyclic ring consisting of the shown nitrogen, 4-10 carbon atoms, and 0-2 additional heteroatoms selected from nitrogen, oxygen, and sulfur, wherein this ring is substituted with 0-3 substituents selected from the group consisting of $C_1$-$C_6$alkyl, aryl, hetaryl, aryl$C_1$-$C_6$alkylene, hetaryl$C_1$-$C_6$alkylene, hydroxy, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarbonyl, arylcarbonyl, hetarylcarbonyl, aryl$C_1$-$C_6$alkylcarbonyl, hetaryl$C_1$-$C_6$alkylcarbonyl, $C_1$-$C_6$alkylcarboxy, arylcarboxy, hetarylcarboxy, aryl$C_1$-$C_6$alkyl-carboxy, and hetaryl$C_1$-$C_6$alkylcarboxy;
$R^{16}$ is selected from the group consisting of H and $C_1$-$C_6$alkyl;
$R^{17}$ is selected from the group consisting of H, $C_1$-$C_6$alkyl, 3-10 membered cycloalkyl, halo, OH, cyano, —C(=O)$R^{12}$, —S(=O)$_n R^{12}$, S(=O)$_n NR^{14}R^{15}$, —N($R^{14}$)S(O)$_n R^{12}$, aryl, and hetaryl, wherein the alkyl and cycloalkyl groups are substituted with 0-3 $R^{20}$;
$R^{18}$ is selected from the group consisting of halo, OH, oxo, COOH, S(O)$_2 R^{12}$, C(=O)O$C_1$-$C_6$alkyl, cyano, $C_1$-$C_6$alkyloxy, $C_3$-$C_{10}$ cycloalkyloxy, aryloxy, hetaryloxy, hetarylthio, and aryl$C_1$-$C_6$alkyloxy;
$R^{20}$ is selected from the group consisting of H, OH, oxo, halo, cyano, nitro, $C_1$-$C_6$alkyl, $C_1$-$C_6$-alkyloxy, $NR^{21}R^{22}$, methylendioxo, dihalomethylendioxo, trihalomethyl, and trihalomethyloxy;
$R^{21}$ and $R^{22}$ are independently selected from the group consisting of H, $C_1$-$C_6$alkyl, and aryl$C_1$-$C_6$alkyl;
$Rn^1$ is H; and $Rn^2$ is an adamantyl group substituted with 0-3 $R^{18}$; and
n is 0, 1 or 2.

2. A method of lowering intracellular glucocorticoid levels in a subject, the method comprising administering to a subject a compound, which is a compound selected from the group consisting of:
1-[4-(Adamantan-1-ylcarbamoyl)-phenyl]-pyrrolidine-3-carboxylic acid;
4-(3-Acetylamino-pyrrolidin-1-yl)-N-adamantan-2-yl-benzamide;

4-[3-(4-Chloro-phenyl)-pyrrolidin-1-yl]-N-adamantan-2-yl-benzamide;
4-[3-(Pyridin-2-yloxymethyl)-pyrrolidin-1-yl]-N-adamantan-2-yl-benzamide;
4-(3-Methanesulfonyl-pyrrolidin-1-yl)-N-adamantan-2-yl-benzamide;
4-[(R)-3-(3-Isopropyl-ureido)-pyrrolidin-1-yl]-N-adamantan-2-yl-benzamide;
Morpholine-4-carboxylic acid {(R)-1-[4-(adamantan-2-ylcarbamoyl)-phenyl]-pyrrolidin-3-yl}-amide; and
1-{(R)-1-[4-(adamantan-2-yl-phenyl]-pyrrolidin-3-yl}-3-N,N-dimethyl-sulfamide;
or a pharmaceutically acceptable salt thereof.

3. A method of lowering intracellular glucocorticoid levels in a subject, the method comprising administering to a subject a compound, which is a compound selected from the group consisting of:

4-(3-Acetylamino-pyrrolidin-1-yl)-N-(3-hydroxymethyl-adamantan-1-yl)-benzamide;
4-(3-Acetylamino-pyrrolidin-1-yl)-N-(5-hydroxy-adamantan-2-yl)-benzamide;
4-(3-Acetylamino-pyrrolidin-1-yl)-N-(5-hydroxy-adamantan-2-yl)-N-methyl-benzamide;
N-Adamantan-2-yl-4-((R)-3-benzyloxy-pyrrolidin-1-yl)-benzamide;
4-((R)-3-Benzyloxy-pyrrolidin-1-yl)-N-(1-hydroxy-adamantan-2-yl)-benzamide;
4-((S)-3-Acetylamino-pyr-rolidin-1-yl)-N-adamantan-2-yl-benzamide;
4-(3-Acetylamino-pyrrolidin-1-yl)-N-(3-hydroxy-adamantan-1-yl)-benzamide;
N-{(S)-1-[4-(Adamantan-2-ylcarbamoyl)-phenyl]-pyrrolidin-3-yl}-6-chloro-nicotin-amide;
N-Adamantan-2-yl-4-[(1S,5R)-3-(pyridin-2-yloxy)-8-aza-bicyclo[3.2.1]oct-8-yl]-benzamide; and
2-[4-(Adamantan-2-yl-carbamoyl)-phenyl]-octahydro-pyrrolo[3,4-c]pyridine-5-carboxylic acid isopropylamide;
or a pharmaceutically acceptable salt thereof.

* * * * *